United States Patent
Ryu et al.

(10) Patent No.: US 10,381,571 B2
(45) Date of Patent: Aug. 13, 2019

(54) COMPOUND, ORGANIC LIGHT EMITTING ELEMENT COMPRISING SAME, AND DISPLAY DEVICE COMPRISING ORGANIC LIGHT EMITTING ELEMENT

(71) Applicant: SAMSUNG SDI CO., LTD., Yongin-si, Gyeonggi-do (KR)

(72) Inventors: Dong-Wan Ryu, Suwon-si (KR); Dal-Ho Huh, Suwon-si (KR); Sung-Hyun Jung, Suwon-si (KR); Jin-Seok Hong, Suwon-si (KR); Jun-Seok Kim, Suwon-si (KR); Dong-Kyu Ryu, Suwon-si (KR); Seung-Jae Lee, Suwon-si (KR); Han-Ill Lee, Suwon-si (KR); Yu-Na Jang, Suwon-si (KR); Young-Kyoung Jo, Suwon-si (KR); Mi-Young Chae, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 283 days.

(21) Appl. No.: 14/844,439

(22) Filed: Sep. 3, 2015

(65) Prior Publication Data
US 2015/0380659 A1 Dec. 31, 2015

Related U.S. Application Data

(63) Continuation-in-part of application No. PCT/KR2013/007135, filed on Aug. 7, 2013.

(30) Foreign Application Priority Data

May 27, 2013 (KR) ........................ 10-2013-0059800

(51) Int. Cl.
| | | |
|---|---|---|
| H01L 51/54 | (2006.01) | |
| C09K 11/06 | (2006.01) | |
| H01L 51/00 | (2006.01) | |
| C07D 333/76 | (2006.01) | |
| C07D 307/91 | (2006.01) | |
| H01L 51/05 | (2006.01) | |
| C07D 405/14 | (2006.01) | |
| C07D 413/14 | (2006.01) | |
| C07D 405/12 | (2006.01) | |
| C07D 409/12 | (2006.01) | |
| C07D 409/14 | (2006.01) | |
| C07D 413/12 | (2006.01) | |
| C07D 417/12 | (2006.01) | |
| C07D 417/14 | (2006.01) | |
| H01L 51/50 | (2006.01) | |

(52) U.S. Cl.
CPC ........ *H01L 51/0061* (2013.01); *C07D 307/91* (2013.01); *C07D 333/76* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C09K 11/06* (2013.01); *H01L 51/006* (2013.01); *H01L 51/0052* (2013.01); *H01L 51/0059* (2013.01); *H01L 51/0071* (2013.01); *H01L 51/0072* (2013.01); *H01L 51/0073* (2013.01); *H01L 51/0074* (2013.01); *H01L 51/052* (2013.01); *C09K 2211/1077* (2013.01); *C09K 2211/1081* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC . C09K 11/06; C09K 2211/00; C09K 2211/10; C09K 2211/1003; C09K 2211/1007; C09K 2211/1018; C09K 2211/1074; C09K 2211/1077; C09K 2211/1081
See application file for complete search history.

(56) References Cited

U.S. PATENT DOCUMENTS

| 5,985,417 A | 11/1999 | Shi et al. |
| 2012/0248426 A1 | 10/2012 | Kato |

FOREIGN PATENT DOCUMENTS

| CN | 1458141 A | 11/2003 |
| CN | 101143830 A | 3/2008 |
| CN | 101432272 A | 5/2009 |
| CN | 101971384 A | 2/2011 |
| CN | 102858912 A | 1/2013 |
| JP | 01-219838 A | 9/1989 |
| JP | 04-126790 A | 4/1992 |
| JP | 08-048974 A | 2/1996 |
| JP | 11-185965 A | 7/1999 |
| JP | 11-185966 A | 7/1999 |
| JP | 11-233260 A | 8/1999 |

(Continued)

OTHER PUBLICATIONS

Machine translation of JP11-233260. Date of publication: Aug. 27, 1999.*
Pu et al. Organic Electronics 2010, 11, 479-485. Date of online publication: Dec. 16, 2009.*
Chang Woo Seo, et al., "Thin Solid Films", 2012, vol. 520, pp. 7022-7025.
Yong Joo Cho, et al., "Low Driving Voltage, H igh Quantum Efficiency, High Power Efficiency, and Little Efficiency Roll-Off in Red, Green, and Deep-Blue Phosphorescent Organic Light-Emitting diodes Using a High-Triplet-Energy Hole Transport Material", Advanced Materials, 2011, vol. 23, pp. 4568-4572.

(Continued)

*Primary Examiner* — Andrew K Bohaty
(74) *Attorney, Agent, or Firm* — Lee & Morse, P.C.

(57) ABSTRACT

A compound, an organic light emitting element including the same, and a display device including the organic light emitting element are disclosed, and the compound for an organic optoelectric device represented by Chemical Formula 1 is provided.

19 Claims, 3 Drawing Sheets

(56) References Cited

FOREIGN PATENT DOCUMENTS

| | | |
|---|---|---|
| JP | 2004-095491 A | 3/2001 |
| JP | 2005-044791 A | 2/2005 |
| JP | 3835918 B2 | 10/2006 |
| JP | 2007-088430 A | 4/2007 |
| JP | 2007-180148 A | 7/2007 |
| JP | 2010-056364 A | 3/2010 |
| JP | 2010-280635 A | 12/2010 |
| JP | 2011-160003 A | 8/2011 |
| KR | 10-2005-0107802 A | 11/2005 |
| KR | 10-2005-0118098 A | 12/2005 |
| KR | 10-2006-0043123 A | 5/2006 |
| KR | 10-2006-0121215 A | 11/2006 |
| KR | 10-2007-0016418 A | 2/2007 |
| KR | 10-2007-0024409 A | 3/2007 |
| KR | 10-2008-0047209 A | 5/2008 |
| KR | 10-2008-0104344 A | 12/2008 |
| KR | 10-0903841 B1 | 6/2009 |
| KR | 10-2009-0120699 A | 11/2009 |
| KR | 10-2010-0033265 A | 3/2010 |
| KR | 10-2011-0041727 A | 4/2011 |
| KR | 10-2011-0051256 A | 5/2011 |
| KR | 10-2011-0061792 A | 6/2011 |
| KR | 10-2012-0104172 A | 9/2012 |
| KR | 10-2013-0020399 A | 2/2013 |
| WO | WO 2007/046486 A1 | 4/2007 |
| WO | WO 2007/125714 A1 | 11/2007 |
| WO | WO 2011/133007 A2 | 10/2011 |
| WO | WO 2012/143079 A1 | 10/2012 |

OTHER PUBLICATIONS

Extended European Search Report dated Sep. 27, 2016 in Corresponding European Patent Application No. 13885531.7.

Chinese Search Report dated Jul. 13, 2016 in Corresponding Chinese Patent Application No. 201380076919.2.

* cited by examiner

COMPOUND, ORGANIC LIGHT EMITTING ELEMENT COMPRISING SAME, AND DISPLAY DEVICE COMPRISING ORGANIC LIGHT EMITTING ELEMENT

CROSS-REFERENCE TO RELATED APPLICATIONS

This application is a continuation-in-part of pending International Application No. PCT/KR2013/007135, entitled "Compound, Organic Light Emitting Element Comprising Same, and Display Device Comprising Organic Light Emitting Element," which was filed on Aug. 7, 2013, the entire contents of which are hereby incorporated by reference.

Korean patent Application No. 10-2013-0059800, filed on May 27, 2013, in the Korean Intellectual Property Office, and entitled: "Compound, Organic Light Emitting Element Comprising Same, and Display Device Comprising Organic Light Emitting Element," is incorporated by reference herein in its entirety.

BACKGROUND OF THE INVENTION (a) Field

A compound, an organic light emitting element including the same, and a display device including the organic light emitting element are disclosed.

(b) Description of the Related Art

An organic optoelectric device is a device requiring a charge exchange between an electrode and an organic material by using holes or electrons.

An organic optoelectric device may be classified as follows in accordance with its driving principles. A first organic optoelectric device is an electronic device driven as follows: excitons are generated in an organic material layer by photons from an external light source; the excitons are separated into electrons and holes; and the electrons and holes are transferred to different electrodes as a current source (voltage source).

A second organic optoelectric device is an electronic device driven as follows: a voltage or a current is applied to at least two electrodes to inject holes and/or electrons into an organic material semiconductor positioned at an interface of the electrodes, and the device is driven by the injected electrons and holes.

Examples of the organic optoelectric device includes organic photoelectric device, an organic light emitting element, an organic solar cell, an organic photo conductor drum, and an organic transistor, and the like, which requires a hole injecting or transport material, an electron injecting or transport material, or a light emitting material.

Particularly, an organic light emitting element (organic light emitting diode, OLED) has recently drawn attention due to an increasing demand for a flat panel display. In general, organic light emission refers to conversion of electrical energy into photo-energy.

Such an organic light emitting element converts electrical energy into light by applying current to an organic light emitting material. It has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light emitting element.

In such an organic light emitting element, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material can be used for a light emitting material of an organic light emitting element in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting element, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect, and therefore, a host/dopant system is included as a light emitting material in order to improve color purity and increase luminous efficiency and stability through energy transfer.

In order to implement excellent performance of an organic light emitting element, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting element has thus far not been satisfactory and thus there is a need for a novel material. This material development is also required for other organic optoelectric devices.

The low molecular organic light emitting element is manufactured as a thin film in a vacuum deposition method and can have good efficiency and life-span performance. A polymer organic light emitting element is manufactured in an Inkjet or spin coating method has an advantage of low initial cost and being large-sized.

Both low molecular organic light emitting and polymer organic light emitting elements have an advantage of self-light emitting, high speed response, wide viewing angle, ultra-thin, high image quality, durability, large driving temperature range, and the like. In particular, they have good visibility due to self-light emitting characteristic compared with a conventional LCD (liquid crystal display) and have an advantage of decreasing thickness and weight of LCD up to a third, because they do not need a backlight.

In addition, since they have a response speed of a microsecond unit, which is 1000 time faster than LCD, they can realize a perfect motion picture without after-image. Based on these advantages, they have been remarkably developed to have 80 times efficiency and more than 100 times life-span since they come out for the first time in the later 1980s and recently, they keep being rapidly larger such as a 40-inch organic light emitting element panel.

They are simultaneously required to have improved luminous efficiency and life-span in order to be larger. Therefore, a stable and efficient organic material layer material for an organic light emitting element needs to be developed.

SUMMARY

One embodiment provides a compound being capable of providing an organic optoelectric device having high efficiency and long life-span.

Another embodiment provides an organic light emitting element including the compound and a display device including the organic light emitting element.

In one embodiment of the present invention, a compound represented by Chemical Formula 1 is provided.

[Chemical Formula 1]

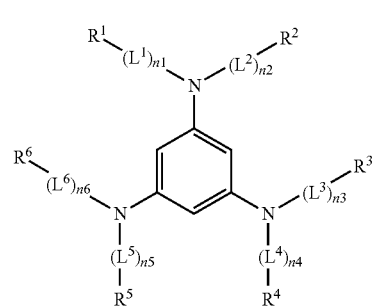

In Chemical Formula 1, $L^1$ to $L^6$ are each independently a substituted or unsubstituted C6 to C30 arylene group, or a substituted or unsubstituted C2 to C30 heteroarylene group except a substituted or unsubstituted fluorenylene group, n1 to n6 are each independently integers ranging from 0 to 3, $R^1$ to $R^6$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group or a substituted or unsubstituted silyl group, and at least one of the $R^1$ to $R^6$ is a substituent represented by Chemical Formula 2.

[Chemical Formula 2]

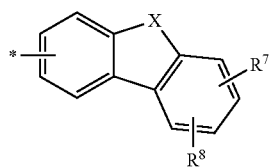

In Chemical Formula 2, X is O or S, $R^7$ or $R^8$ are selected from hydrogen, deuterium, a substituted or unsubstituted C1 to C30 alkyl group, a substituted or unsubstituted C6 to C30 aryl group and a substituted or unsubstituted C2 to C30 heteroaryl group, and * indicates a point where the substituent is linked to a carbon atom or an atom except carbon.

In Chemical Formula 1, $R^1$ and $R^2$ are independently present or are linked to each other to form a condensed ring, $R^3$ and $R^4$ are independently present or are linked to each other to form a condensed ring, $R^5$ and $R^6$ are independently present or are linked to each other to form a condensed ring, and when one of $R^1$ to $R^6$ is a substituted or unsubstituted fluorenyl group, the substituted or unsubstituted fluorenyl group is not directly bonded with the "N" of Chemical Formula 1.

The Chemical Formula 1 may be represented by one of Chemical Formulae 3 to 29.

[Chemical Formula 3]

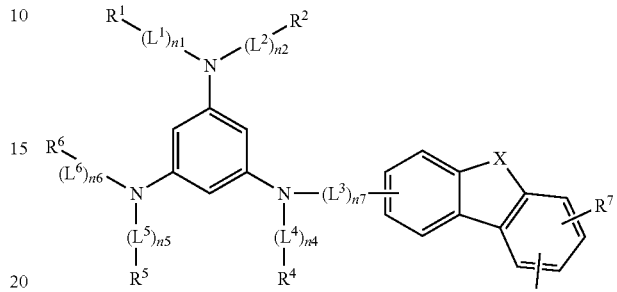

[Chemical Formula 4]

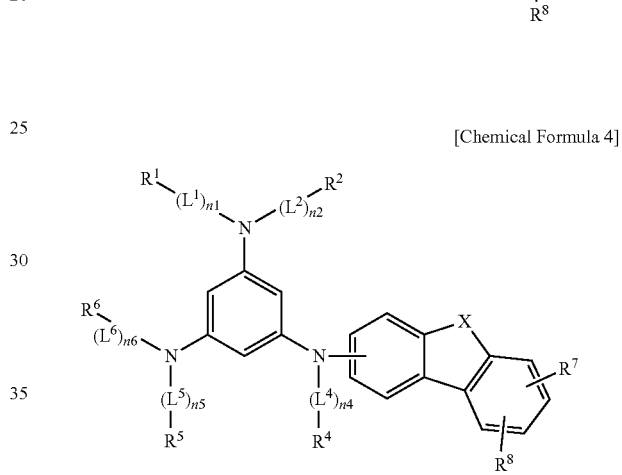

[Chemical Formula 5]

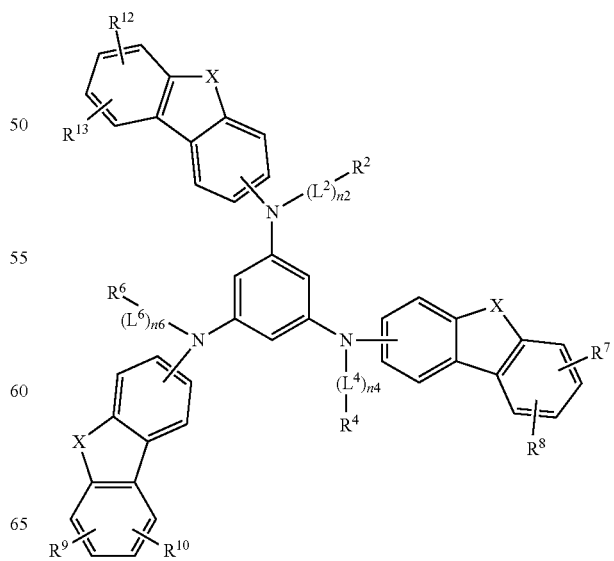

[Chemical Formula 6]
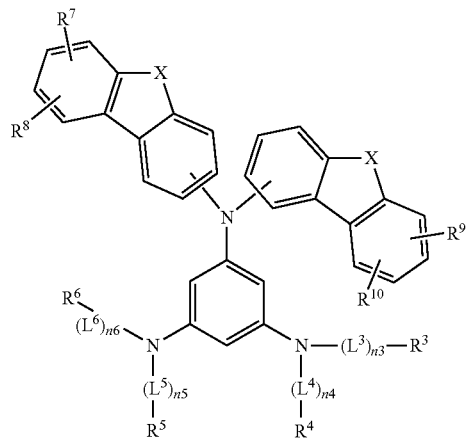
[Chemical Formula 7]
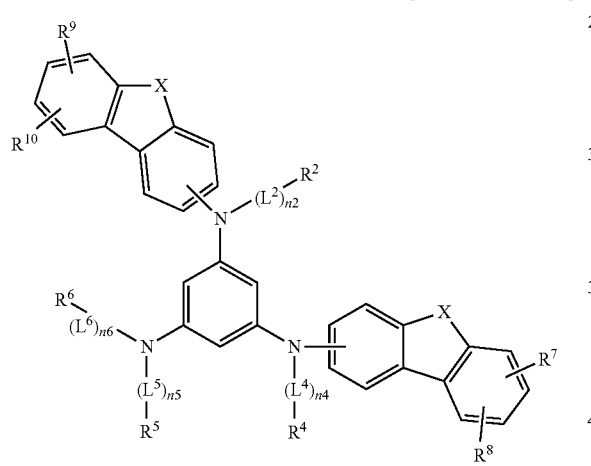
[Chemical Formula 8]
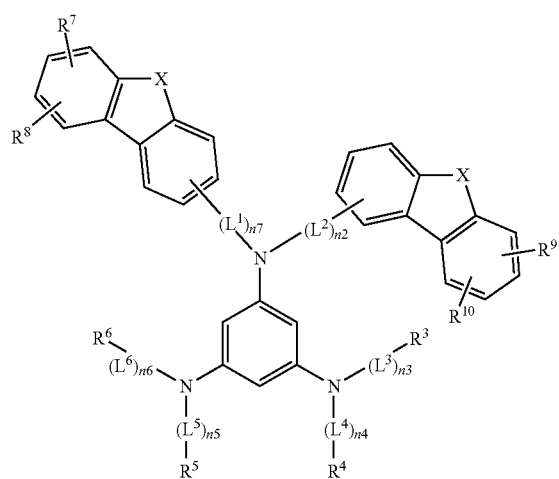
[Chemical Formula 9]
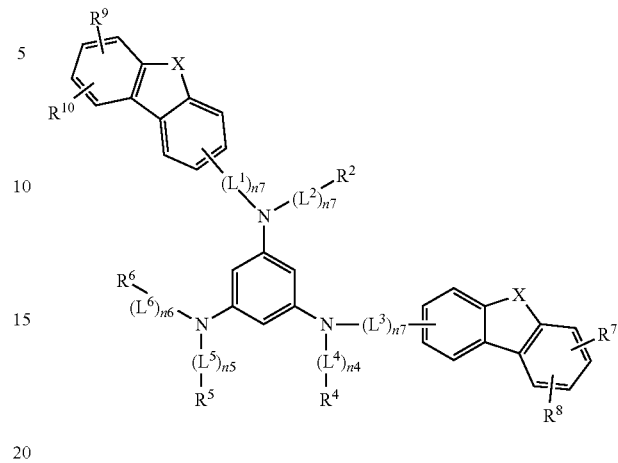
[Chemical Formula 10]
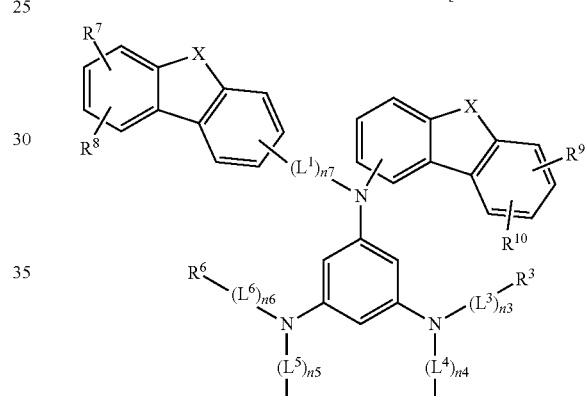
[Chemical Formula 11]
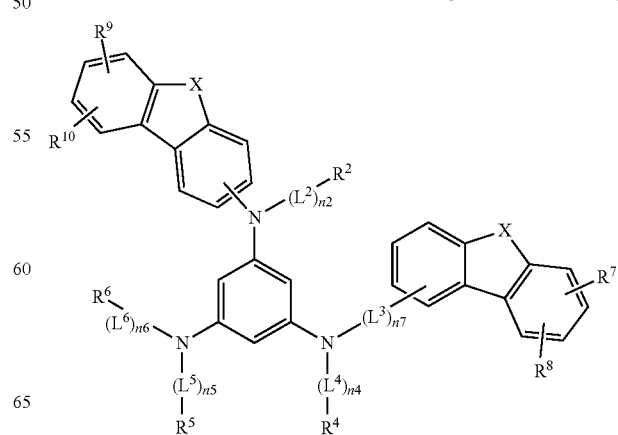

[Chemical Formula 12]
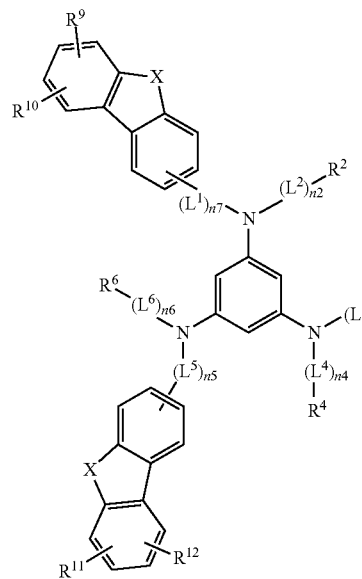
[Chemical Formula 13]
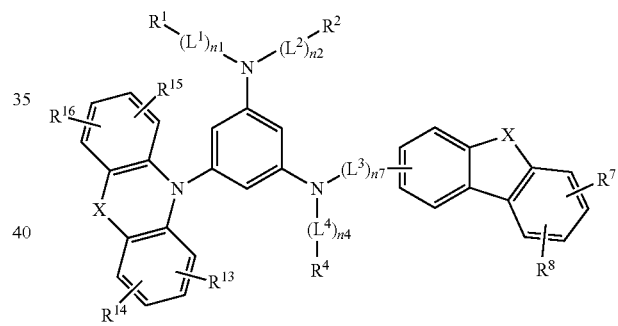
[Chemical Formula 14]
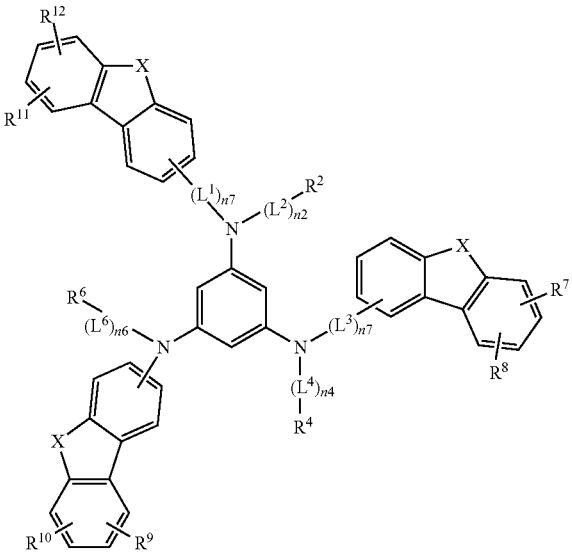
[Chemical Formula 15]
[Chemical Formula 16]
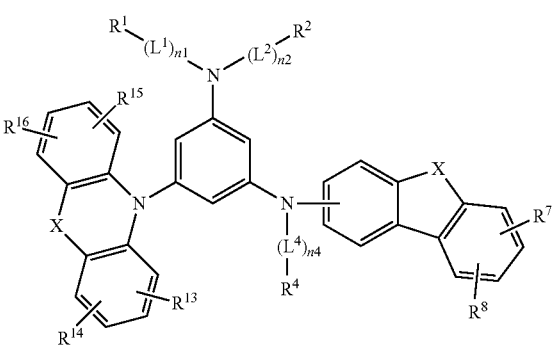

[Chemical Formula 17]
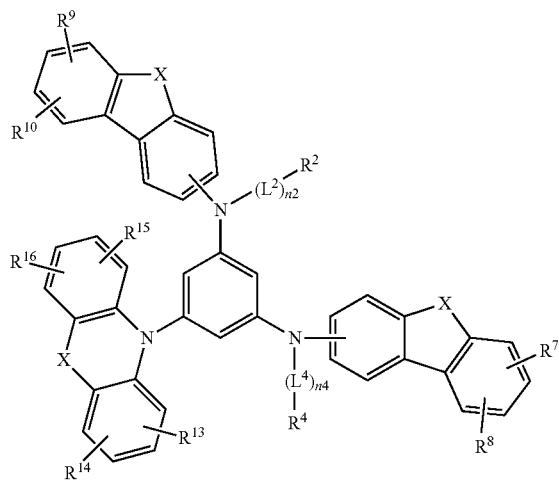
[Chemical Formula 18]
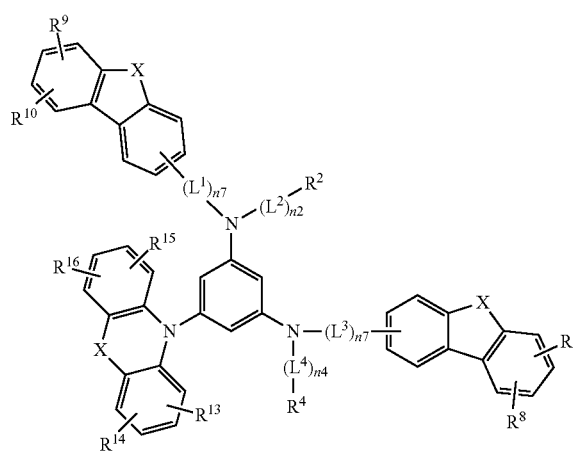
[Chemical Formula 19]
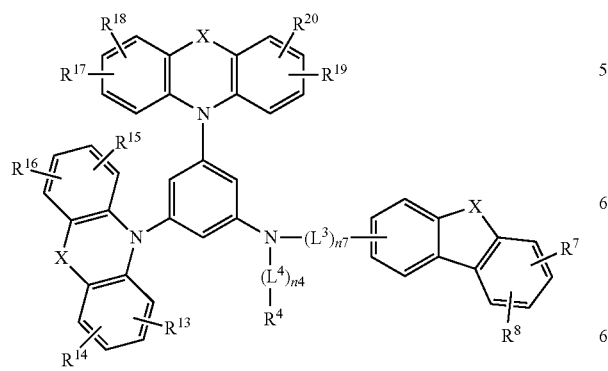
[Chemical Formula 20]
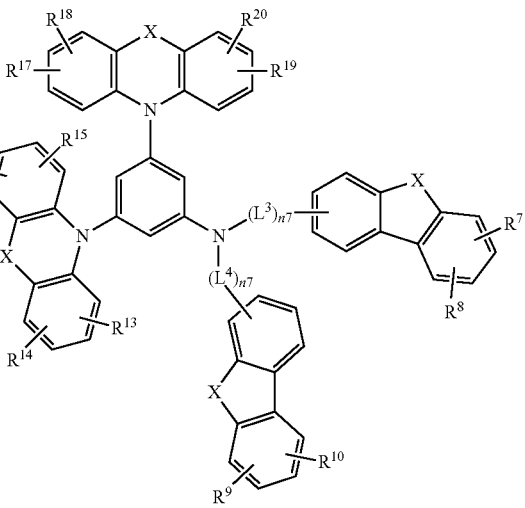
[Chemical Formula 21]
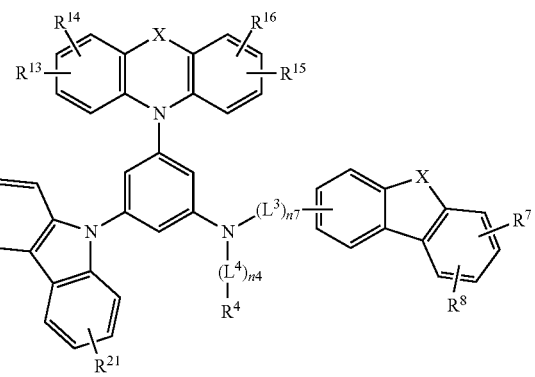
[Chemical Formula 22]
[Chemical Formula 23]
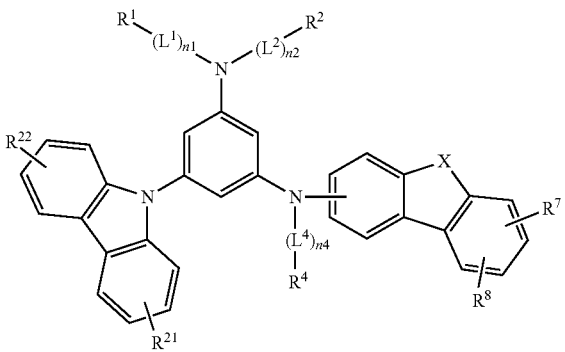

-continued

[Chemical Formula 24]

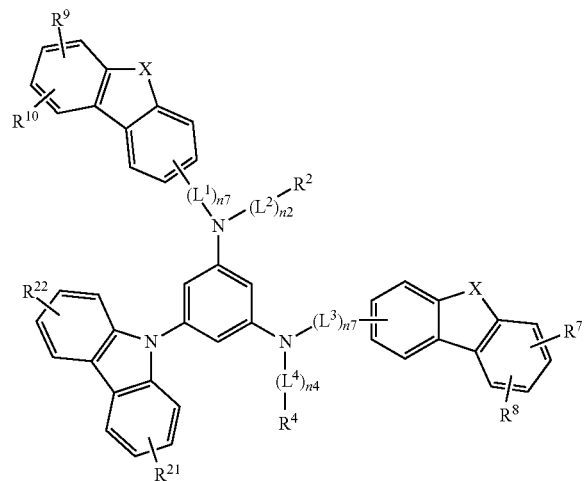

[Chemical Formula 25]

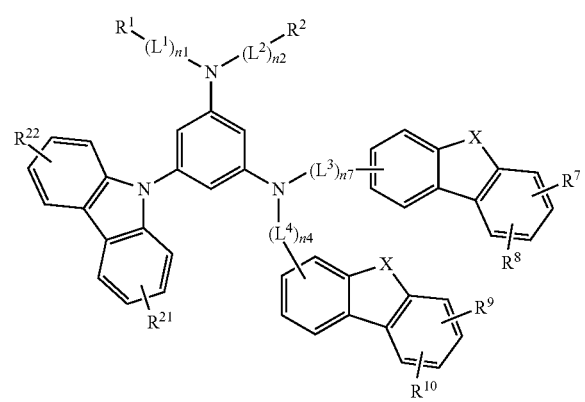

[Chemical Formula 26]

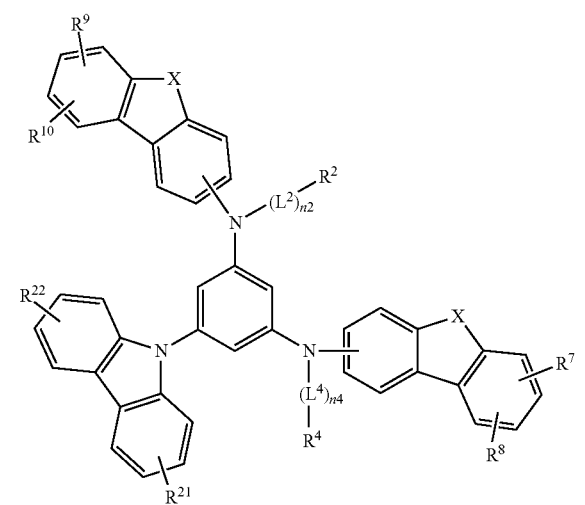

-continued

[Chemical Formula 27]

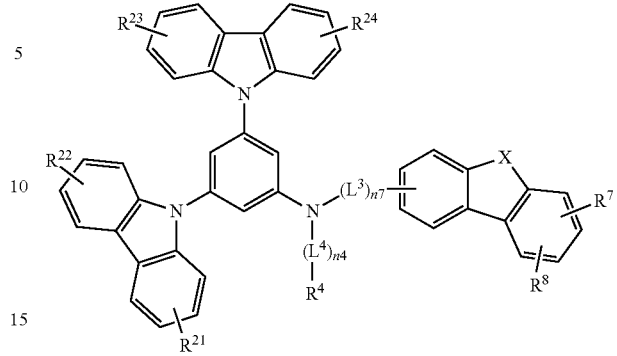

[Chemical Formula 28]

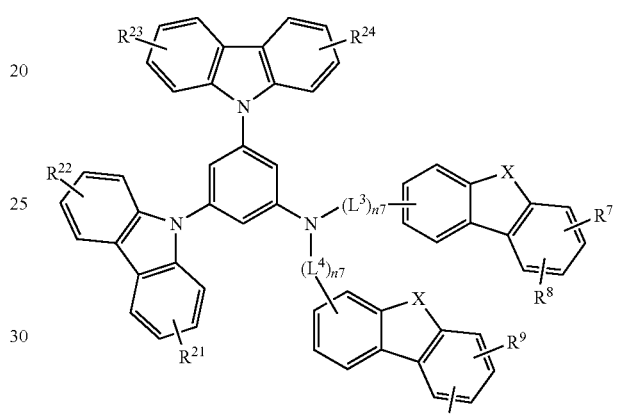

[Chemical Formula 29]

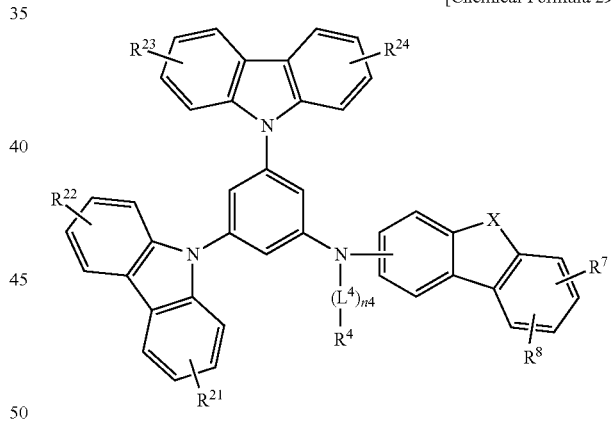

group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, or a combination thereof, but are not limited thereto.

In Chemical Formulae 3 to 29, $L^1$ to $L^6$ are each independently a substituted or unsubstituted C6 to C30 arylene group, or a substituted or unsubstituted C2 to C30 heteroarylene group except a substituted or unsubstituted fluorenylene group, n1 to n6 are each independently an integer of 0 to 3, n7 is an integer of 1 to 3, $R^1$ to $R^6$ are each independently selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, and a substituted or unsubstituted silyl group, when one of $R^1$ to $R^6$ is a substituted or unsubstituted fluorenyl group, the substituted or unsubstituted fluorenyl group is not directly bonded with "N" of Chemical Formula 1, X is O or S, and $R^7$ to $R^{24}$ are each independently selected from deuterium, a substituted or unsubstituted C1 to C30 alkyl group, a substituted or unsubstituted C6 to C30 aryl group and a substituted or unsubstituted C2 to C30 heteroaryl group.

$L^3$ of Chemical Formula 3, $L^1$ and $L^2$ of Chemical Formula 8, $L^1$ and $L^3$ of Chemical Formula 9, $L^2$ of Chemical Formula 10, $L^3$ of Chemical Formula 11, $L^1$, $L^3$ and $L^5$ of chemical Formula 12, $L^5$ of Chemical Formula 13, $L^1$ and $L^3$ of Chemical Formula 14, $L^3$ of Chemical Formula 15, $L^1$ and $L^3$ of Chemical Formula 18, $L^3$ of Chemical Formula 19, $L^3$ and $L^4$ of Chemical Formula 20, $L^3$ of Chemical Formula 21, $L^3$ of Chemical Formula 22, $L^1$ and $L^3$ of Chemical Formula 24, $L^3$ and $L^4$ of Chemical Formula 25, $L^3$ of Chemical Formula 27 and $L^3$ and $L^4$ of Chemical Formula 28 may be each independently a substituted or unsubstituted C6 to C30 arylene group, or a substituted or unsubstituted C2 to C30 heteroarylene group except a substituted or unsubstituted fluorenylene group.

The $L^1$ and $L^6$ may be each independently a substituted or unsubstituted C6 to C30 arylene group except a substituted or unsubstituted fluorenylene group.

In another embodiment of the present invention, provided is an organic light emitting element that includes an anode, a cathode and at least one organic thin layer between the anode and the cathode, wherein at least one layer of the organic thin layer includes the compound according to the embodiment of the present invention.

The organic thin layer may be an electron injection layer (EIL), an electron transport layer (ETL), a hole injection layer (HIL), a hole transport layer (HTL), an auxiliary hole transport layer (HTL), or emission layer.

The organic thin layer may be a hole injection layer (HIL) or a hole transport layer (HTL).

The organic thin layer may be an auxiliary hole transport layer (HTL).

The organic thin layer may be an emission layer.

The compound may be used as a host in an emission layer.

In yet another embodiment of the present invention, a display device including the organic light emitting element according to the embodiment of the present invention is provided.

An organic optoelectric device including the compound according to the embodiment of the present invention has excellent electrochemical and thermal stability, improved life-span characteristics, and high luminous efficiency at a low driving voltage. In addition, the compound may be appropriate for a solution process.

Figure 1:
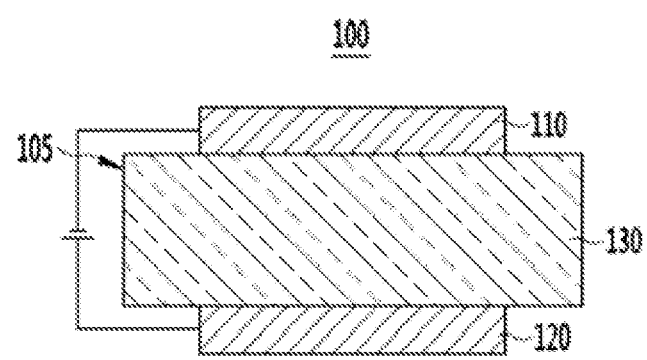
FIGS. 1 and 2 are cross-sectional views showing various embodiments of organic light emitting elements according to embodiments of the present invention.

<Description of Reference Numerals Indicating Primary Elements in the Drawings>

100, 200: organic light emitting element 110: cathode
120: anode 105: organic thin layer
130: emission layer 140: hole transport layer (HTL)
230: emission layer + electron transport layer (ETL)

DETAILED DESCRIPTION

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium, a halogen, hydroxy group, an amino group, a substituted or unsubstituted C1 to C30 amine group, a nitro group, a substituted or unsubstituted C1 to C40 silyl group, C1 to C30 alkyl group, C1 to C10 alkylsilyl group, C3 to C30 cycloalkyl group, C6 to C30 aryl group, C1 to C20 alkoxy group, a fluoro group, a C1 to C10 trifluoralkyl group such as a trifluoromethyl group, or a cyano group instead of at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused with each other to form a ring. Specifically, the substituted C6 to C30 aryl group is fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, and P, and remaining carbons in a functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, cyclopropyl group, a cyclobutyl group, a cyclopentyl group, a cyclohexyl group, and the like.

In the present specification, "aryl group" refers to a cyclic substituent where all elements have p-orbitals, and these p-orbitals forms conjugation, and includes a monocyclic or fused ring polycyclic (i.e., rings sharing adjacent pairs of carbon atoms) functional group.

In the present specification, "heteroaryl group" refers to aryl group including 1 to 3 hetero atoms selected from N, O, S, and P, and remaining carbons. When the heteroaryl group is a fused ring, each ring may include 1 to 3 hetero atoms.

More specifically, the substituted or unsubstituted C6 to C30 aryl group and/or the substituted or unsubstituted C2 to C30 heteroaryl group refer to a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, or a combination thereof, but are not limited thereto.

For more specific examples, the substituted or unsubstituted fluorenyl group included in the substituted C6 to C30 aryl group may be Chemical Formula 30 or 31.

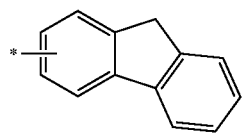

[Chemical Formula 30]

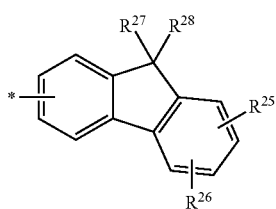

[Chemical Formula 31]

In Chemical Formulae 30 and 31, $R^{25}$ to $R^{28}$ are independently hydrogen, deuterium, a halogen, hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, C3 to C30 cycloalkyl group, a C6 to C30 aryl group, a C1 to C20 alkoxy group, a fluoro group, a C1 to C10 trifluoroalkyl group such as a trifluoromethyl group and the like or a cyano group, and * indicates a point where the substituent is linked to a carbon atom or an atom except carbon.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level. More specifically, it is similar to electron-withdrawing characteristics.

In one embodiment of the present invention, a compound represented by Chemical Formula 1 is provided.

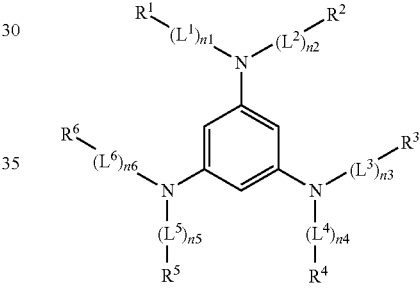

[Chemical Formula 1]

In Chemical Formula 1, $L^1$ to $L^6$ are each independently a substituted or unsubstituted C6 to C30 arylene group, or a substituted or unsubstituted C2 to C30 heteroarylene group except a substituted or unsubstituted fluorenylene group, n1 to n6 are each independently integers ranging from 0 to 3, R1 to R6 are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group, and at least one of the R1 to R6 is a substituent represented by Chemical Formula 2.

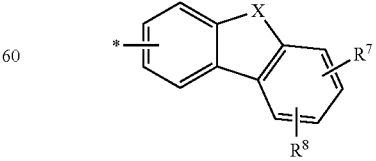

[Chemical Formula 2]

In Chemical Formula 2, X is O or S, $R^7$ or $R^8$ are hydrogen, deuterium, a substituted or unsubstituted C1 to C30 alkyl group, a substituted or unsubstituted C6 to C30 aryl group, or a substituted or unsubstituted C2 to C30 heteroaryl group, and * indicates a point where the substituent is linked to a carbon atom or an atom except carbon.

In Chemical Formula 1, $R^1$ and $R^2$ are independently present or are linked to each other to form a condensed ring, $R^3$ and $R^4$ are independently present or are linked to each other to form a condensed ring, and $R^5$ and $R^6$ are independently present or are linked to each other to form a condensed ring. When one of $R^1$ to $R^6$ is a substituted or unsubstituted fluorenyl group, the substituted or unsubstituted fluorenyl group is not directly bonded with the "N" of Chemical Formula 1.

The compound according to one embodiment of the present invention has a substituent represented by Chemical Formula 2 at at least one of the $R^1$ to $R^6$ and thus has an increased glass transition temperature and thus, may have improved thermal stability and in addition, has improved hole transport capability and thus, may improve a driving voltage, efficiency and a life-span when used to form hole injection and transport layers of an organic light emitting element.

In addition, the compound represented by Chemical Formula 1 may have various energy bandgaps due to various substituents.

More specifically, the Chemical Formula 1 may be represented by one of Chemical Formulae 3 to 29.

[Chemical Formula 3]

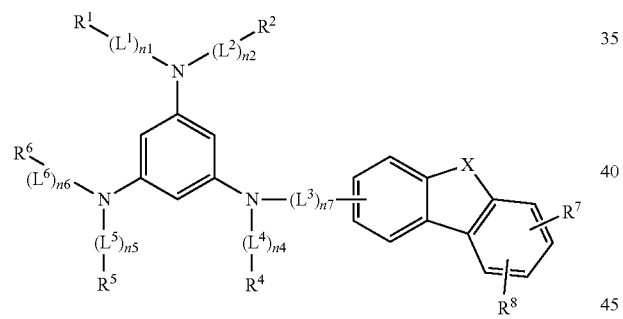

[Chemical Formula 4]

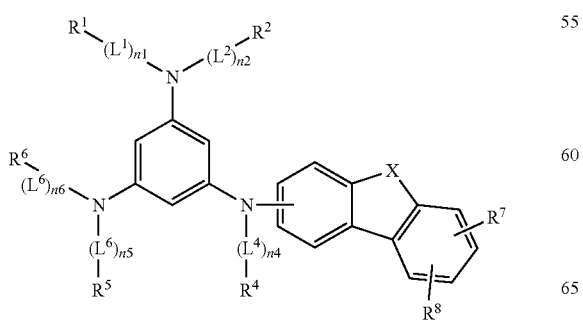

[Chemical Formula 5]

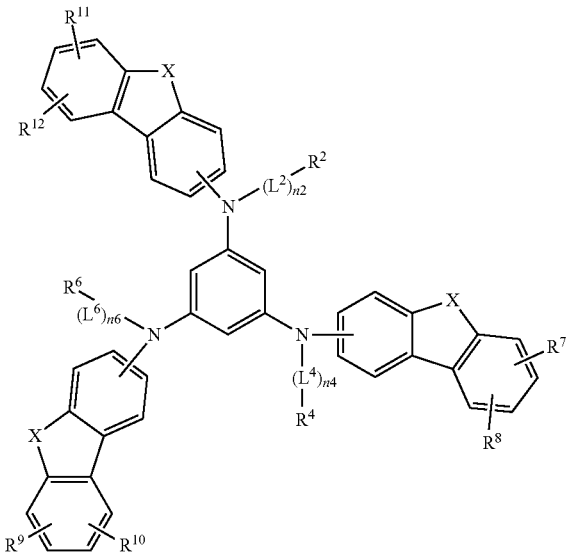

[Chemical Formula 6]

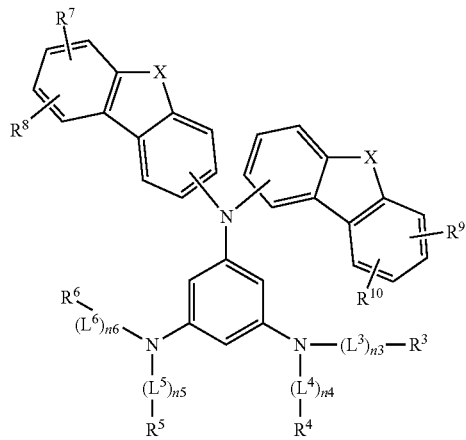

[Chemical Formula 7]

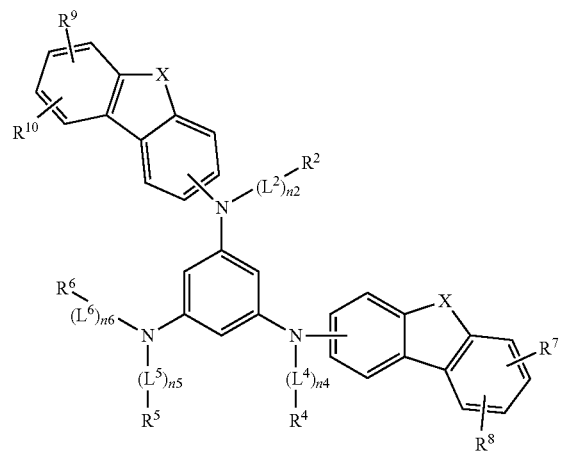

[Chemical Formula 8]
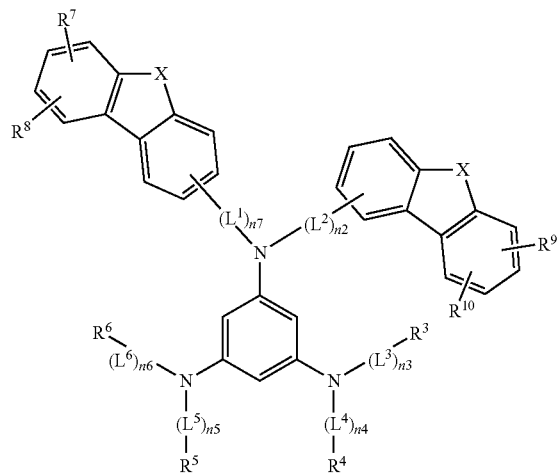
[Chemical Formula 9]
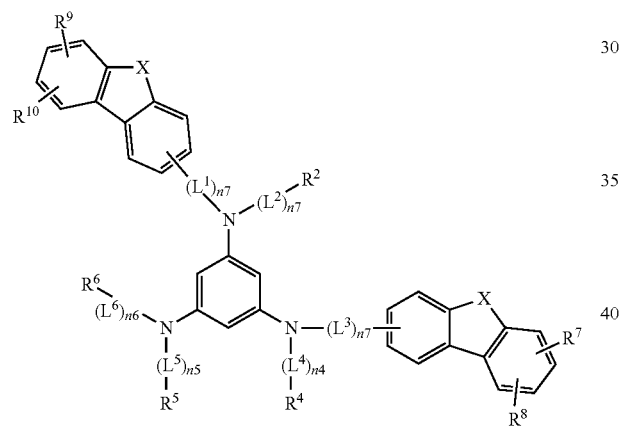
[Chemical Formula 10]
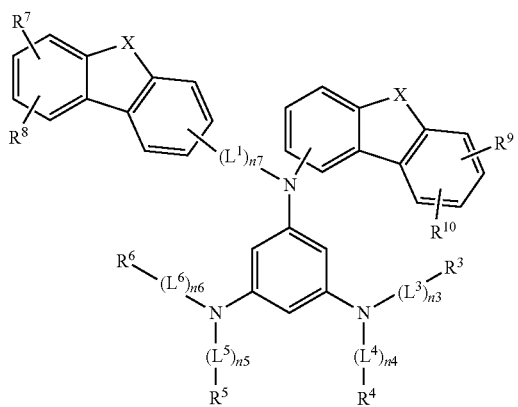
[Chemical Formula 11]
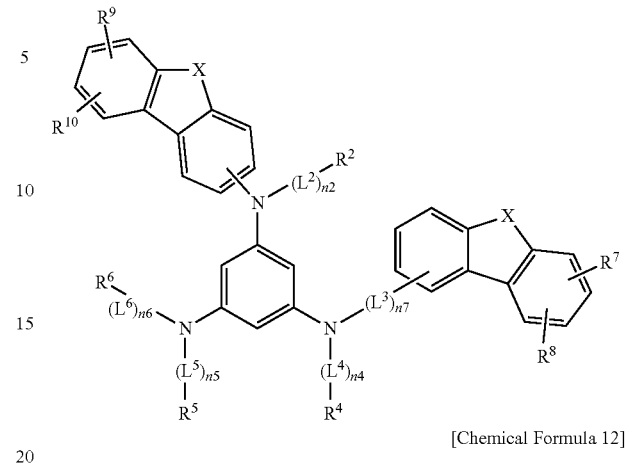
[Chemical Formula 12]
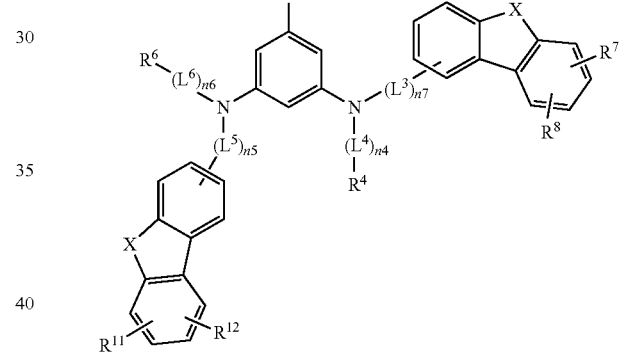
[Chemical Formula 13]
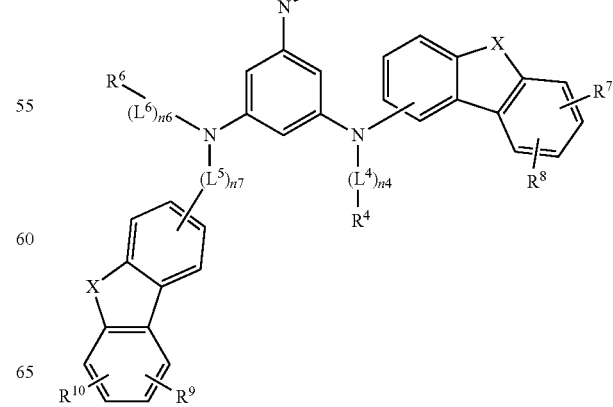

-continued
[Chemical Formula 14]
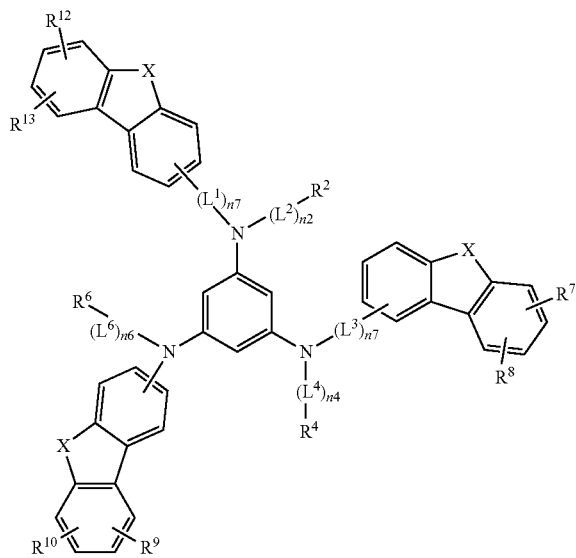
[Chemical Formula 15]
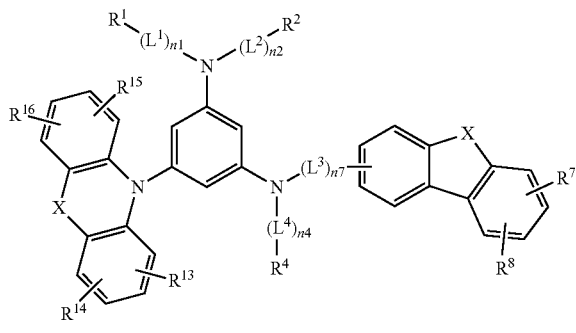
[Chemical Formula 16]
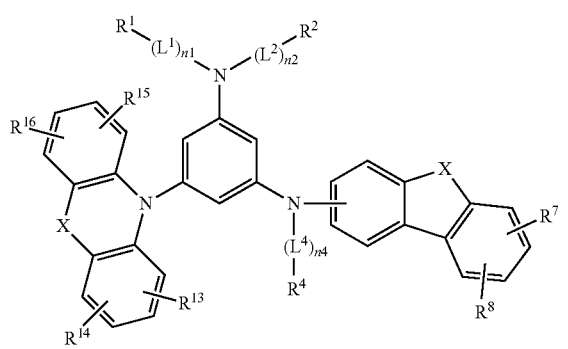
[Chemical Formula 17]
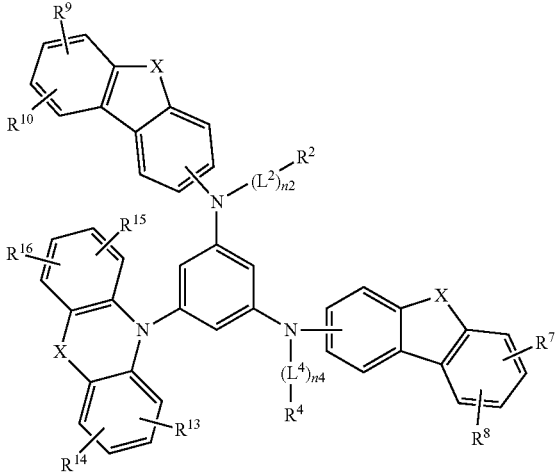
[Chemical Formula 18]
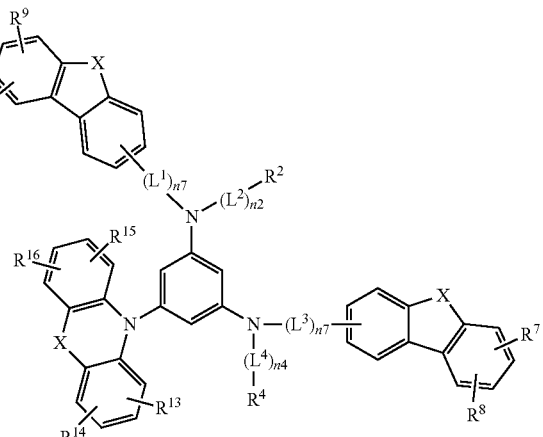
[Chemical Formula 19]
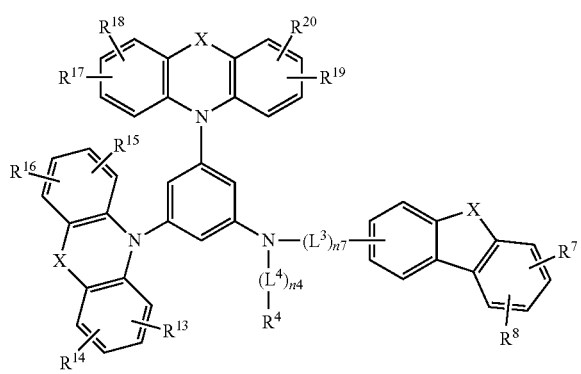

[Chemical Formula 20]
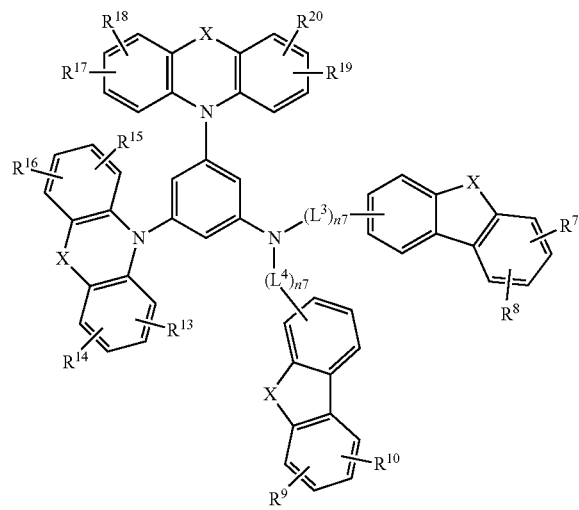
[Chemical Formula 21]
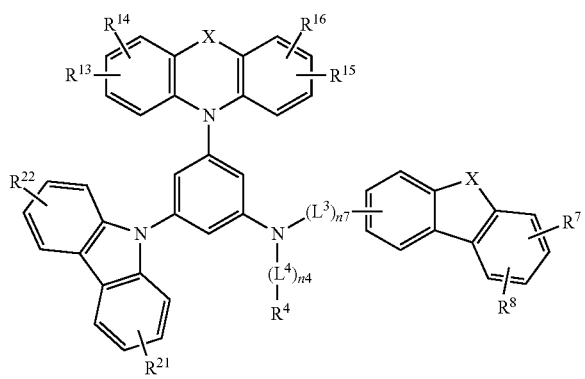
[Chemical Formula 22]
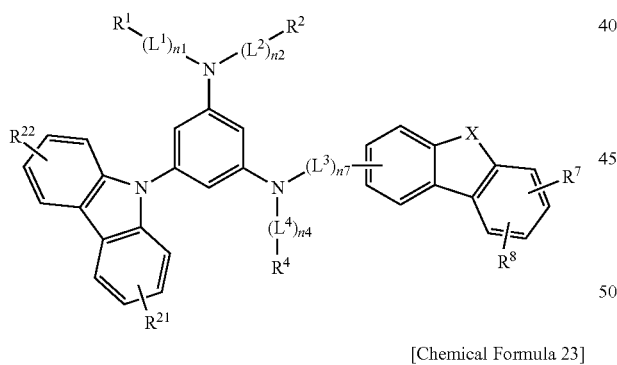
[Chemical Formula 23]
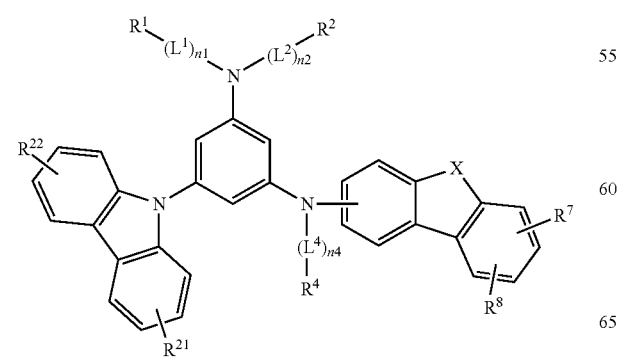
[Chemical Formula 24]
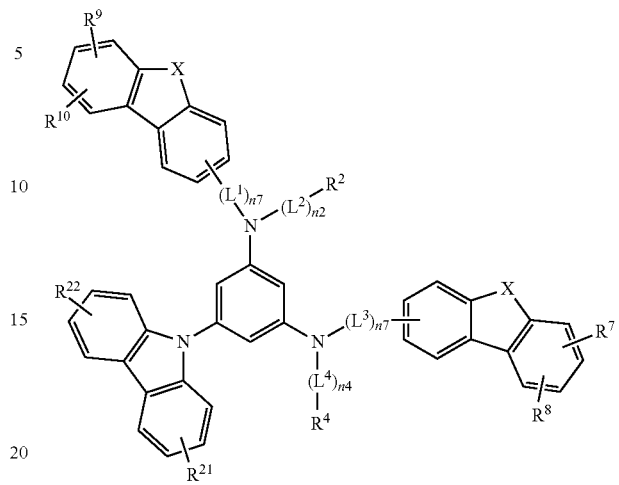
[Chemical Formula 25]
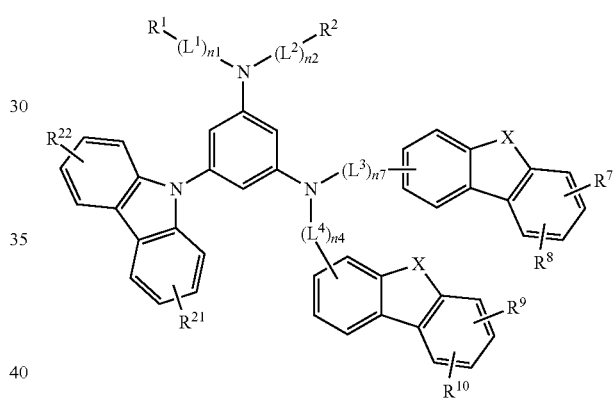
[Chemical Formula 26]
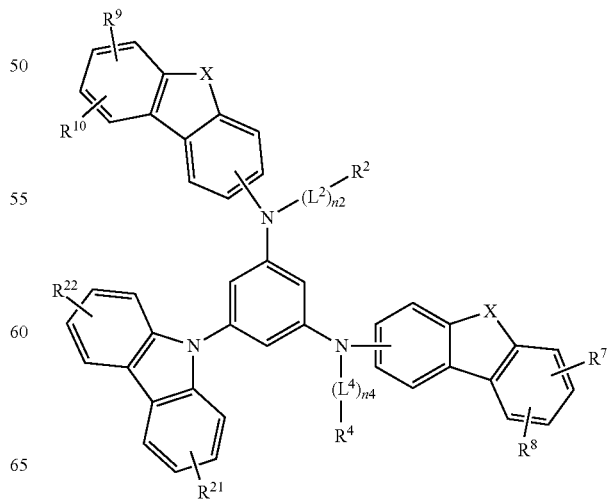

[Chemical Formula 27]

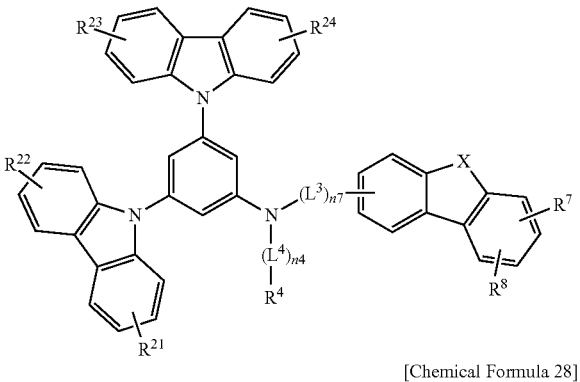

[Chemical Formula 28]

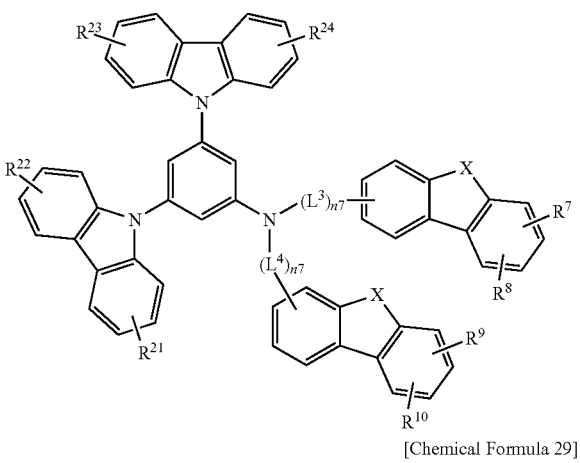

[Chemical Formula 29]

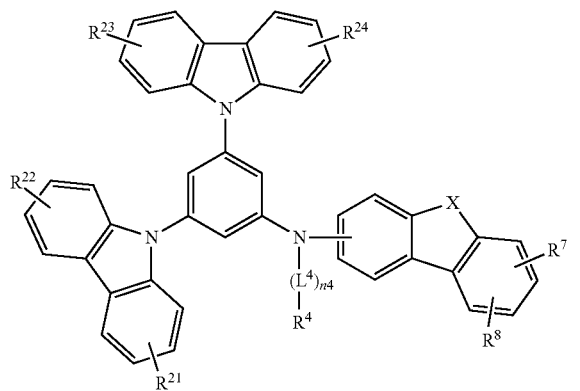

In Chemical Formulae 3 to 29, $L^1$ to $L^6$ are each independently a substituted or unsubstituted C6 to C30 arylene group, or a substituted or unsubstituted C2 to C30 heteroarylene group except a substituted or unsubstituted fluorenylene group, n1 to n6 are each independently an integer of 0 to 3, n7 is an integer of 1 to 3, $R^1$ to $R^6$ are each independently selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group and a substituted or unsubstituted silyl group, and when one of $R^1$ to $R^6$ is a substituted or unsubstituted fluorenyl group, the substituted or unsubstituted fluorenyl group is not directly bonded with the "N" of Chemical Formula 1.

X is O or S, and $R^7$ to $R^{24}$ are each independently selected from hydrogen, deuterium, a substituted or unsubstituted C1 to C30 alkyl group, a substituted or unsubstituted C6 to C30 aryl group and a substituted or unsubstituted C2 to C30 heteroaryl group.

The Chemical Formulae 3 to 29 may have an increased glass transition temperature and may have improved thermal stability due to at least one substituent represented by Chemical Formula 2, and in addition, have improved hole transport capability and resultantly, may improve efficiency and a life-span when used to form hole injection and transport layers of an organic light emitting element.

In addition, the compounds represented by Chemical Formulae 15 to 21 additionally include an amine compound except carbazole in addition to the substituent represented by Chemical Formula 2 and thus, improved hole injection characteristics since a HOMO energy level is increased, and thus, a hole injection barrier is lowered, and accordingly, may deteriorate a driving voltage when used to form a hole injection layer (HIL).

In addition, the compounds represented by Chemical Formulae 22 to 29 accitionally include an amine compound and/or a carbazolyl group in addition to the substituent represented by Chemical Formula 2 and thus, have improved thermal stability and resultantly, may improve life-span characteristics, and in addition, have a high triplet energy level (T1) and may have appropriate characteristics as a host of a phosphorescent emission layer or a hole transport material for a phosphorescent organic light emitting element.

$L^3$ of Chemical Formula 3, $L^1$ and $L^2$ of Chemical Formula 8, $L^1$ and $L^3$ of Chemical Formula 9, $L^2$ of Chemical Formula 10, $L^3$ of Chemical Formula 11, $L^1$ $L^3$ and $L^5$ of Chemical Formula 12, $L^5$ of Chemical Formula 13, $L^1$ and $L^3$ of Chemical Formula 14, $L^3$ of Chemical Formula 15, $L^1$ and $L^3$ of Chemical Formula 18, $L^3$ of Chemical Formula 19, $L^3$ and $L^4$ of Chemical Formula 20, $L^3$ of Chemical Formula 21, $L^3$ of Chemical Formula 22, $L^1$ and $L^3$ of Chemical Formula 24, $L^3$ and $L^4$ of Chemical Formula 25, $L^3$ of Chemical Formula 27 and $L^3$ and $L^4$ of Chemical Formula 28 may be each independently a substituted or unsubstituted C6 to C30 arylene group, or a substituted or unsubstituted C2 to C30 heteroarylene group except a substituted or unsubstituted fluorenylene group. More specifically, the $L^1$ to $L^6$ may be each independently a substituted or unsubstituted C6 to C30 arylene group except a substituted or unsubstituted fluorenylene group. In this case, the compound may have appropriate hole transport characteristics and from a more stable thin film due to the increased molecular weight and improved packing characteristics.

The $L^1$ to $L^6$ may be selectively adjusted to determine an entire conjugation length of the compound, and a triplet energy bandgap of the compound may be adjusted therefrom. Thereby, characteristics of a material required of an organic optoelectric device may be realised. In addition, the triplet energy bandgap may also be adjusted by changing a bonding position of ortho, para, and meta.

Specific examples of the $L^1$ to $L^6$ may be a substituted or unsubstituted phenylene group, a substituted or unsubstituted biphenylene group, a substituted or unsubstituted p-terphenylene group, a substituted or unsubstituted m-terphenylene group, a substituted or unsubstituted o-terphenylene group, a substituted or unsubstituted naphthylene group, a substituted or unsubstituted anthracenylene group, a substituted or unsubstituted phenanthrylene group, a substituted or unsubstituted pyrenylene group, and the like, but is not limited thereof.

The $R^1$ to $R^6$ may be each independently hydrogen, or a substituted or unsubstituted C6 to C30 aryl group. In this case, since hole and/or electron characteristics of the compound may be appropriately adjusted, the compound may be used as an emission layer material as well as a hole transport material by adjusting a bandgap and a light emitting wavelength.

Specific examples of the $R^1$ to $R^6$ may be hydrogen, a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenyl group, or a substituted, or unsubstituted fluorenyl group, and when one of $R^1$ to $R^6$ is a substituted or unsubstituted fluorenyl group, in Chemical Formulae 1 and Chemical Formulae 3 to 29, the substituted or unsubstituted fluorenyl group is not directly bonded with the "N."

Specific examples of the compound according to one embodiment of the present invention are as follows, but are not limited thereto.

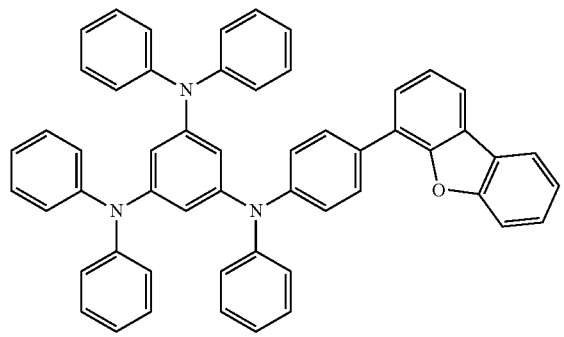

[A-1]

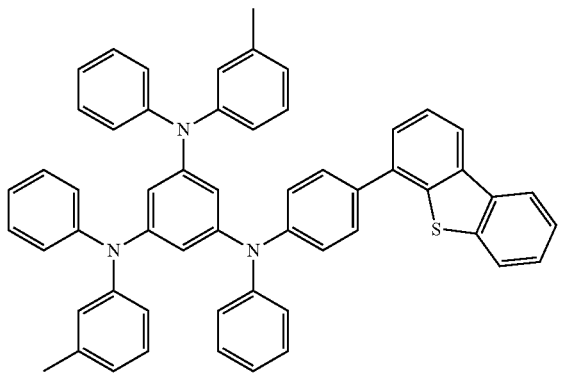

[A-2]

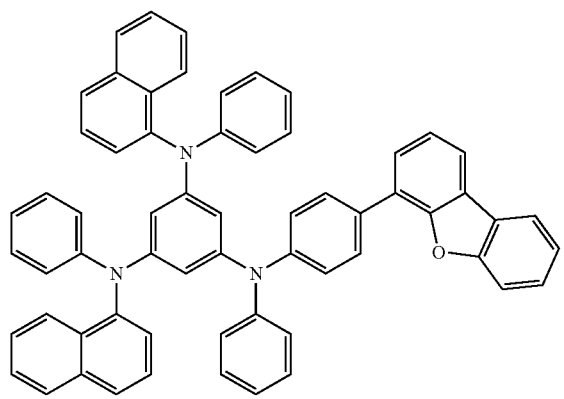

[A-3]

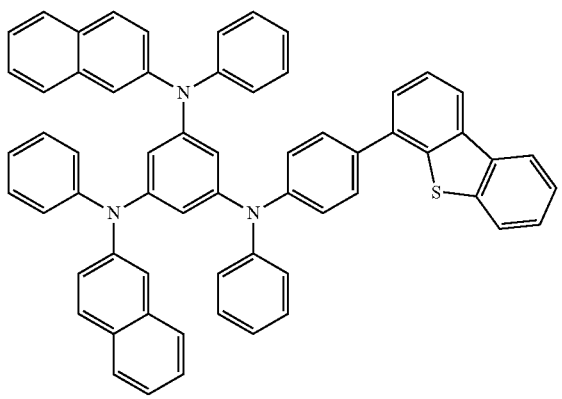

[A-4]

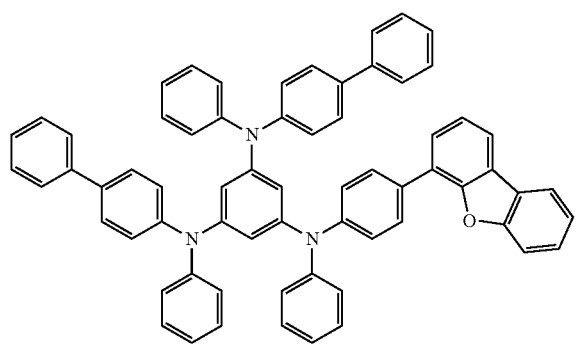

[A-5]

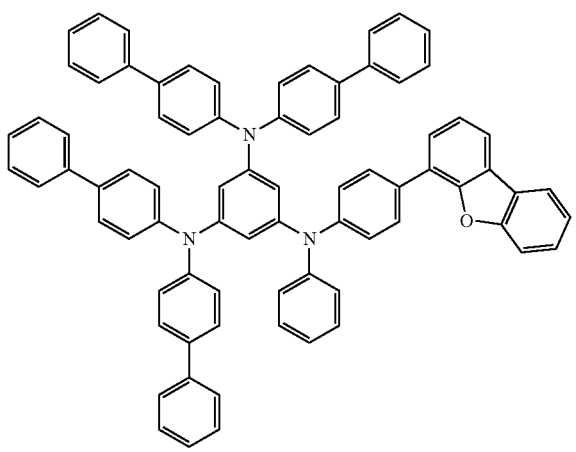

[A-6]

-continued
[A-7]
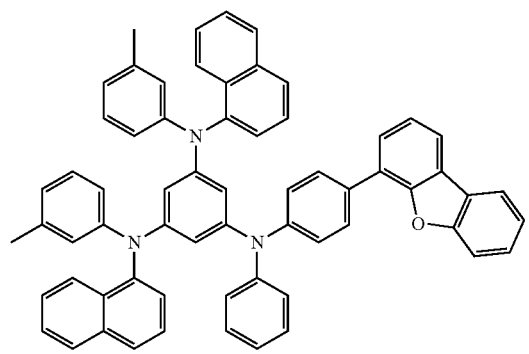
[A-8]
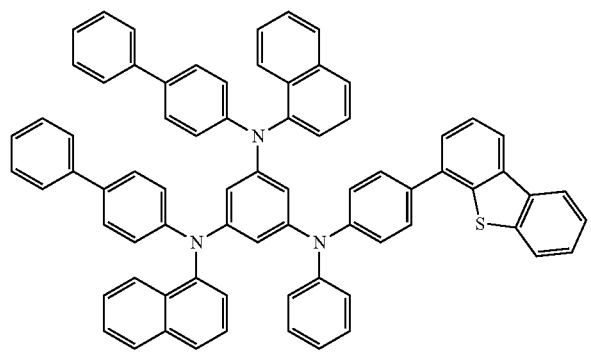
[A-9]
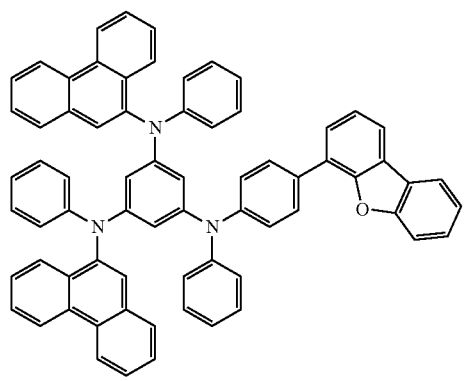
[A-10]
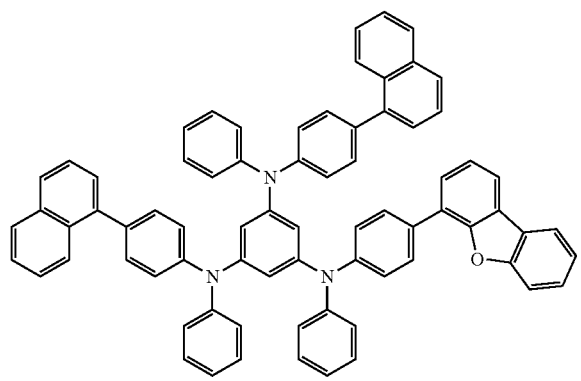
[A-11]
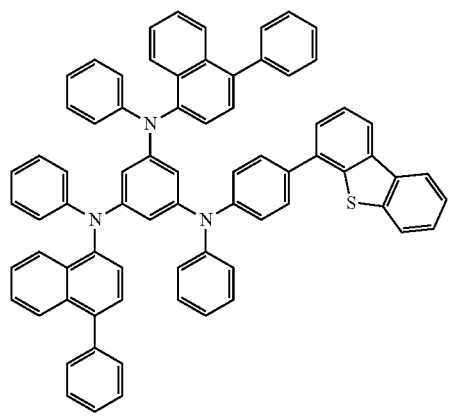
[A-12]
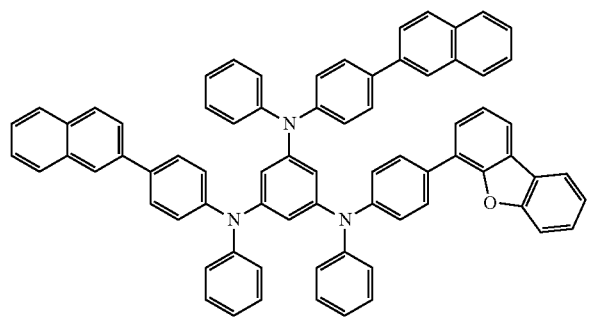

-continued
[A-13]
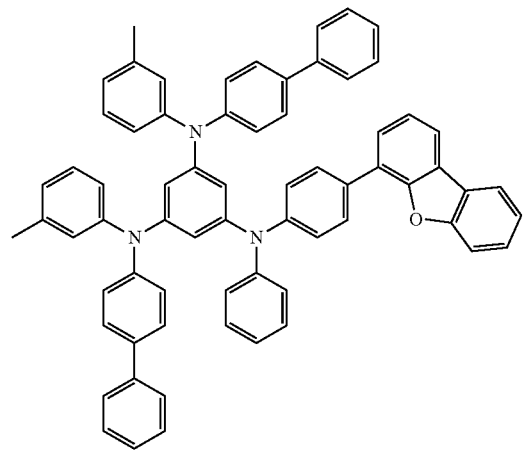
[A-14]
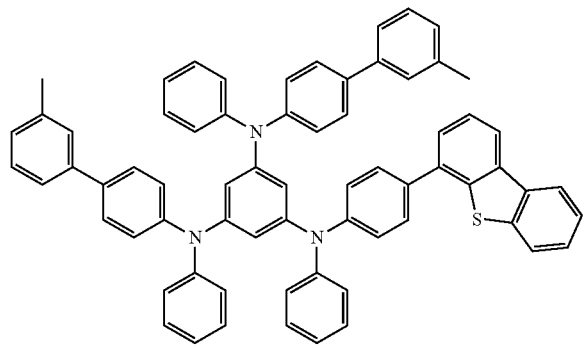
[A-15]
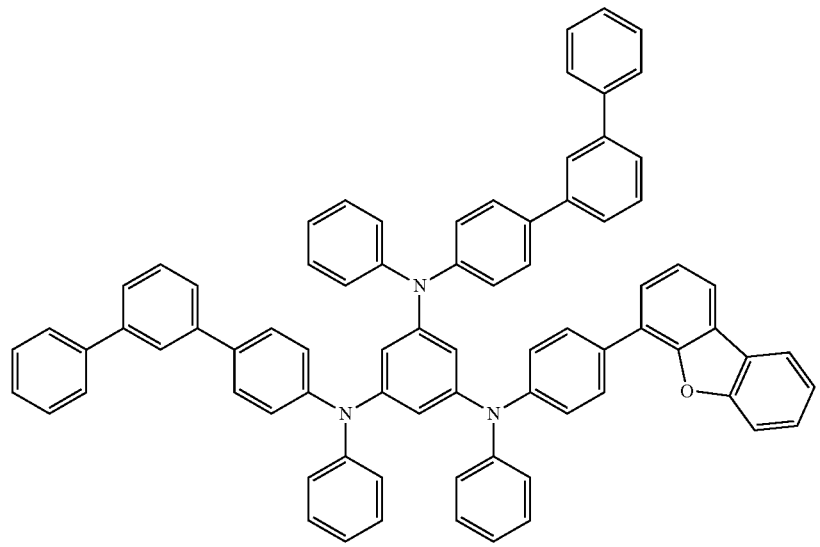
[A-16]
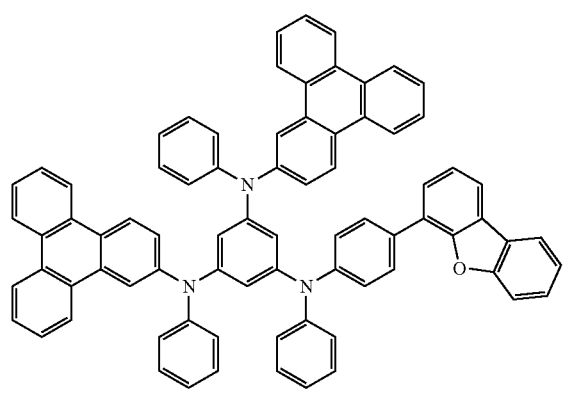
[A-17]
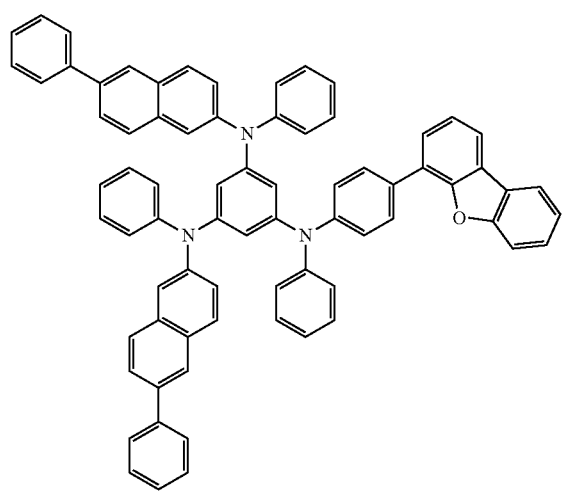

-continued
[A-18]
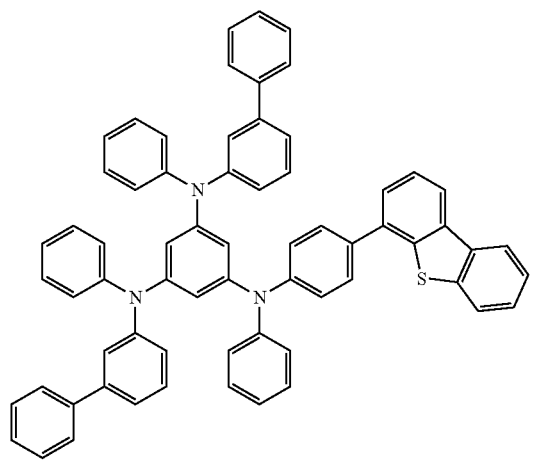
[A-19]
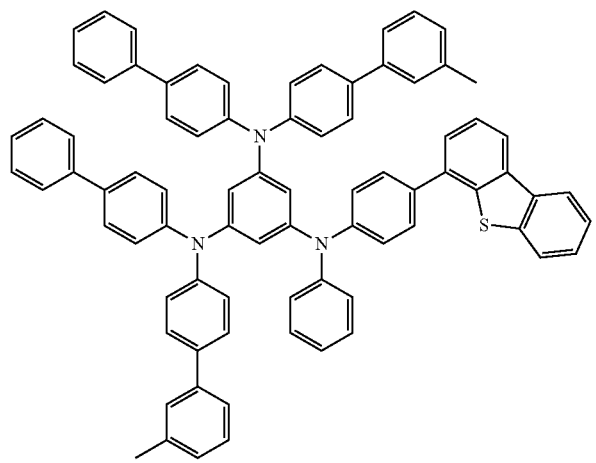
[A-20]
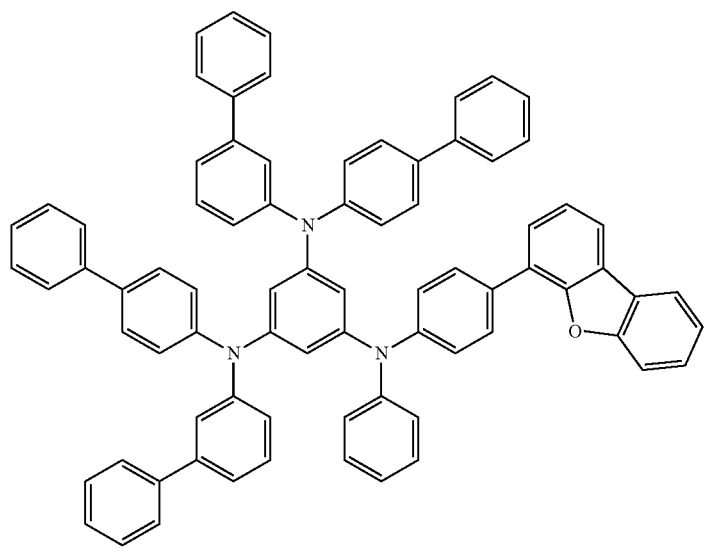
[A-21]
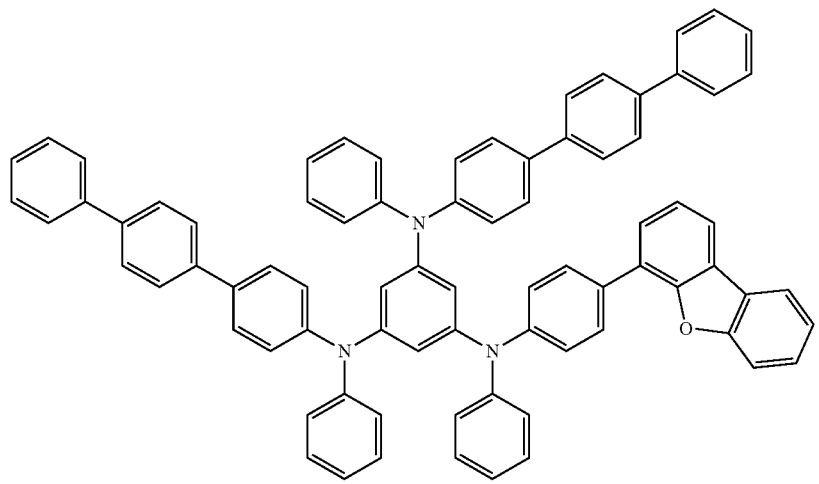

-continued
[A-22]
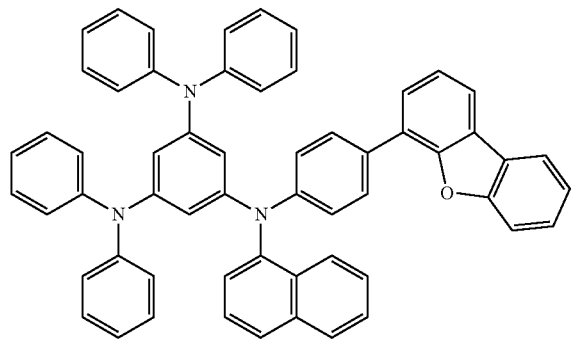
[A-23]
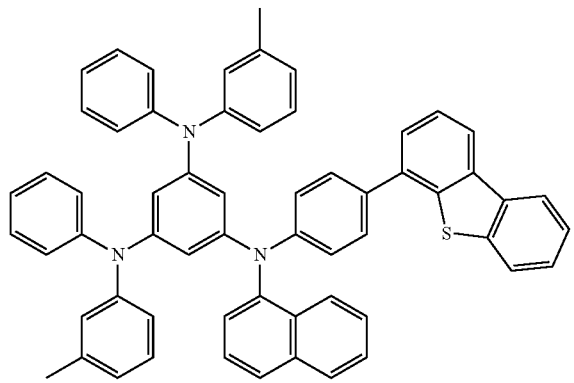
[A-24]
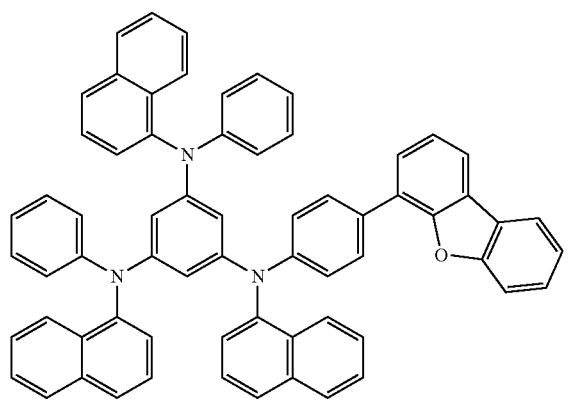
[A-25]
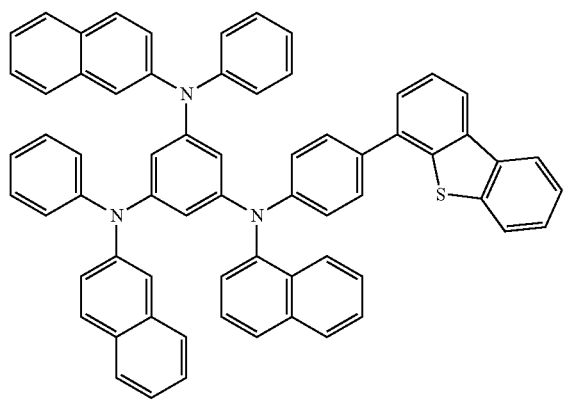
[A-26]
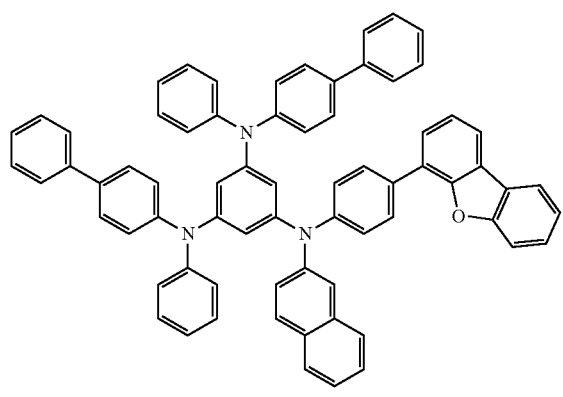
[A-27]
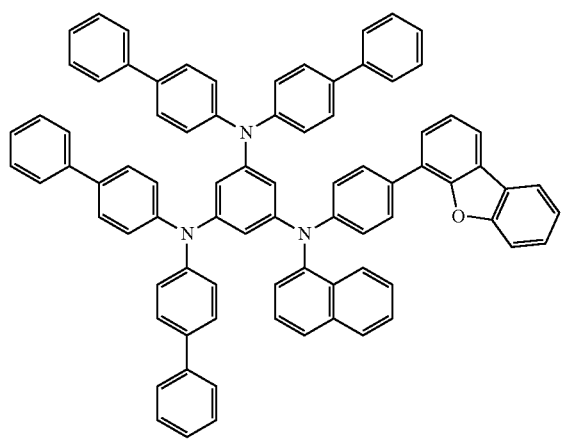

-continued
[A-28]
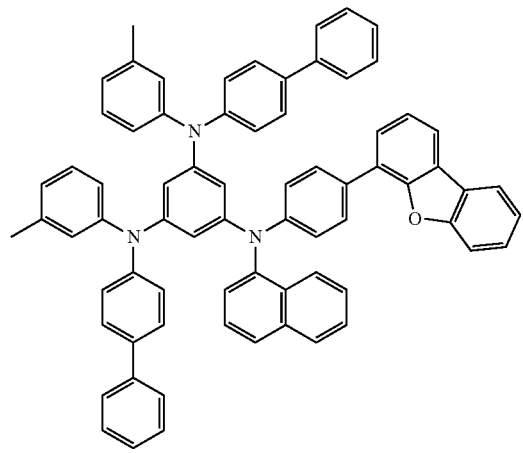
[A-29]
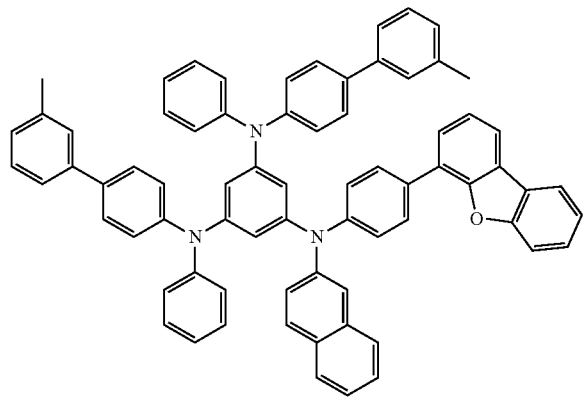
[A-30]
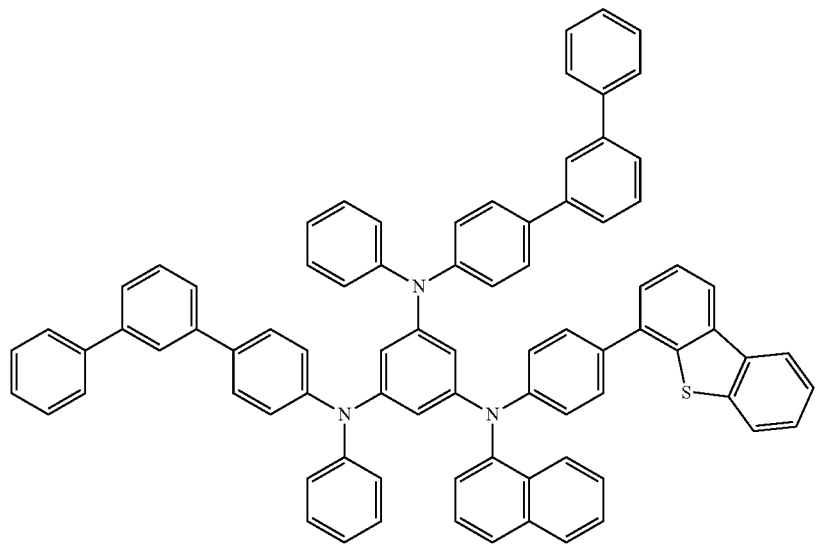
[A-31]
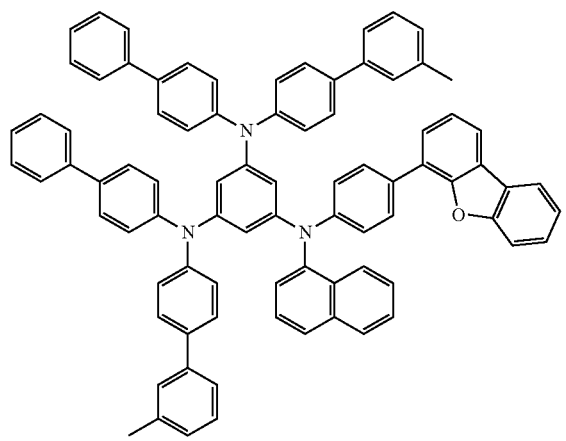
[A-32]
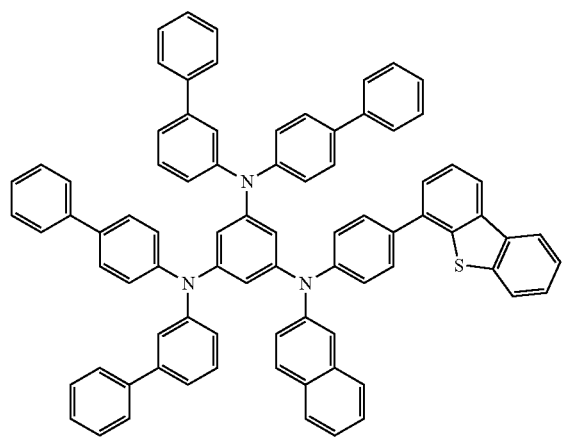

[A-33]
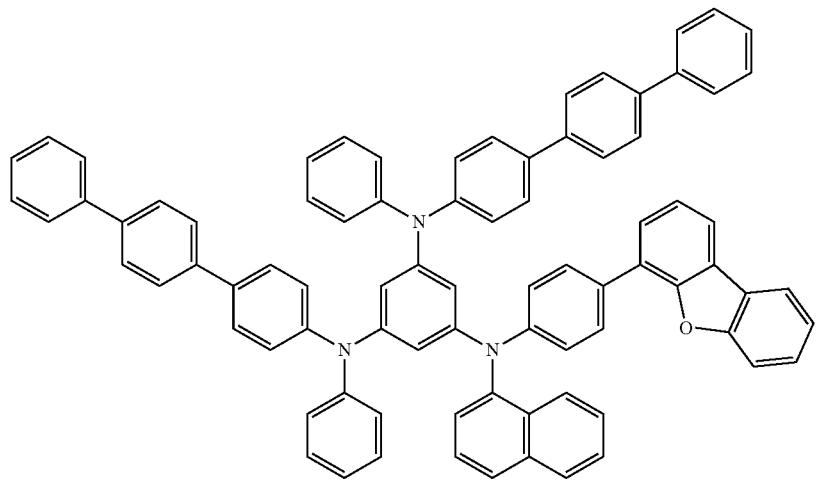
[A-34]
[A-35]
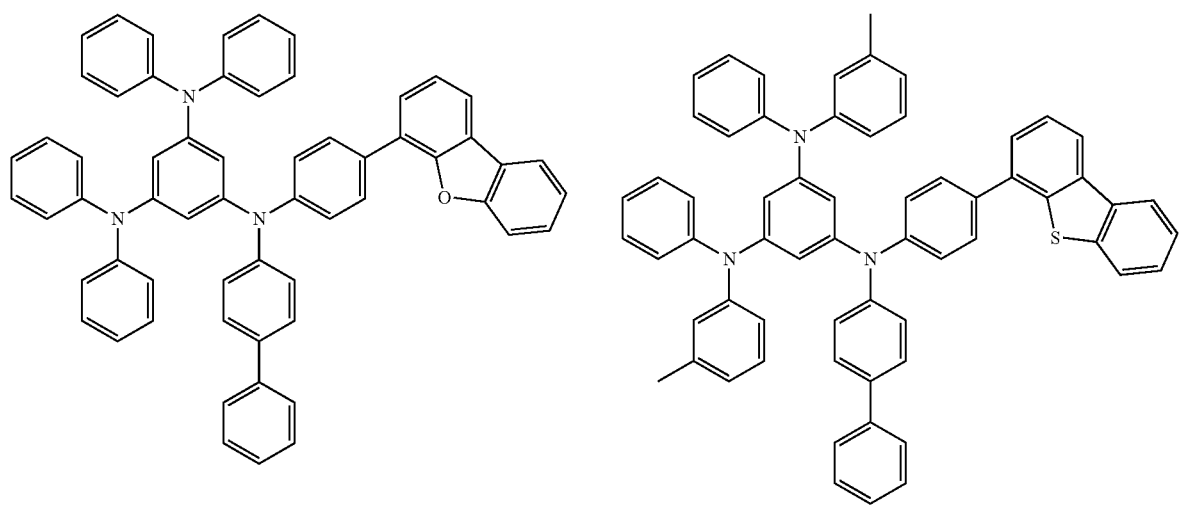
[A-36]
[A-37]
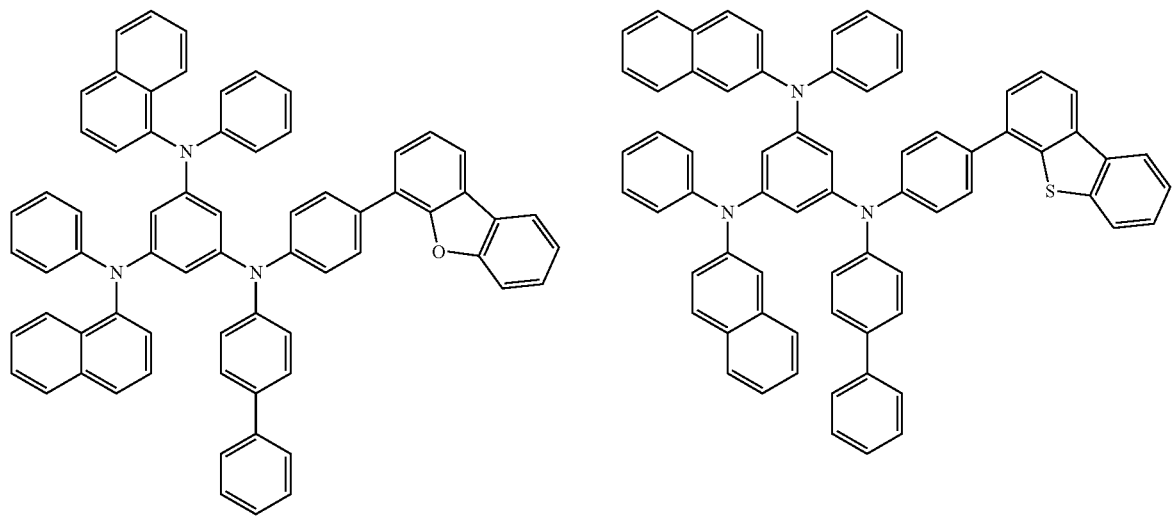

-continued
[A-38]
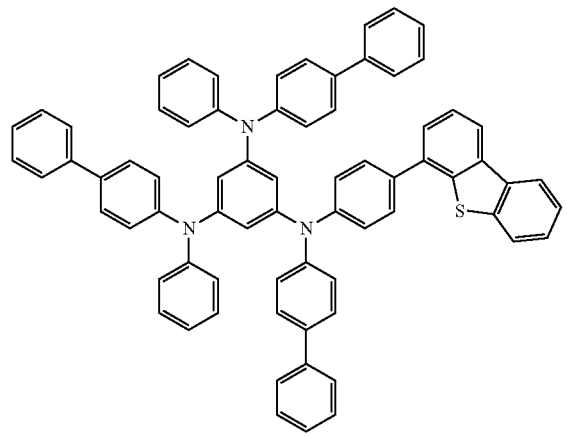
[A-39]
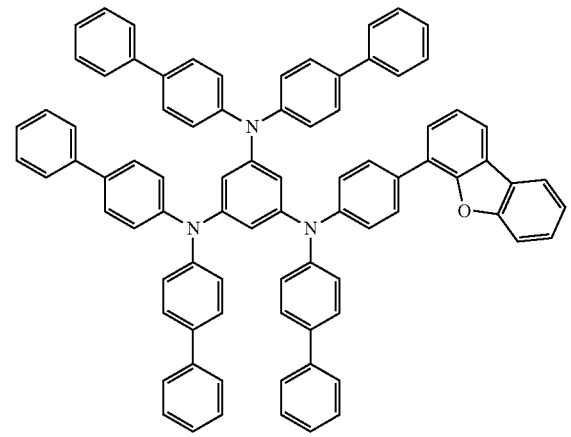
[A-40]
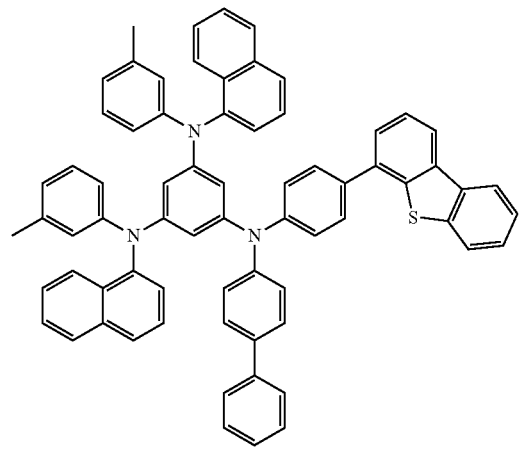
[A-41]
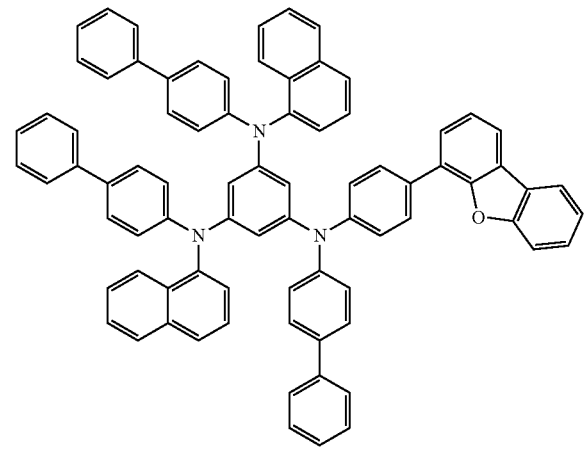
[A-42]
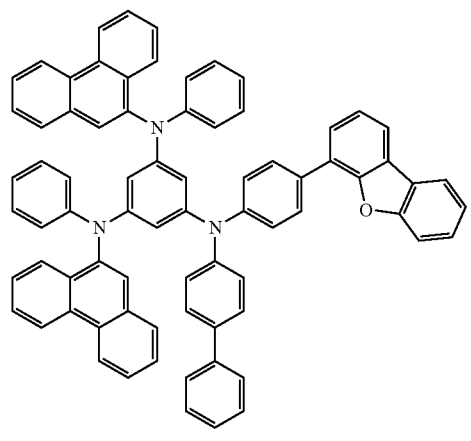
[A-43]
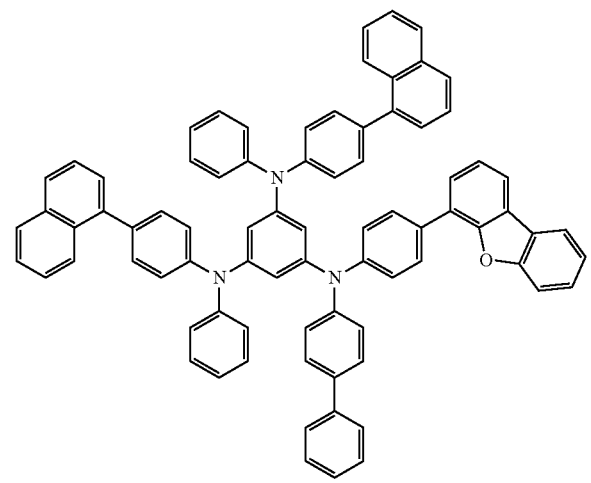

-continued
[A-44]
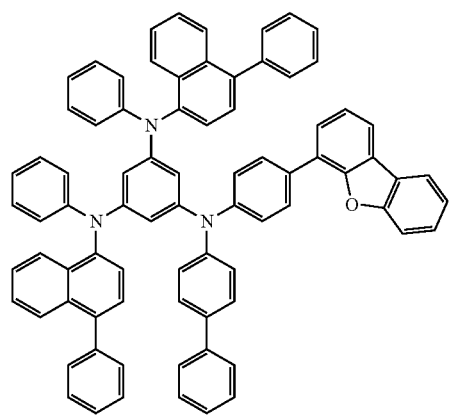
[A-45]
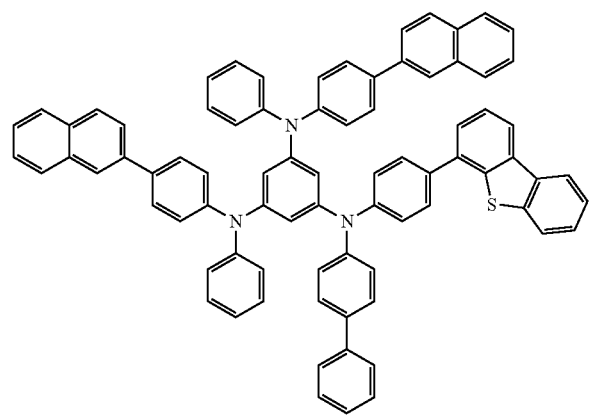
[A-46]
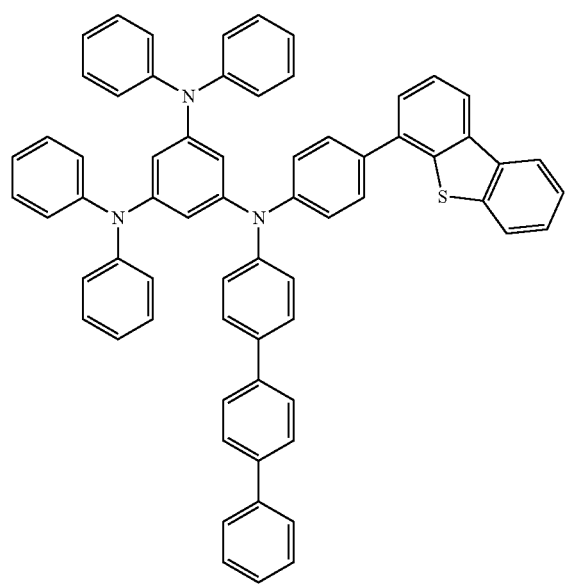
[A-47]
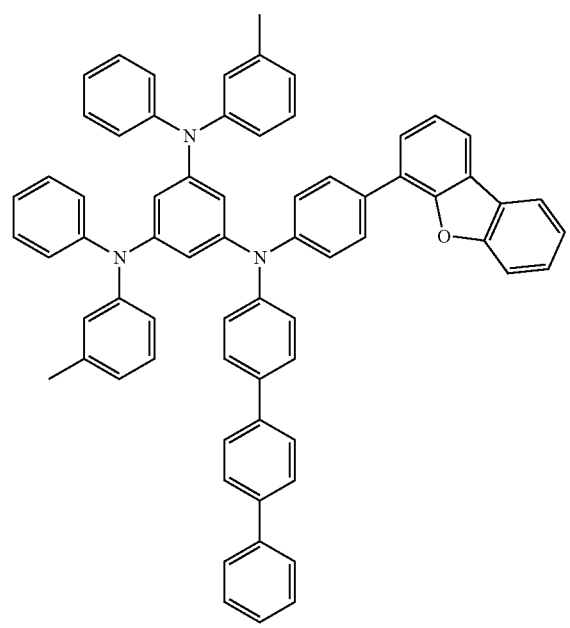

-continued
[A-48]
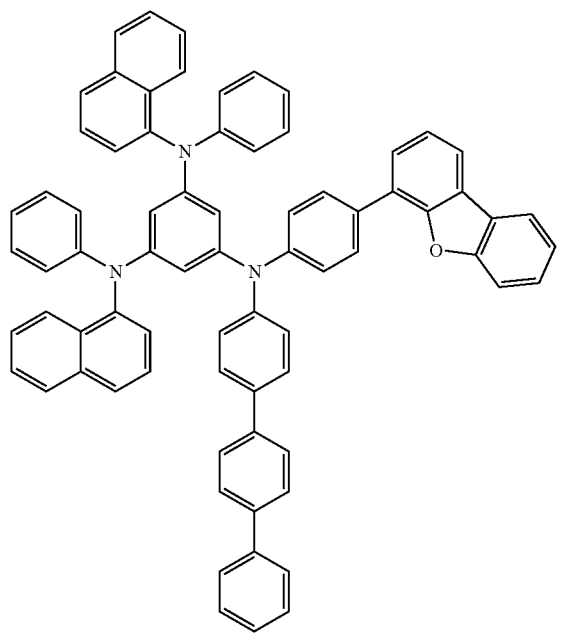
[A-49]
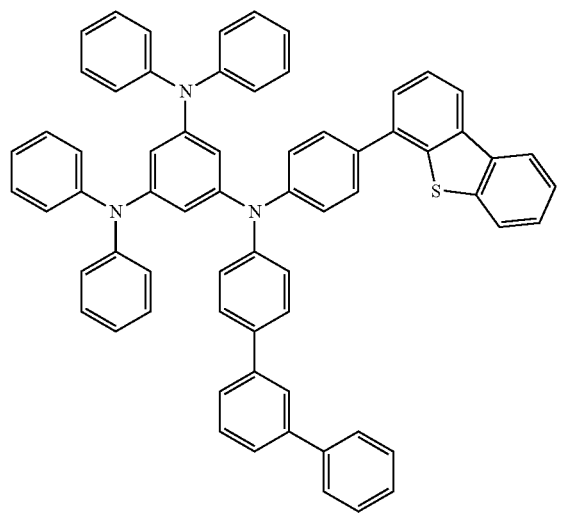
[A-50]
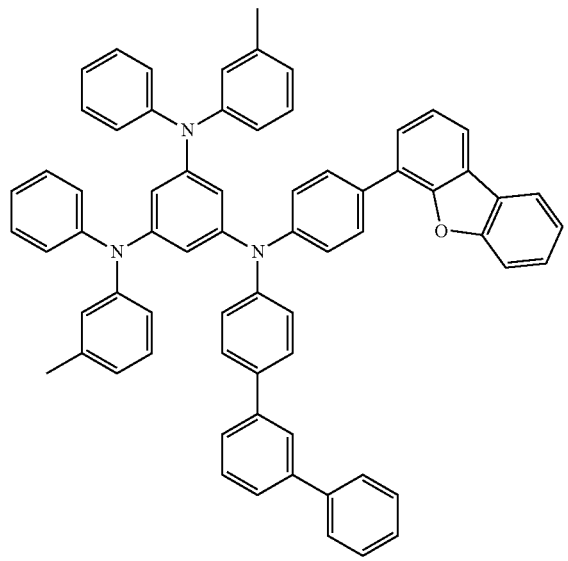
[A-51]
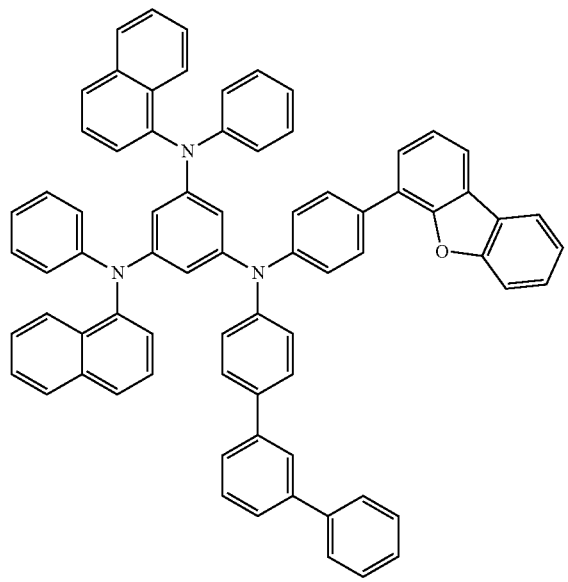
[A-52]
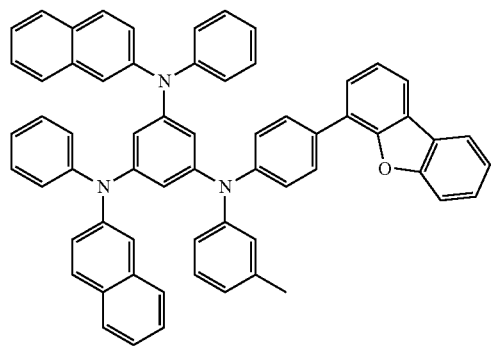
[A-53]
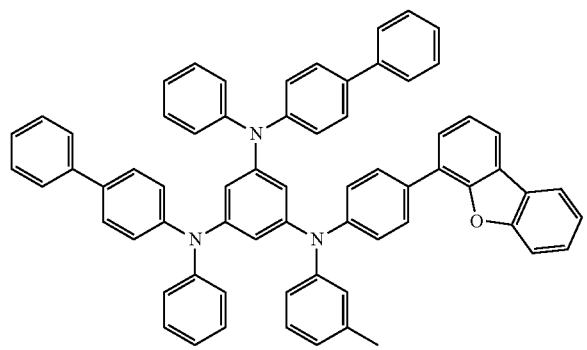

-continued
[A-54]
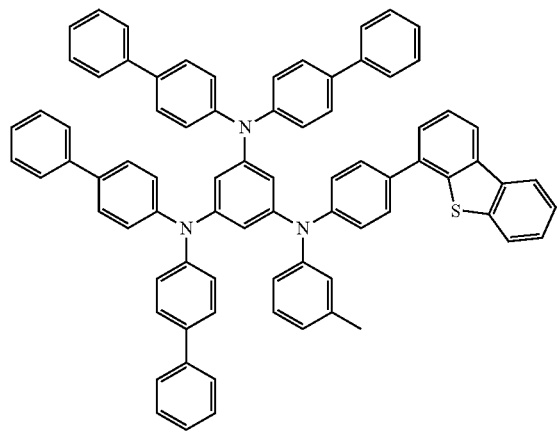
[A-55]
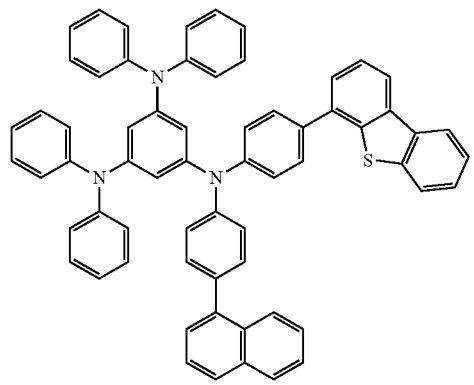
[A-56]
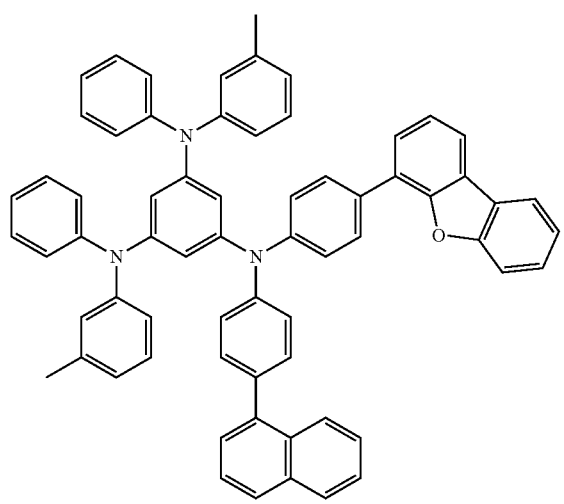
[A-57]
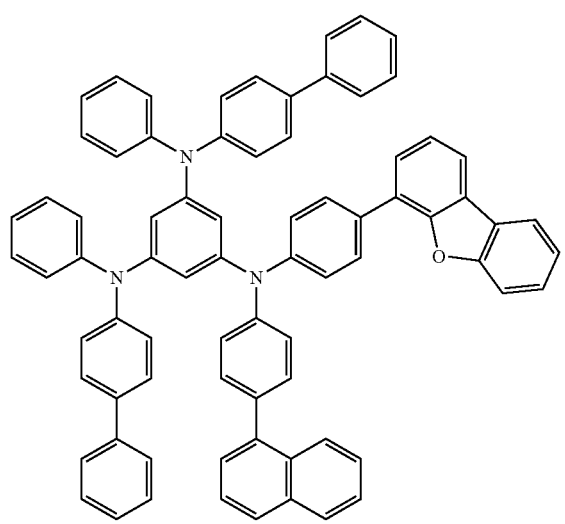
[A-58]
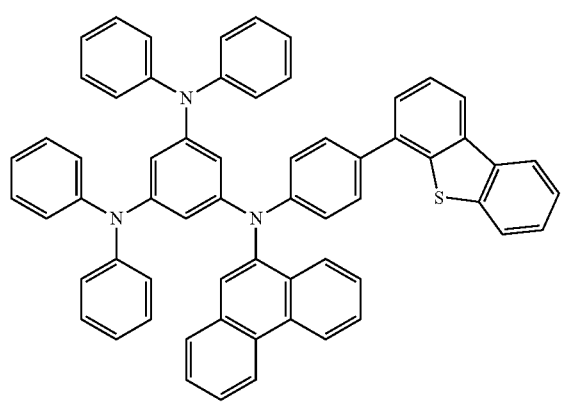
[A-59]
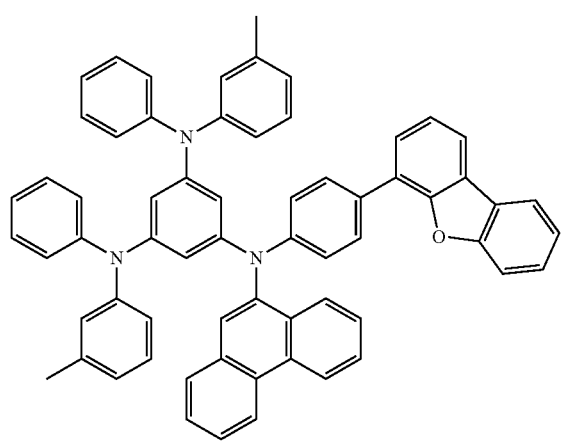

-continued
[A-60]
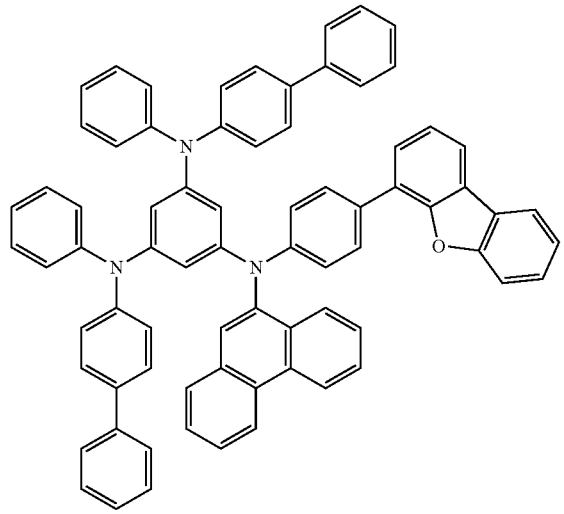
[A-61]
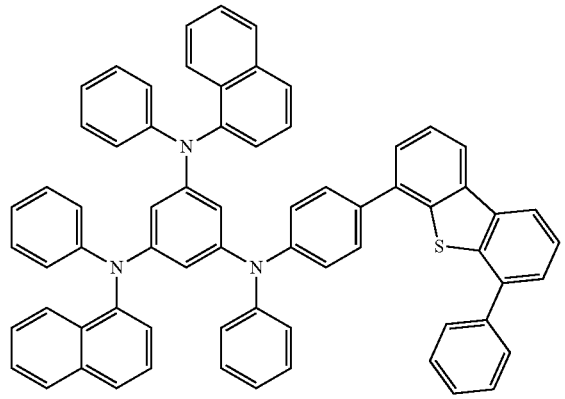
[A-62]
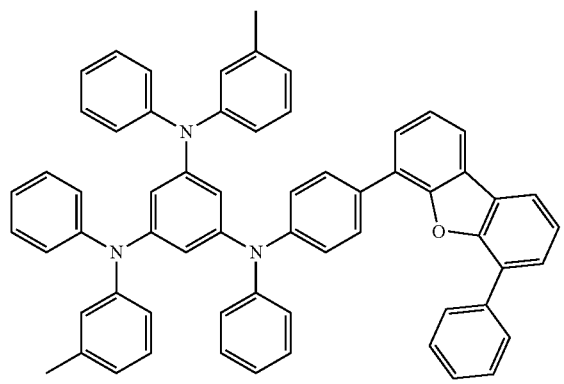
[A-63]
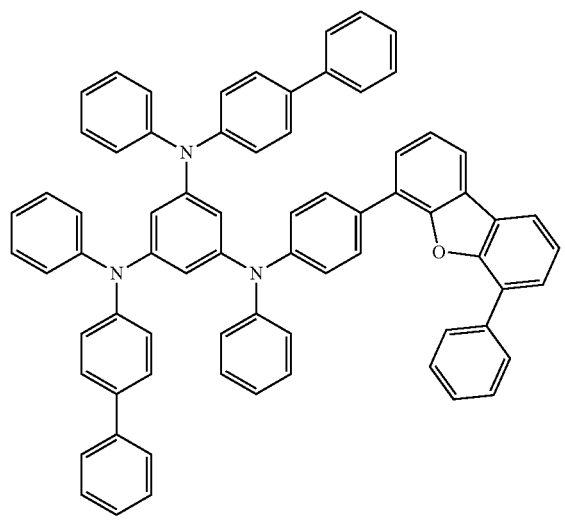
[A-64]
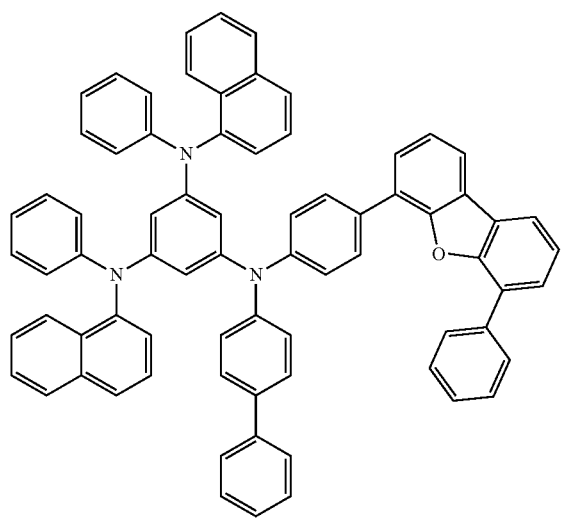
[A-65]
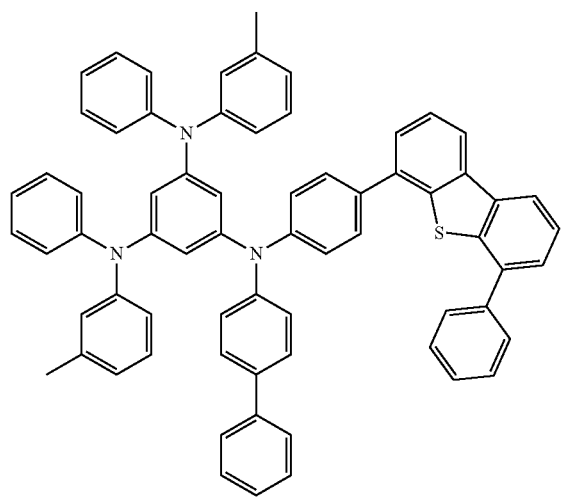

-continued
[A-66]
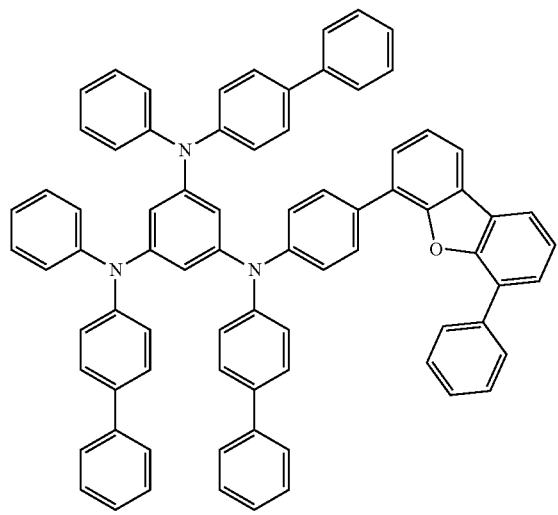
[A-67]
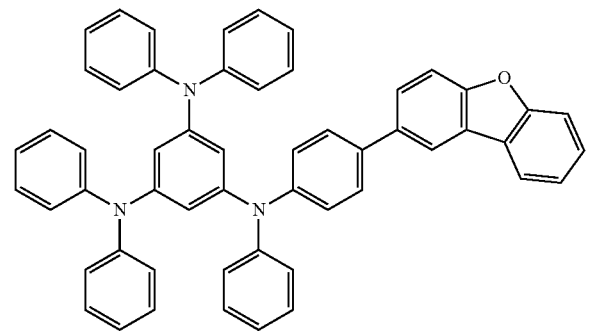
[A-68]
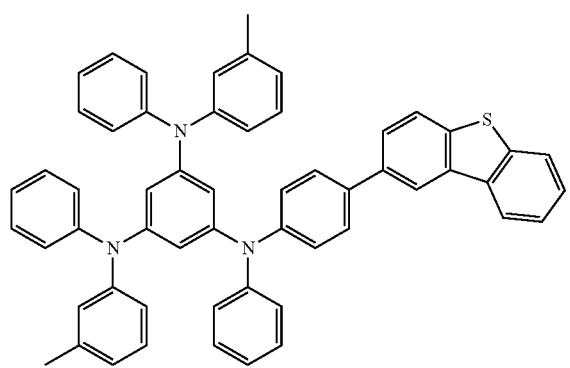
[A-69]
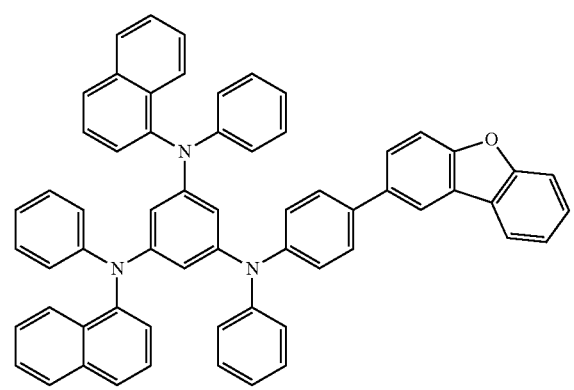
[A-70]
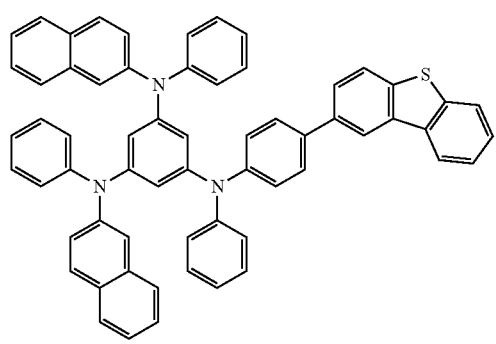
[A-71]
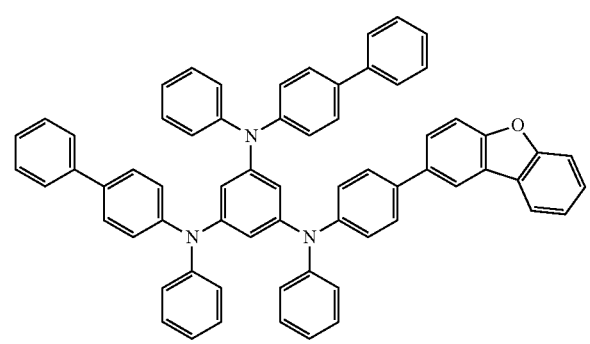

-continued
[A-72]
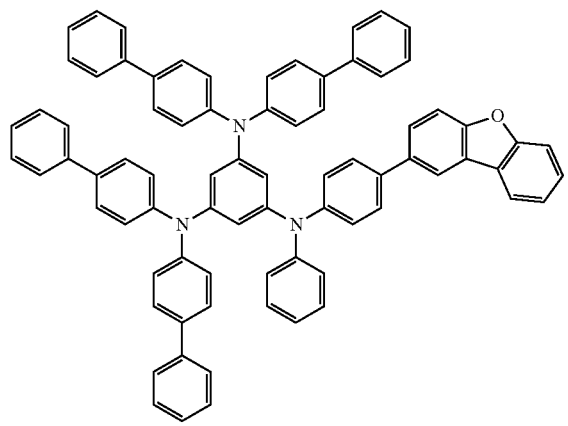
[A-73]
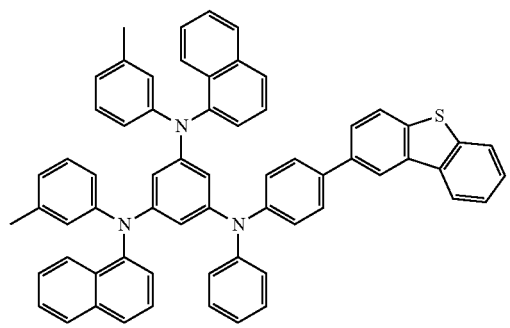
[A-74]
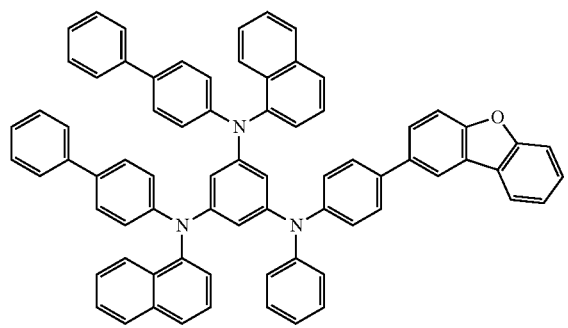
[A-75]
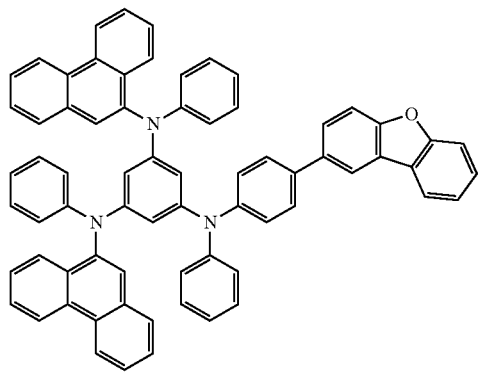
[A-76]
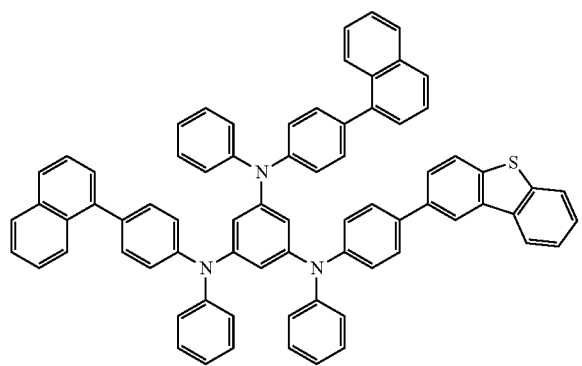
[A-77]
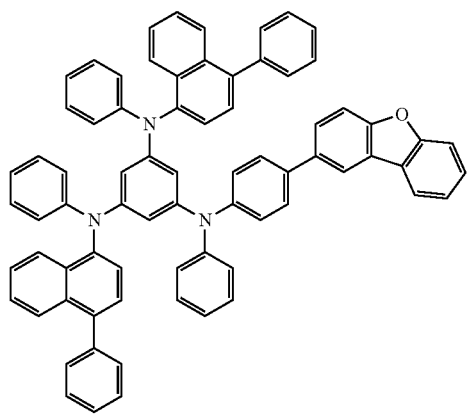

[A-78]
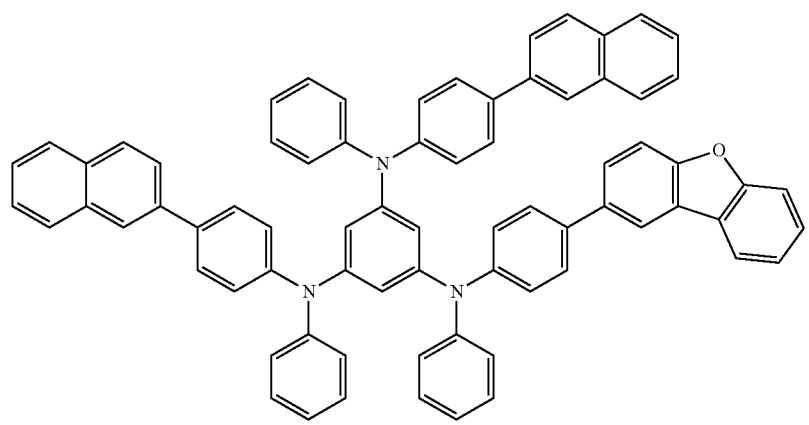
[A-79]
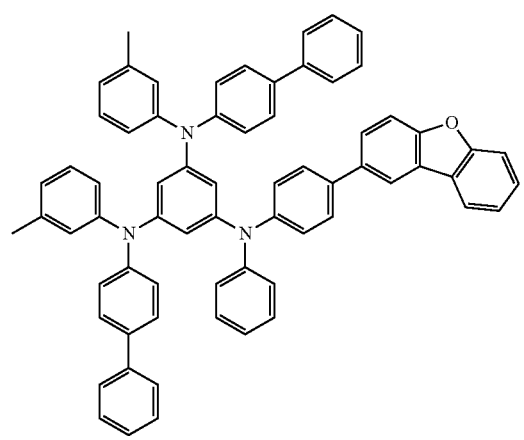
[A-80]
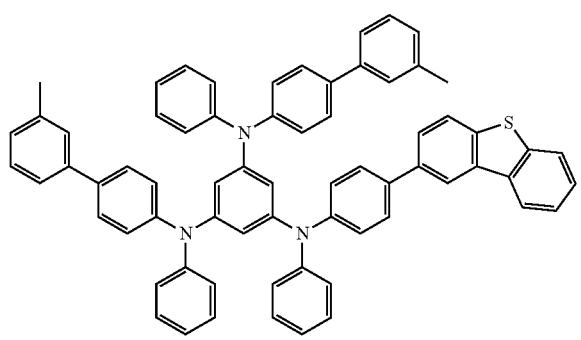
[A-81]
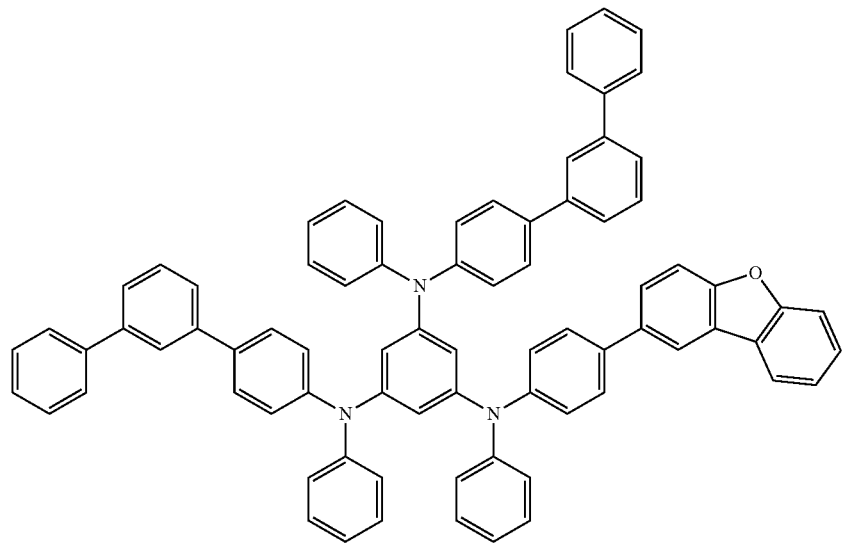

-continued
[A-82]
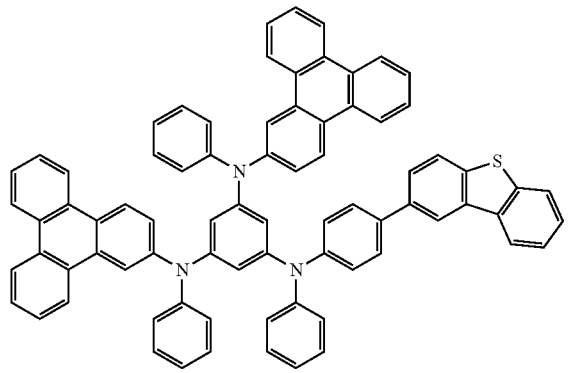
[A-83]
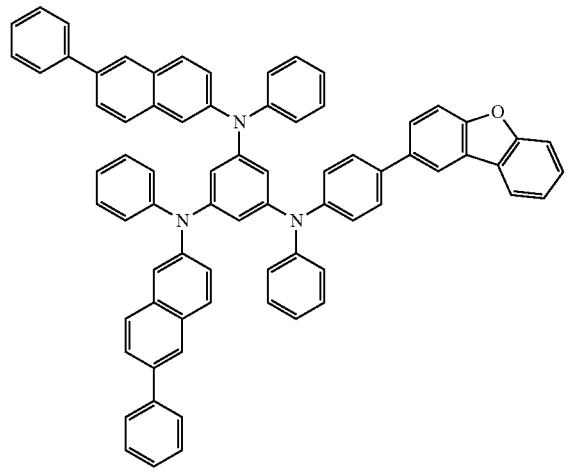
[A-84]
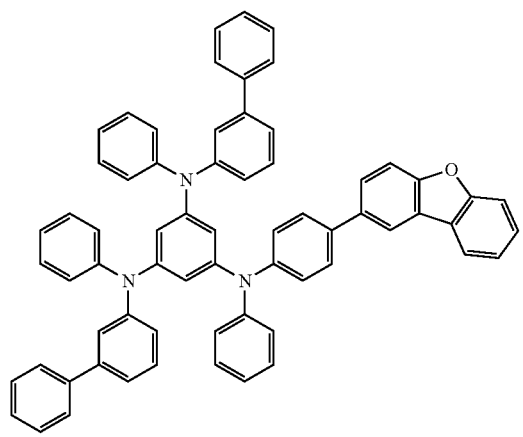
[A-85]
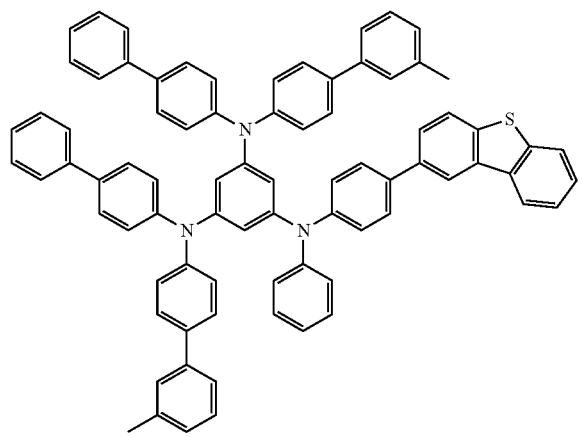
[A-86]
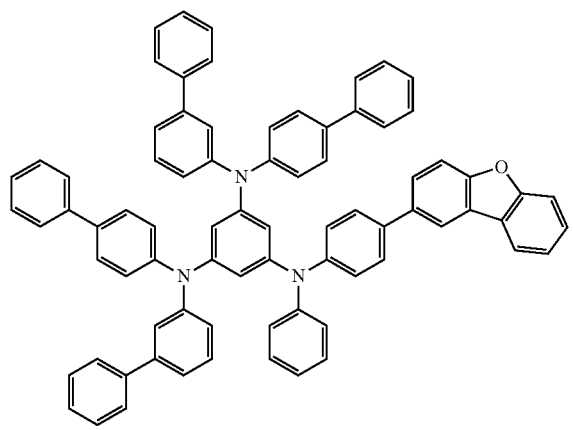
[A-87]
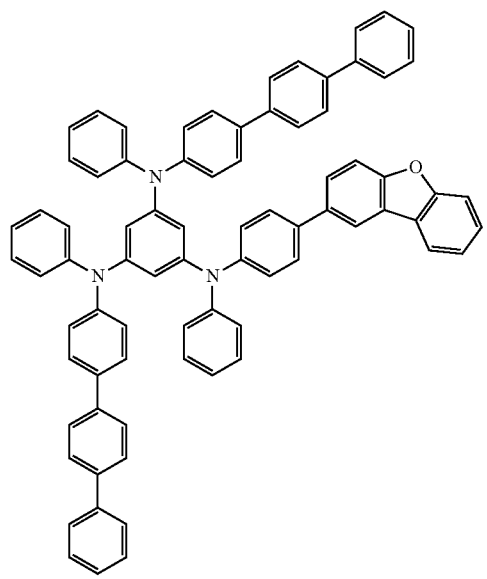

-continued
[A-88]
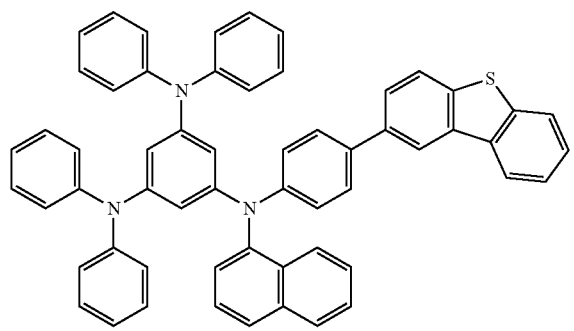
[A-89]
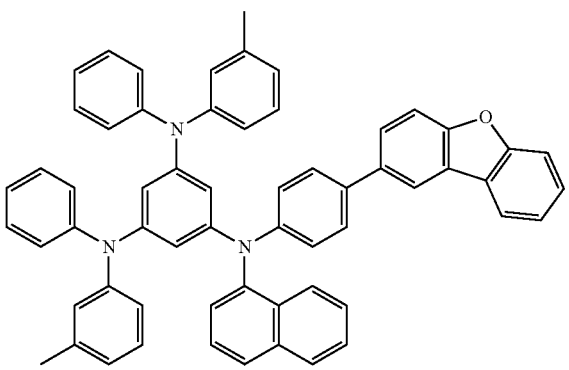
[A-90]
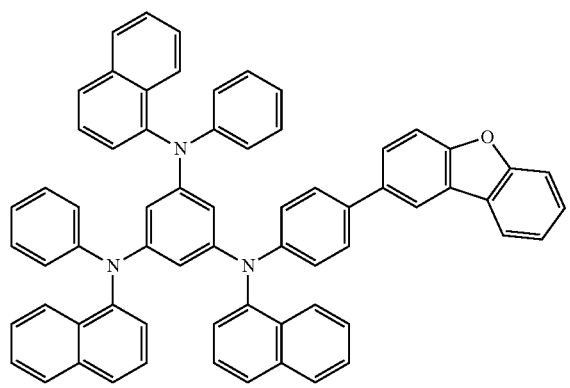
[A-91]
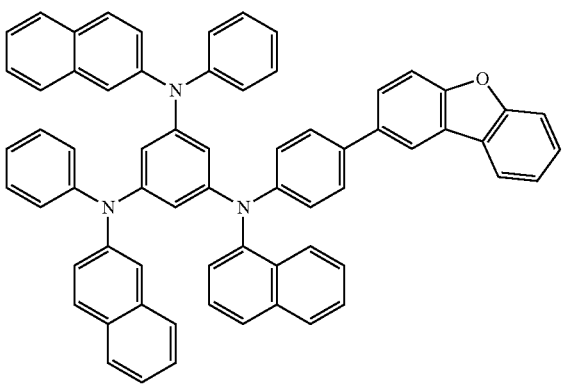
[A-92]
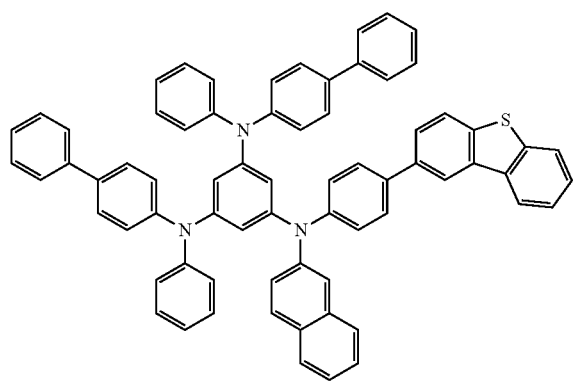
[A-93]
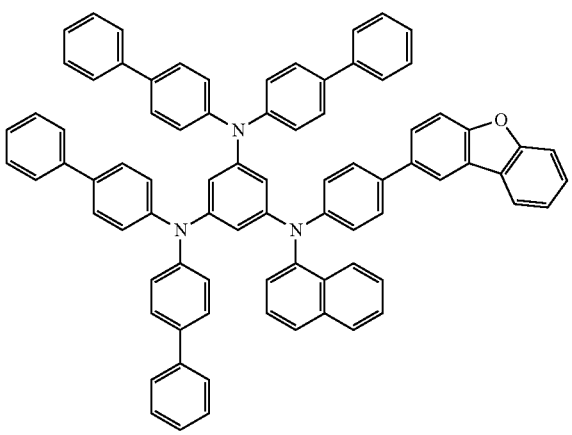

-continued
[A-94]
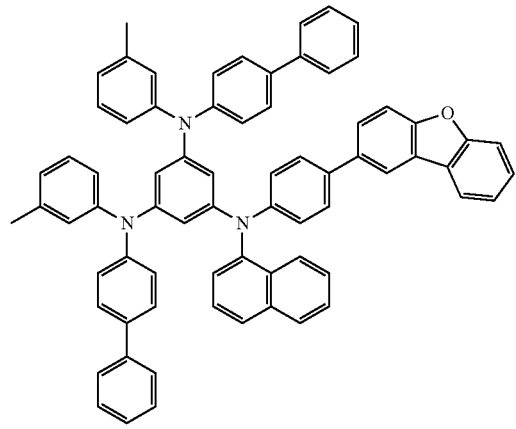
[A-95]
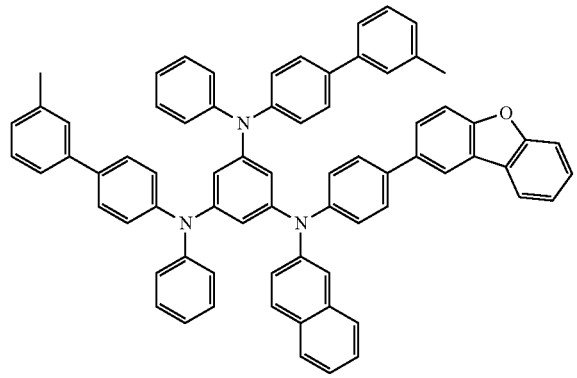
[A-96]
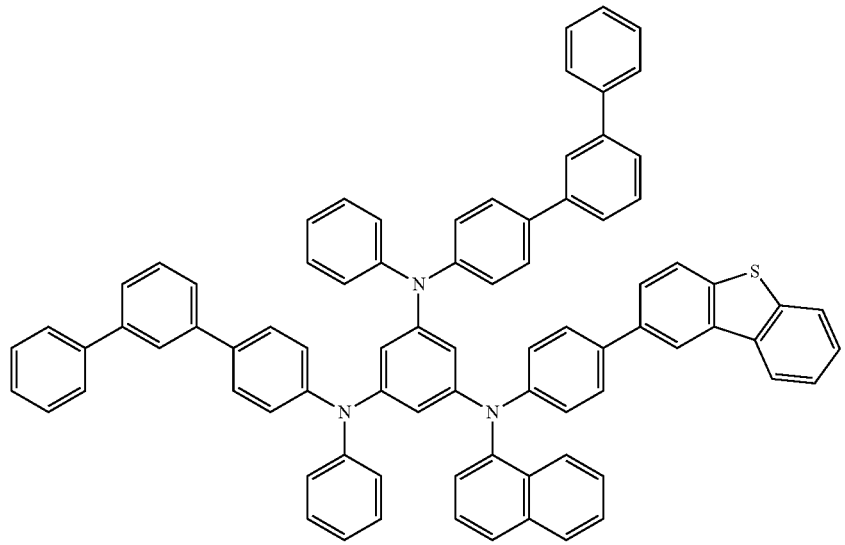
[A-97]
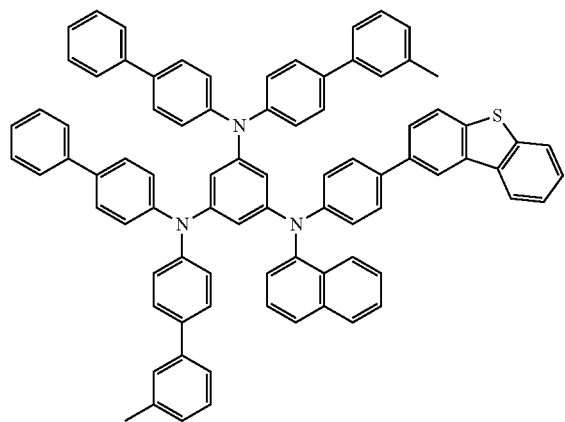
[A-98]
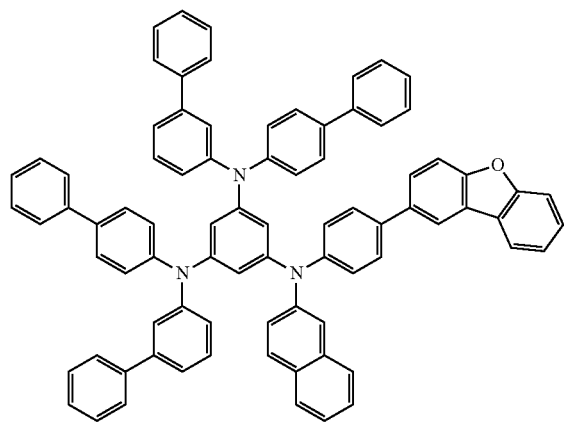

[A-99]
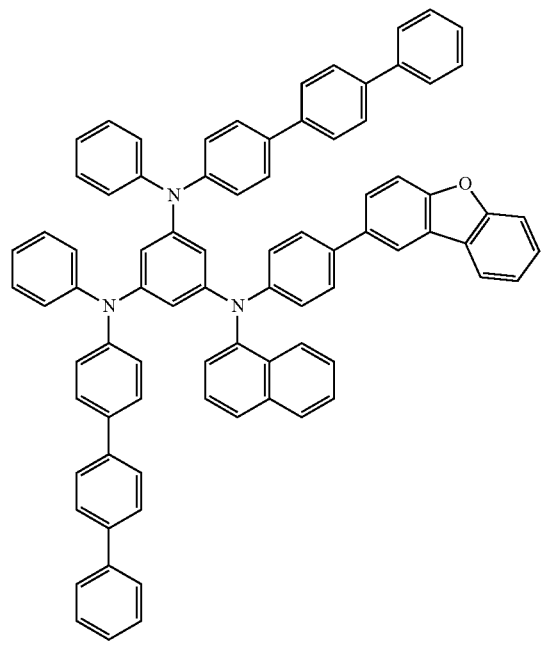
[A-100]
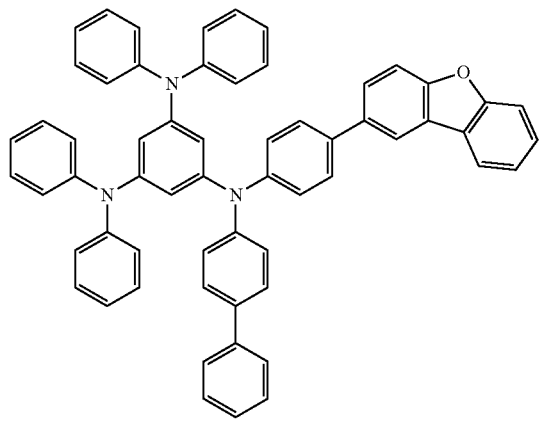
[A-101]
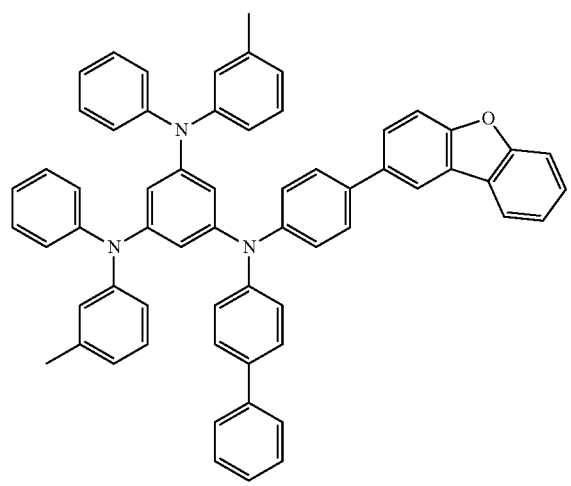
[A-102]
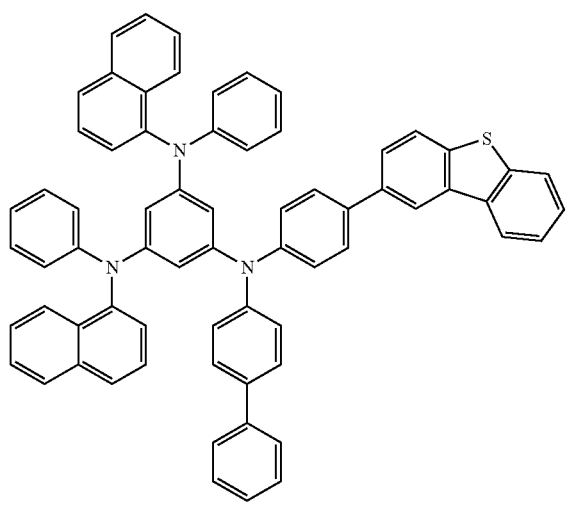

[A-103]
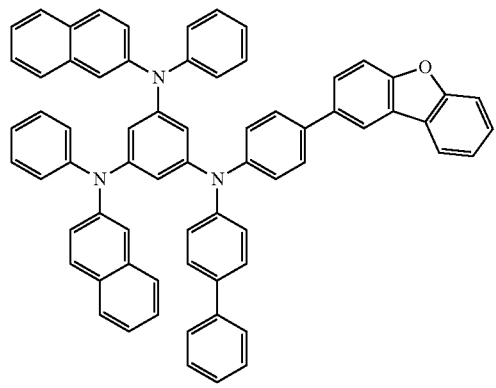
[A-104]
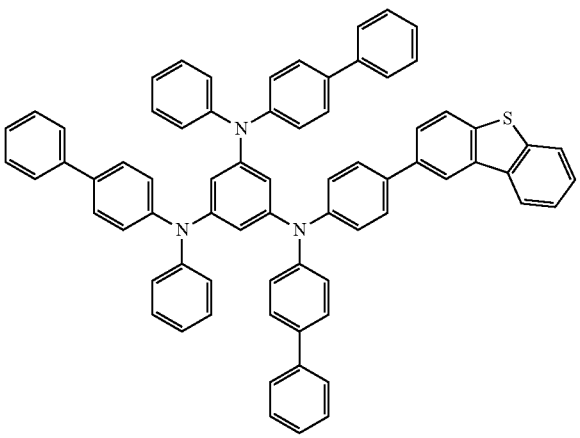
[A-105]
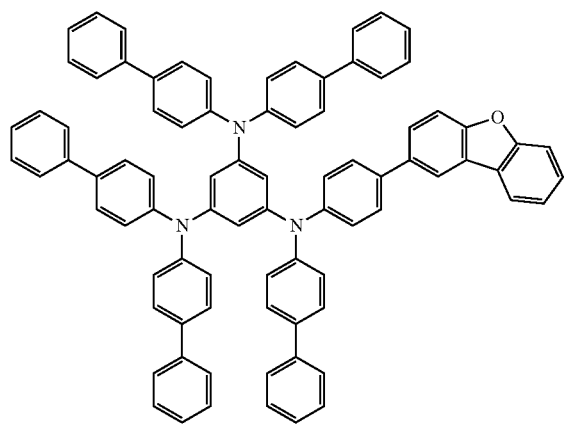
[A-106]
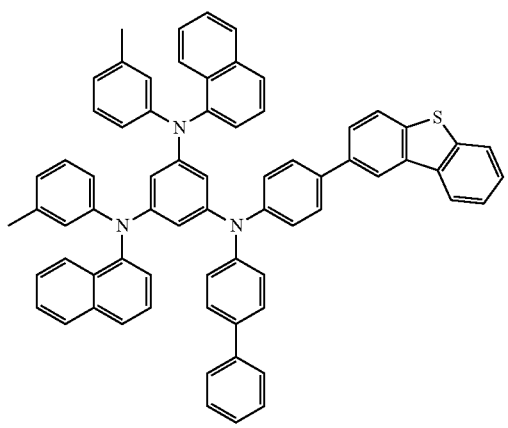
[A-107]
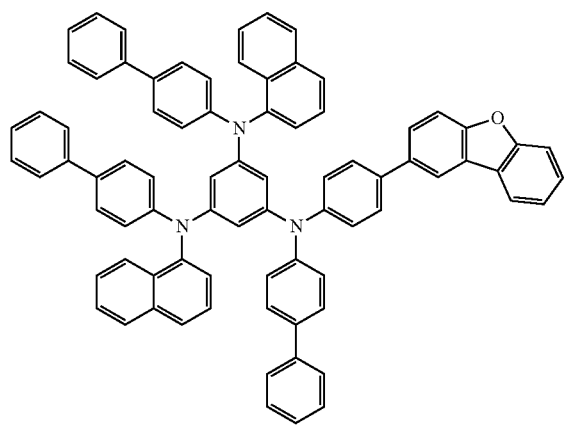
[A-108]
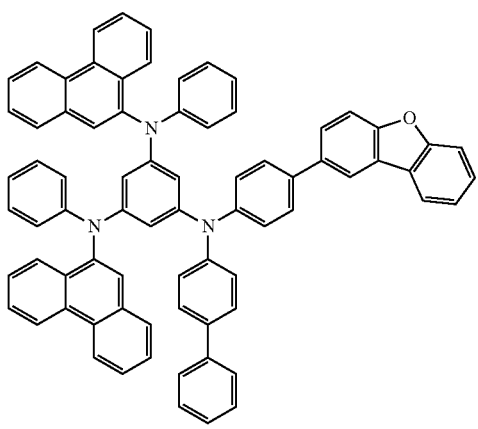

[A-109]
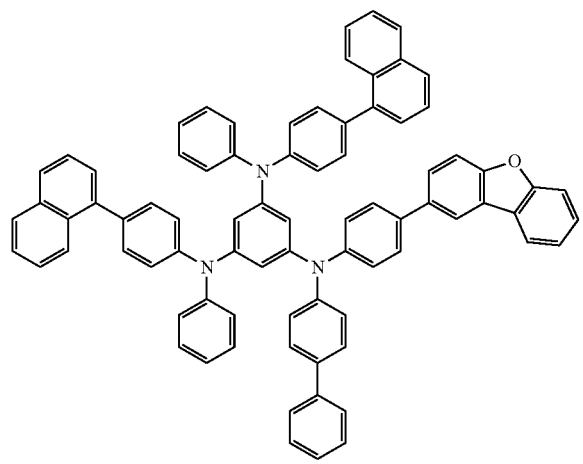
[A-110]
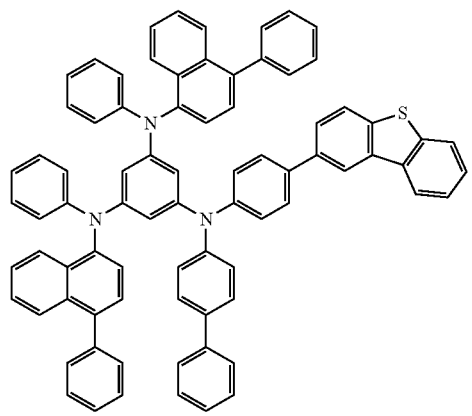
[A-111]
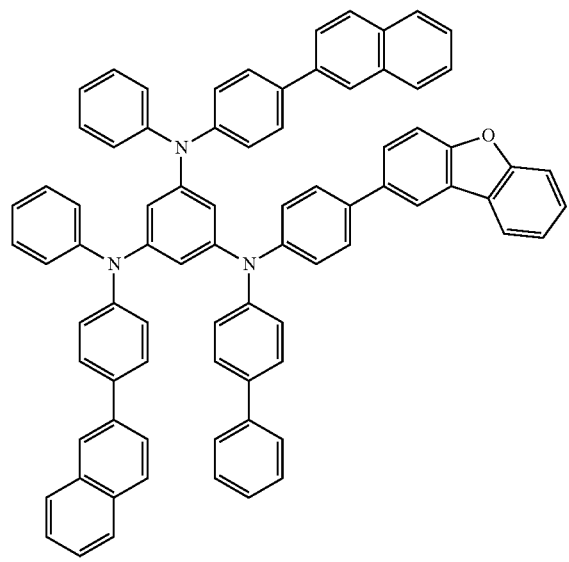
[A-112]
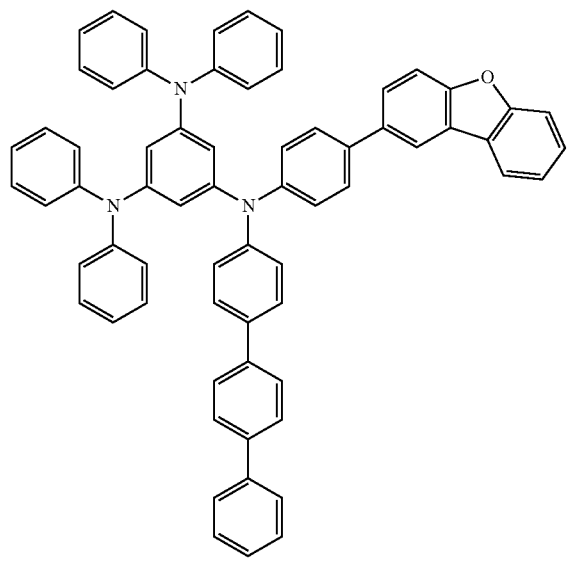

-continued
[A-113]
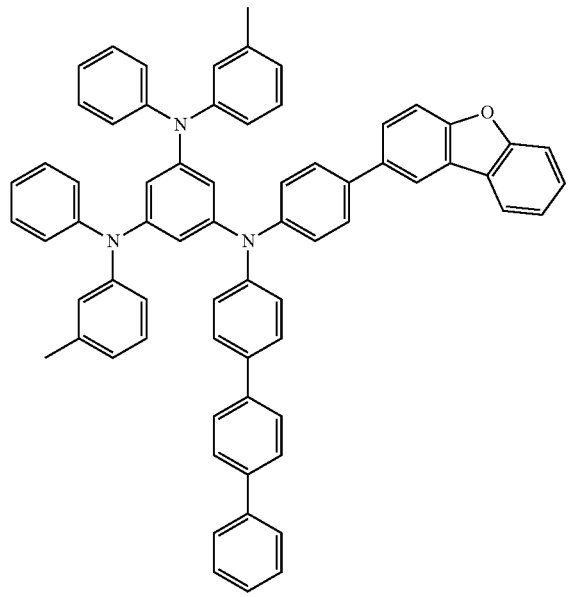
[A-114]
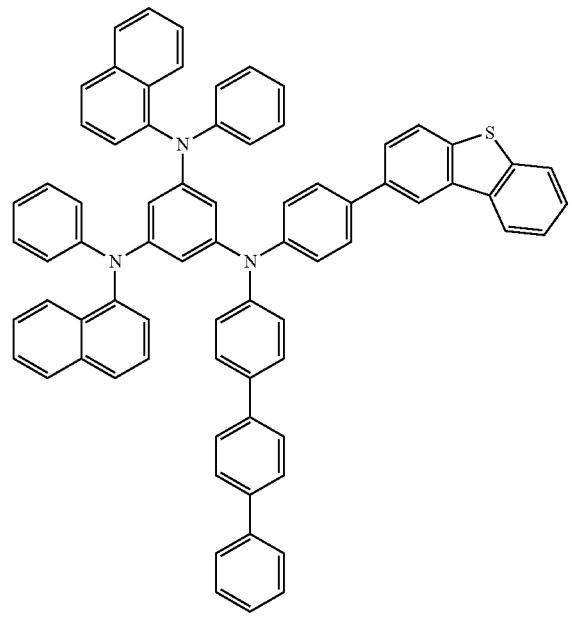
[A-115]
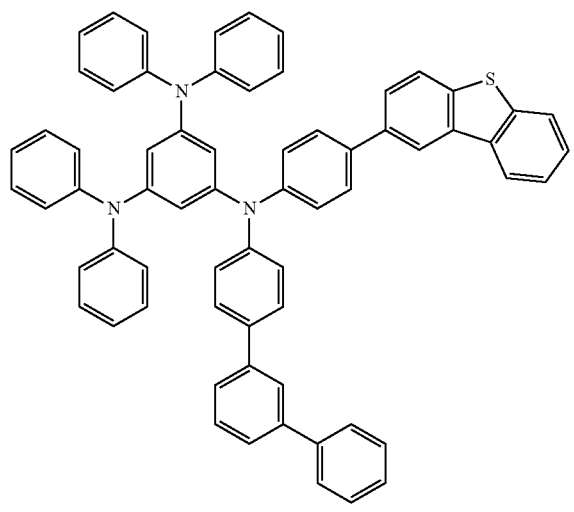
[A-116]
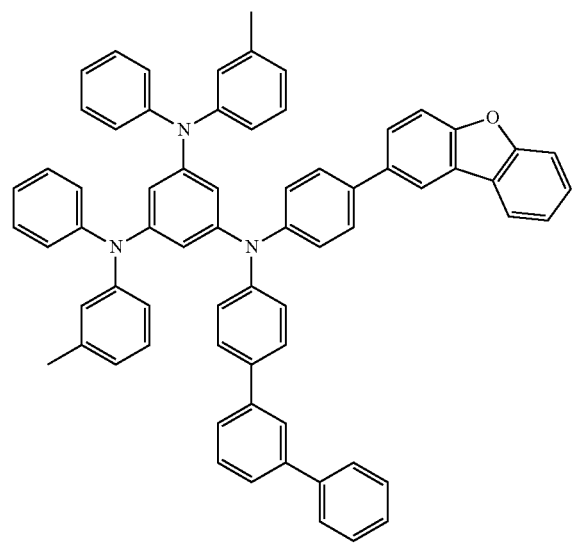

-continued
[A-117]
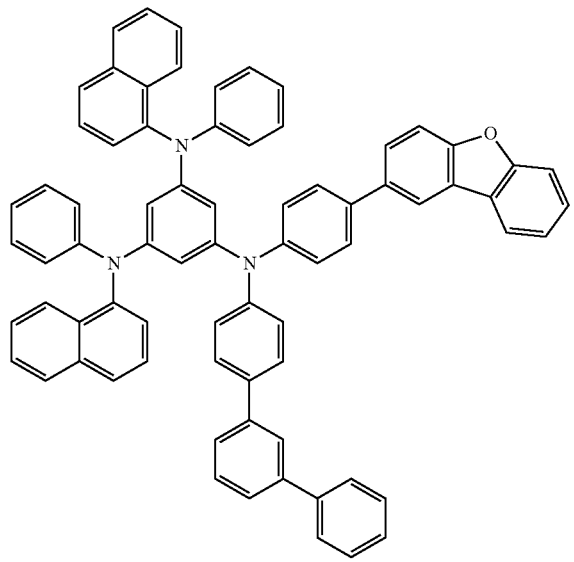
[A-118]
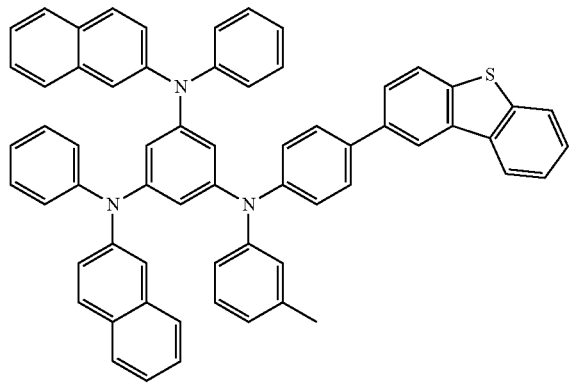
[A-119]
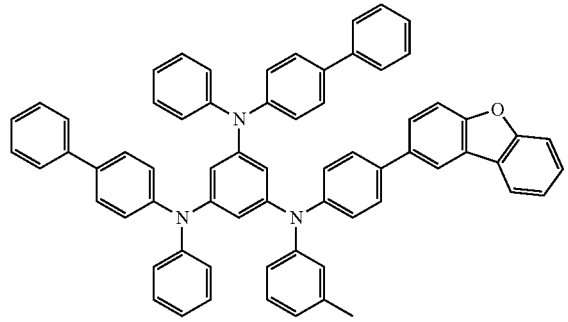
[A-120]
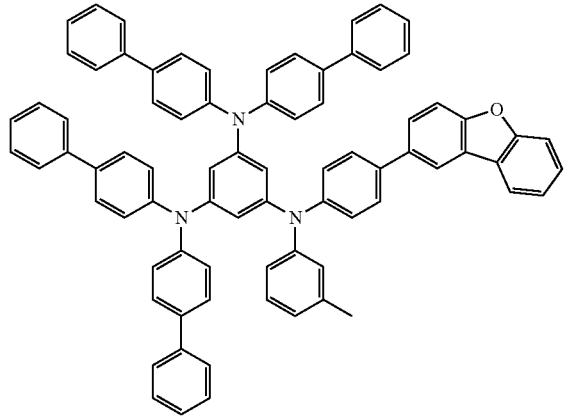
[A-121]
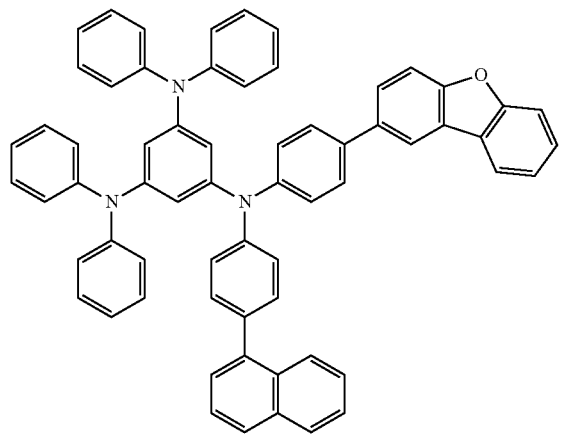
[A-122]
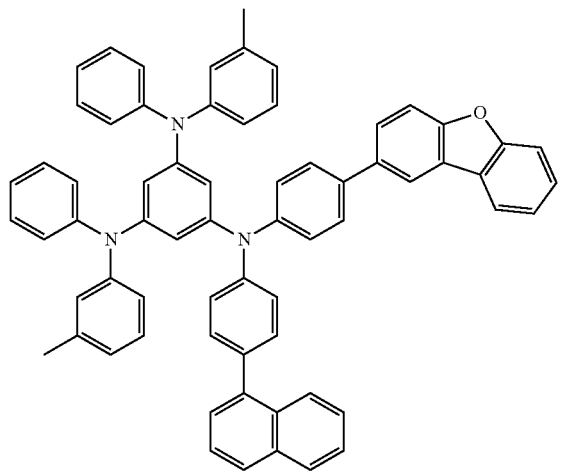

-continued
[A-123]
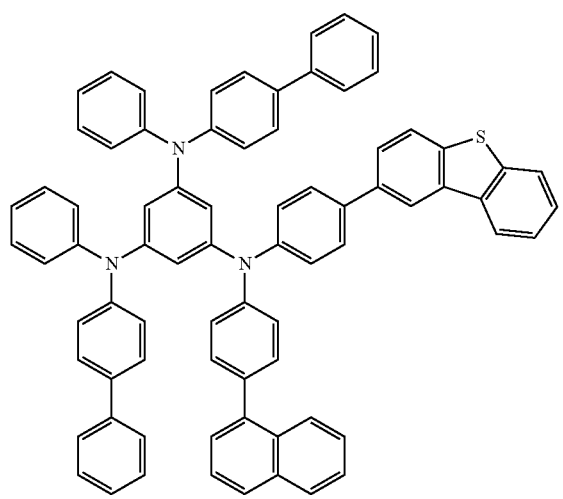
[A-124]
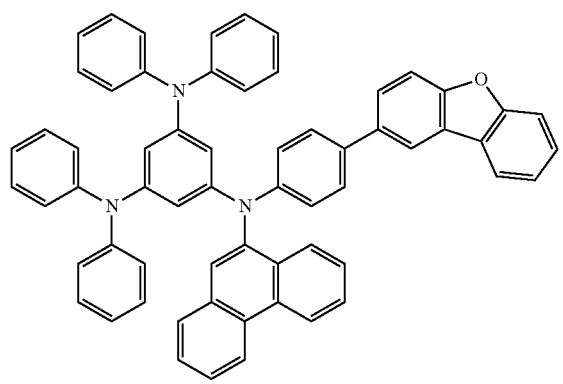
[A-125]
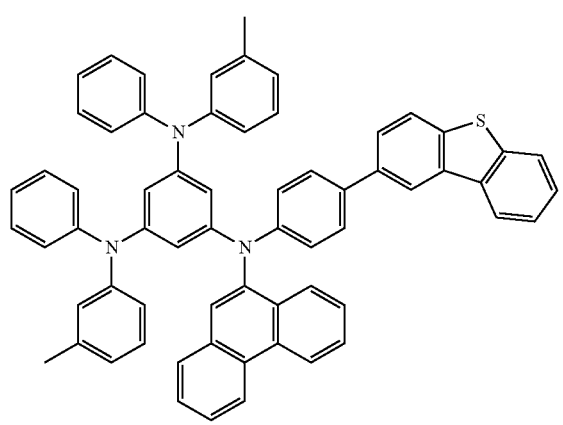
[A-126]
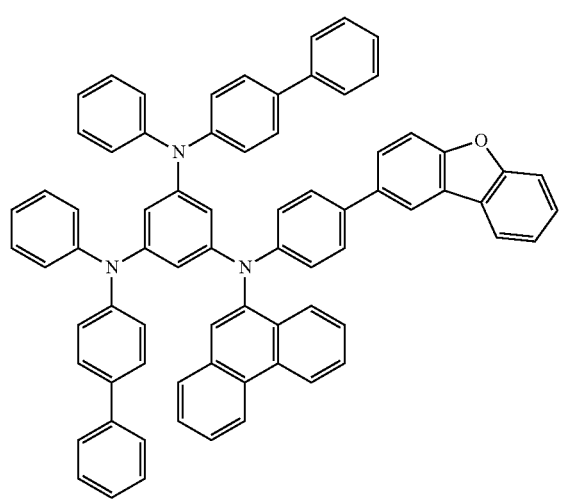
[A-127]
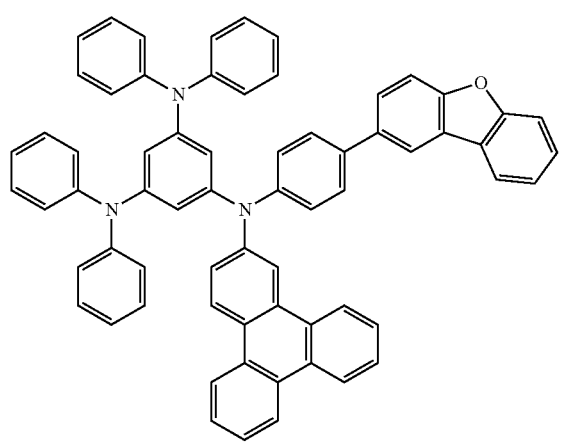
[A-128]
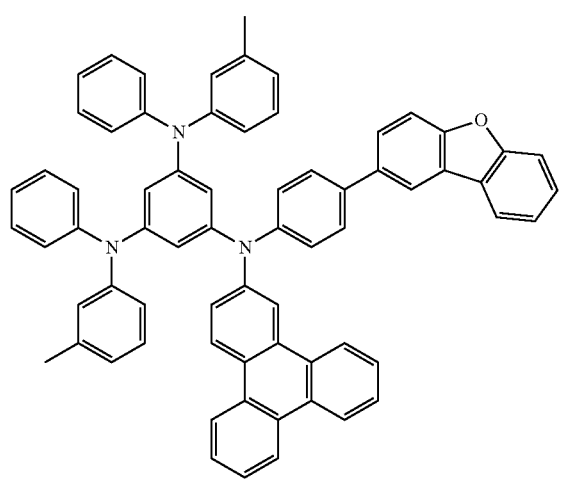

-continued
[A-129]
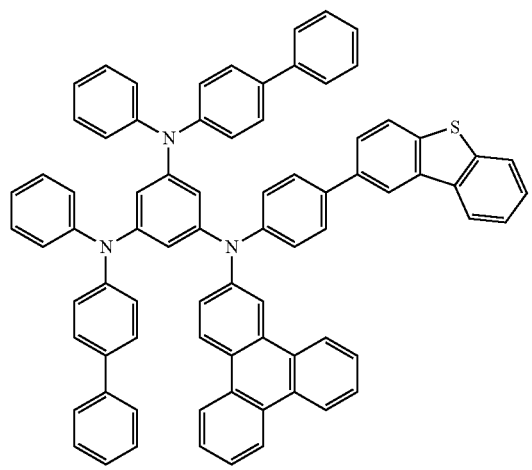
[A-130]
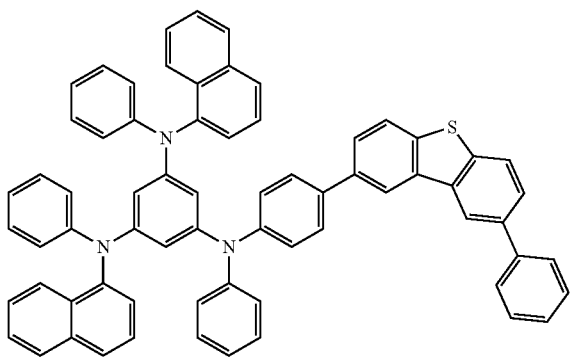
[A-131]
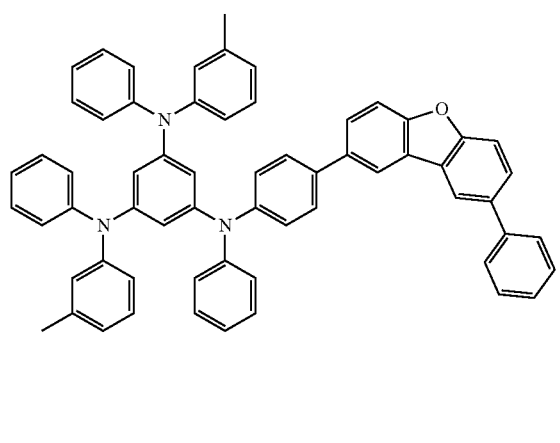
[A-132]
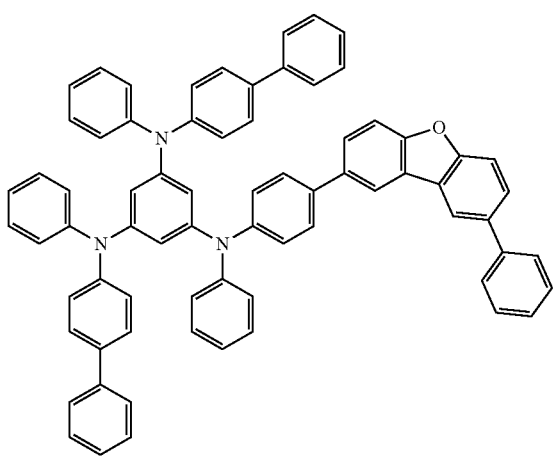
[A-133]
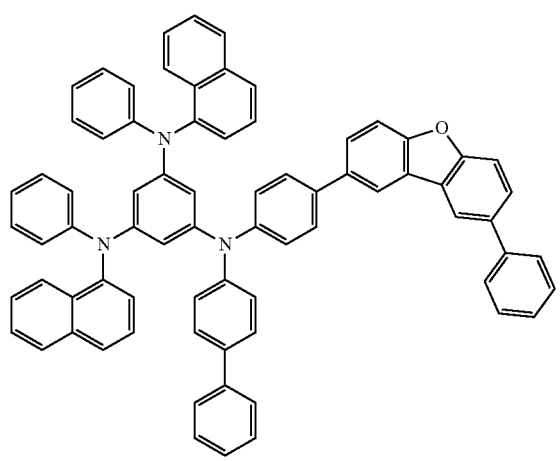
[A-134]
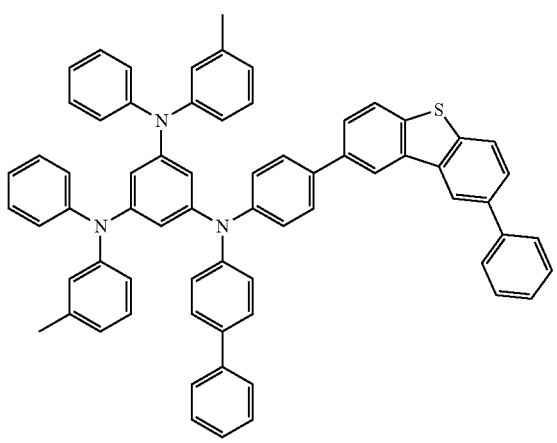

-continued
[A-135]
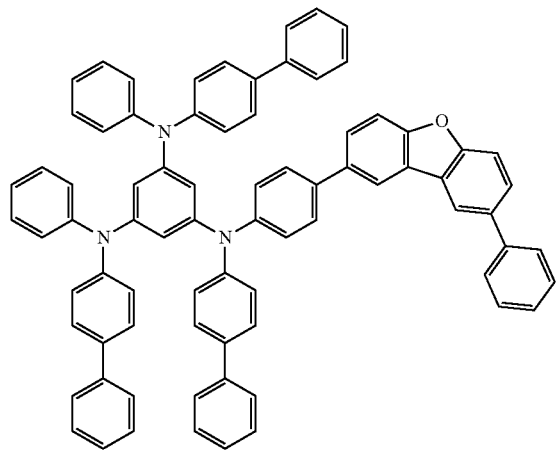
[A-136]
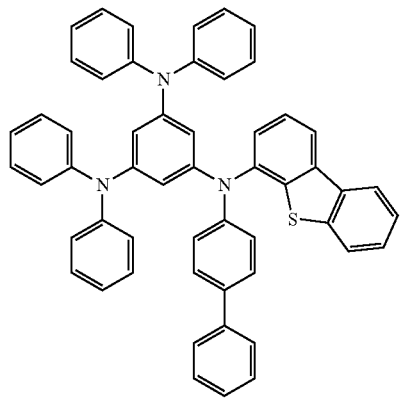
[A-137]
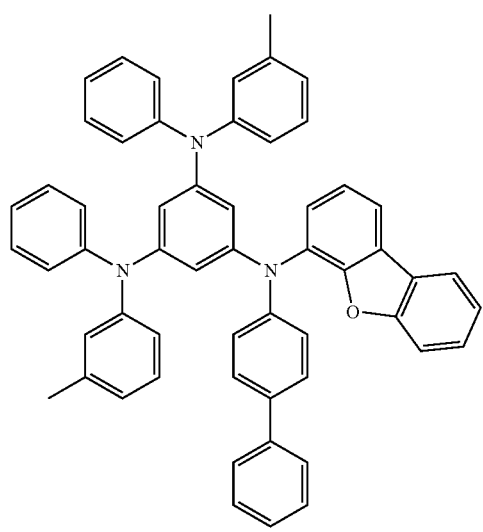
[A-138]
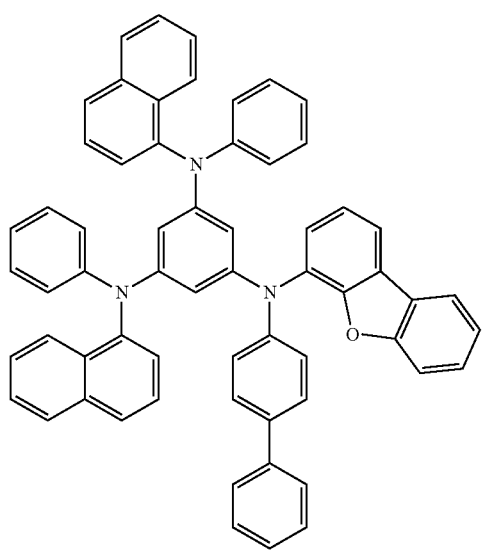
[A-139]
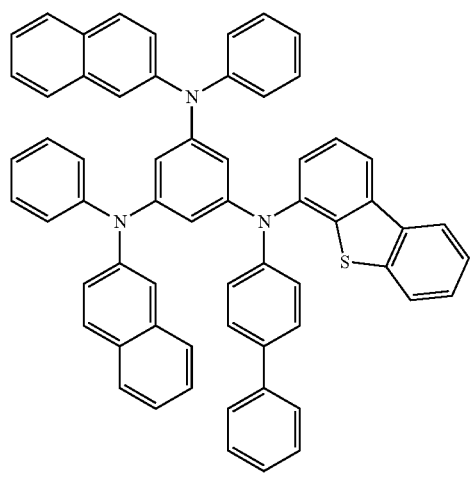
[A-140]
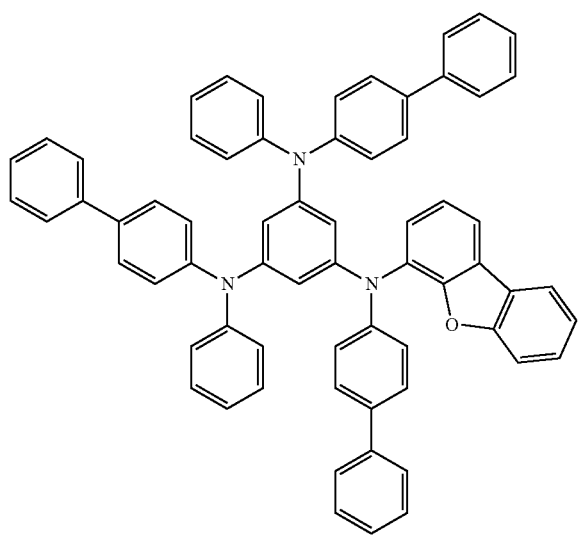

-continued
[A-141]
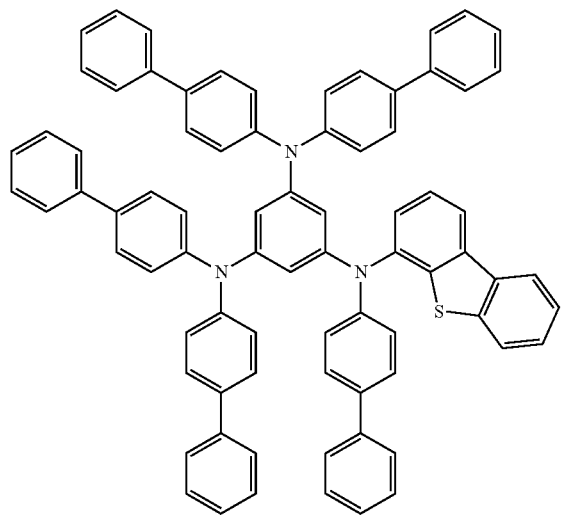
[A-142]
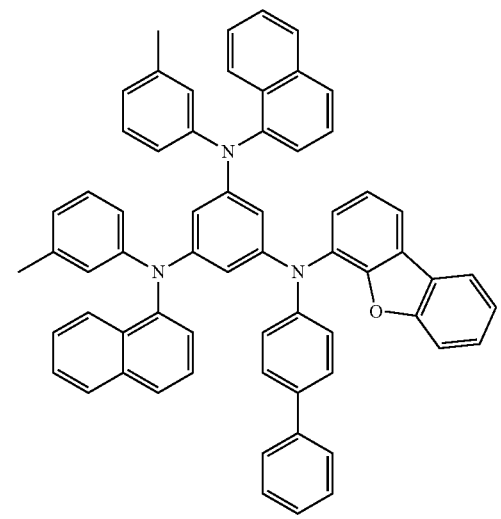
[A-143]
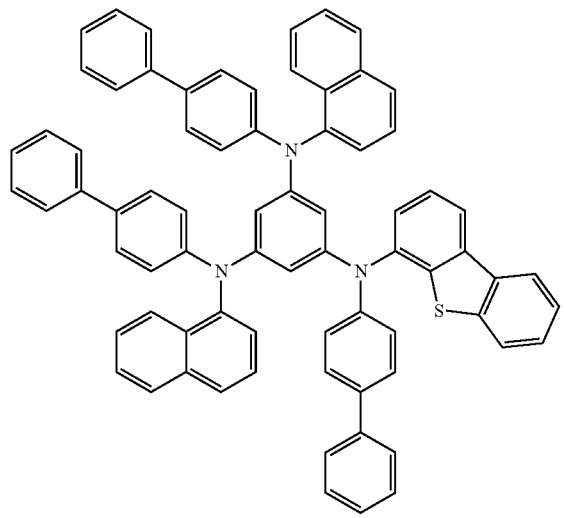
[A-144]
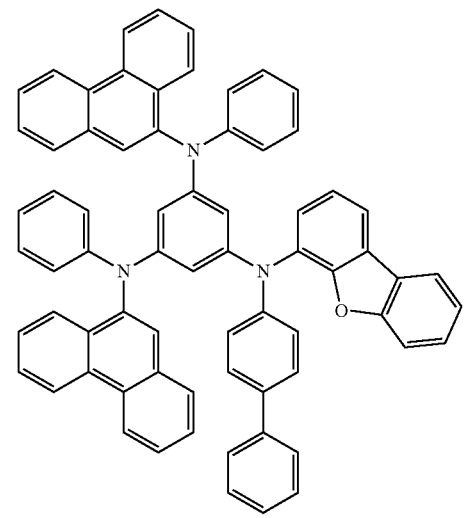
[A-145]
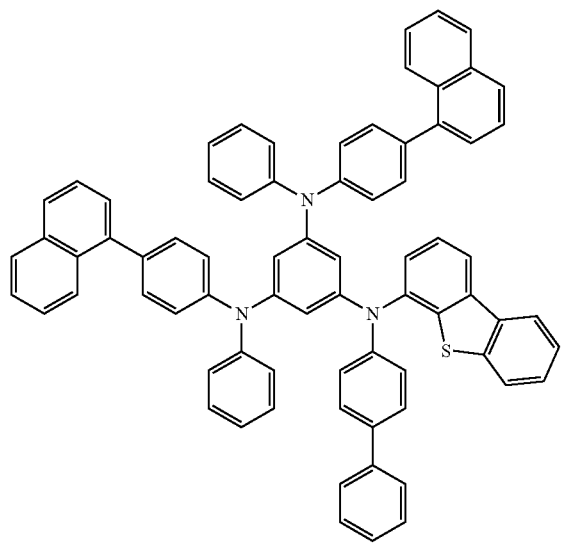
[A-146]
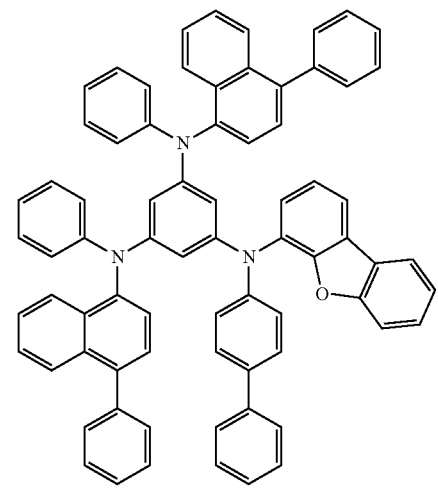

-continued
[A-147]
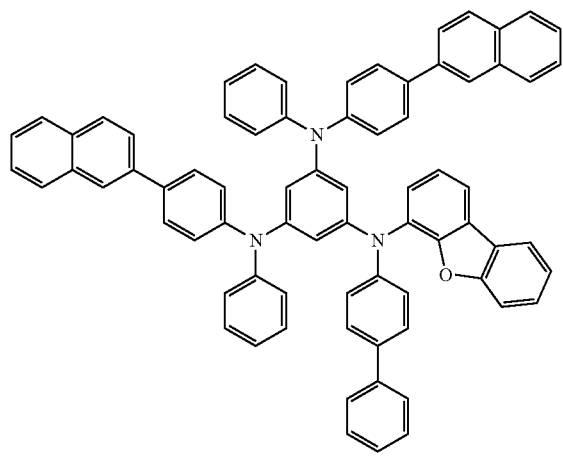
[A-148]
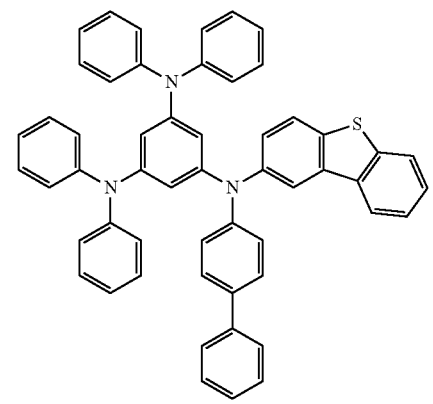
[A-149]
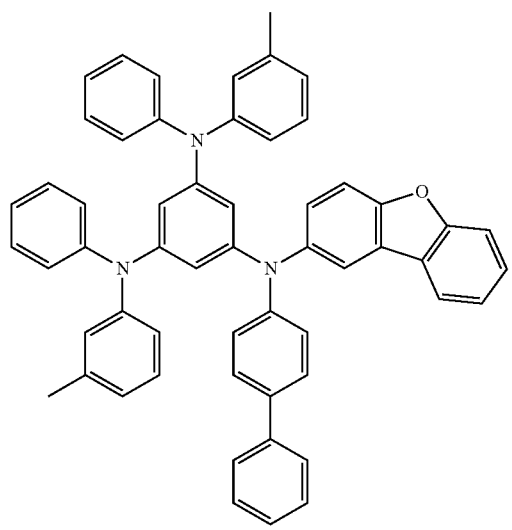
[A-150]
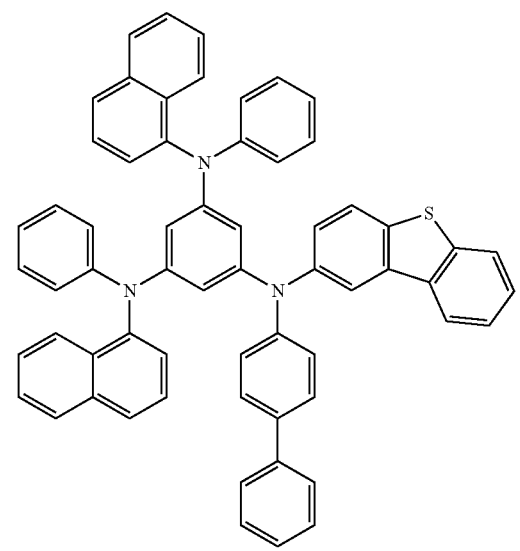
[A-151]
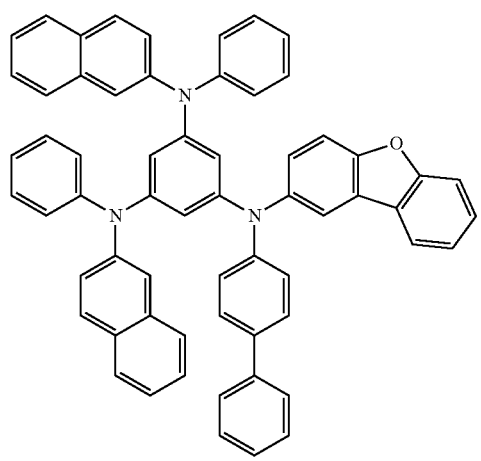
[A-152]
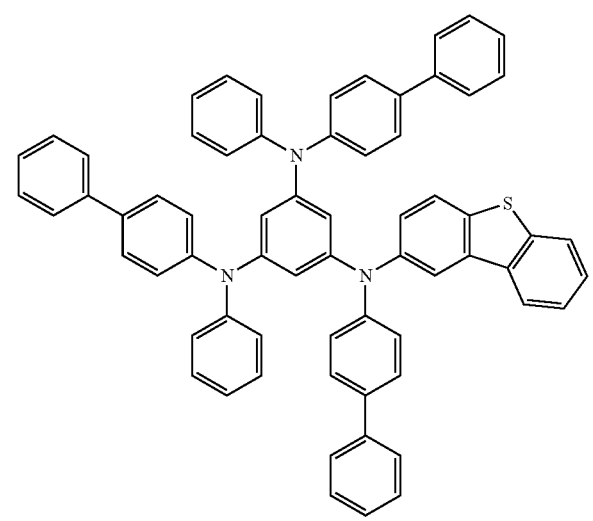

[A-153]
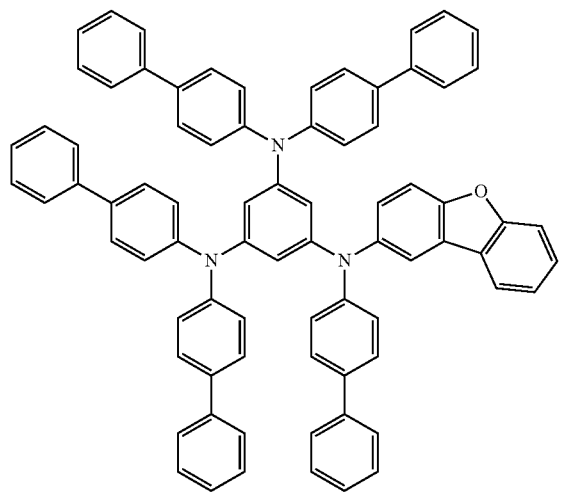
[A-154]
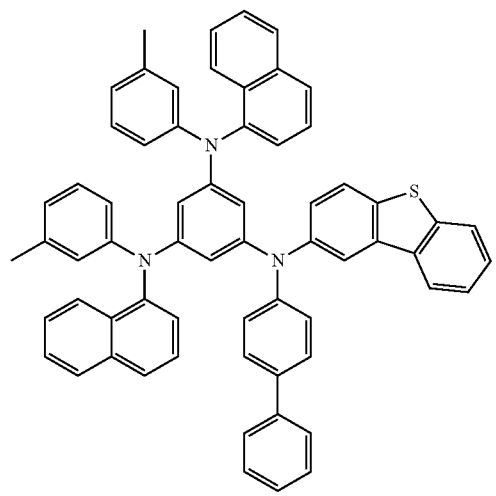
[A-155]
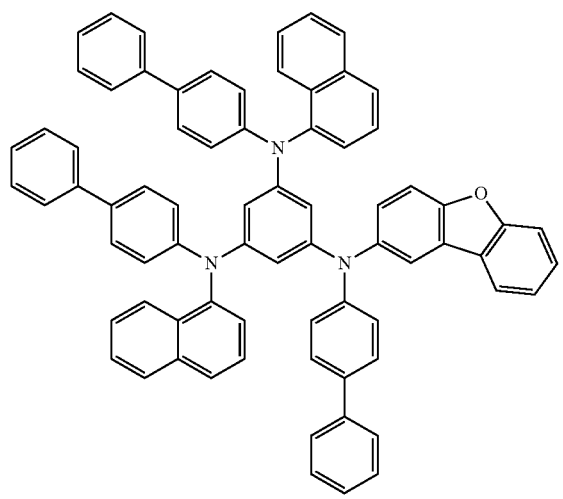
[A-156]
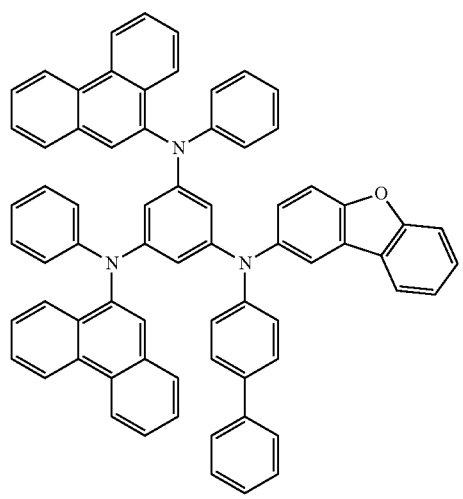
[A-157]
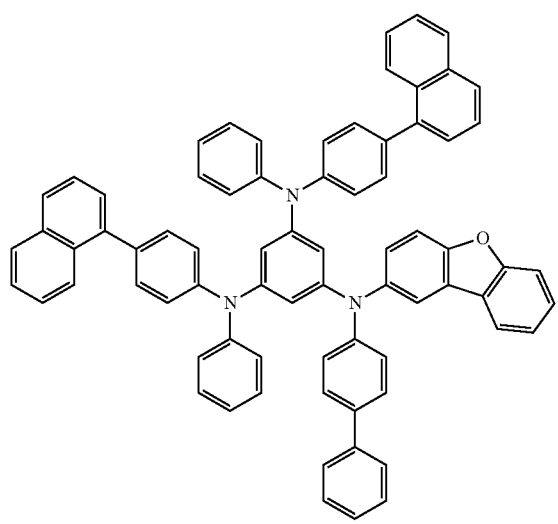
[A-158]
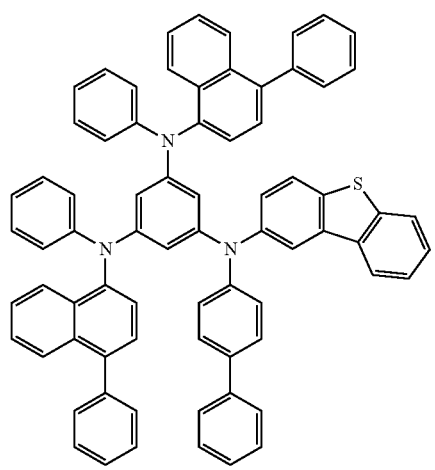

-continued
[A-159]
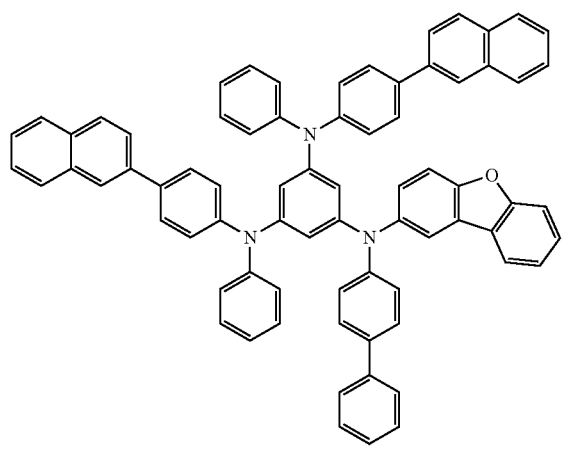
[A-160]
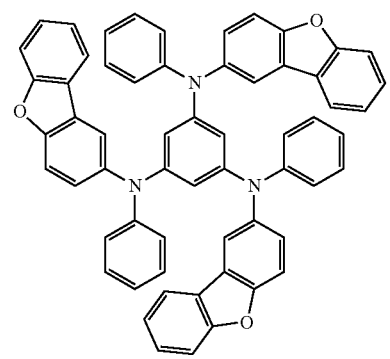
[A-161]
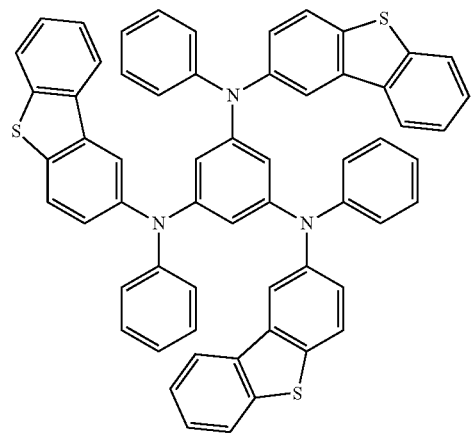
[A-162]
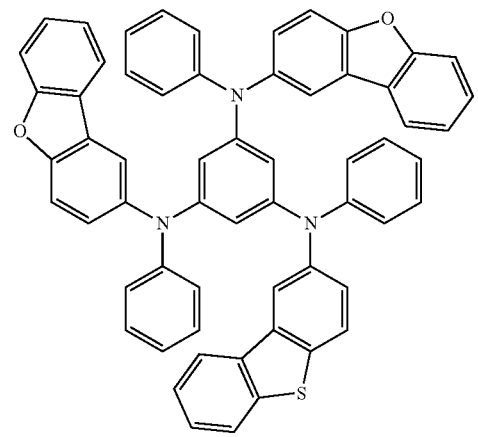
[A-163]
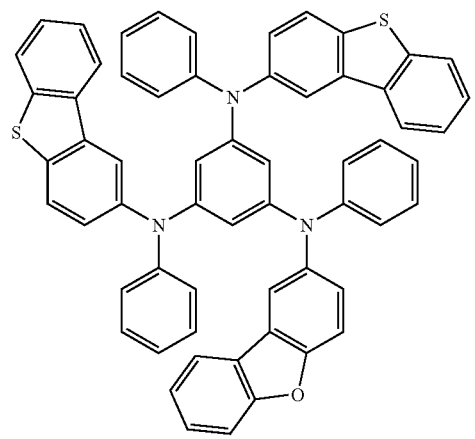
[A-164]
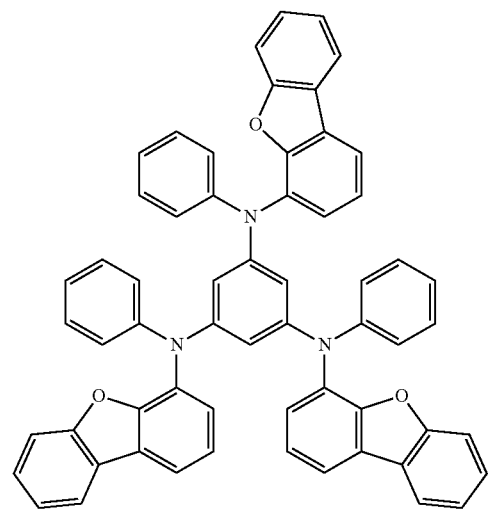

-continued
[A-165]
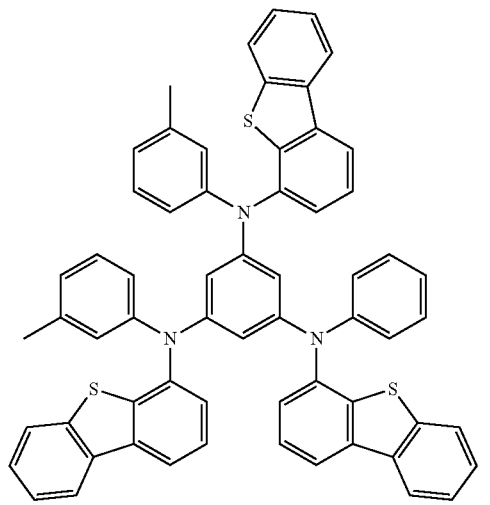
[A-166]
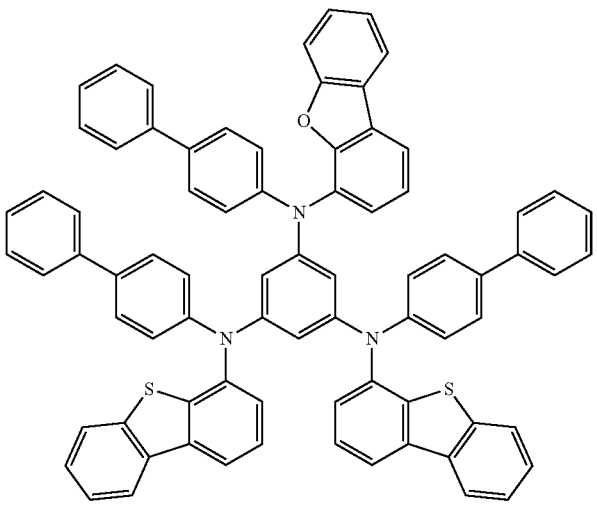
[A-167]
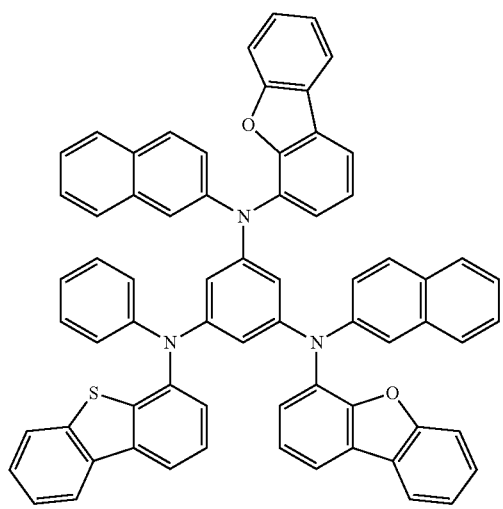
[A-168]
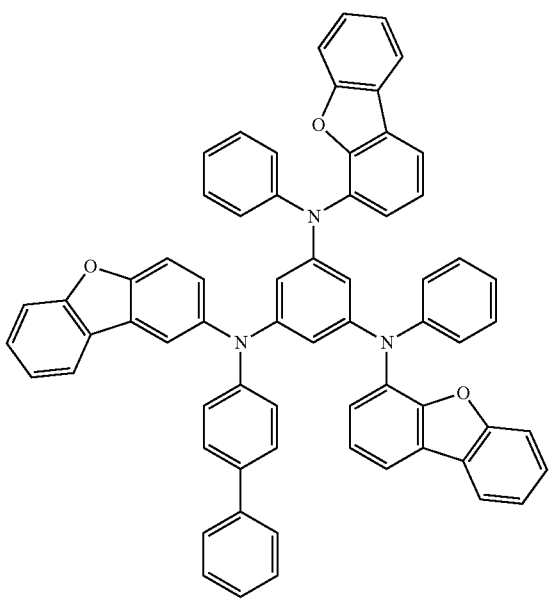
[A-169]
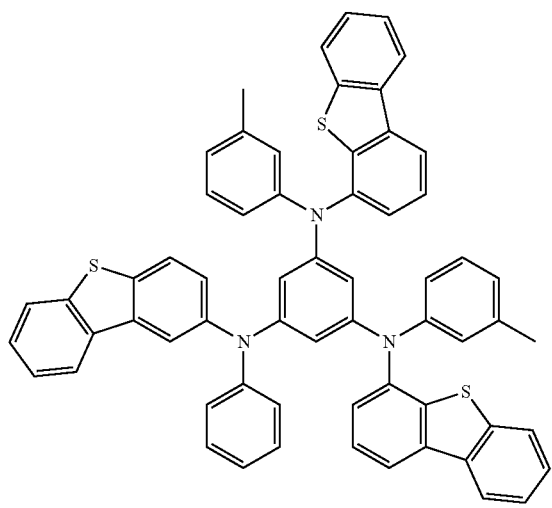
[A-170]
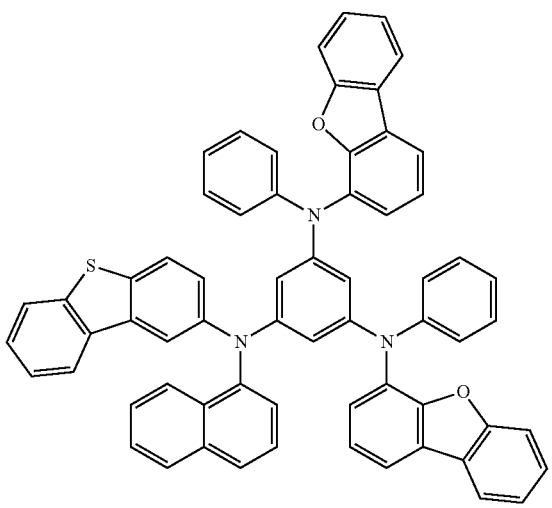

-continued
[A-171]
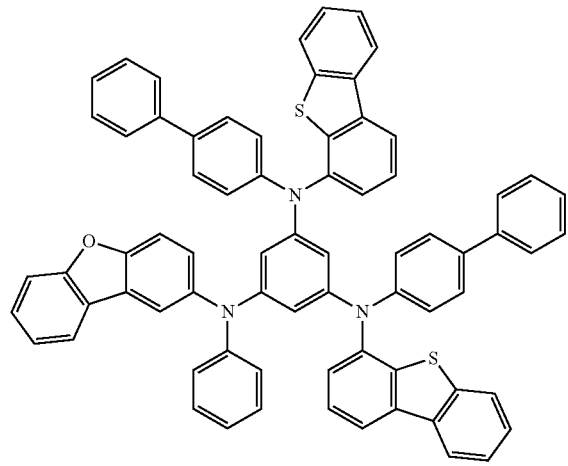
[A-172]
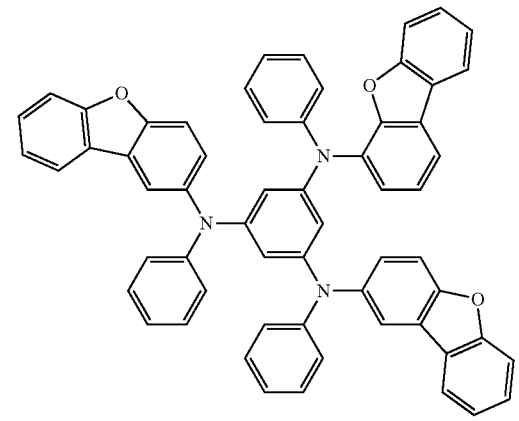
[A-173]
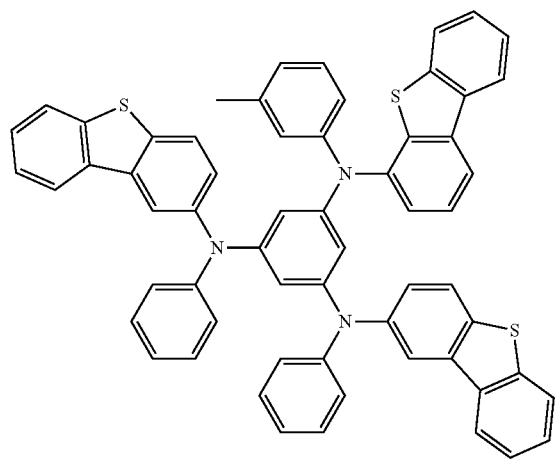
[A-174]
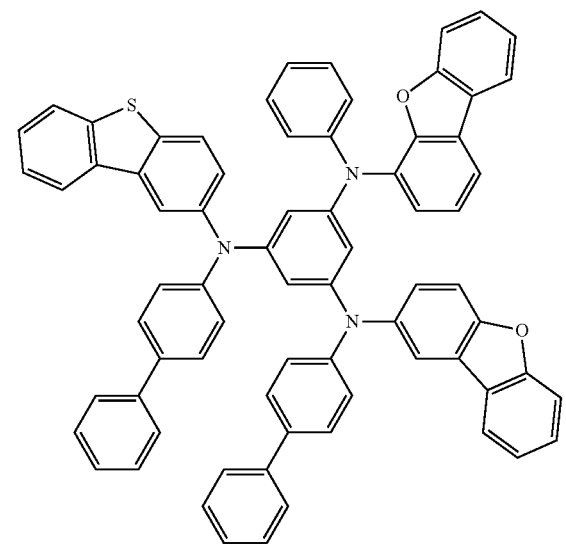
[A-175]
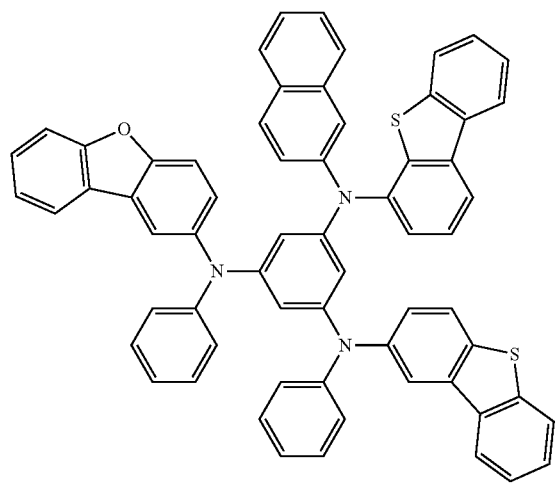
[A-176]
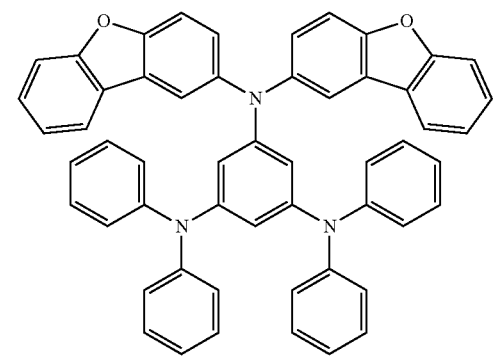

-continued
[A-177]
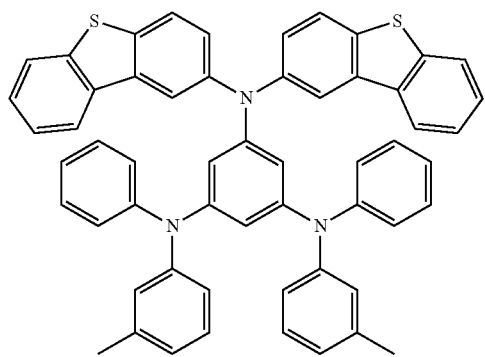
[A-178]
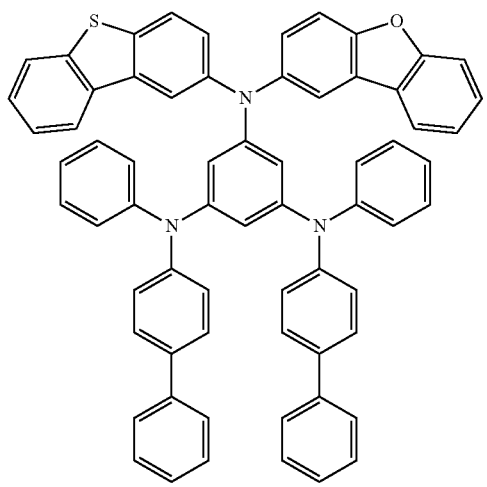
[A-179]
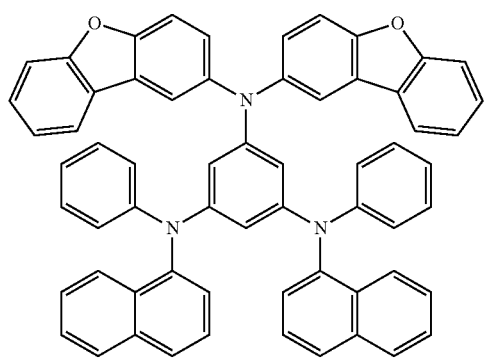
[A-180]
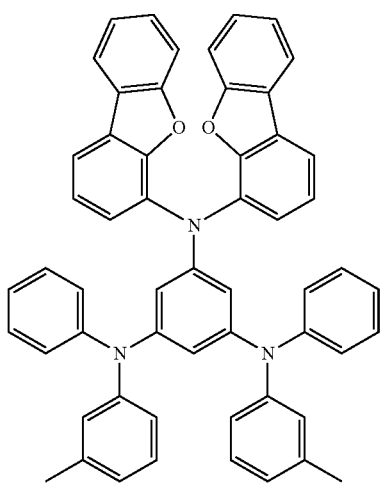
[A-181]
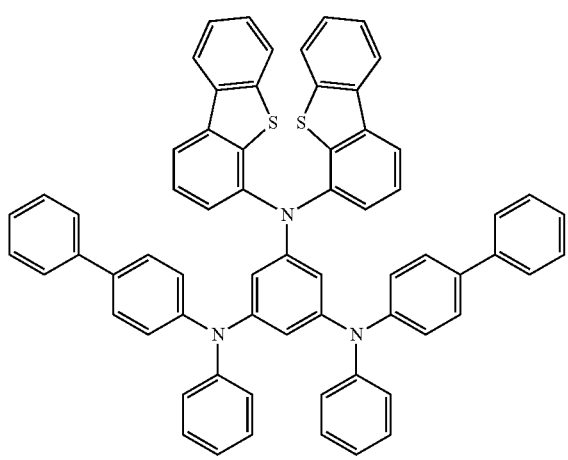
[A-182]
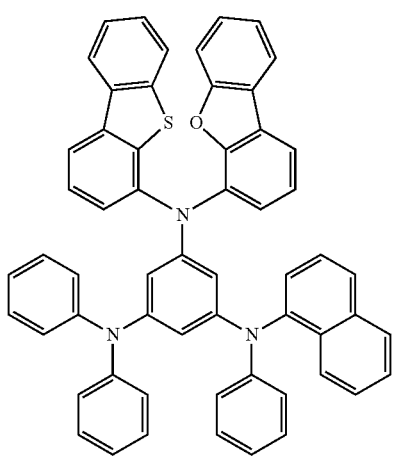

[A-183]
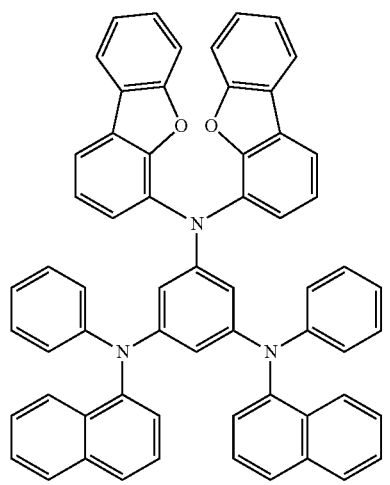
[A-184]
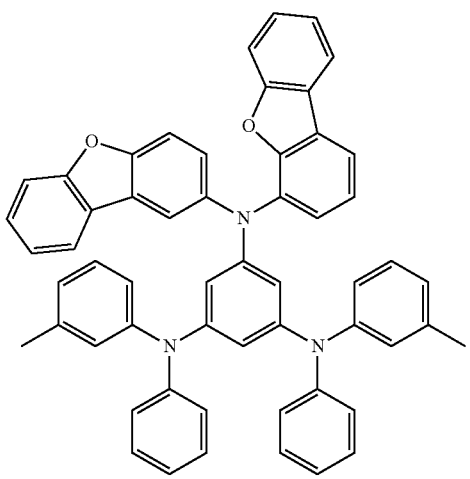
[A-185]
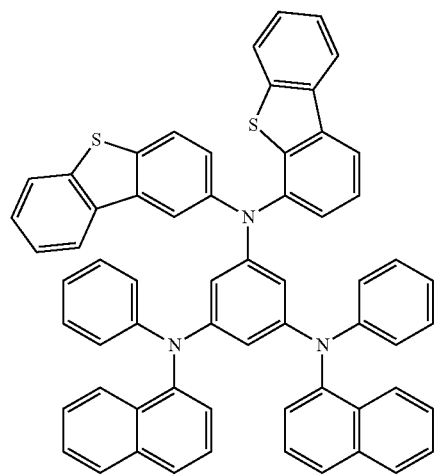
[A-186]
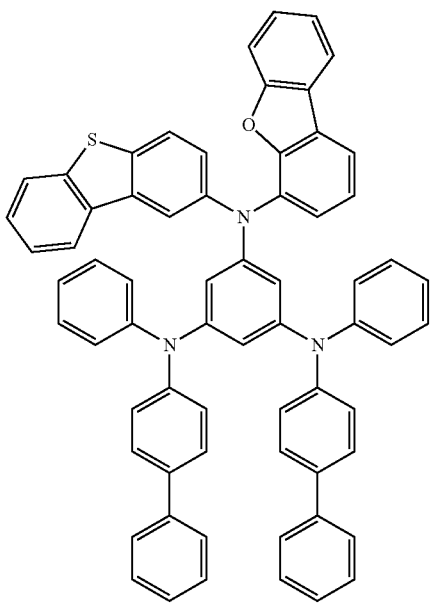
[A-187]
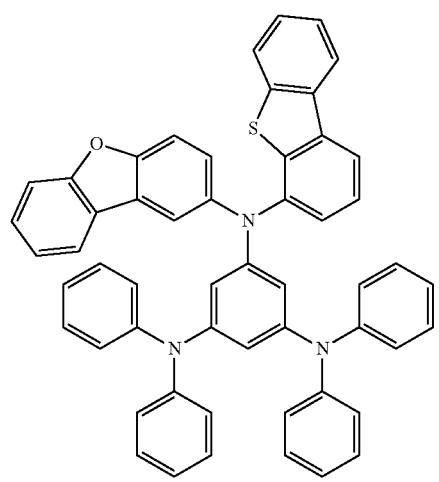
[A-188]
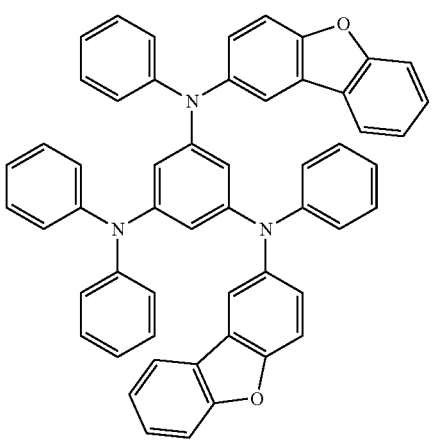

-continued
[A-189]
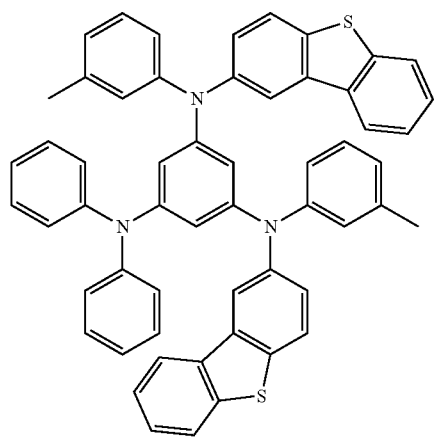
[A-190]
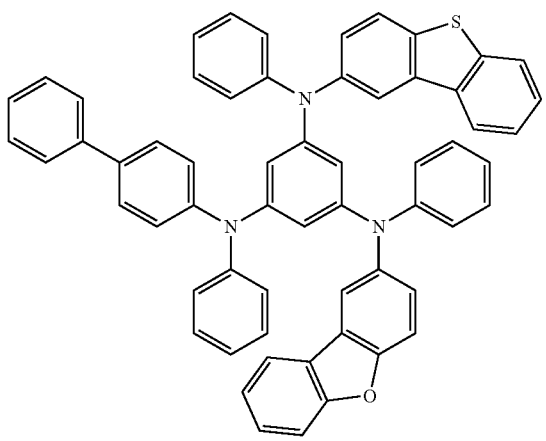
[A-191]
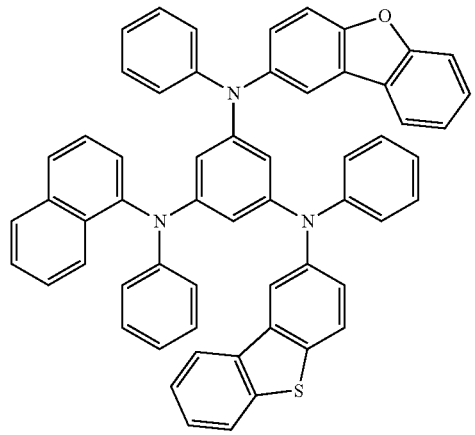
[A-192]
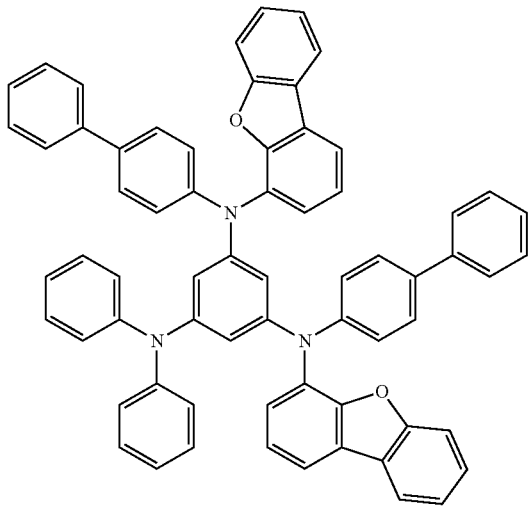
[A-193]
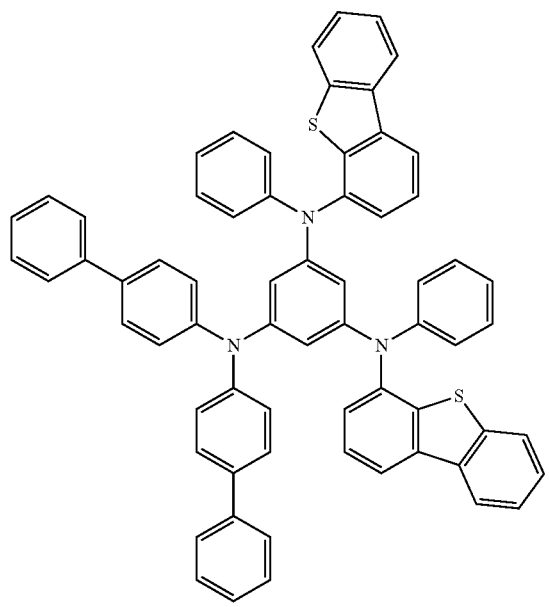
[A-194]
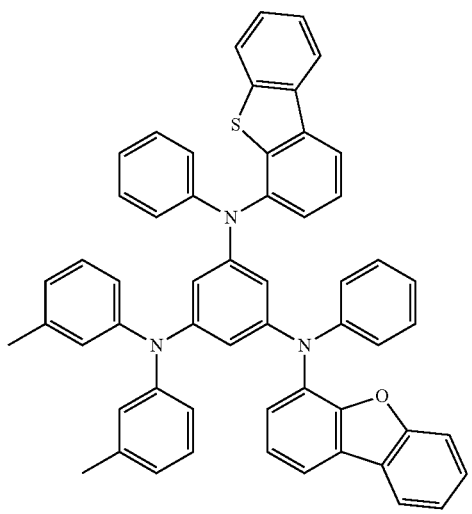

-continued
[A-195]
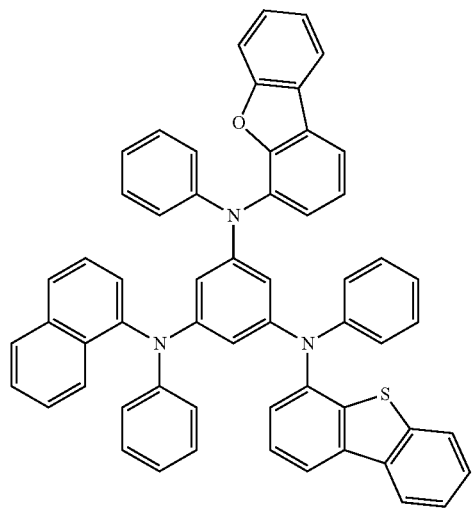
[A-196]
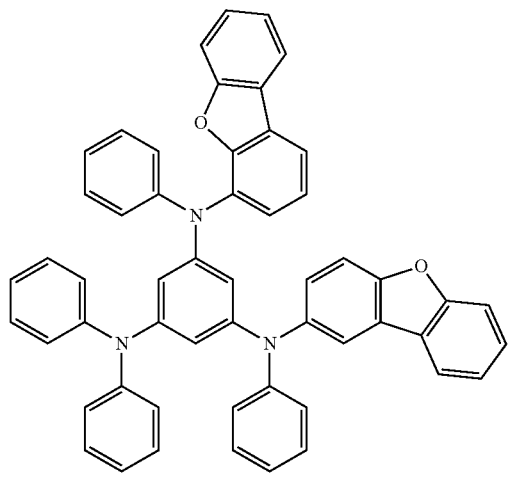
[A-197]
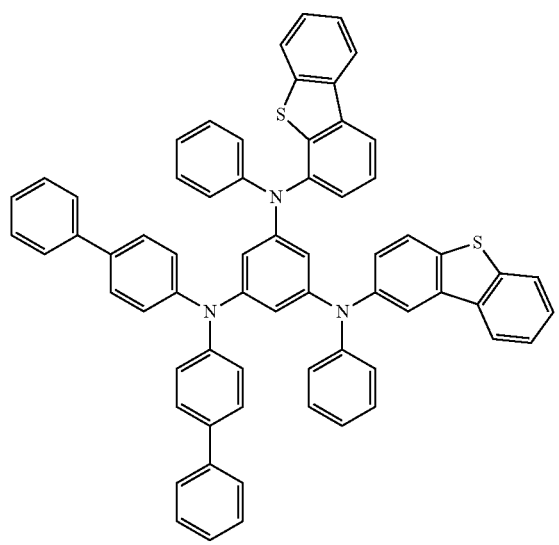
[A-198]
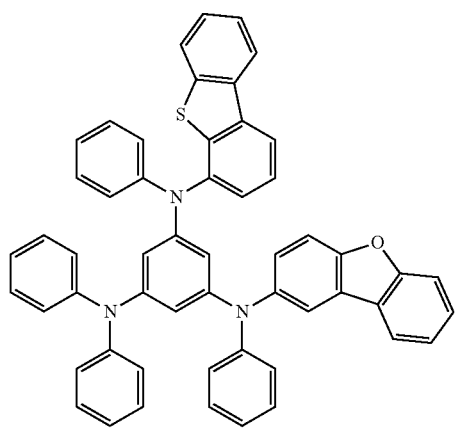
[A-199]
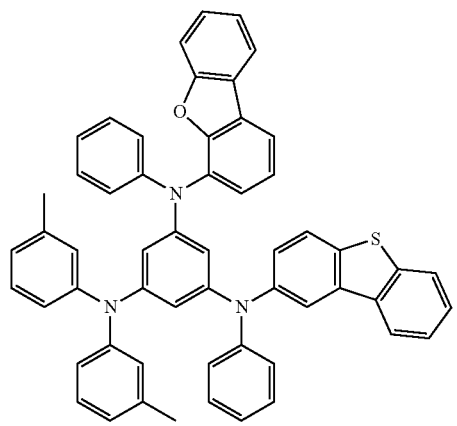
[A-200]
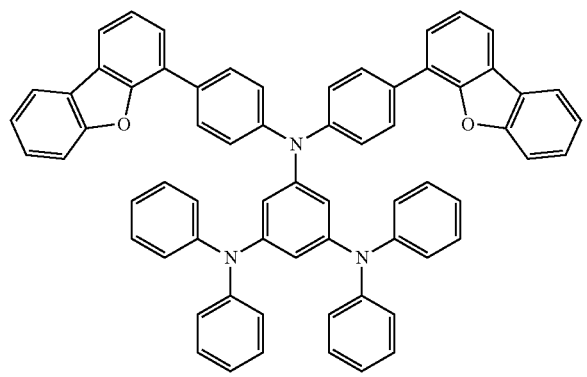

-continued
[A-201]
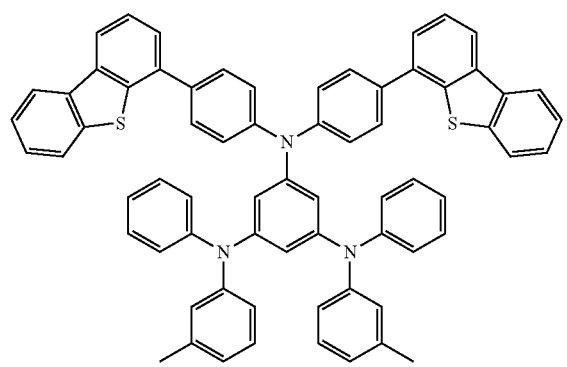
[A-202]
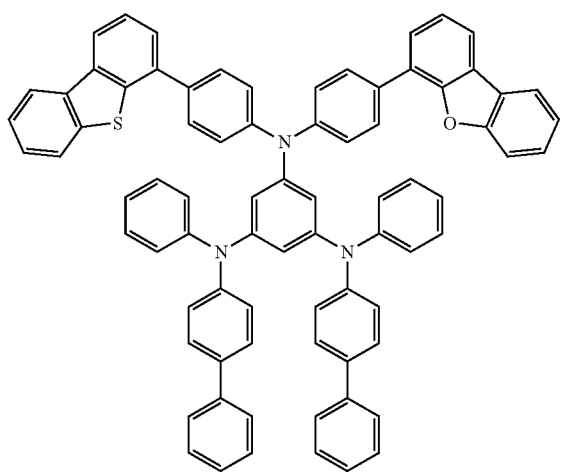
[A-203]
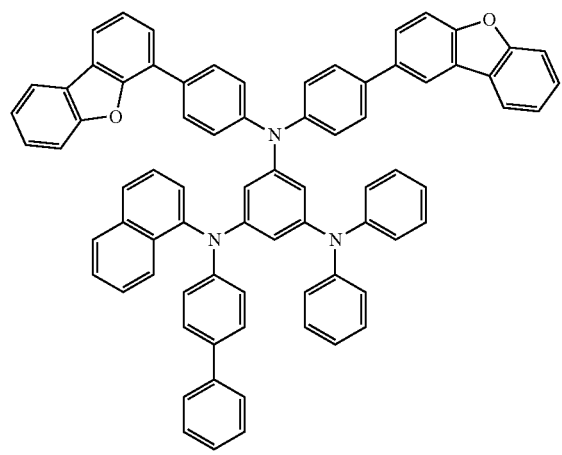
[A-204]
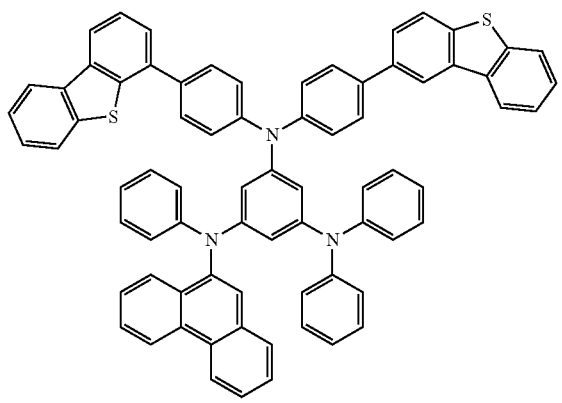
[A-205]
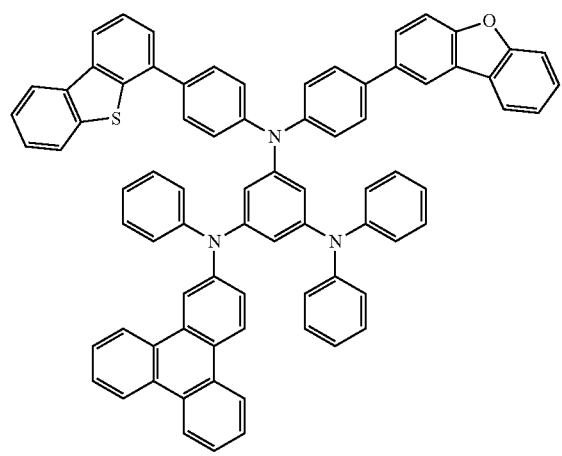
[A-206]
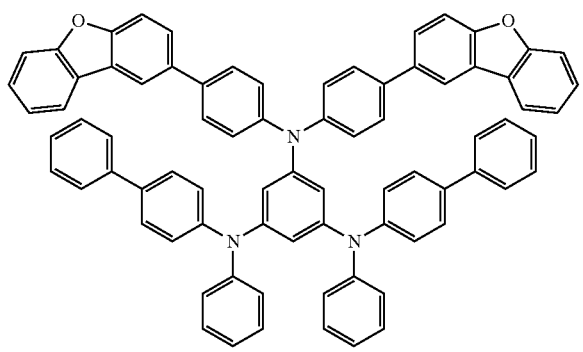

-continued
[A-207]
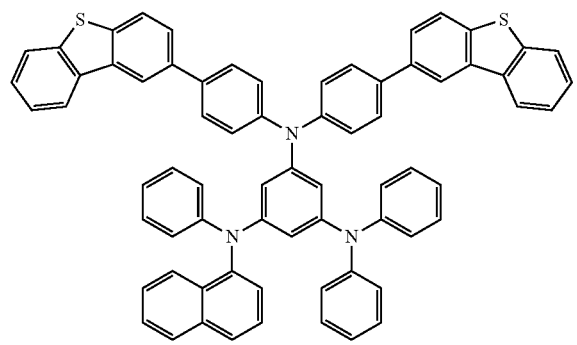
[A-208]
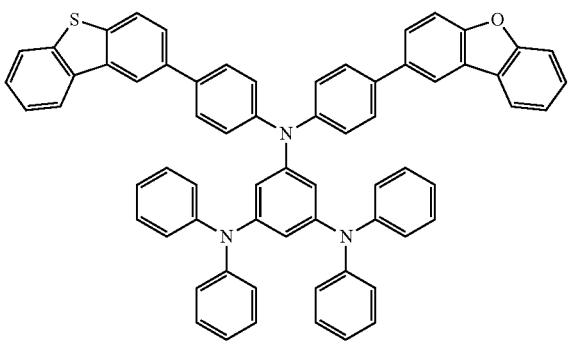
[A-209]
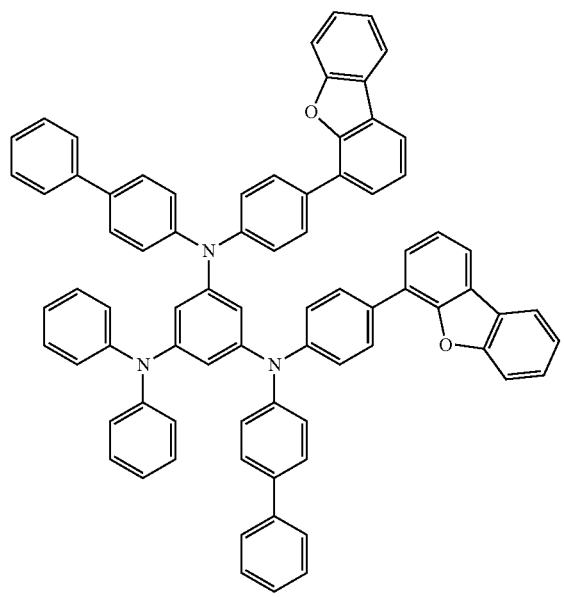
[A-210]
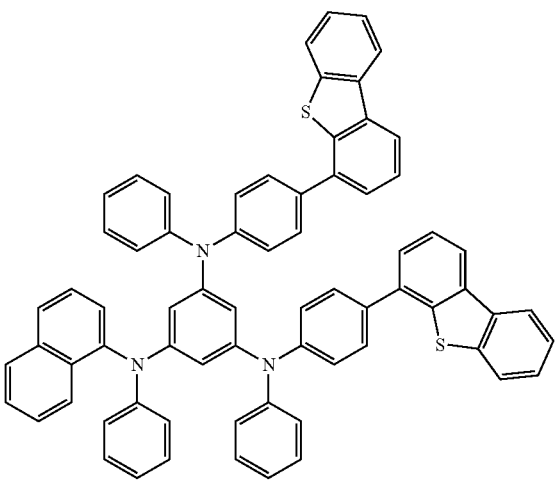
[A-211]
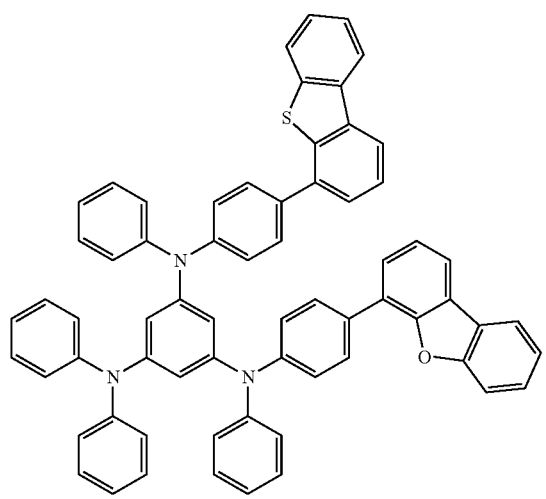
[A-212]
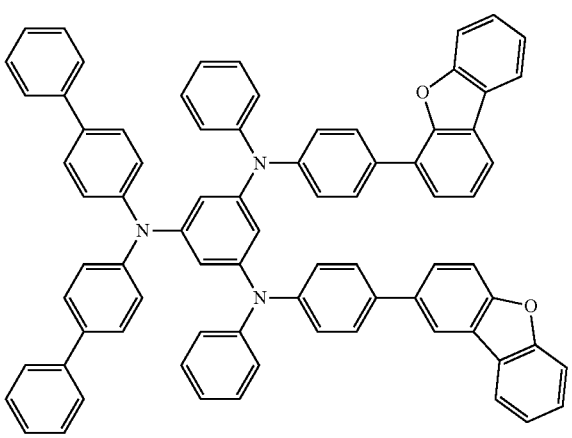

-continued
[A-213]
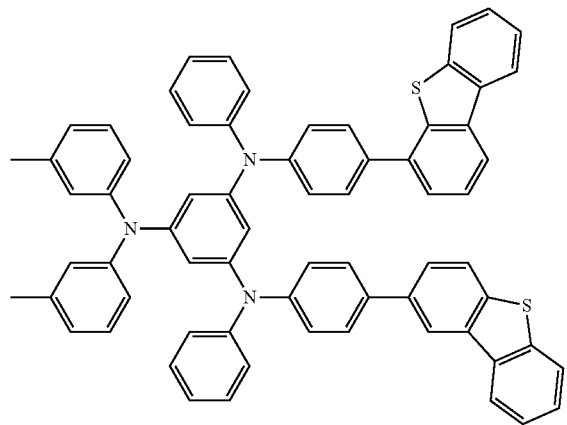
[A-214]
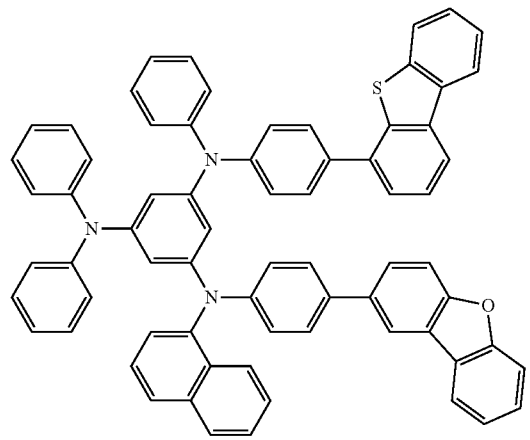
[A-215]
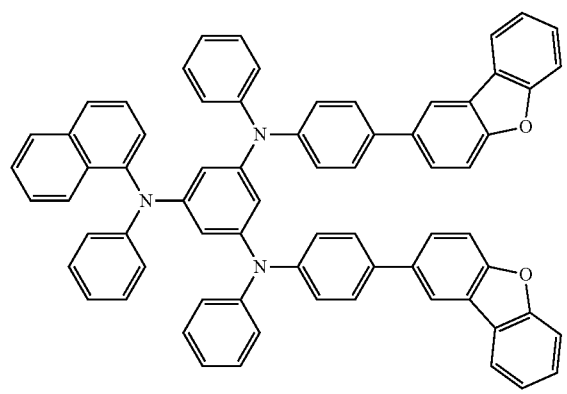
[A-216]
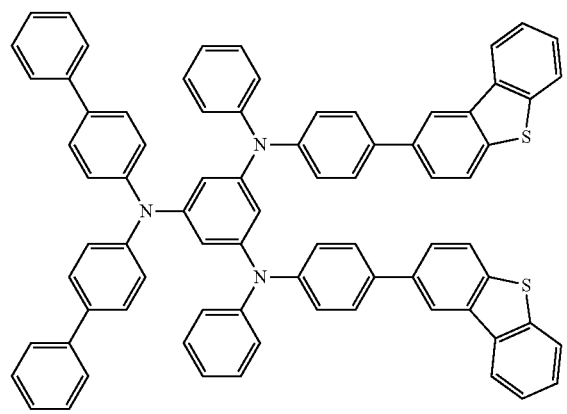
[A-217]
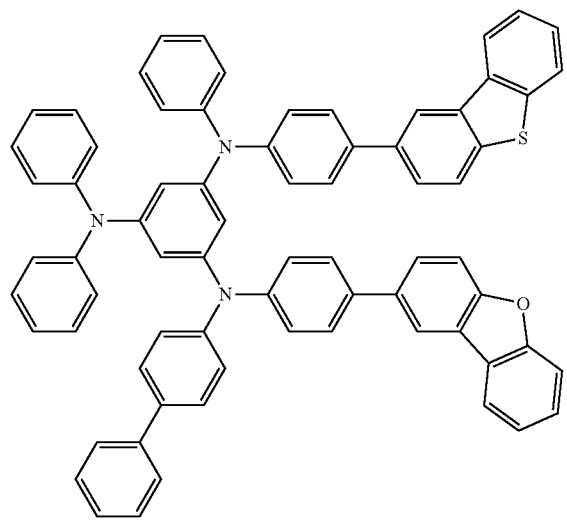
[A-218]
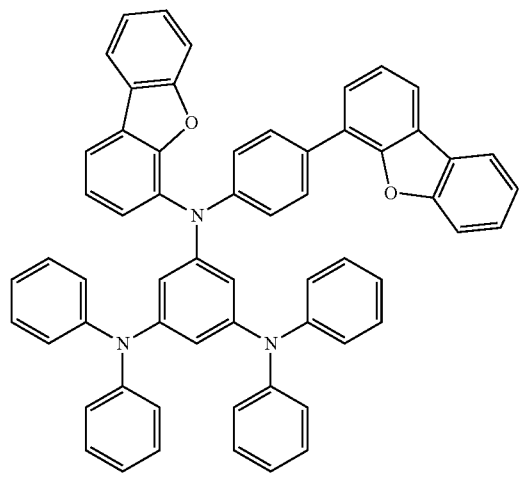

-continued
[A-219]
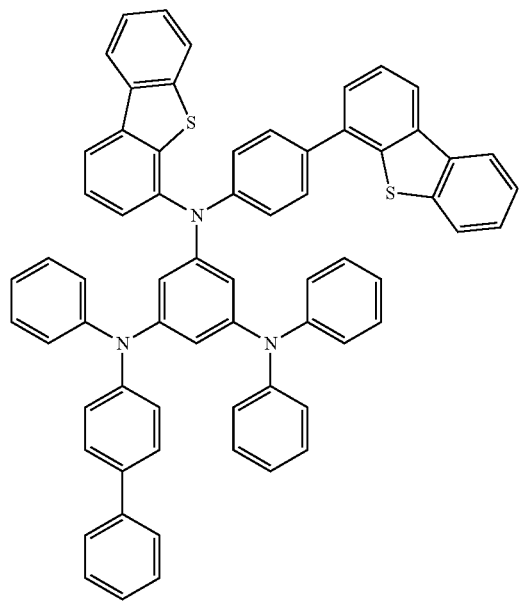
[A-220]
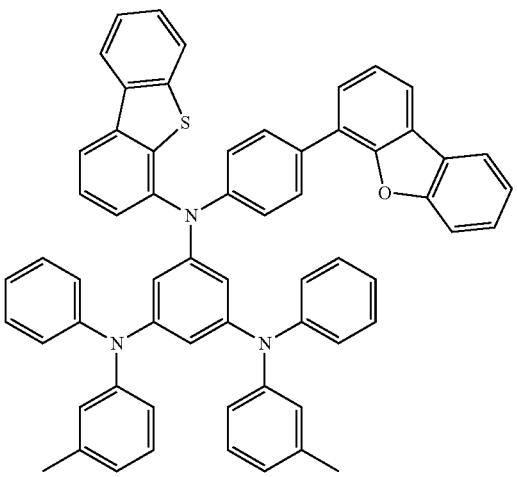
[A-221]
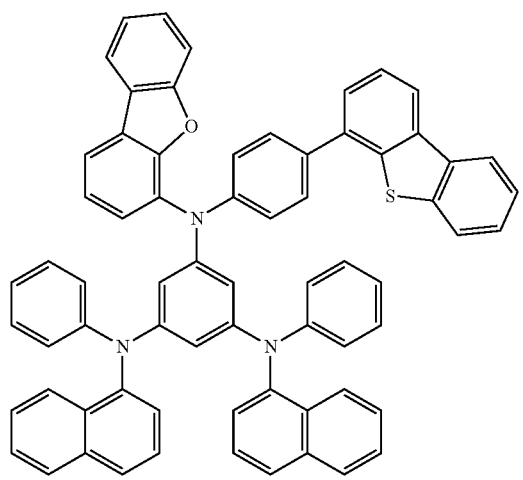
[A-222]
[A-223]
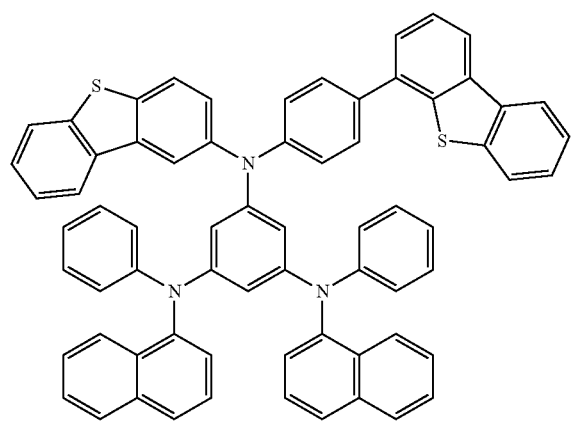
[A-224]
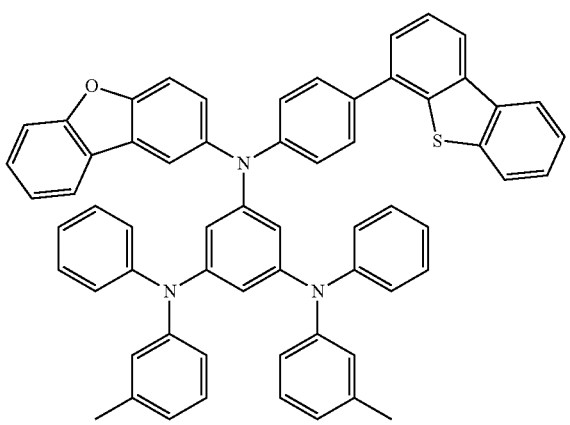

[A-225] 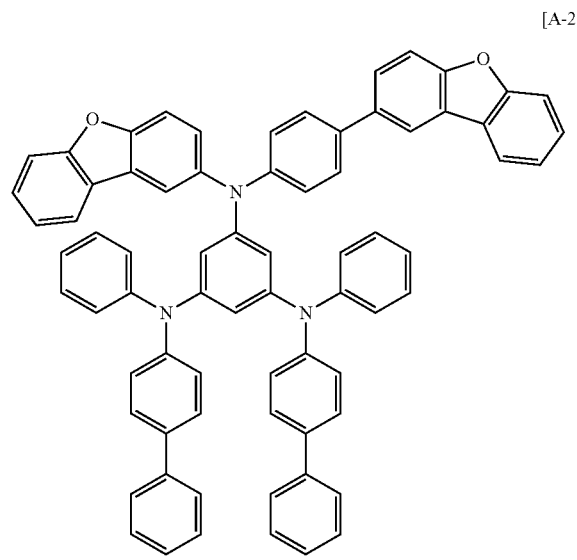
[A-226] 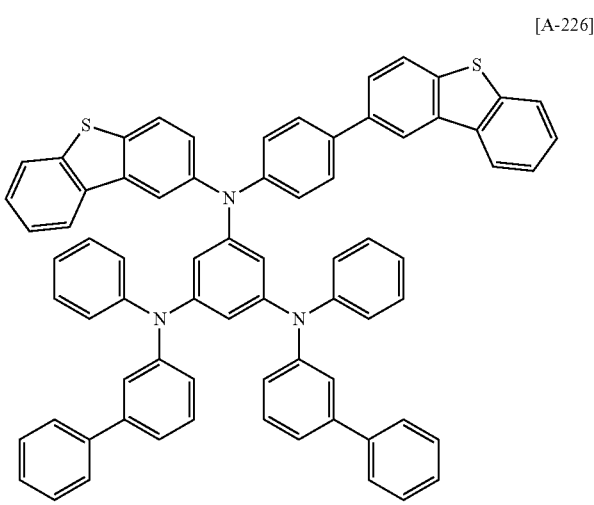
[A-227] 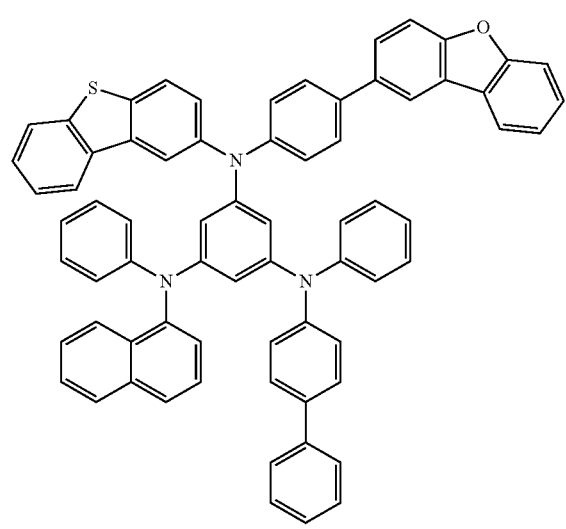
[A-228] 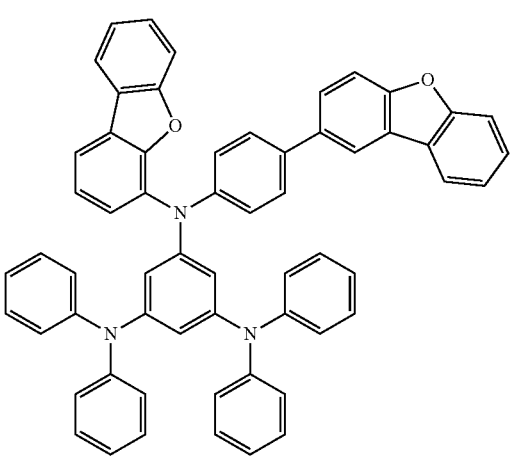
[A-229] 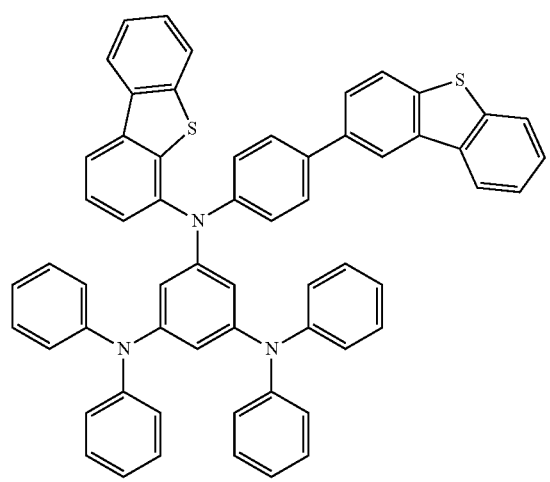
[A-230] 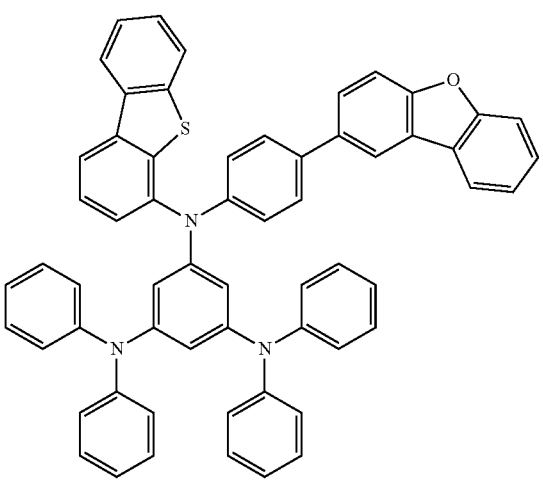

-continued
[A-231]
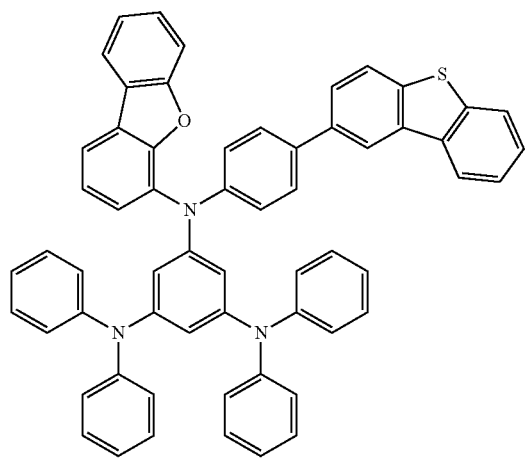
[A-232]
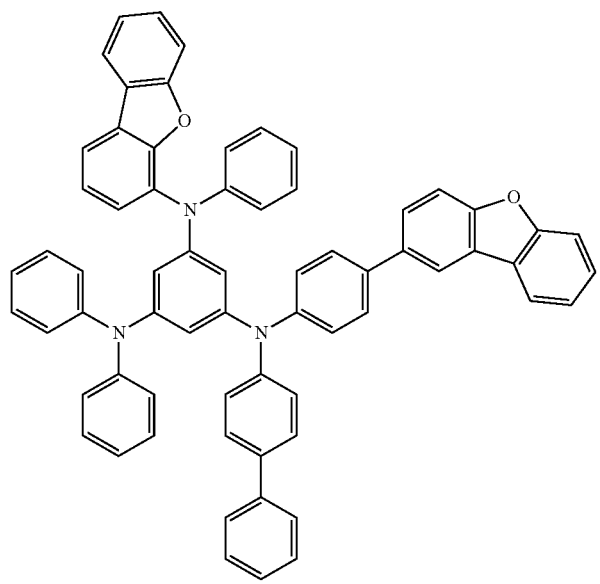
[A-233]
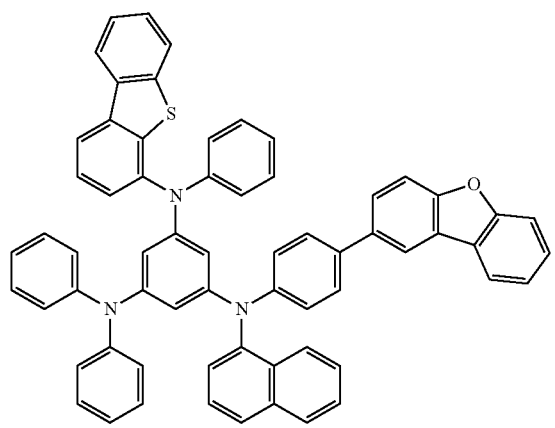
[A-234]
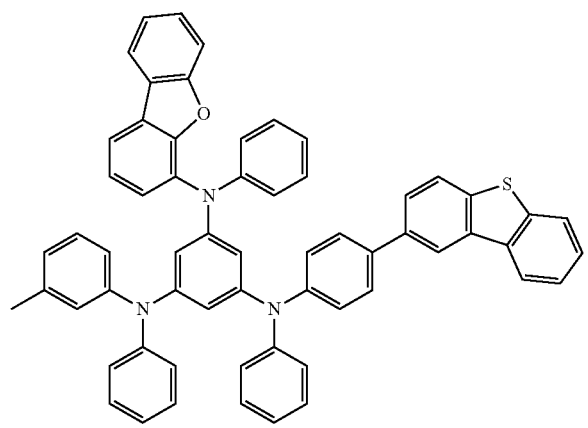
[A-235]
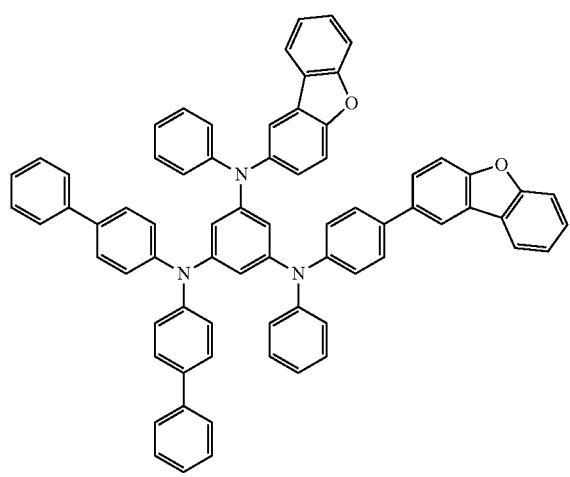
[A-236]
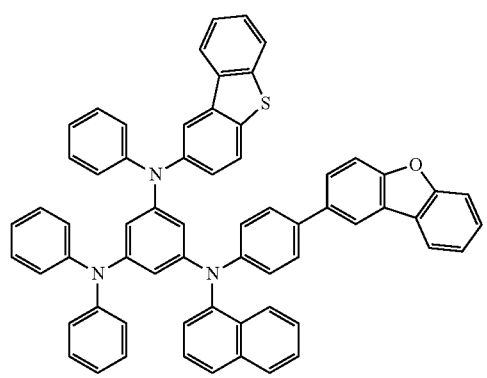

-continued
[A-237]
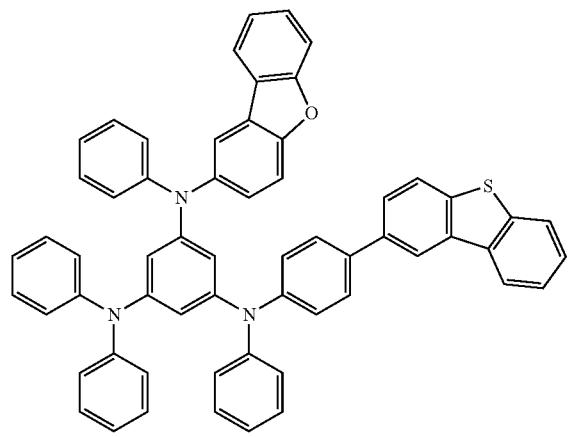
[A-238]
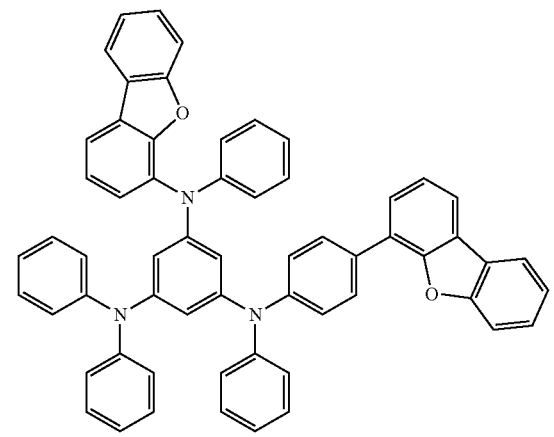
[A-239]
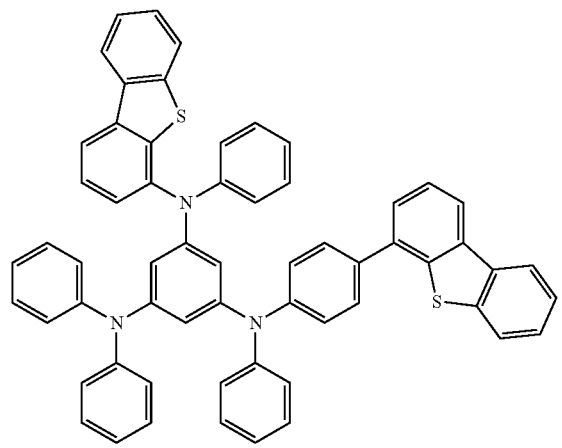
[A-240]
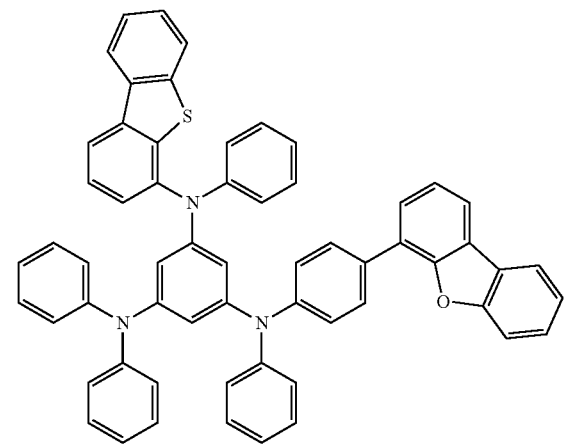
[A-241]
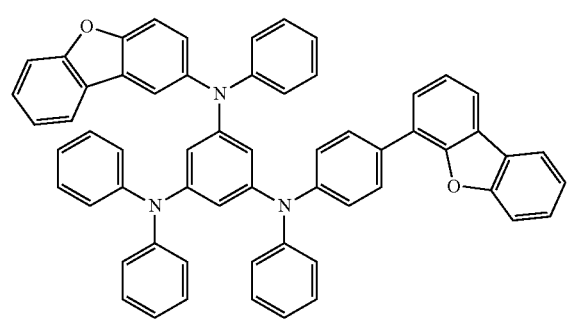
[A-242]
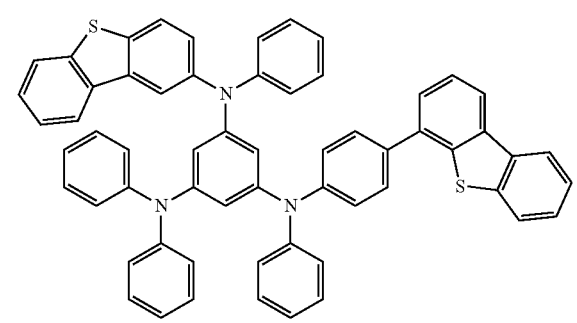
[A-243]
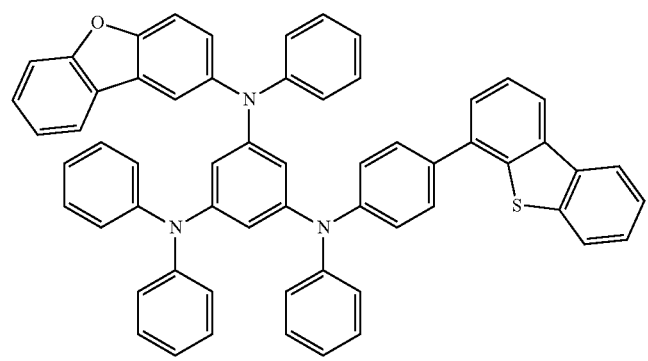

[A-244]
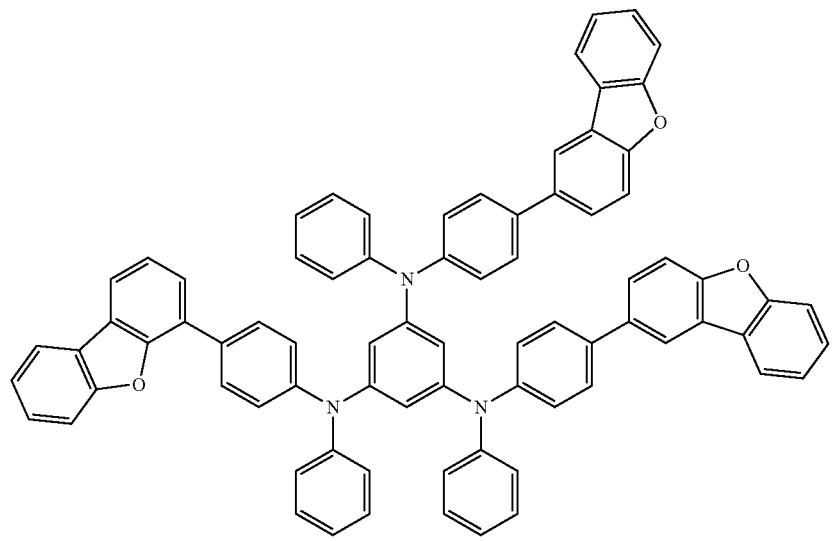
[A-245]
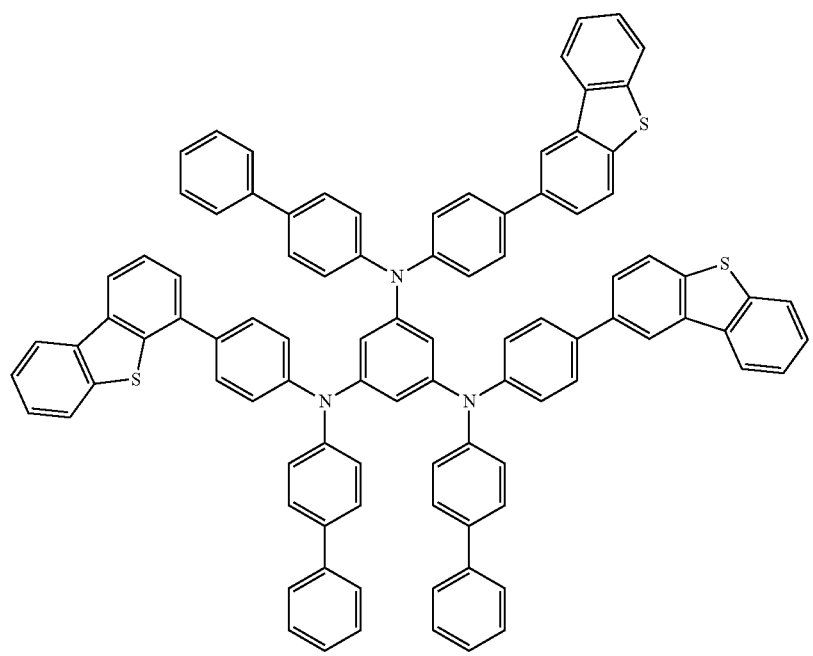

[A-246]
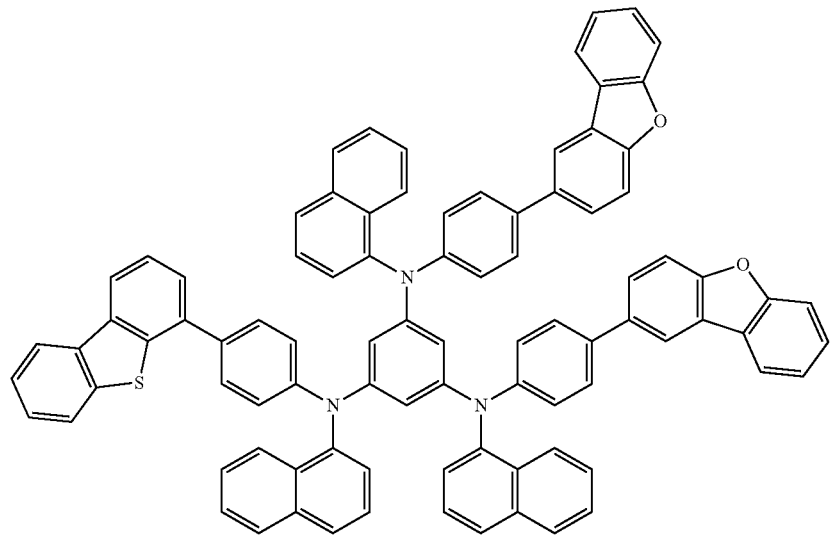
[A-247]
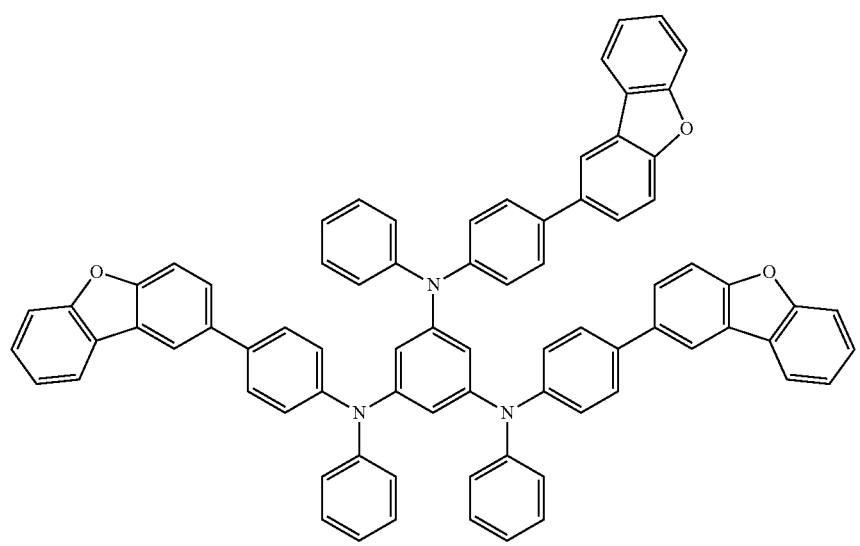
[A-248]
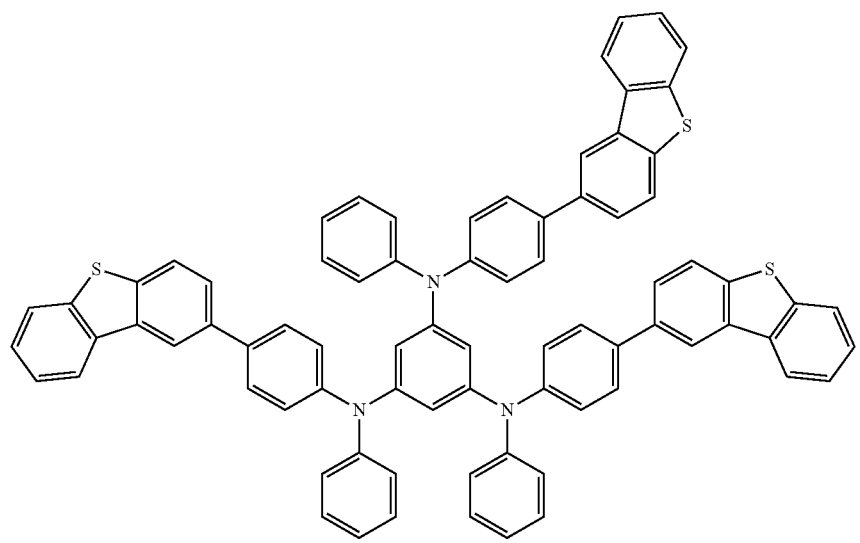

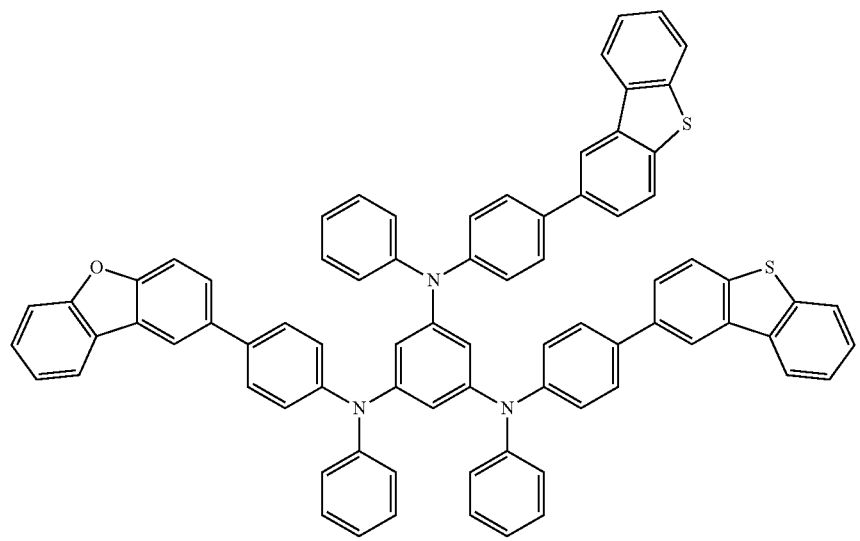
[A-249]
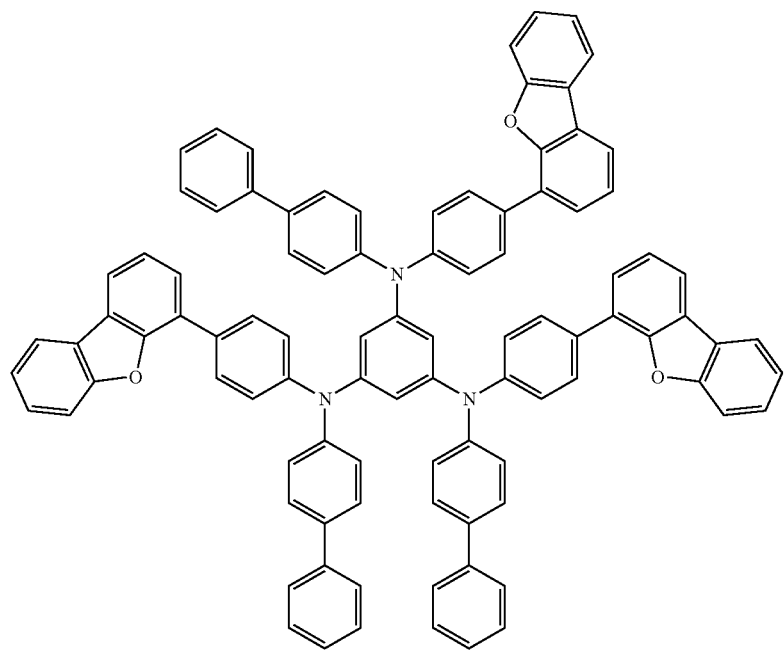
[A-250]

-continued
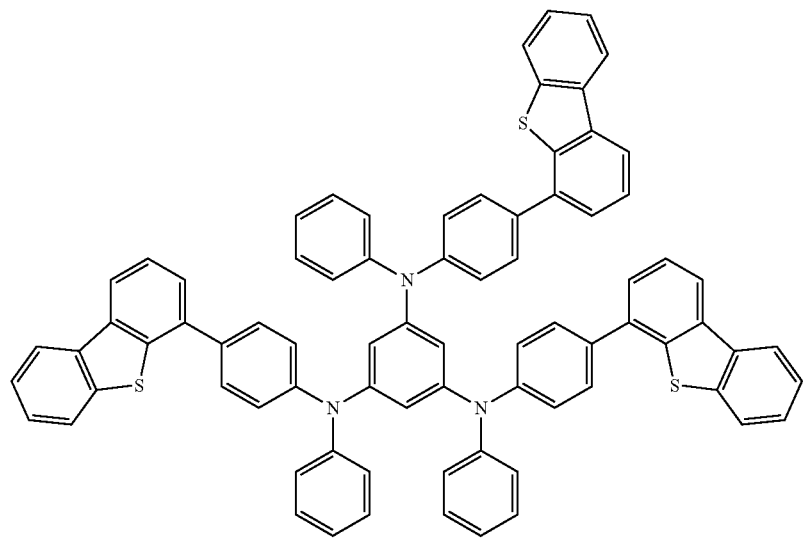
[A-251]
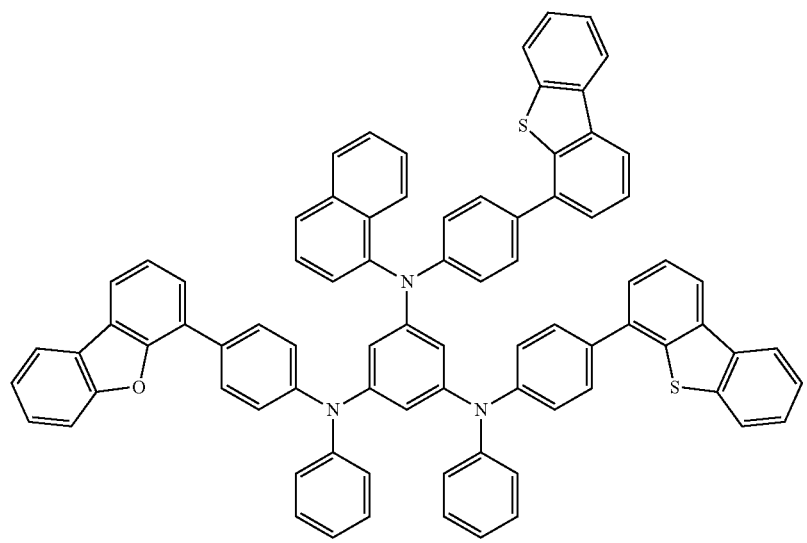
[A-252]
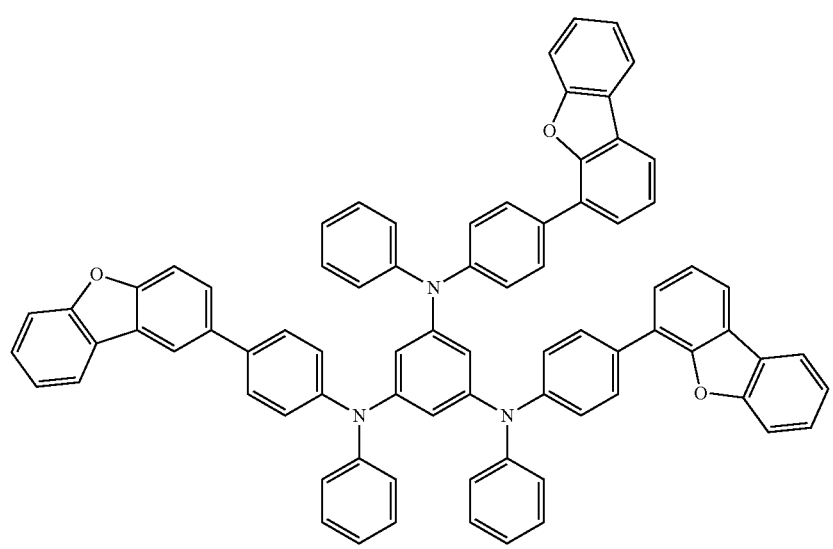
[A-253]

-continued
[A-254]
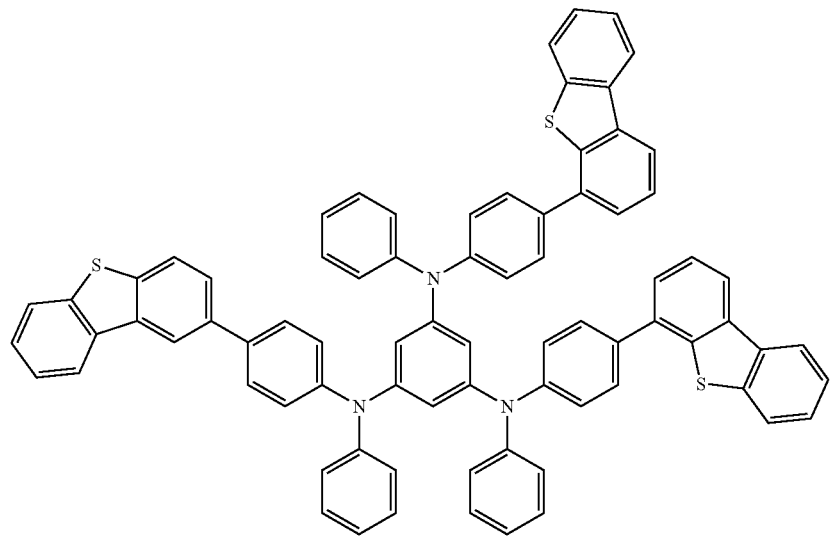
[A-255]
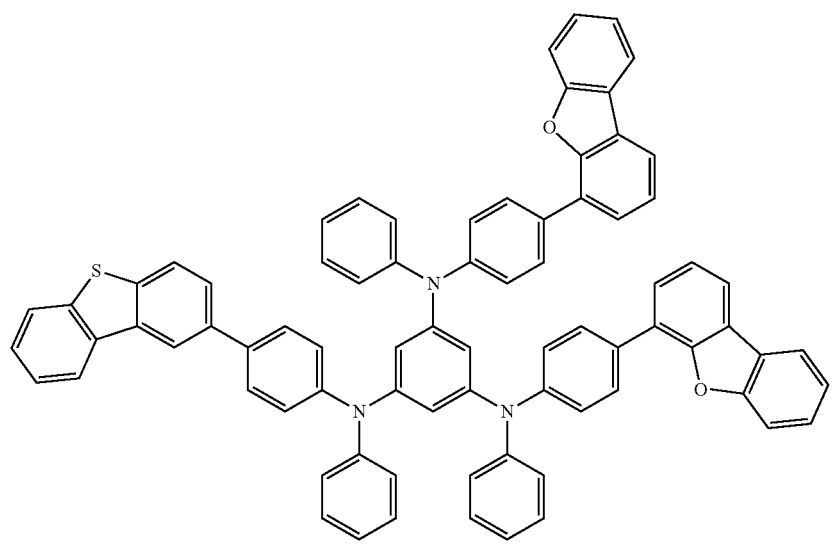
[A-256]
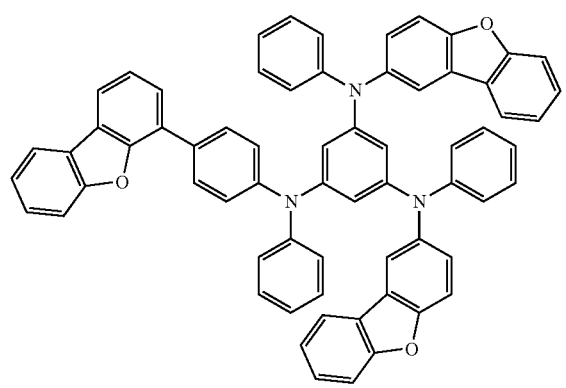
[A-257]
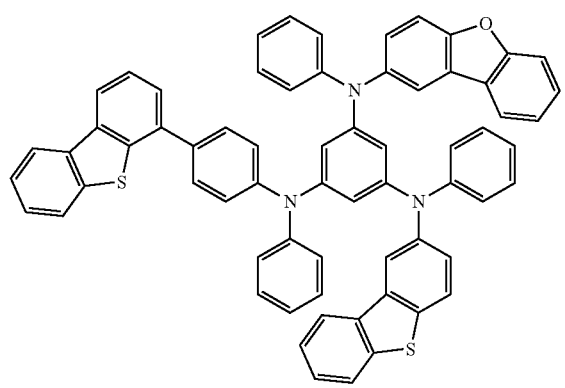

-continued
[A-258]
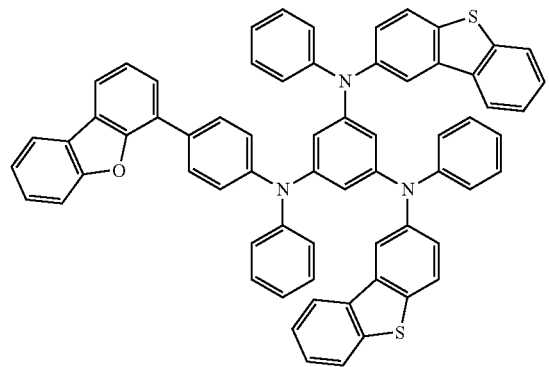
[A-259]
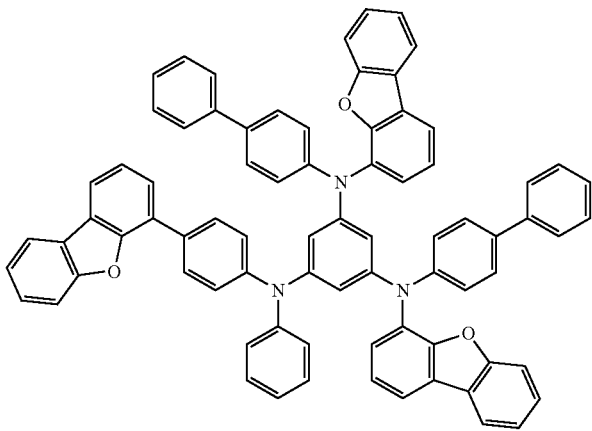
[A-260]
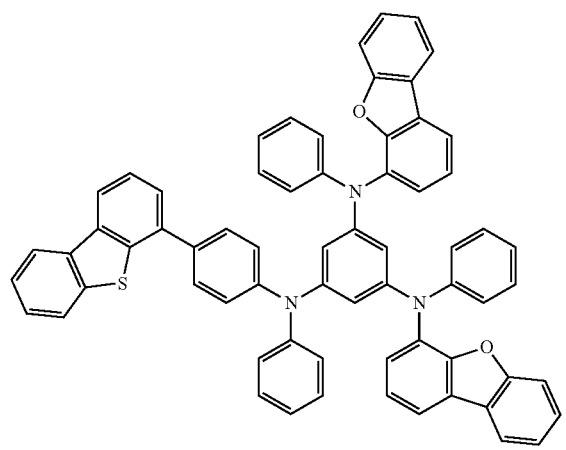
[A-261]
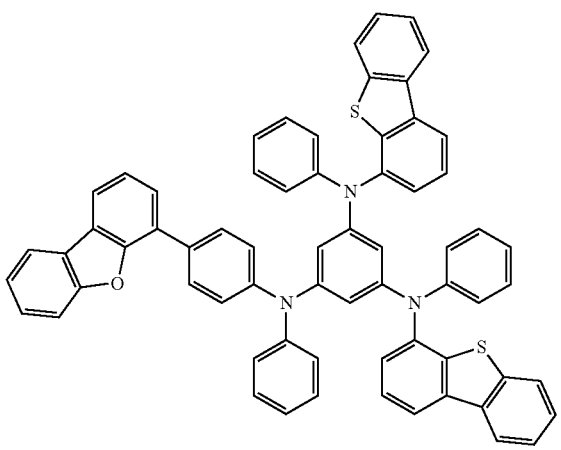
[A-262]
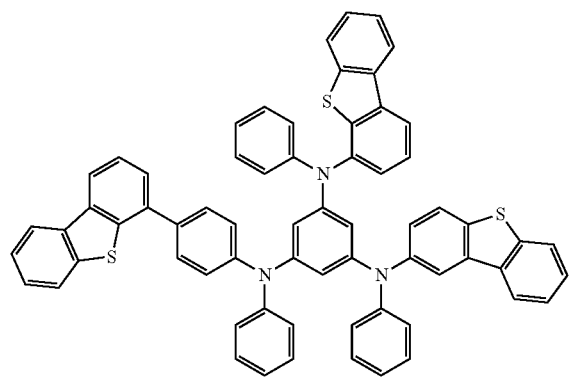
[A-263]
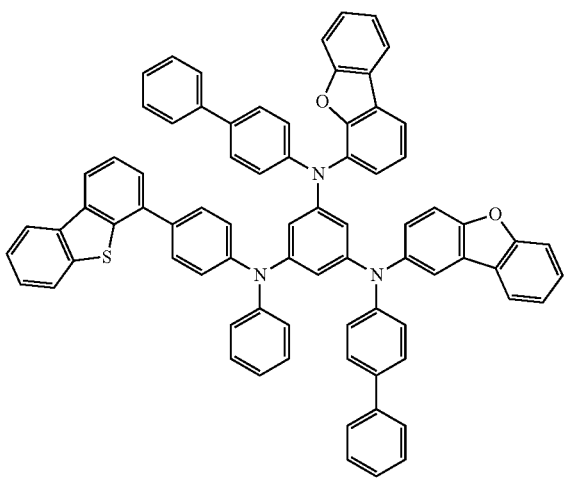

-continued
[A-264]
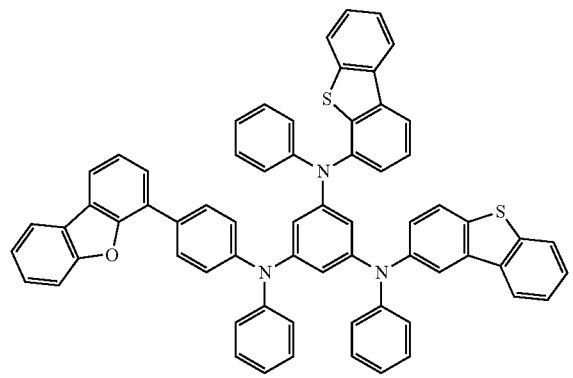
[A-265]
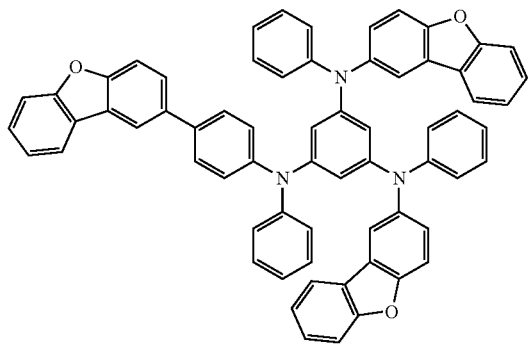
[A-266]
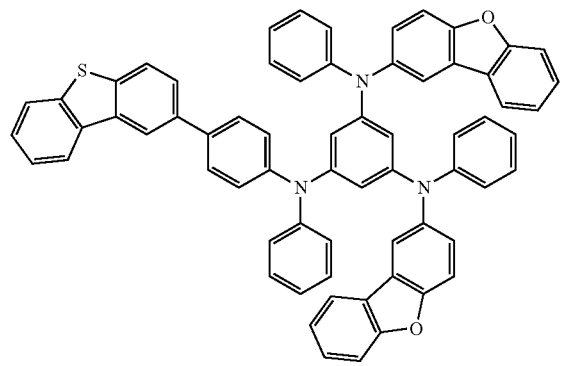
[A-267]
[A-268]
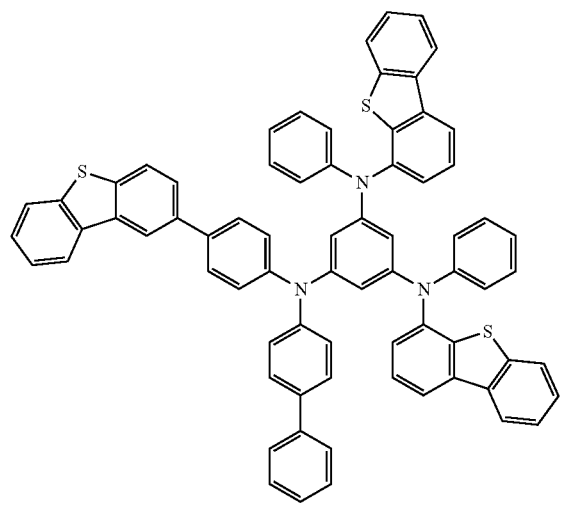
[A-269]
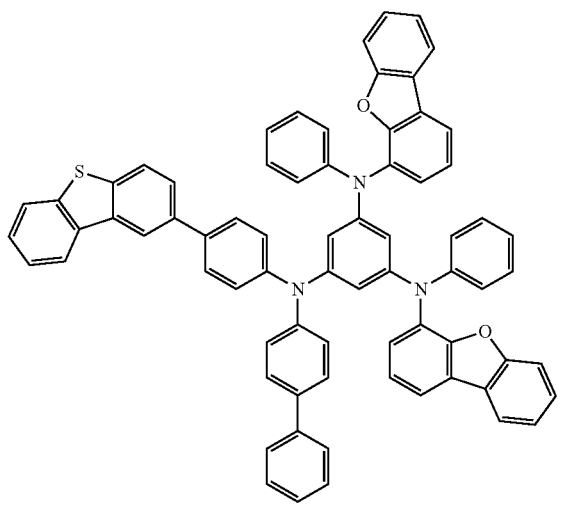

-continued
[A-270]
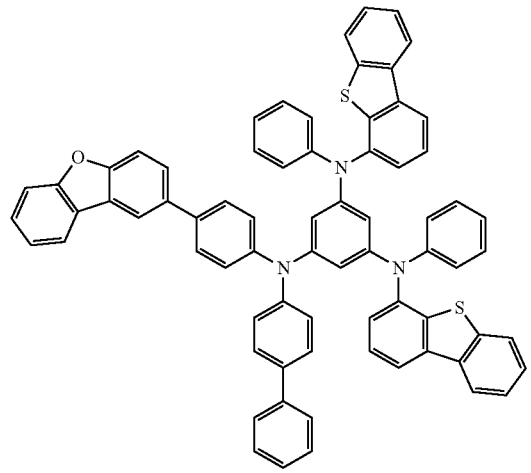
[A-271]
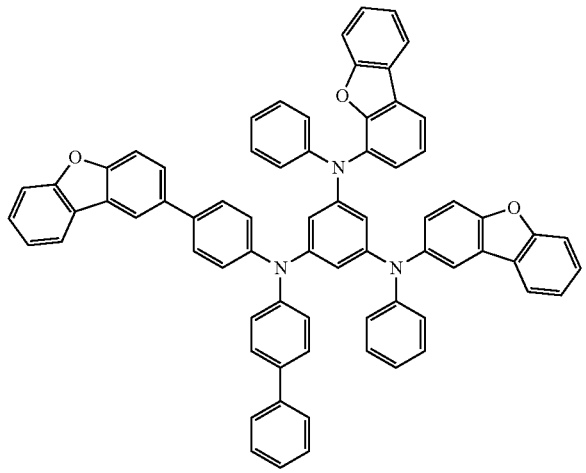
[A-272]
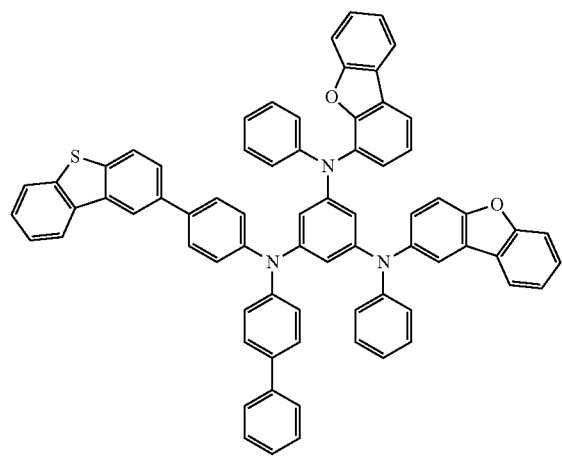
[A-273]
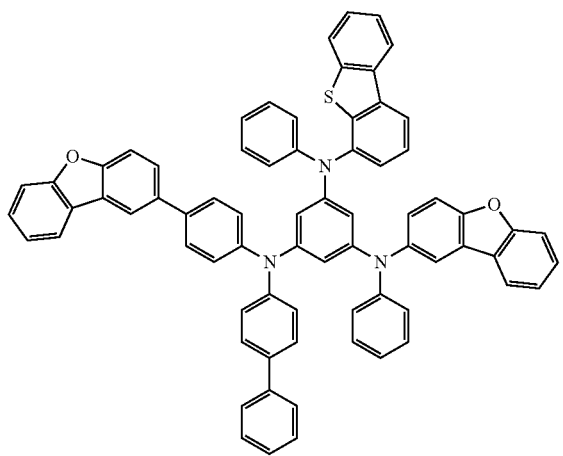
[A-274]
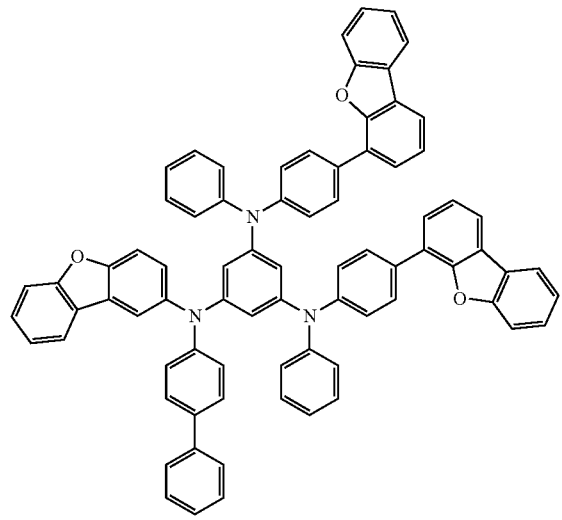
[A-275]
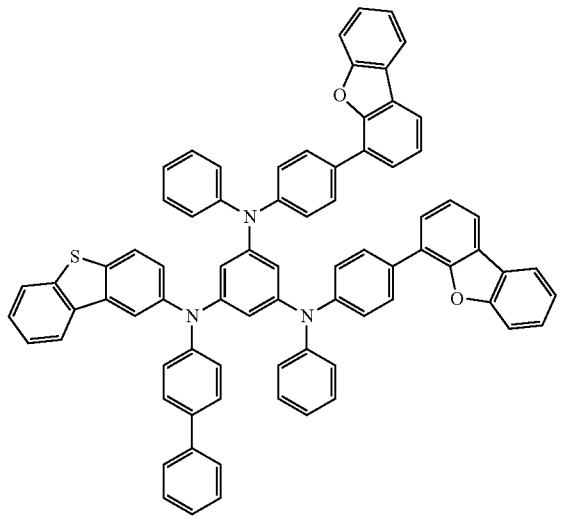

-continued
[A-276]
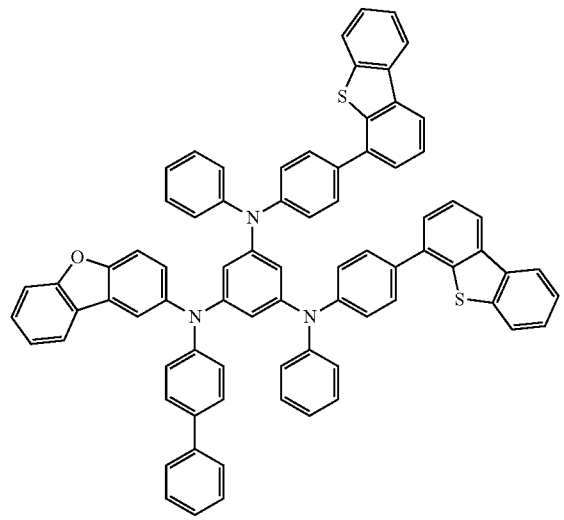
[A-277]
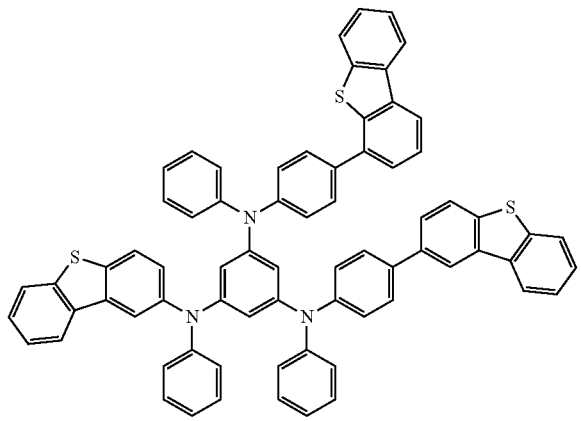
[A-278]
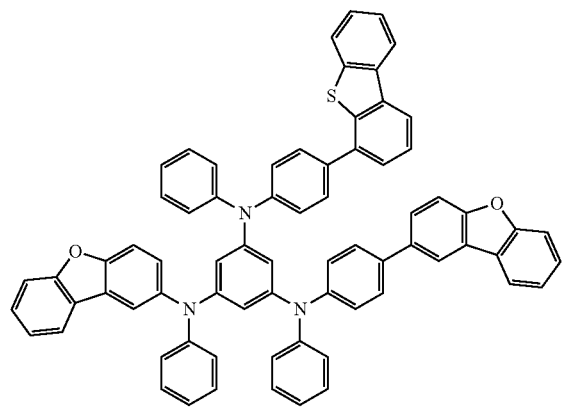
[A-279]
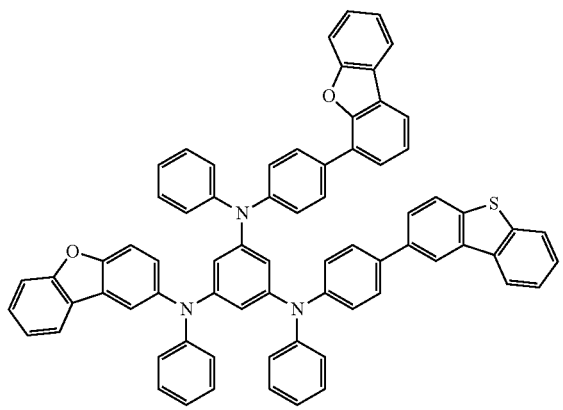
[A-280]
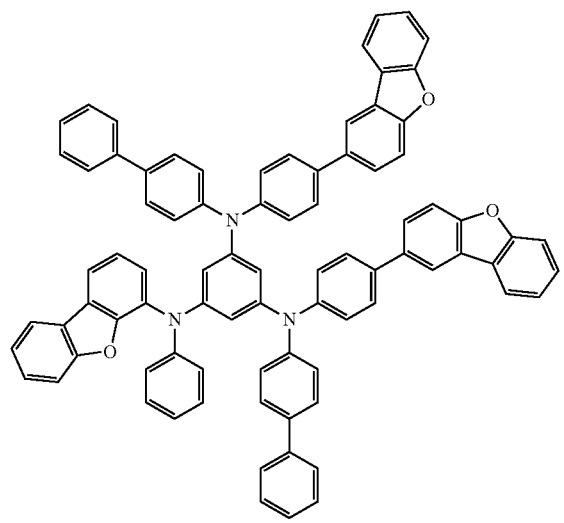
[A-281]
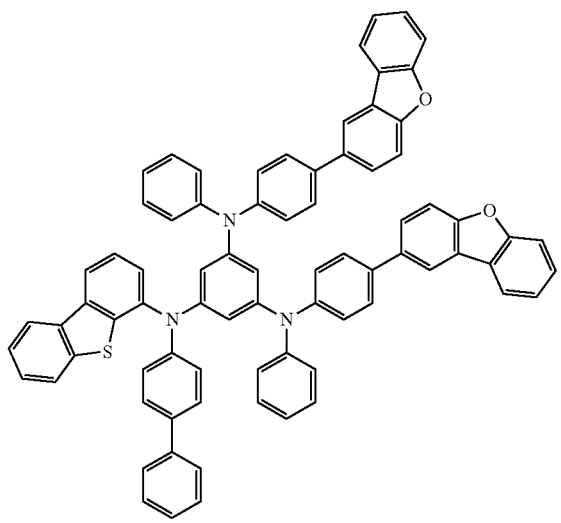

-continued
[A-282]
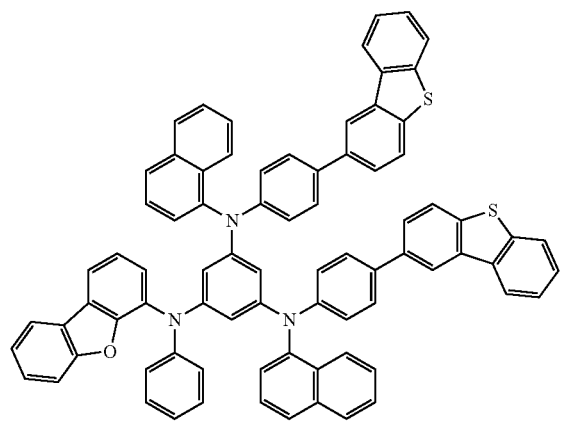
[A-283]
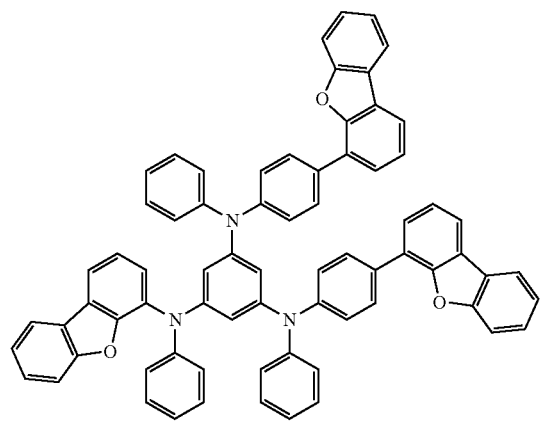
[A-284]
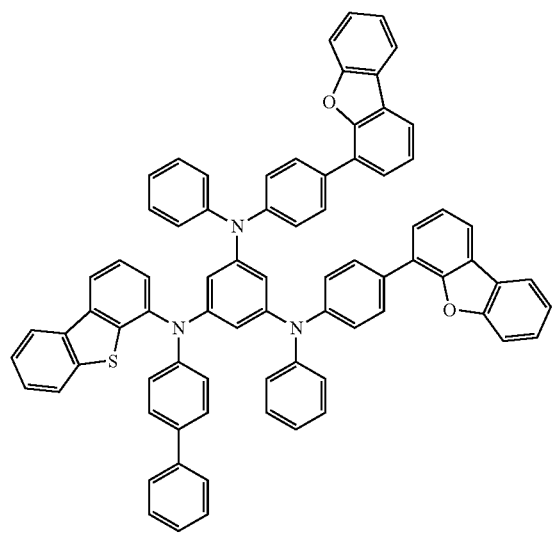
[A-285]
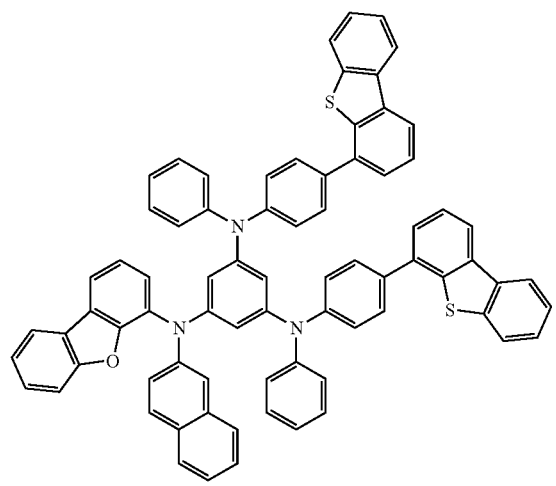
[A-286]
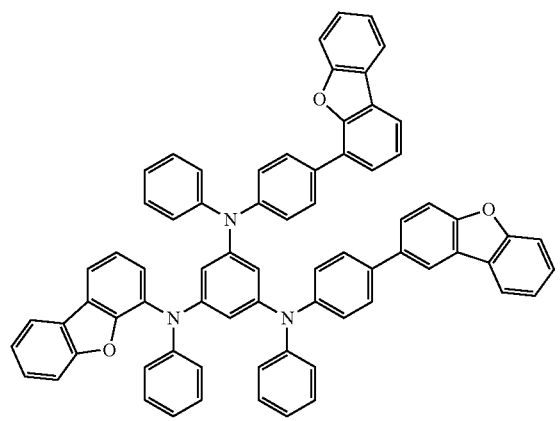
[A-287]
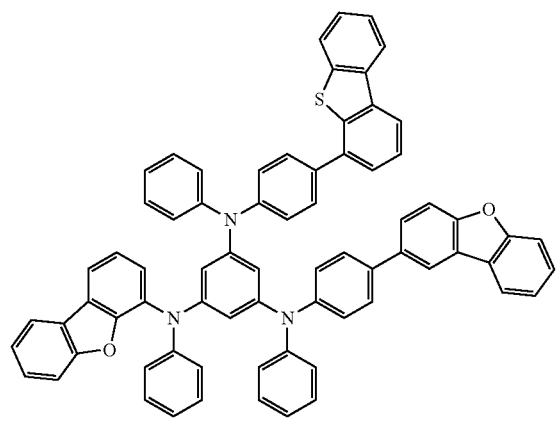

-continued
[A-288]
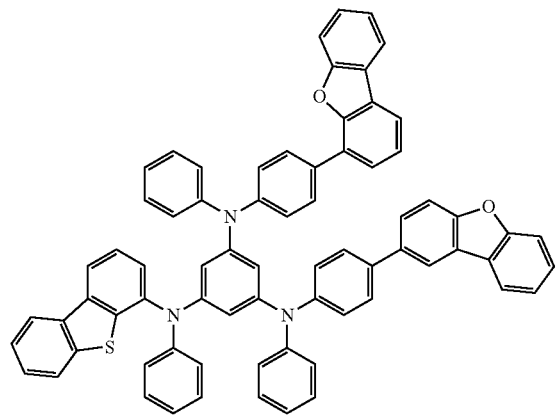
[A-289]
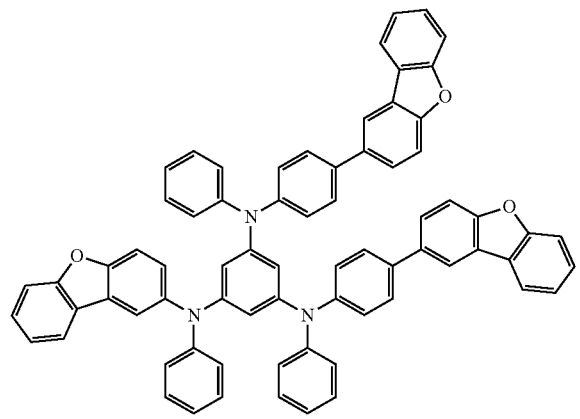
[A-290]
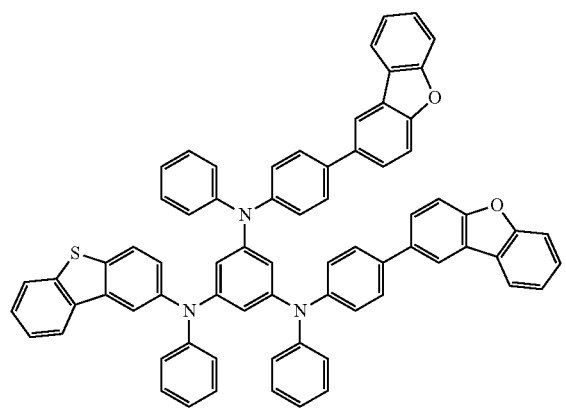
[A-291]
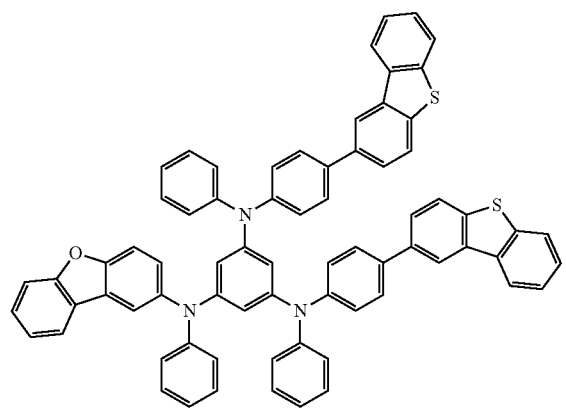
[A-300]
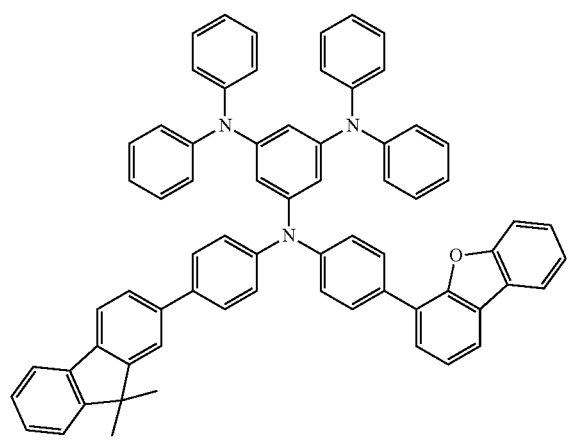
[B-1]
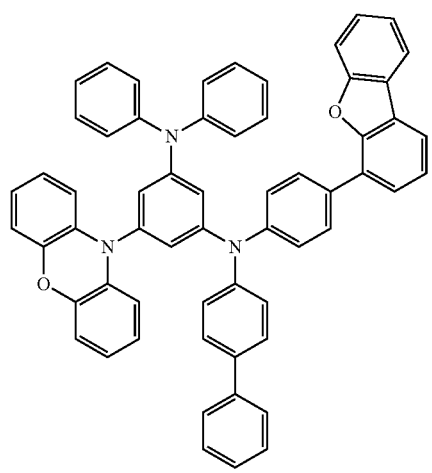

-continued
[B-2]
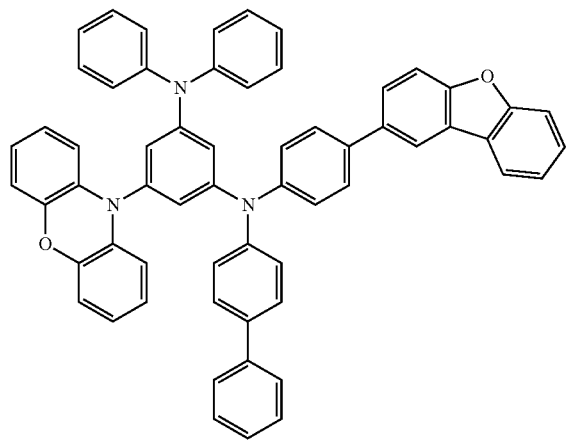
[B-3]
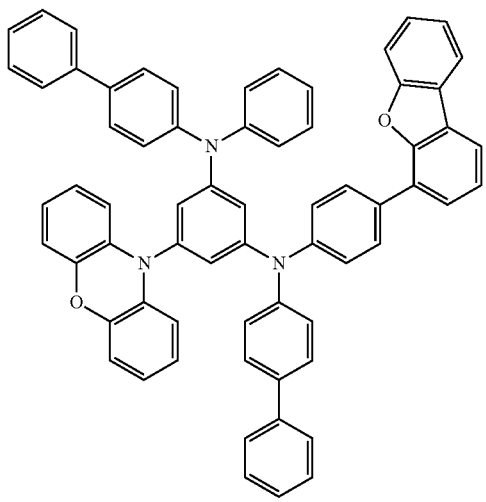
[B-4]
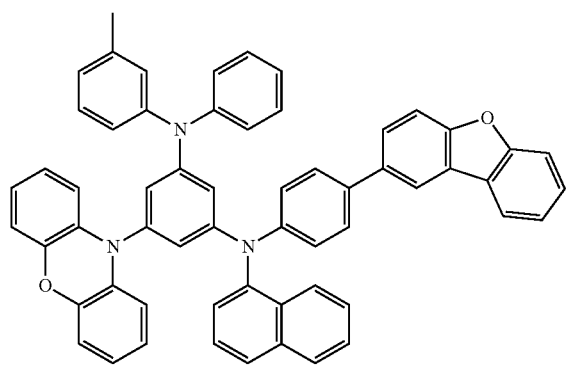
[B-5]
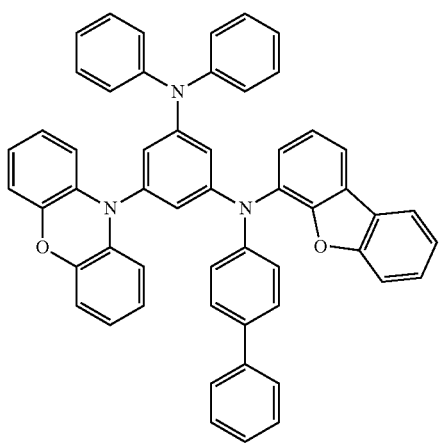
[B-6]
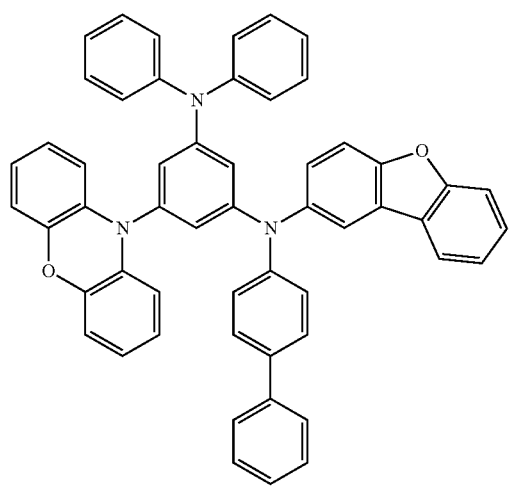
[B-7]
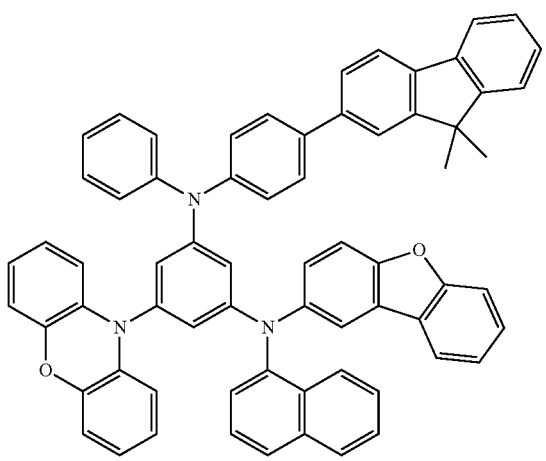

[B-8]
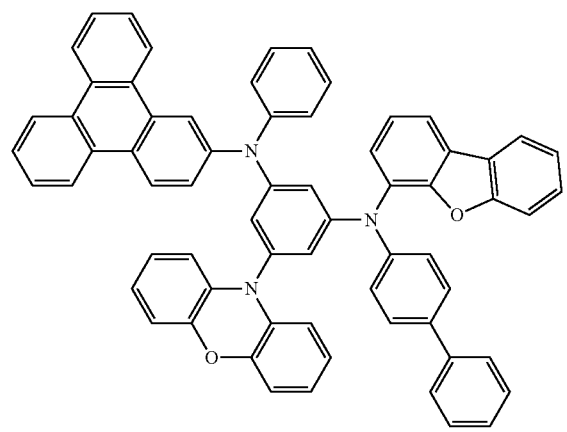
[B-9]
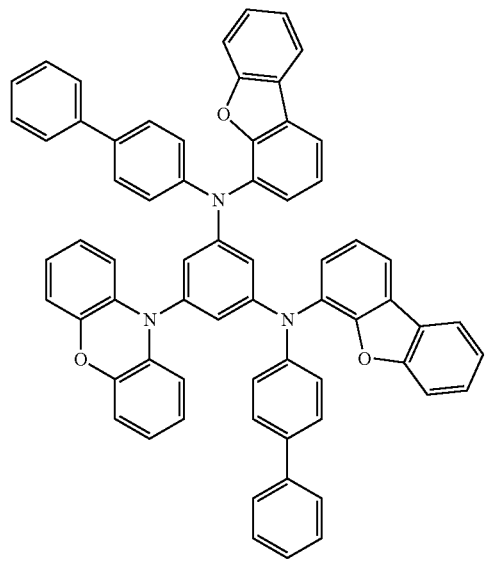
[B-10]
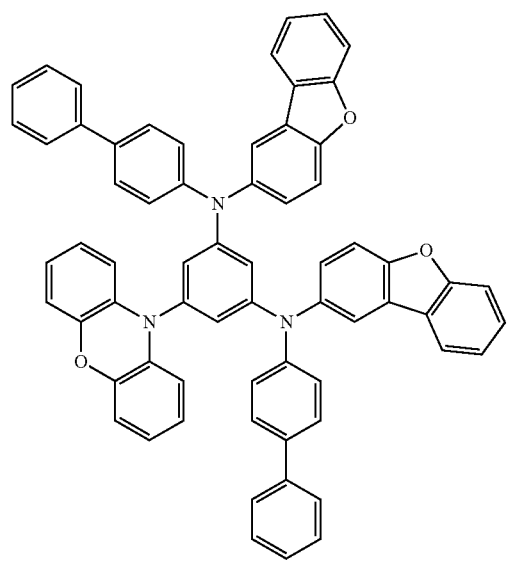
[B-11]
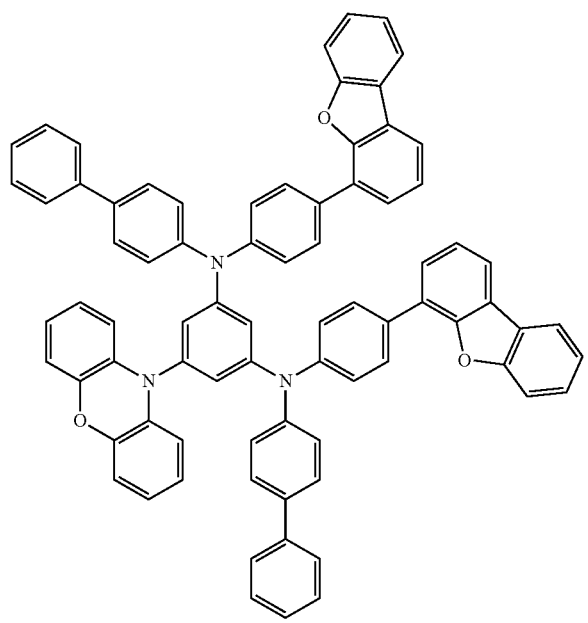

-continued
[B-12]
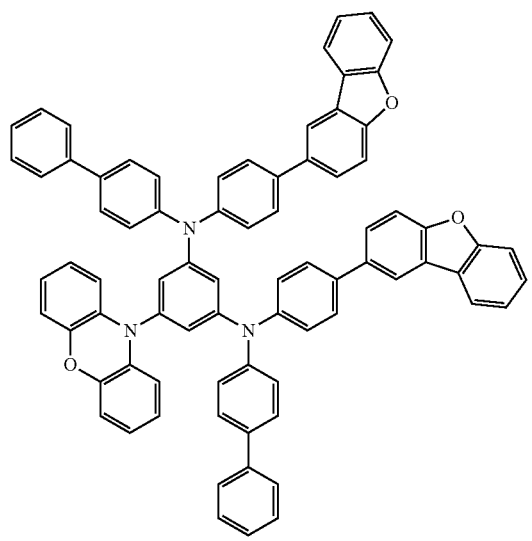
[B-13]
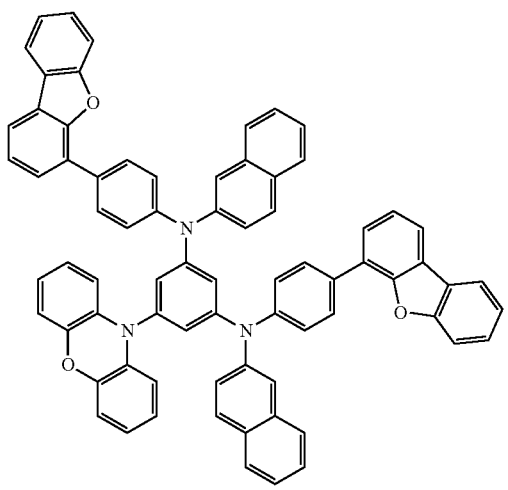
[B-14]
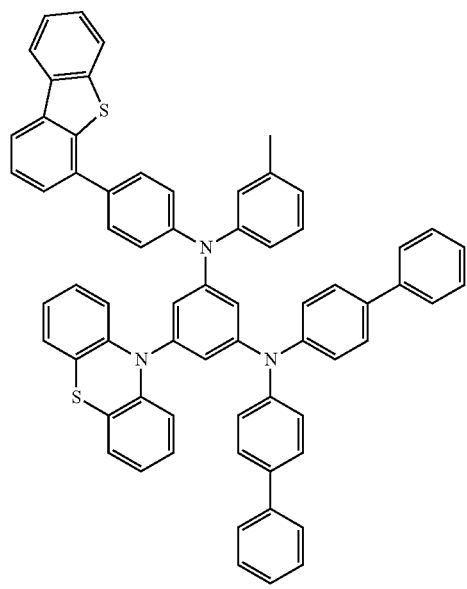
[B-15]
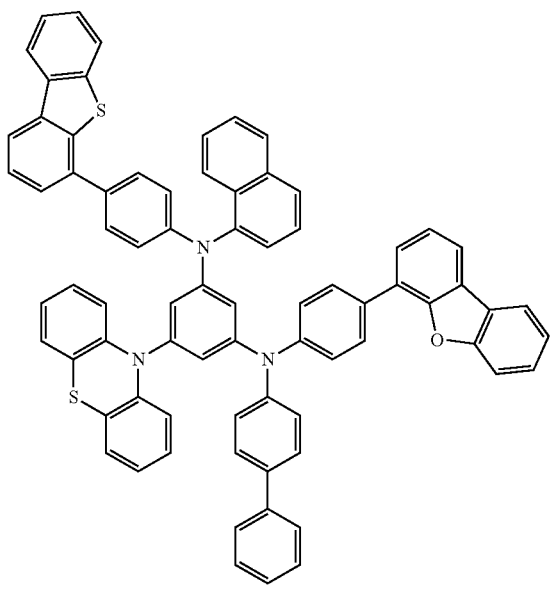
[B-16]
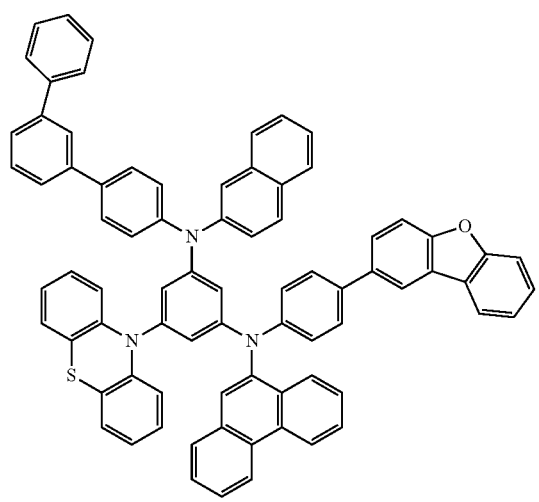
[B-17]
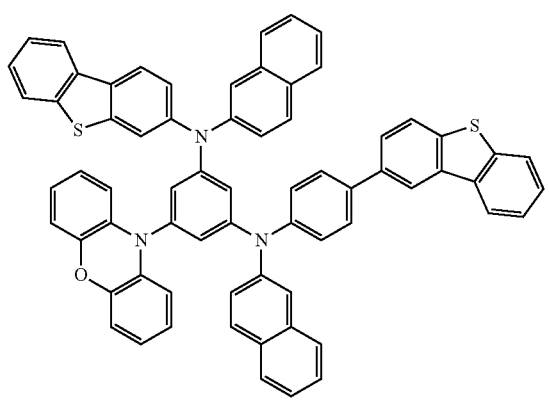

-continued
[B-18]
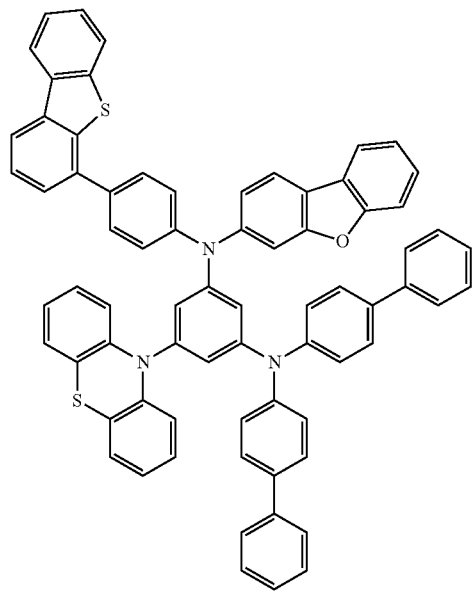
[B-19]
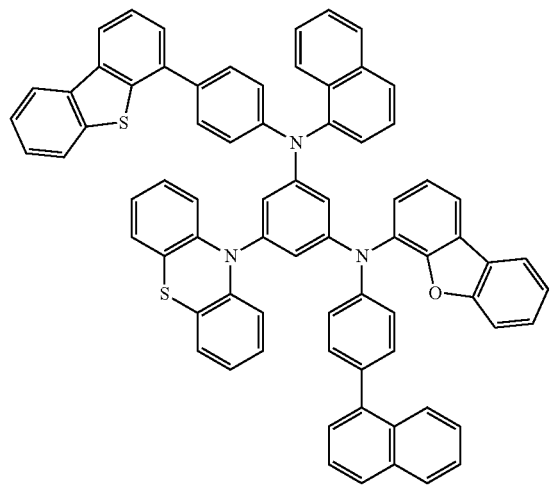
[B-20]
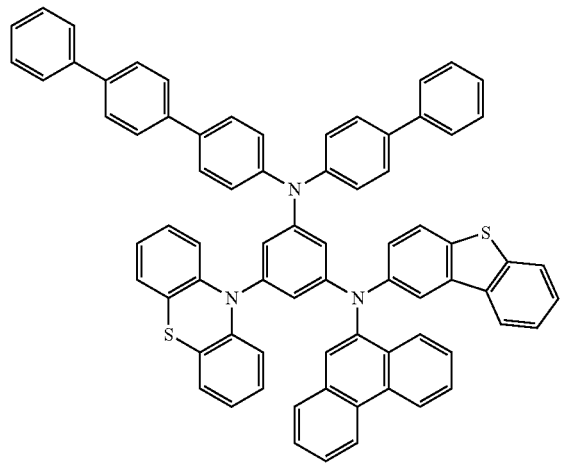
[C-1]
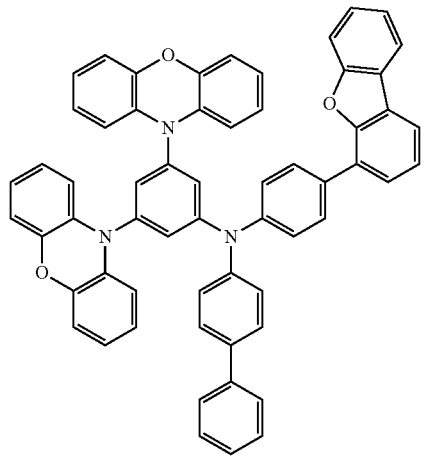
[C-2]
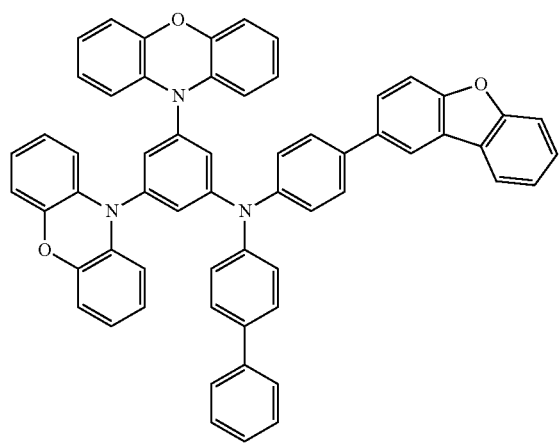
[C-3]
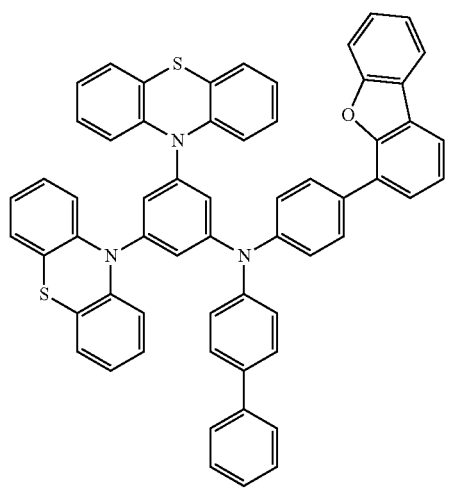

-continued
[C-4]
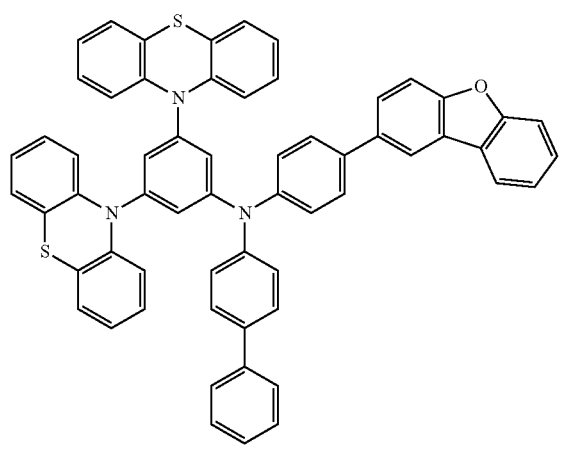
[C-5]
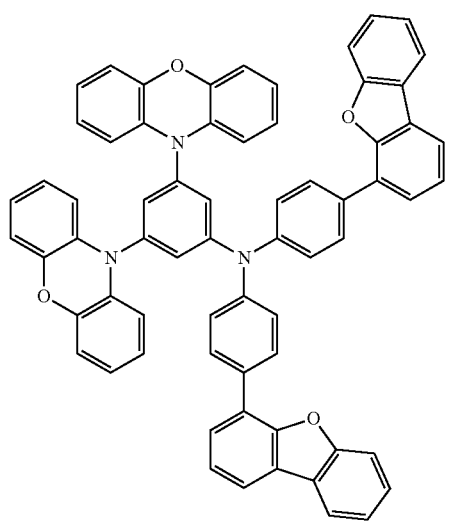
[C-6]
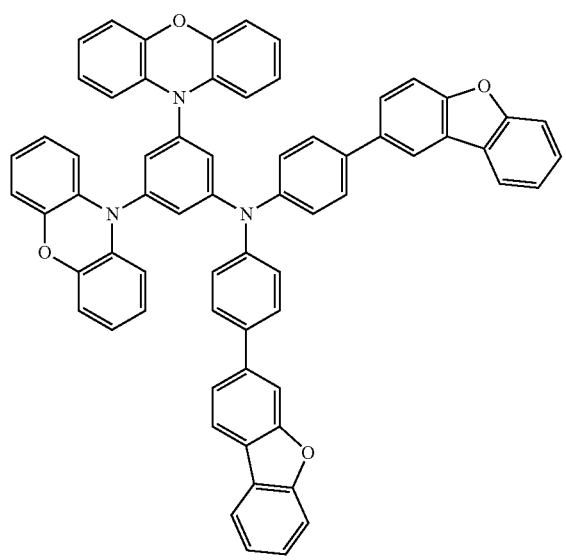
[C-7]
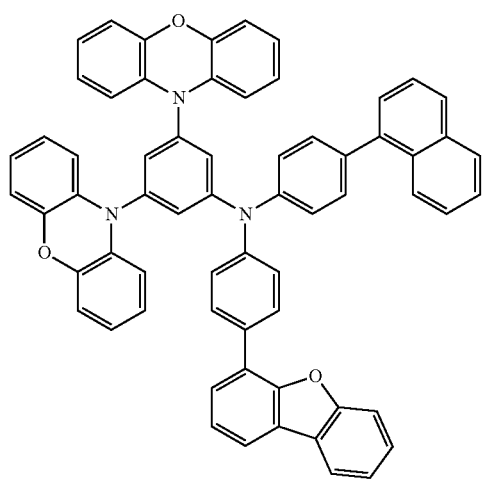
[C-8]
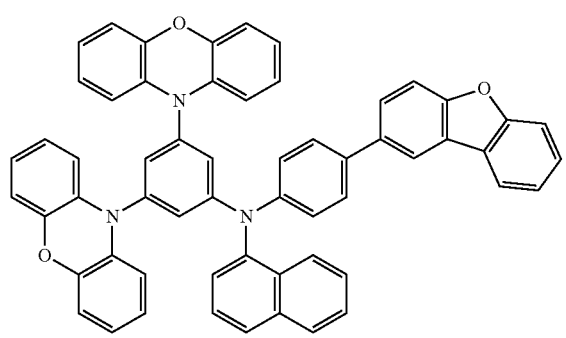
[C-9]
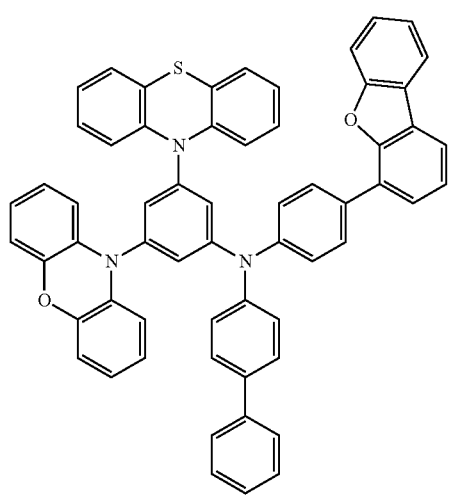

-continued
[C-10]
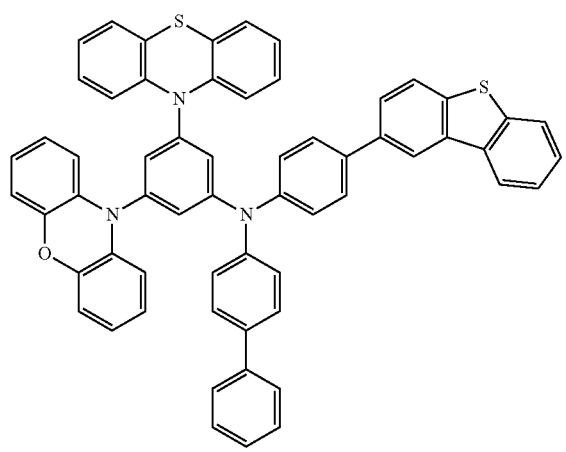
[C-11]
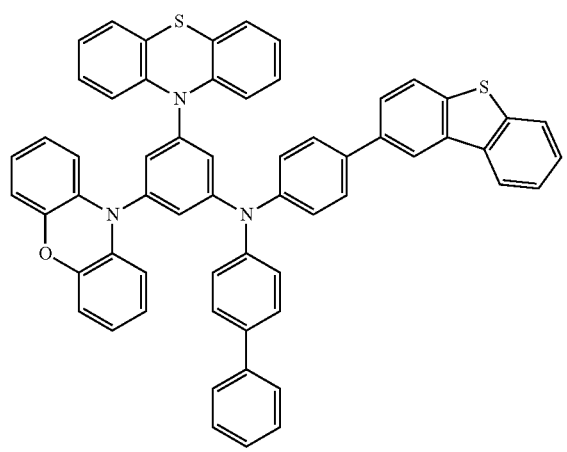
[C-12]
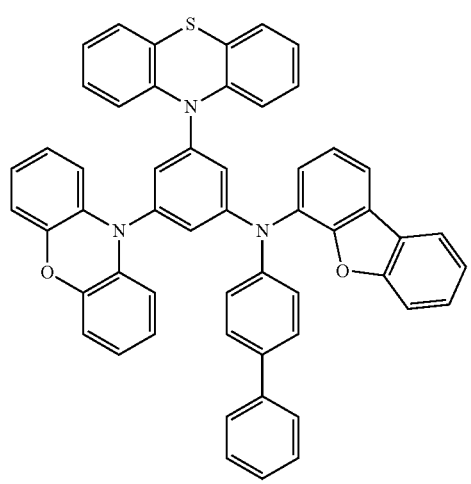
[D-1]
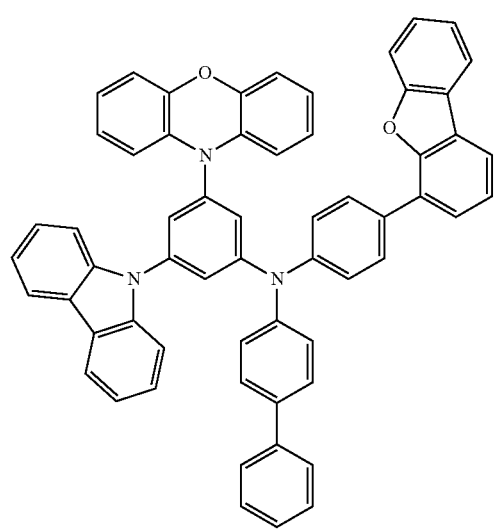
[D-2]
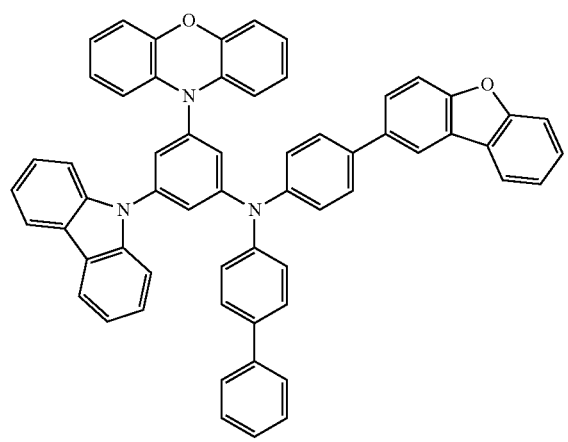
[D-3]
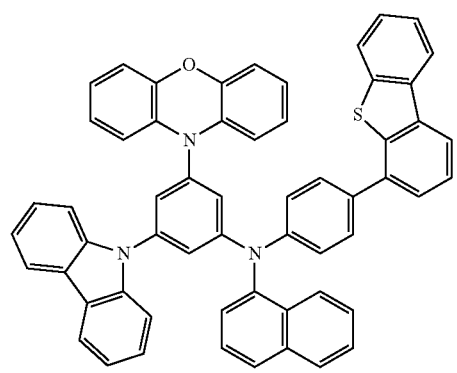

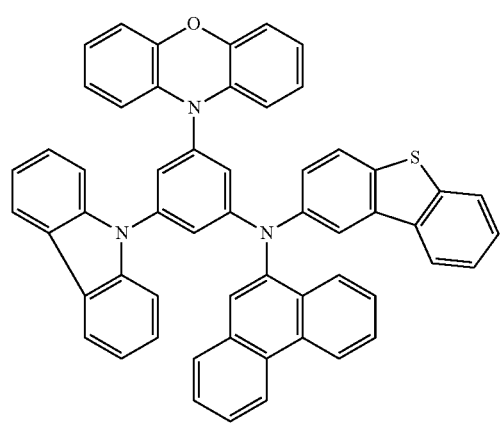
[D-4]
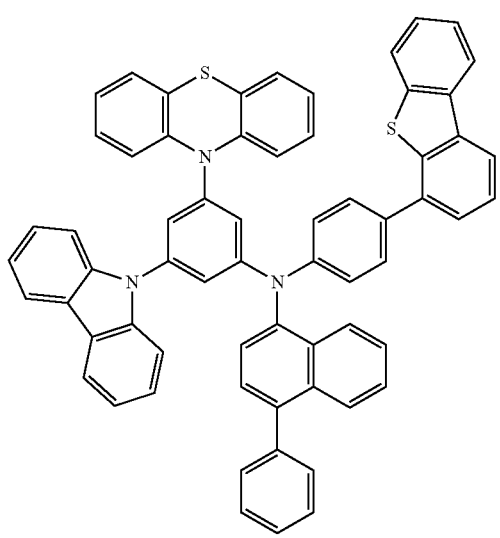
[D-5]
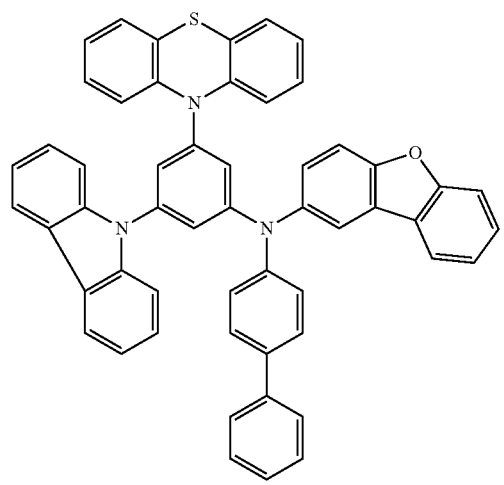
[D-6]
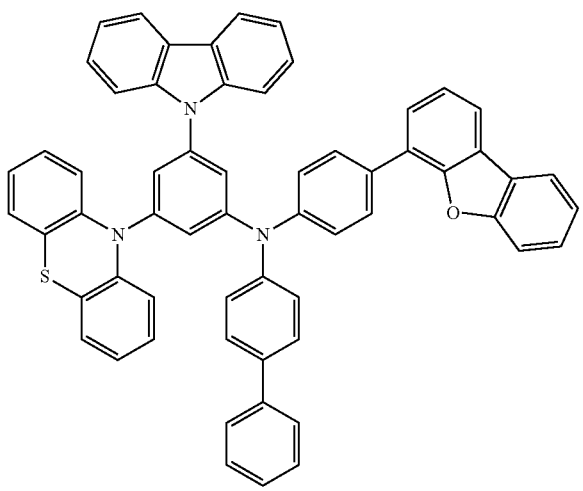
[D-7]
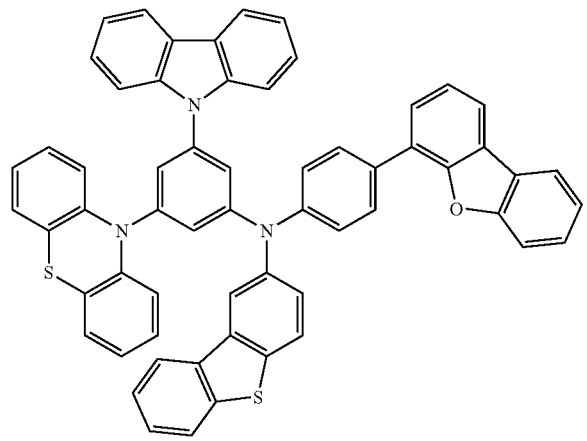
[D-8]
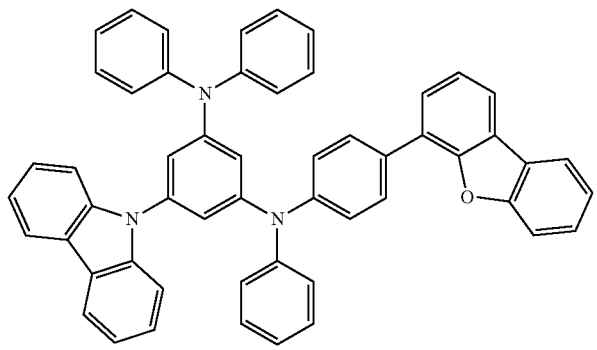
[E-1]

-continued
[E-2]
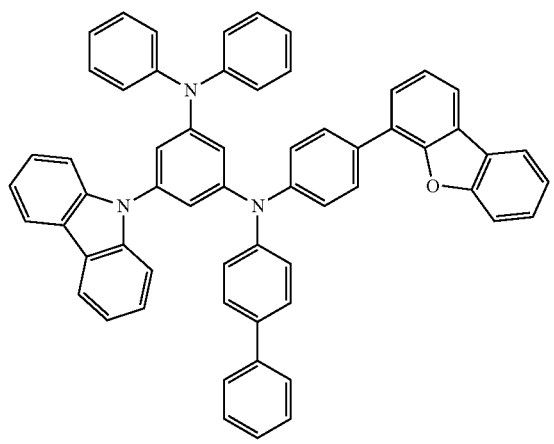
[E-3]
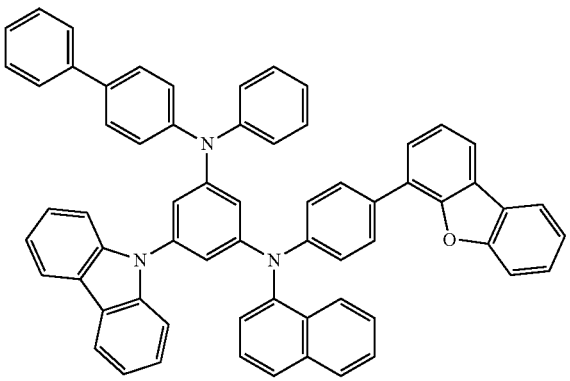
[E-4]
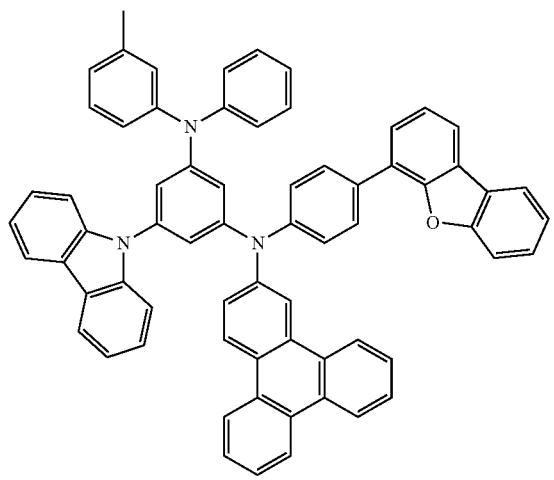
[E-5]
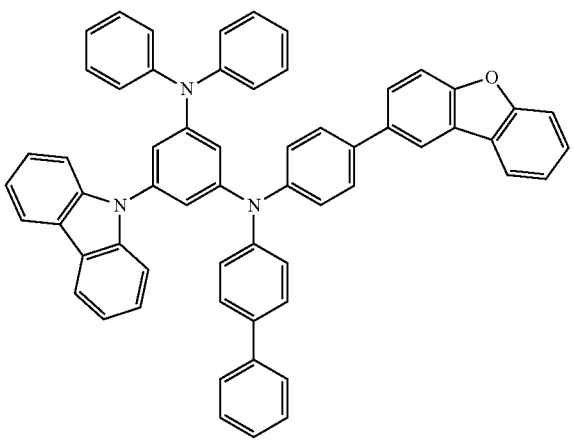
[E-6]
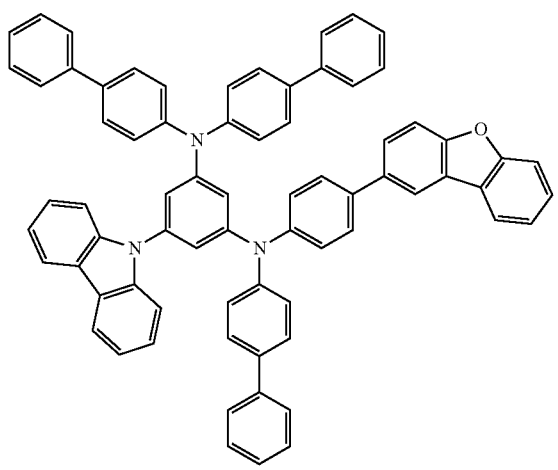
[E-7]
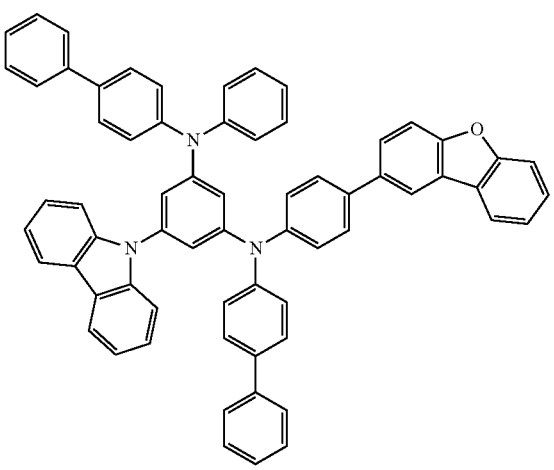

[E-8]
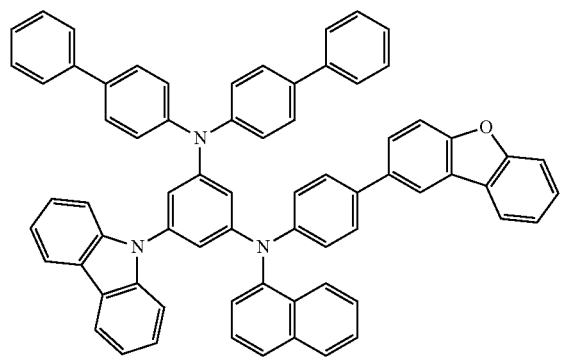
[E-9]
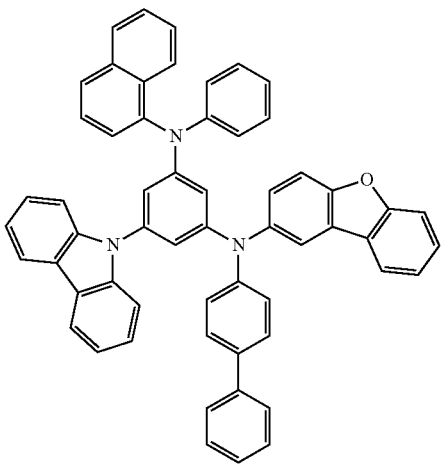
[E-10]
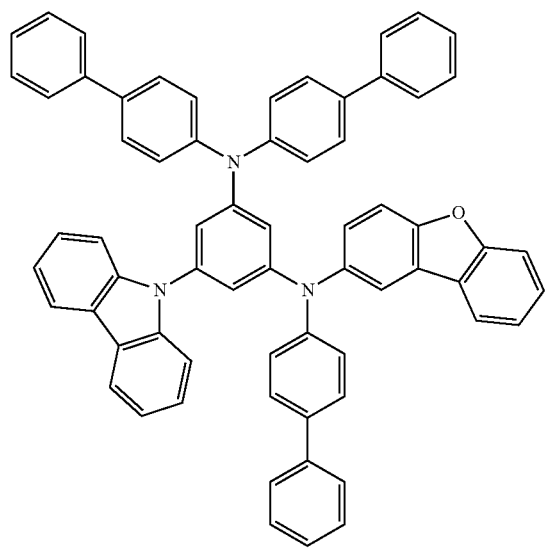
[E-11]
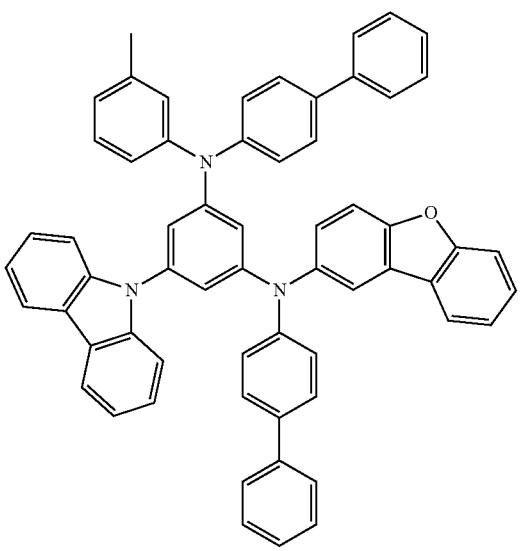
[E-12]
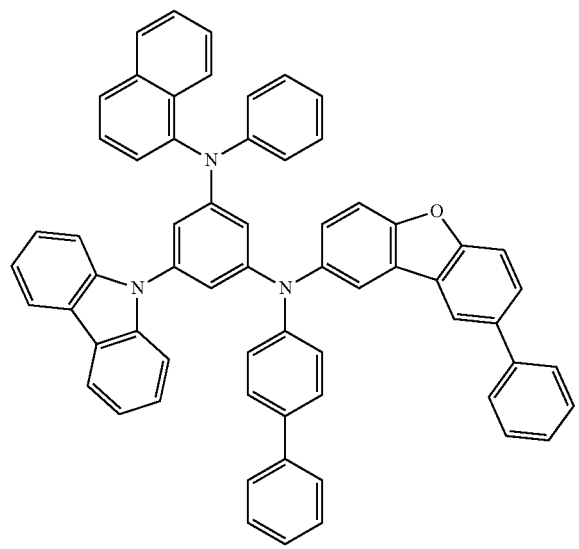
[E-13]
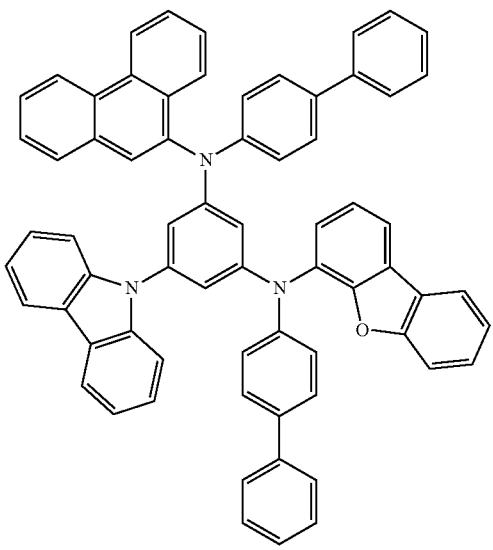

-continued
[E-14]
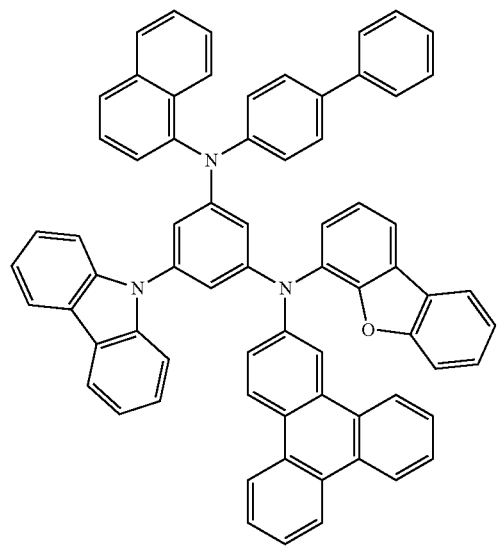
[E-15]
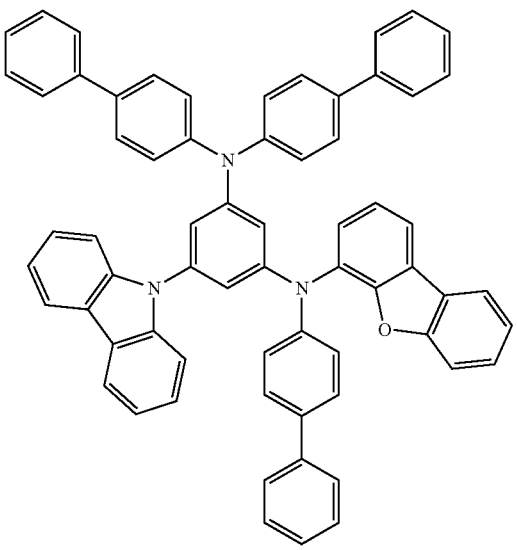
[E-16]
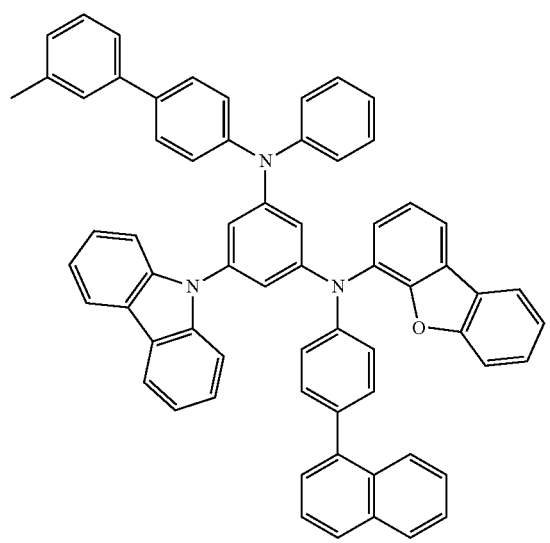
[E-17]
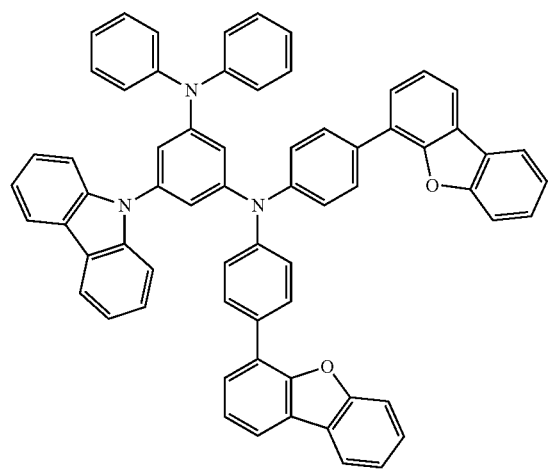
[E-18]
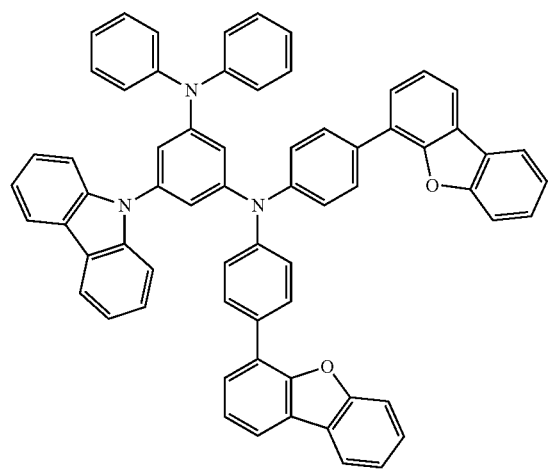
[E-19]
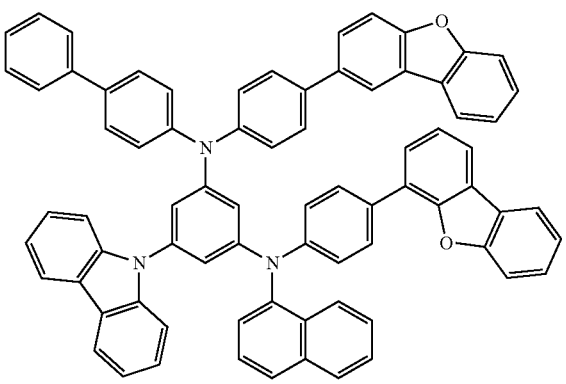

-continued
[E-20]
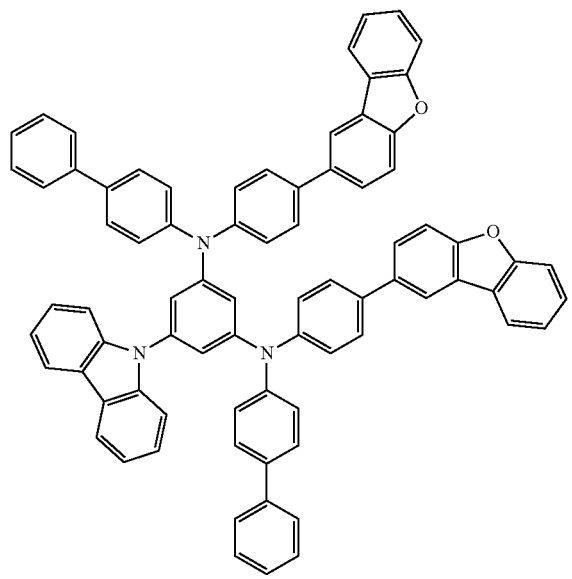
[E-21]
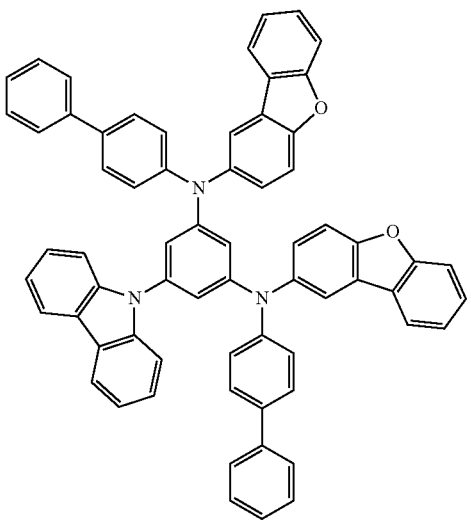
[E-22]
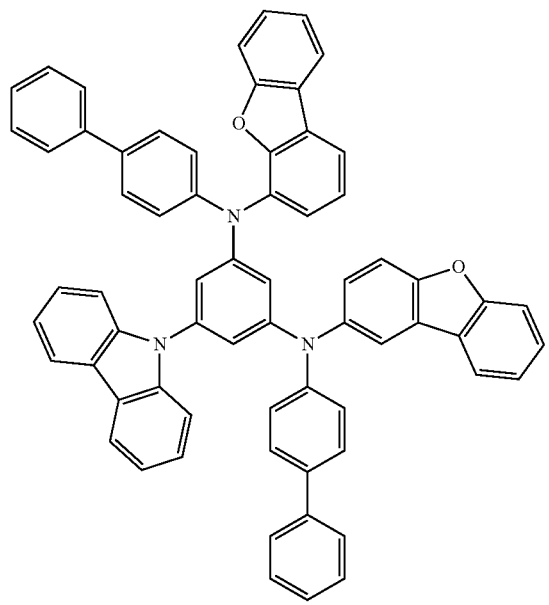
[E-23]
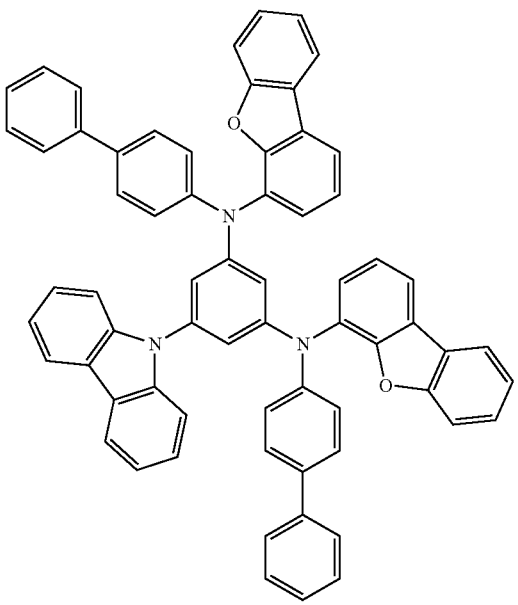

-continued
[E-24]
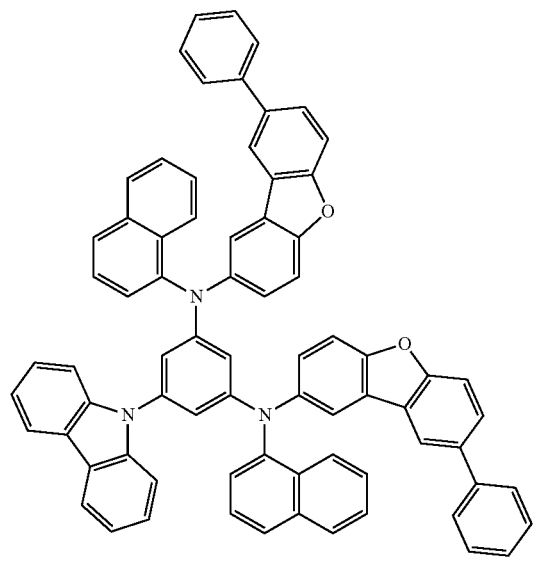
[E-25]
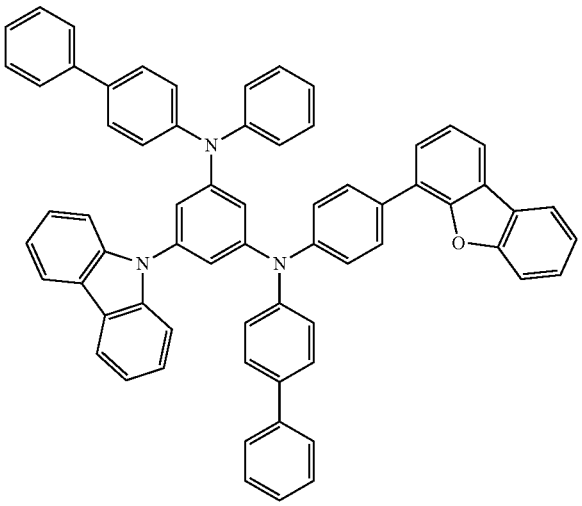
[E-26]
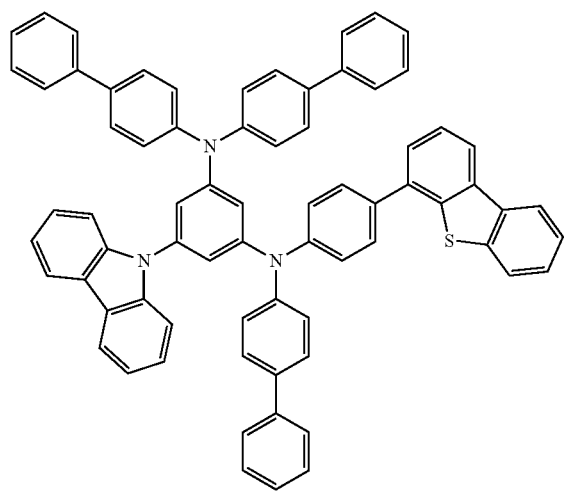
[E-27]
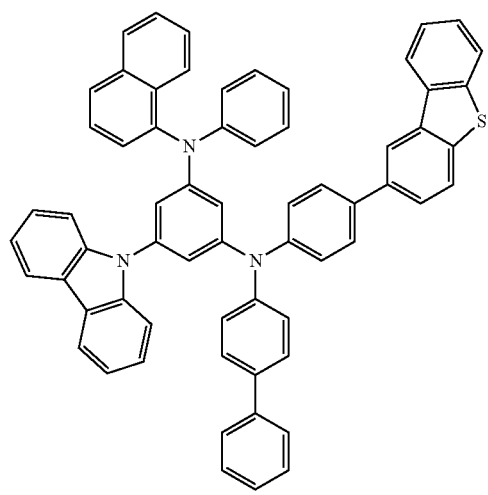
[E-28]
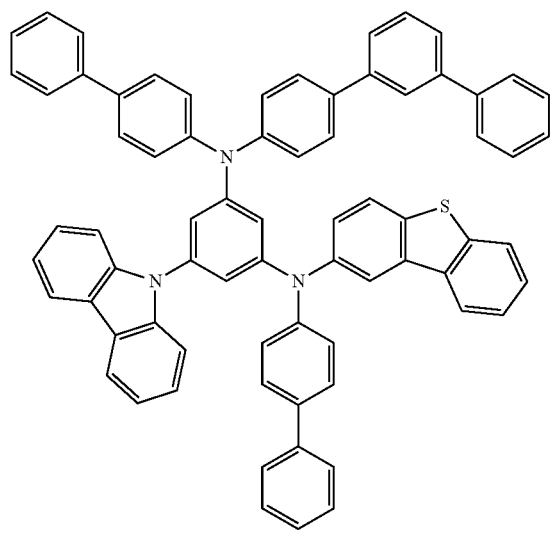
[F-1]
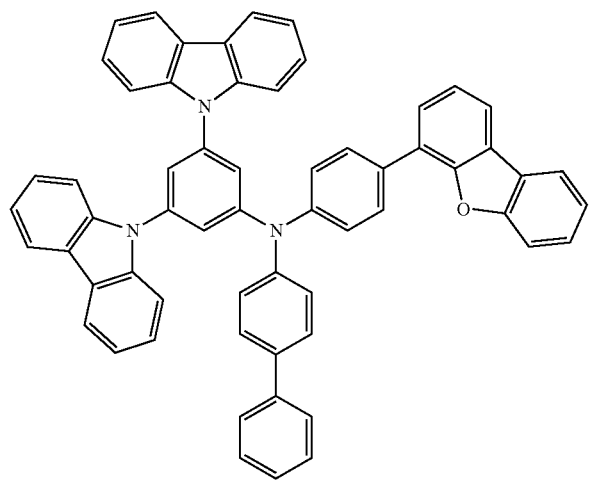

-continued
[F-2]
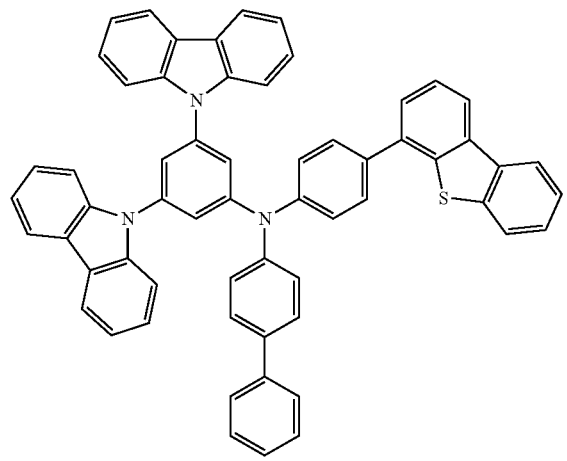
[F-3]
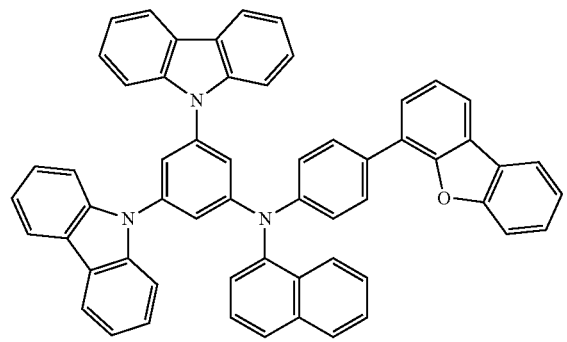
[F-4]
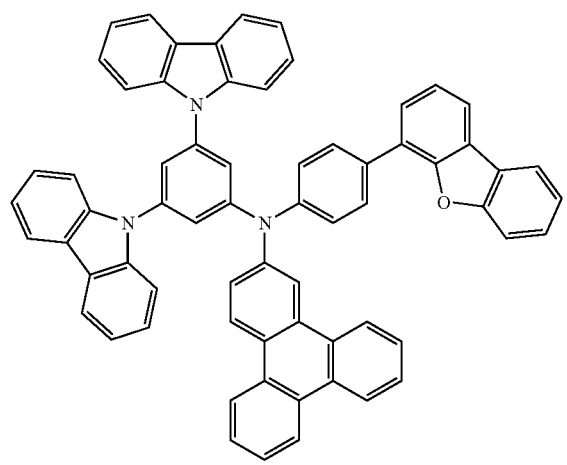
[F-5]
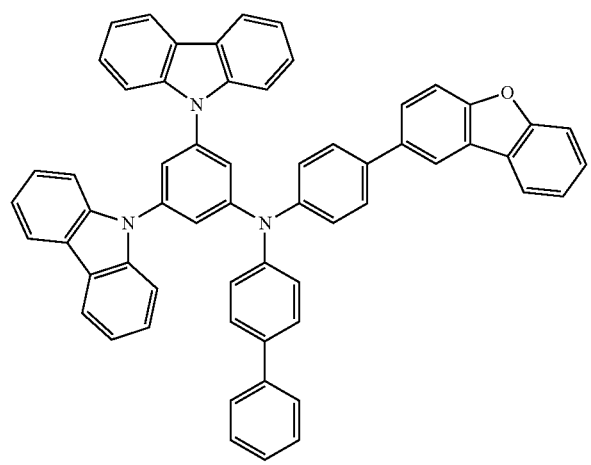
[F-6]
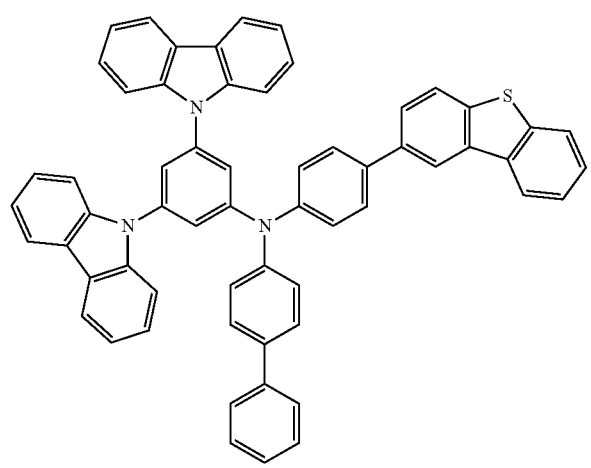
[F-7]
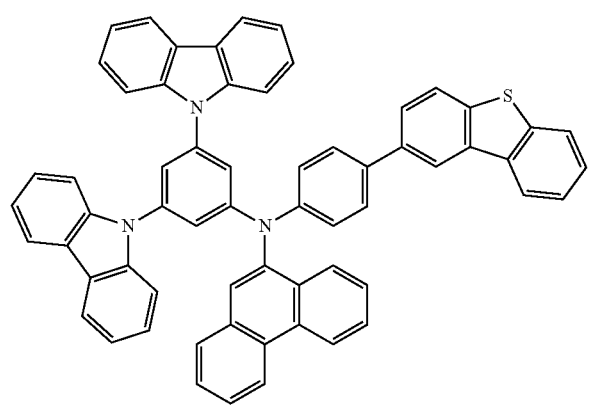

-continued
[F-8]
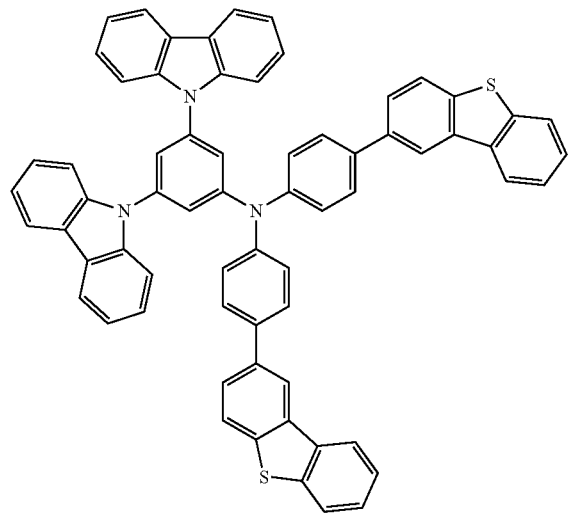
[F-9]
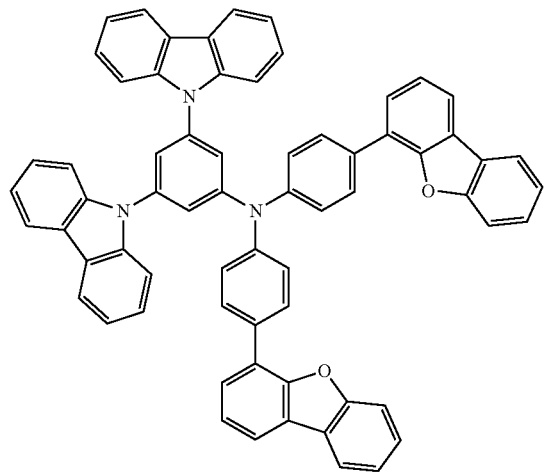
[F-10]
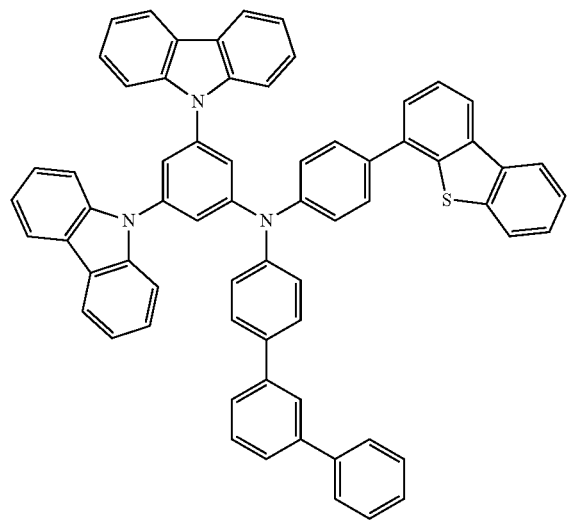
[F-11]
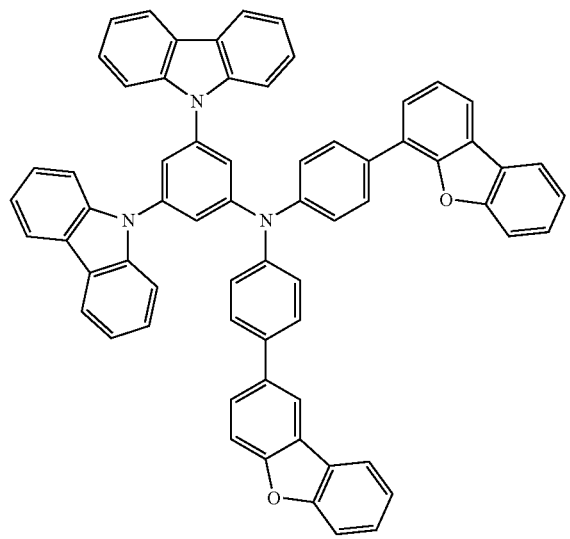

-continued
[F-12]
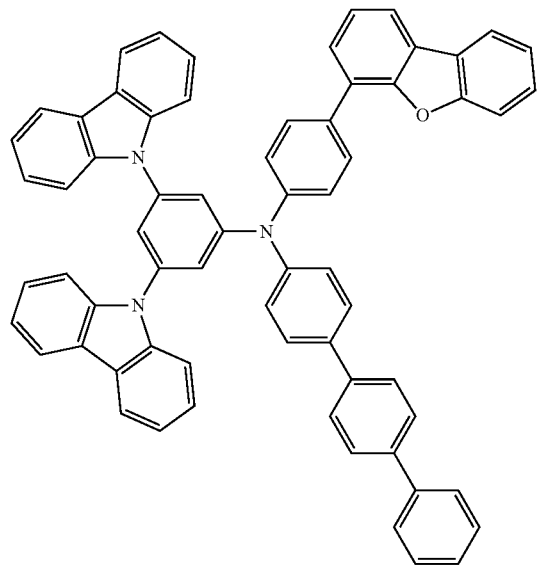
[F-13]
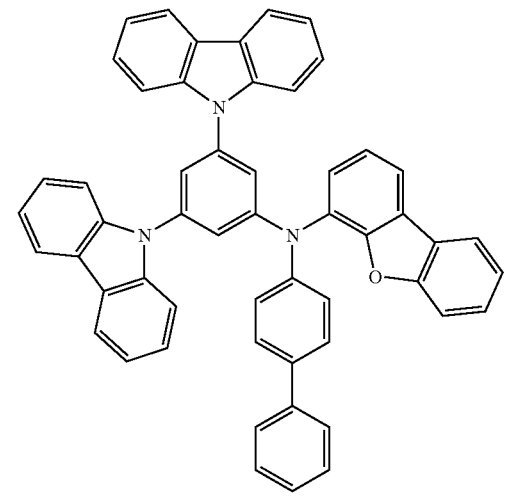
[F-14]
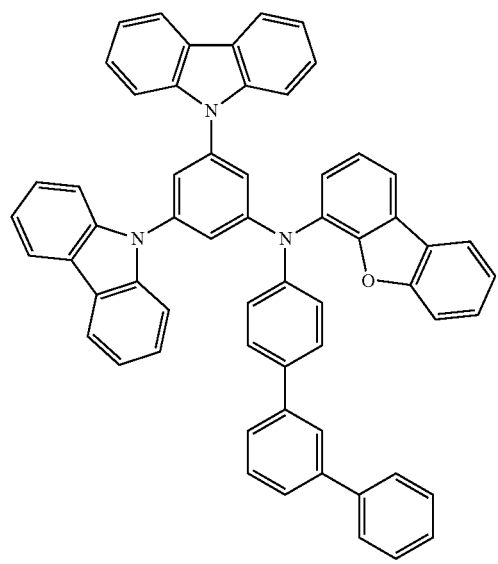
[F-15]
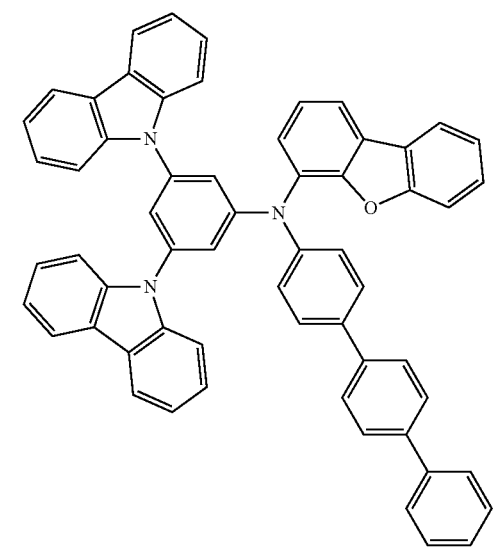
[F-16]
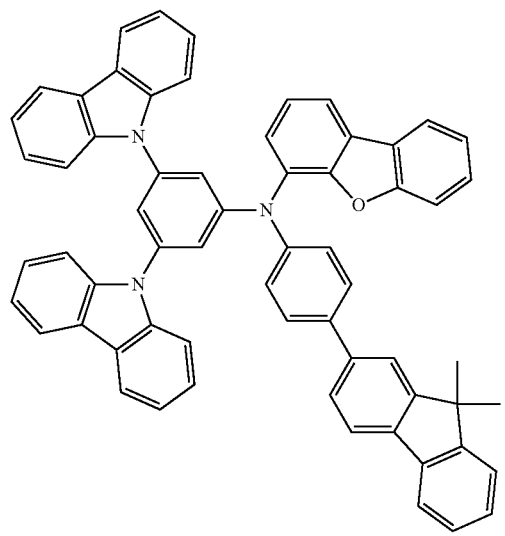
[F-17]
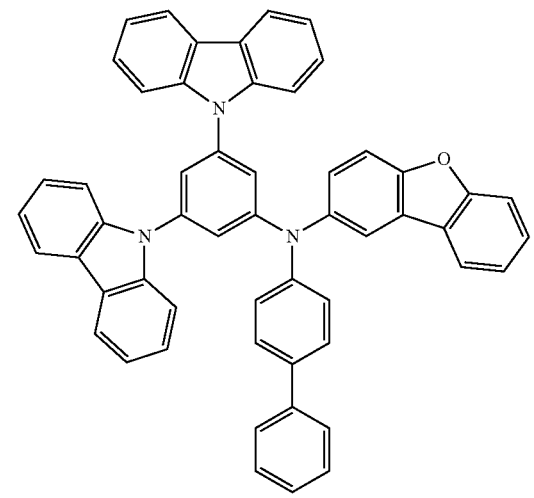

[F-18]
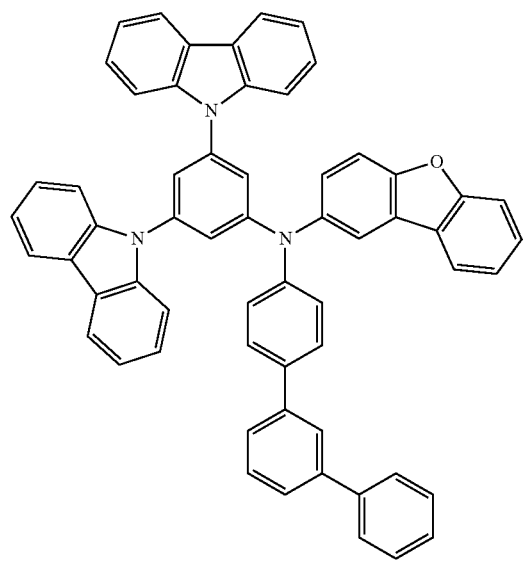

[F-19]
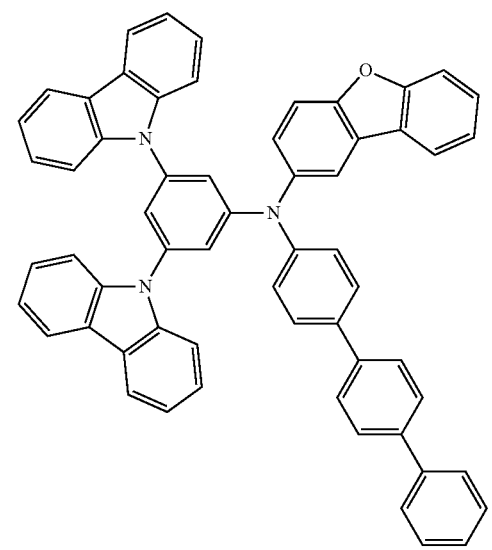

[F-20]
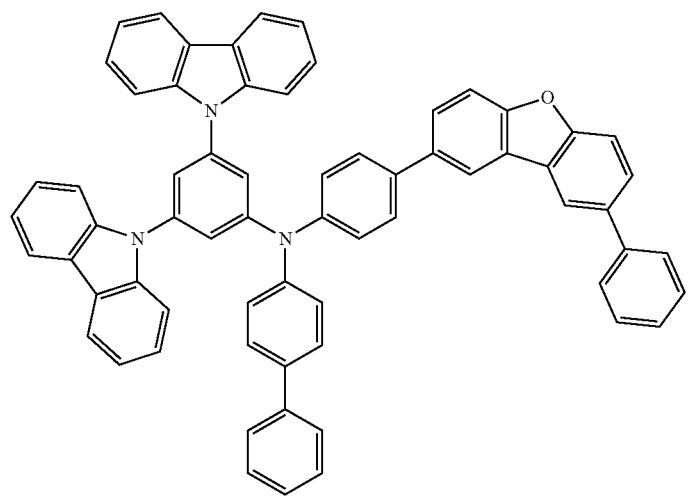

In another embodiment of the present invention, provided is an organic optoelectric device that includes an anode, cathode, and an organic thin layer interposed between the anode and the cathode, wherein at least one layer of the organic thin layer includes the compound according to one embodiment of the present invention.

The compound for an organic optoelectric device is used in an organic thin layer and thus improves life-span characteristics, efficiency characteristic, electrochemical stability and thermal stability of an organic optoelectric device, and lowers a driving voltage.

The organic thin layer may be specifically a hole injection layer (HIL), a hole transport layer (HTL), an auxiliary hole transport layer (HTL), or an emission layer.

The organic optoelectric device may be an organic light emitting element, an organic photoelectric device, an organic solar cell, an organic transistor, an organic photo conductor drum, or an organic memory device.

Figure 2:
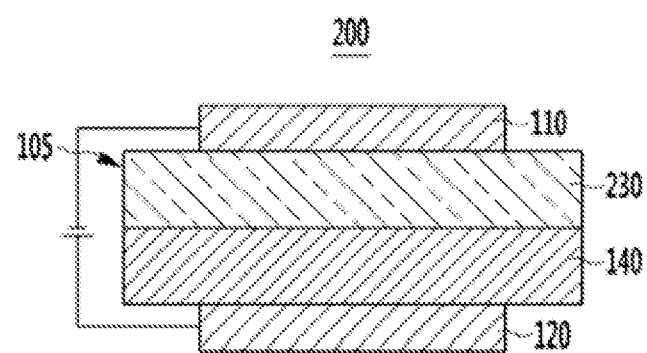

More specifically, the organic optoelectric device may be an organic light emitting element. FIGS. 1 and 2 are cross-sectional views of an organic light emitting element according to one embodiment.

Referring to FIGS. 1 and 2, organic light emitting elements 100 and 200 according to one embodiment include an anode 120, a cathode 110 and an organic layer 105 between the anode 120 and the cathode 110.

The anode 120 includes an anode material having a large work function to help hole injection into an organic thin layer. The anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combination of a metal and an oxide such as ZnO:Al and SnO$_2$:Sb; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. It is preferable to include a metal electrode including aluminum as a cathode.

First, referring to FIG. 1, FIG. 1 shows an organic light emitting element 100 including an emission layer 130 as an organic thin layer 105, and the organic thin layer 105 may consist of an emission layer 130.

Referring to FIG. 2, a double-layered organic light emitting element 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and the hole transport layer (HTL) 140. The emission layer 130 also functions as an electron transport layer (ETL), and the hole transport layer (HTL) 140 layer has an improved binding property with a transparent electrode such as ITO or an improved hole transport capability. The organic thin layer 105 may further include an electron injection layer (EIL), an electron transport layer (ETL), an auxiliary electron transport layer (ETL), an auxiliary hole transport layer, a hole injection layer and a combination thereof even though they are not shown in FIG. 1 or 2. In FIGS. 1 and 2, at least one organic thin layer 105 selected from the emission layers 130 and 230, the hole transport layer (HTL) 140, even though being not shown, the electron injection layer (EIL), the electron transport layer (ETL), the auxiliary electron transport layer (ETL), the auxiliary hole transport layer (HTL), the hole infection layer (HIL), and a combination thereof may include the compound.

Particularly the compound may be used in the hole transport layer (HTL) 140, the auxiliary hole transport layer (HTL), or the emission layers 130 and 230, and when the compound is used in the emission layers 130 and 230, it may be used as a host material in the emission layer.

The organic light emitting element may be fabricated by: forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment of the present invention provides a display device including the organic light emitting element according to the embodiment.

Hereinafter, the embodiments are illustrated in more detail with reference to examples. These examples, however, are not in any sense to be interpreted as limiting the scope of the invention.

(Preparation of Compound for Organic Optoelectric Device)

SYNTHESIS OF INTERMEDIATE

Synthesis Example 1: Synthesis of Intermediate M-1

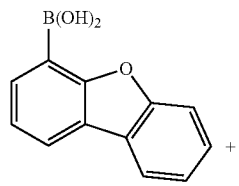

+

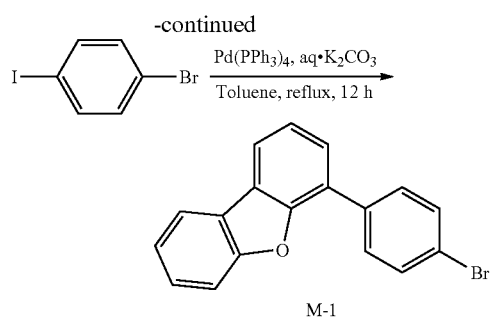

20 g (943 mmol) of 4-dibenzofuranboronic acid and 26.7 g (94.3 mmol) of 1-bromo-4-iodobenzene were put in a round-bottomed flask and dissolved by adding 313 ml of toluene thereto, and 117 ml of an aqueous solution obtained by dissolving 19.5 g (141.5 mmol) of potassium carbonate was added thereto, and the mixture was agitated. Then, 1.09 g (0.94 mmol) of tetrakistriphenylphosphinepalladium was added thereto, and the resulting mixture was refluxed and agitated under a nitrogen atmosphere for 12 hours. When the reaction was complete, the resultant was extracted with ethylacetate, the extracted solution was dried with magnesium sulfate, filtered and concentrated under a reduced pressure. Subsequently, a product therein was purified with n-hexane/dichloromethane (9:1 of a volume ratio) through silica gel column chromatography, obtaining 27 g of a target compound of a white solid intermediate M-1 (a yield of 89%). (Calculation value: 322.00 g/mol, Measurement value: M+=322.09 g/mol, M+2=324.04 g/mol)

Synthesis Example 2: Synthesis of Intermediate M-2

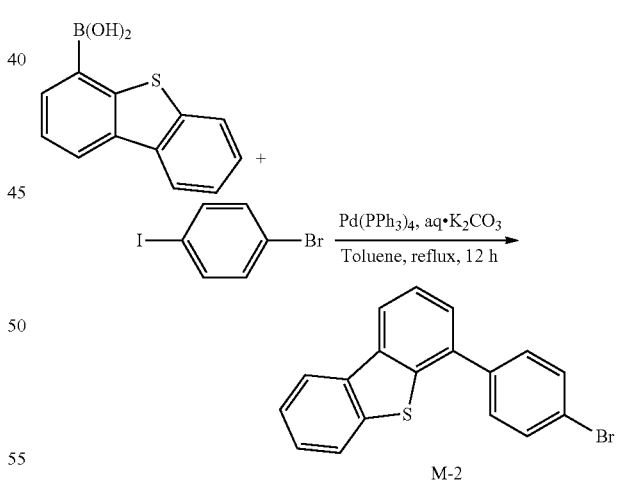

215 g (94.3 mmol) of 4-dibenzothiopheneboronic acid and 26.7 g (94.3 mmol) of 1-bromo-4-iodobenzene were put in a round-bottomed flask and dissolved by adding 313 ml of toluene thereto, and 117 ml of an aqueous solution obtained by dissolving 19.5 g (141.5 mmol) of potassium carbonate was added thereto, and the mixture was agitated. Then, 1.09 g (0.94 mmol) of tetrakistriphenylphosphinepalladium was added thereto, and the mixture was refluxed and agitated under a nitrogen atmosphere for 12 hours. When the reaction was complete, the resultant was extracted with ethylacetate, and the extracted solution was dried with magnesium sulfate, filtered and concentrated under a reduced pressure. Then, a product therefrom was purified with n-hexane/dichloromethane (9:1 of a volume ratio) through silica gel column chromatography, obtaining 29 g of a target compound of a white solid intermediate M-2 (a yield of 91%). (Calculation value: 337.98 g/mol, Measurement value: M+=338.04 g/mol, M+2=340.11 g/mol)

Synthesis Example 3: Synthesis of Intermediate M-3

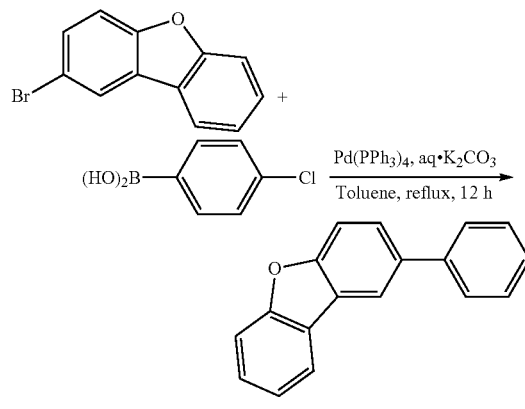

M-3

14.7 g (94.3 mmol) of 4-chlorophenylboronic acid and 23.3 g (94.3 mmol) of 2-bromodibenzofuran were put in a round-bottomed flask and dissolved by adding 313 ml of toluene thereto, 117 ml of an aqueous solution obtained by dissolving 19.5 g (141.5 mmol) of potassium carbonate was added thereto, and the mixture was agitated. Subsequently, 1.09 g (0.94 mmol) of tetrakistriphenylphosphinepalladium was added thereto, and the obtained mixture was refluxed and agitated under a nitrogen atmosphere for 12 hours.

When the reaction was complete, the resultant was extracted with ethylacetate, the extracted solution was dried with magnesium sulfate, filtered and concentrated under a reduced pressure. Subsequently, a product therefrom was purified with n-hexane/dichloromethane (9:1 of a volume ratio) through silica gel column chromatography, obtaining 23.9 g of a target compound of a white sold intermediate M-3 (a yield of 91%). (Calculation value: 278.05 g/mol, Measurement value: M+=278.12 g/mol, M+2=280.13 g/mol)

Synthesis Example 4: Synthesis of Intermediate M-4

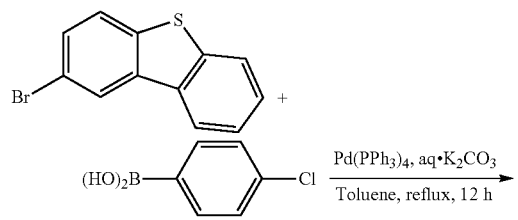

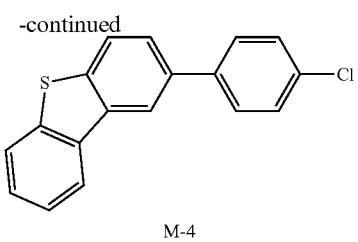

M-4

14.7 g (94.3 mmol) of 4-chlorophenylboronic acid and 24.8 g (94.3 mmol) of 2-bromodibenzothiophene were put in a round-bottomed flask and dissolved by adding 313 ml of toluene thereto, 117 ml of an aqueous solution obtained by dissolving 19.5 g (141.5 mmol) of potassium carbonate was added thereto, and the mixture was agitated. Then, 1.09 g (0.94 mmol) of tetrakistriphenylphosphinepalladium was added thereto, and the resulting mixture was refluxed and agitated under a nitrogen atmosphere for 12 hours. When the reaction was complete, the resultant was extracted with ethylacetate, the extracted solution was dried with magnesium sulfate, filtered and concentrated under a reduced pressure. Then, a product therein was purified with n-hexane/dichloromethane (9:1 of a volume ratio) through silica gel column chromatography, obtaining 25.6 g of a target compound of a white solid intermediate M-4 (a yield of 92%). (Calculation value: 294.03 g/mol, Measurement value: M+=294.16 g/mol, M+2=296.13 g/mol)

Synthesis Example 5: Synthesis of Intermediate M-5

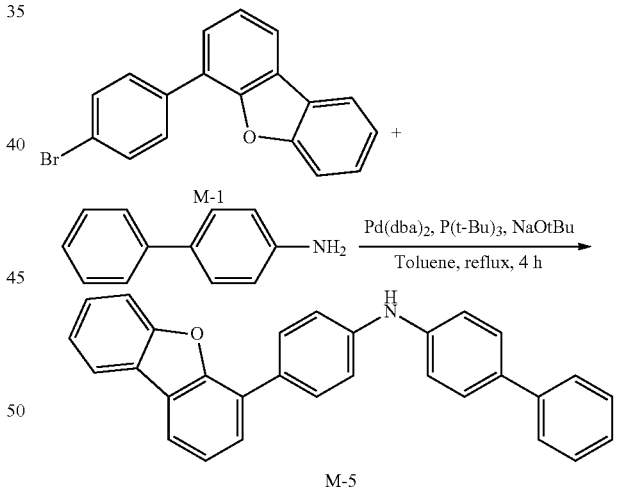

M-5

10 g (30.9 mmol) of the intermediate M-1, 6.3 g (37.08 mmol) of 4-aminobiphenyl, and 5.35 g (55.6 mmol) of sodium t-butoxide were put in a round-bottomed flask and dissolved by adding 155 ml of toluene thereto. Then, 0.178 g (0.31 mmol) of Pd(dba)$_2$ and 0.125 g (0.62 mmol) of tri-tertiary-butylphosphine were sequentially added thereto, and the resulting mixture was refluxed and agitated under a nitrogen atmosphere for 4 hours. When the reaction was complete, the resultant was extracted with ethylacetate and distilled water, an organic layer obtained therefrom was dried with magnesium sulfate, filtered and then, concentrated under a reduced pressure. Then, a product therefrom was purified with n-hexane/dichloromethane (7:3 volume ratio) through silica gel column chromatography, obtaining 9.92 g of a target compound of a white solid intermediate M-5 (a yield of 78%). (Calculation value: 411.16 g/mol, Measurement value: M+=411.21 g/mol)

Synthesis Example 6: Synthesis of Intermediate M-6

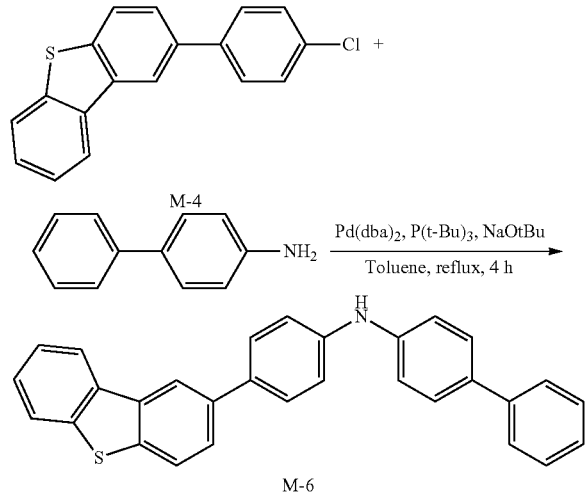

9.1 g (30.9 mmol) of the intermediate M-4 and 6.3 g (37.08 mmol) of 4-aminobiphenyl, and 5.35 g (55.6 mmol) of sodium t-butoxide were put in a round-bottomed flask and dissolved by adding 155 ml of toluene thereto. Then, 0.178 g (0.31 mmol) of Pd(dba)₂ and 0.125 g (0.62 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 10.6 g of a target compound of a white solid intermediate M-6 (a yield of 80%). (Calculation value: 427.14 g/mol, Measurement value: M+=427.19 g/mol)

Synthesis Example 7: Synthesis of Intermediate M-7

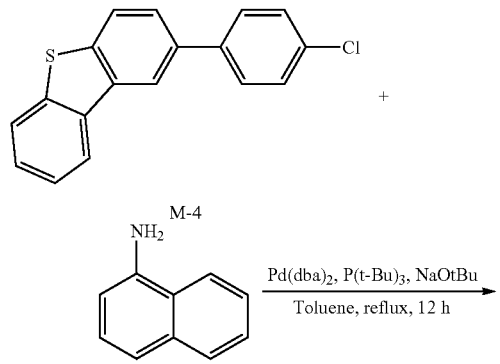

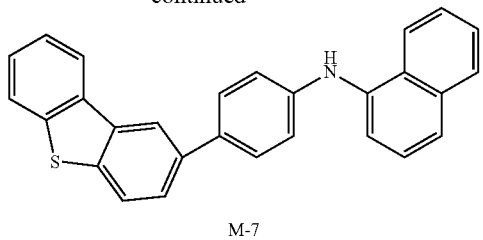

9.1 g (30.9 mmol) of the intermediate M-4, 5.3 g (37.08 mmol) of 1-aminonaphthalene, and 5.35 g (55.6 mmol) of sodium t-butoxide were put in a round-bottomed flask and dissolved by adding 155 ml of toluene thereto. Then, 0.178 g (0.31 mmol) of Pd(dba)₂ and 0.125 g (0.62 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 10 g of a target compound of a white solid intermediate M-7 (a yield of 81%). (Calculation value: 401.12 g/mol, Measurement value: M+=401.15 g/mol)

Synthesis Example 8: Synthesis of Intermediate M-8

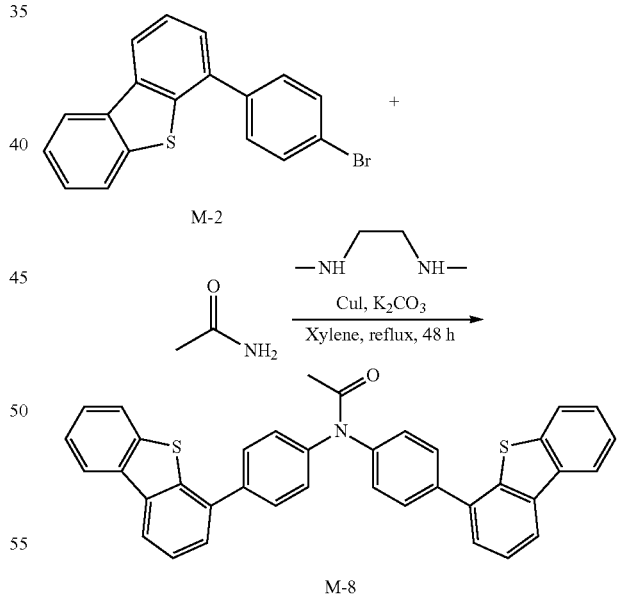

31.9 g (64.7 mmol) of the intermediate M-2, 1.74 g (29.4 mmol) of acetamide, and 17.3 g (117.6 mmol) of potassium carbonate were put in a round-bottomed flask and dissolved by adding 130 ml of xylene thereto. Then, 1.12 g (5.88 mmol) of copper iodide (I) and 1.04 g (11.8 mmol) of N,N-dimethylethylenediamine were sequentially added thereto, and the mixture was refluxed and agitated under a nitrogen atmosphere for 48 hours. When the reaction was complete, the resultant was extracted with toluene and distilled water, and an organic layer obtained therefrom was dried with magnesium sulfate, filtered and concentrated under a reduced pressure. Then, a product therefrom was purified with n-hexane/ethylacetate (7:3 of a volume ratio) through silica gel column chromatography, obtaining 14 g of a target compound of an intermediate M-8 (a yield of 93%). (Calculation value: 575.14 g/mol, Measurement value: M+=575.31 g/mol)

Synthesis Example 9: Synthesis of Intermediate M-9

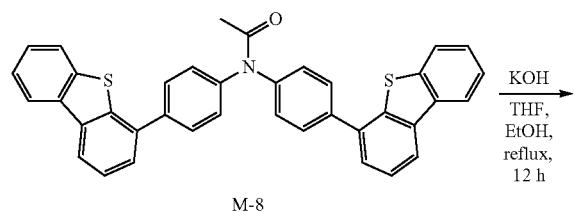

M-8

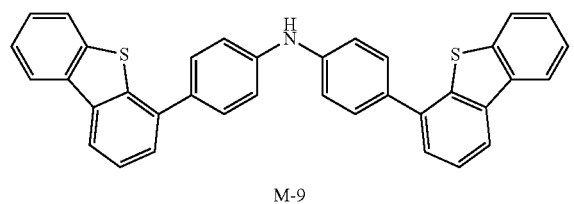

M-9

13 g (252 mmol) intermediate M-8 and 4.2 g (75.6 mmol) of potassium hydroxide were put in a round-bottomed flask and dissolved by adding 80 ml of tetrahydrofuran and 80 mL of ethanol thereto. The mixture was refluxed and agitated under a nitrogen atmosphere for 12 hours. When the reaction was complete, the reaction solution was concentrated under a reduced pressure, extracted with diclomethane and distilled water, and an organic layer obtained therefrom was dried with magnesium sulfate, filtered and concentrated under a reduced pressure. Subsequently, a product therefrom was purified with n-hexane/dichloromethane (7:3 of a volume ratio) through silica gel column chromatography, obtaining 12.1 g of a target compound of an intermediate M-9 (a yield of 90%). (Calculation value: 533.13 g/mol, Measurement value: M+=533.26 g/mol)

Synthesis Example 10: Synthesis of Intermediate M-10

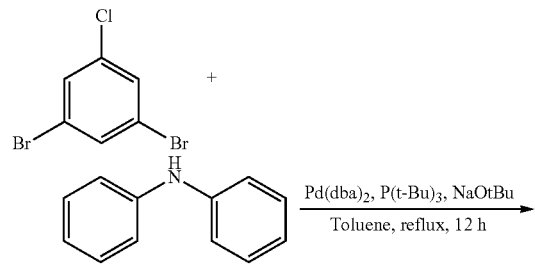

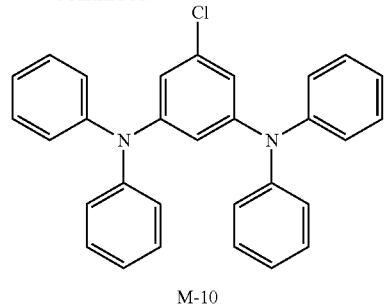

M-10

25 g (92.47 mmol) of 1,3-dibromo-5-chlorobenzene, 31.3 g (184.9 mmol) of diphenylamine, and 26.7 g (277.41 mmol) of sodium t-butoxide were put in a round-bottomed flask and dissolved by adding 463 ml of toluene thereto. Then, 0.266 g (0.462 mmol) of Pd(dba)₂ and 0.187 g (0.924 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (9:1 of a volume ratio) through silica gel column chromatography, obtaining 34.7 g of a target compound of a white solid intermediate M-10 (a yield of 84%). (Calculation value: 446.15 g/mol, Measurement value: M+=446.23 g/mol)

Synthesis Example 11: Synthesis of Intermediate M-11

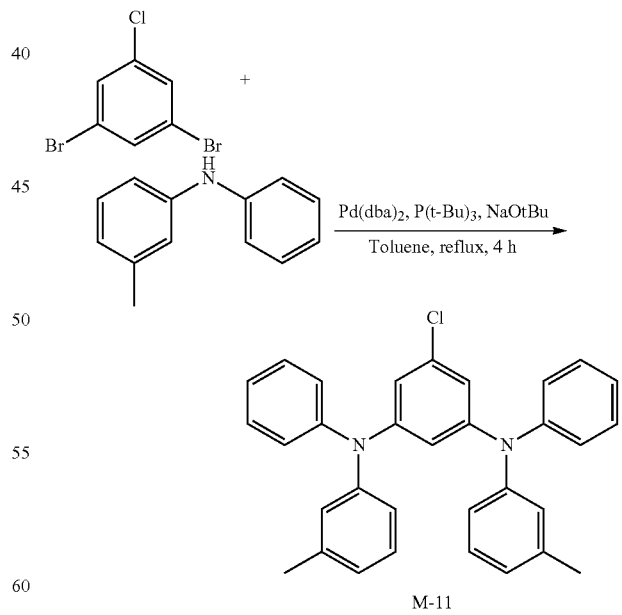

M-11

25 g (92.47 mmol) of 1,3-dibromo-5-chlorobenzene, 33.9 g (184.9 mmol) of 3-methyldiphenylamine, and 26.7 g (277.41 mmol) of sodium t-butoxide were put in a round-bottomed flask and dissolved by adding 463 ml of toluene thereto. Then, 0266 g (0.462 mmol) of Pd(dba)₂ and 0.187 g (0.924 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (9:1 of a volume ratio) through silica gel column chromatography, obtaining 37.3 g of a target compound of a white solid intermediate M-11 (a yield of 85%). (Calculation value: 474.19 g/mol, Measurement value: M+=474.28 g/mol)

Synthesis Example 12: Synthesis of Intermediate M-12

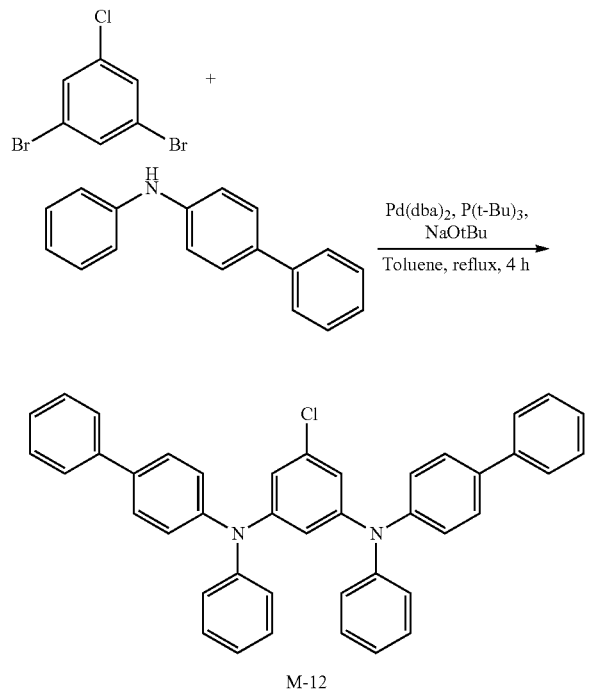

M-12

25 g (92.47 mmol) of 1,3-dibromo-5-chlorobenzene, 45.4 g (184.9 mmol) of biphenyl-4-yl-phenyl amine, and 26.7 g (277.41 mmol) of sodium t-butoxide were put in a round-bottomed flask and dissolved by adding 463 ml of toluene thereto. Then, 0.266 g (0.462 mmol) of Pd(dba)$_2$ and 0.187 g (0.924 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 44.9 g of a target compound of a white solid intermediate M-12 (a yield of 81%). (Calculation value: 598.22 g/mol, Measurement value: M+=598.37 g/mol)

Synthesis Example 13: Synthesis of Intermediate M-13

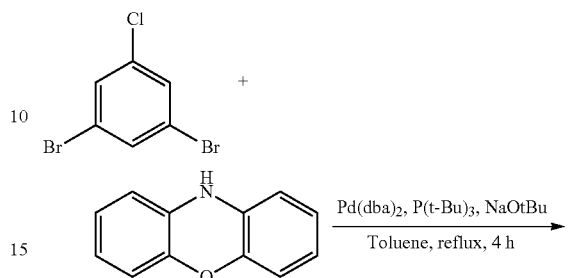

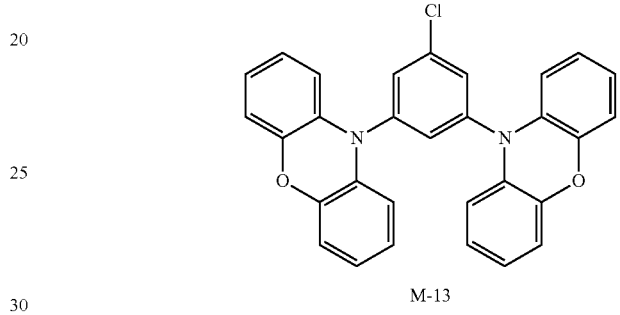

M-13

25 g (92.47 mmol) of 1,3-dibromo-5-chlorobenzene, 33.9 g (184.9 mmol) of phenoxazine, and 26.7 g (277.41 mmol) of sodium t-butoxide were put in a round-bottomed flask and dissolved by adding 463 ml of toluene thereto. Then, 0.266 g (0.462 mmol) of Pd(dba)$_2$ and 0.187 g (0.924 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8.2 of a volume ratio) through silica gel column chromatography, obtaining 36.9 g of a target compound of a white solid intermediate M-13 (a yield of 84%). (Calculation value: 474.11 g/mol, Measurement value: M+=474.26 g/mol)

Synthesis Example 14: Synthesis of Intermediate M-14

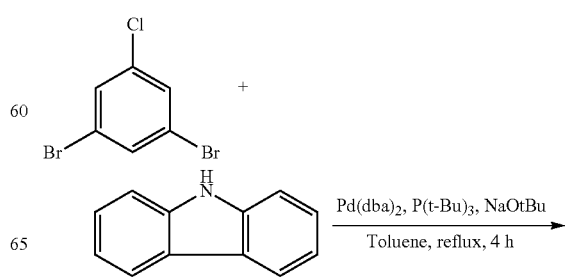

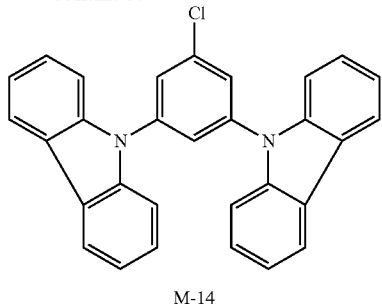

M-14

25 g (92.47 mmol) of 1,3-dibromo-5-chlorobenzene, 30.9 g (184.9 mmol) of carbazole, and 26.7 g (277.41 mmol) of sodium t-butoxide were put in a round-bottomed flask and dissolved by adding 463 ml of toluene thereto. Then, 0.266 g (0.462 mmol) of Pd(dba)$_2$ and 0.187 g (0.924 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8.2 of a volume ratio) through silica gel column chromatography, obtaining 33.2 g of a target compound of a white solid intermediate M-14 (a yield of 81%). (Calculation value: 442.12 g/mol, Measurement value: M+=442.36 g/mol)

Synthesis Example 15: Synthesis of Intermediate M-15

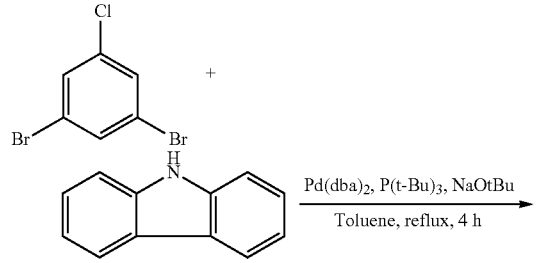

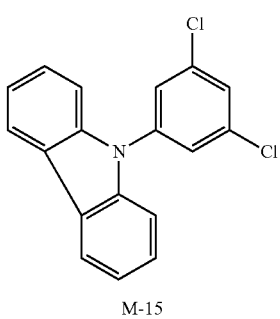

M-15

25 g (92.47 mmol) of 1-bromo-3,5-dichlorobenzene, 15.5 g (92.47 mmol) of carbazole, and 13.4 g (138.7 mmol) of sodium t-butoxide were put in a round-bottomed flask and dissolved by adding 463 ml of toluene thereto. Then, 0.133 g (0.231 mmol) of Pd(dba)$_2$ and 0.094 g (0.462 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (9:1 of a volume ratio) through silica gel column chromatography, obtaining 24.0 g of a target compound of a white solid intermediate M-15 (a yield of 83%). (Calculation value: 311.03 g/mol, Measurement value: M+=311.17 g/mol)

Synthesis Example 16: Synthesis of Intermediate M-16

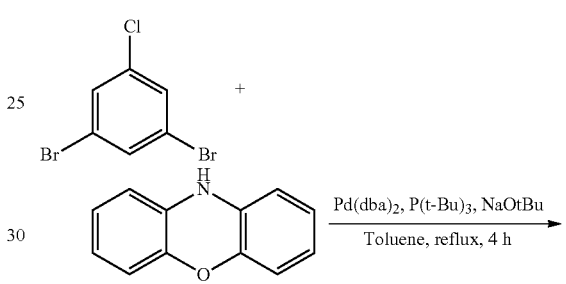

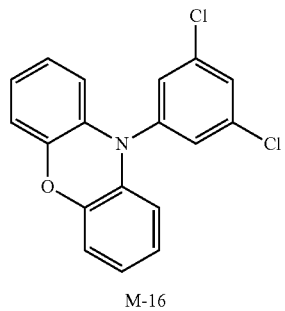

M-16

25 g (92.47 mmol) of 1-bromo-3,5-dichlorobenzene, 16.9 g (92.47 mmol) of phenoxazine, and 13.4 g (138.7 mmol) of sodium t-butoxide were put in a round-bottomed flask and dissolved by adding 463 ml of toluene thereto. Then, 0.133 g (0.231 mmol) of Pd(dba)$_2$ and 0.094 g (0.462 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 25.7 g of a target compound of a white solid intermediate M-16 (a yield of 85%). (Calculation value: 327.02 g/mol, Measurement value: M+=327.27 g/mol)

Synthesis Example 17: Synthesis of Intermediate M-17

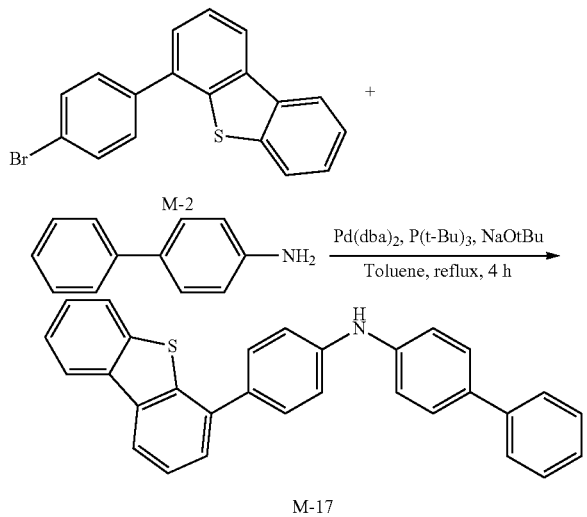

10.5 g (30.9 mmol) of the intermediate M-2, 6.3 g (37.08 mmol) of 4-aminobiphenyl, and 5.35 g (55.6 mmol) of sodium t-butoxide were put in a round-bottomed flask and dissolved in 155 ml of toluene. Then, 0.178 g (0.31 mmol) of Pd(dba)$_2$ and 0.125 g (0.62 mmol) of tri-tertiary-butyl-phosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 9.91 g of a target compound of a white solid intermediate M-17 (a yield of 75%).

(Calculation value: 427.14 g/mol, Measurement value: M+=427.29 g/mol)

Synthesis Example 18: Synthesis of Intermediate M-18

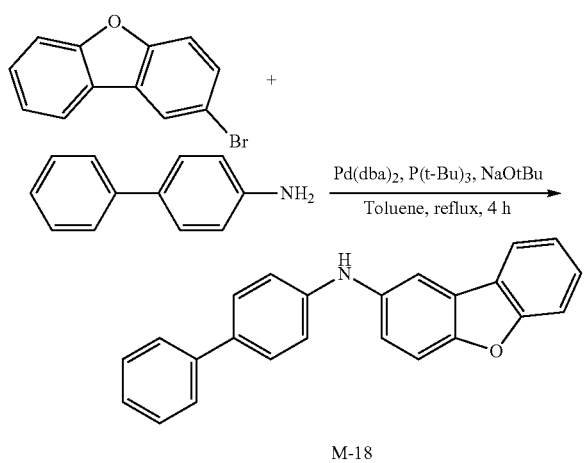

7.6 g (30.9 mmol) of 2-bromodibenzofuran as an intermediate, 63 g (37.08 mmol) of 4-aminobiphenyl, and 5.35 g (55.6 mmol) of sodium t-butoxide were put in a round-bottomed flask and dissolved by adding 155 ml of toluene. Then, 0.178 g (0.31 mmol) of Pd(dba)$_2$ and 0.125 g (0.62 mmol) of tri-tertiary-butylphosphine were sequentially added thereto, and the mixture was refluxed and agitated under a nitrogen atmosphere for 4 hours When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 8.1 g of a target compound of a white solid intermediate M-18 (a yield of 78%).

(Calculation value: 335.13 g/mol, Measurement value: M+=335.42 g/mol)

Synthesis Example 19: Synthesis of Intermediate M-19

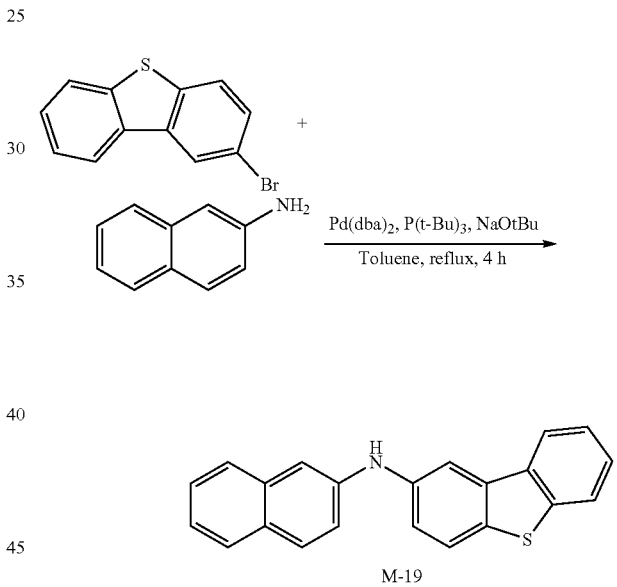

8.1 g (30.9 mmol) of 2-bromodibenzothiophene as an intermediate, 5.3 g (37.08 mmol) of 2-aminonaphthalene, and 5.35 g (55.6 mmol) of sodium t-butoxide were put in a round-bottomed flask and dissolved by adding 155 ml of toluene thereto. Then, 0.178 g (0.31 mmol) of Pd(dba)$_2$ and 0.125 g (0.62 mmol) of tri-tertiary-butylphosphine were sequentially added thereto, and the mixture was refluxed and agitated under a nitrogen atmosphere for 4 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 7.9 g of a target compound of a white solid intermediate M-19 (a yield of 79%).

(Calculation value: 325.09 g/mol, Measurement value: M+=325.33 g/mol)

Synthesis Example 20: Synthesis of Intermediate M-20

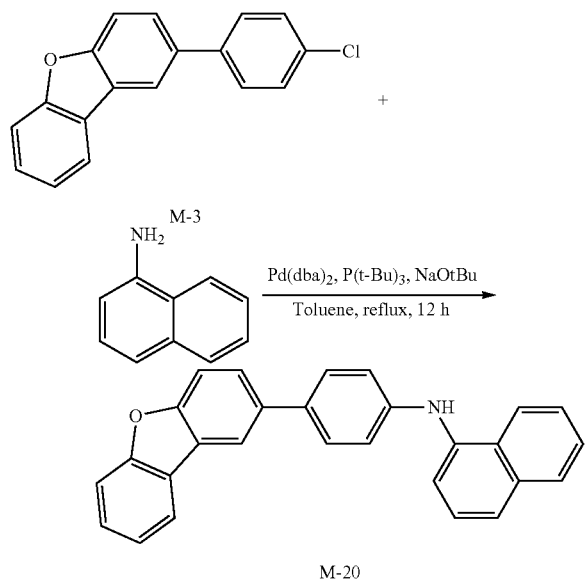

8.6 g (30.9 mmol) of the intermediate M-3, 5.3 g (37.08 mmol) of I-aminonaphthalene, and 5.35 g (55.6 mmol) of sodium t-butoxide were put in a round-bottomed flask and dissolved by adding 155 ml of toluene thereto. Then, 0.178 g (0.31 mmol) of Pd(dba)$_2$ and 0.125 g (0.62 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (7:3 of a volume ratio) through silica gel column chromatography, obtaining 9.5 g of a target compound of a white solid intermediate M-20 (a yield of 80%).

(Calculation value: 385.15 g/mol, Measurement value: M+=385.27 g/mol)

Synthesis Example 21: Synthesis of Intermediate M-21

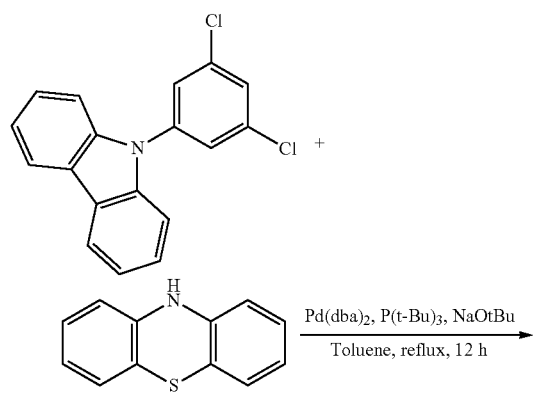

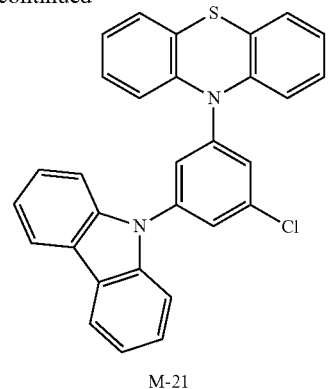

28.9 g (92.47 mmol) of the intermediate M-15, 16.9 g (92.47 mmol) of phenoxazine, and 13.4 g (138.7 mmol) of sodium t-butoxide were put in a round-bottomed flask and dissolved by adding 463 ml of toluene thereto. Then, 0.133 g (0.231 mmol) of Pd(dba)$_2$ and 0.094 g (0.462 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8.2 of a volume ratio) through silica gel column chromatography, obtaining 35.6 g of a target compound of a white solid intermediate M-21 (a yield of 81%).

(Calculation value: 474.10 g/mol, Measurement value: M+=474.38 g/mol)

Synthesis Example 22: Synthesis of Intermediate M-22

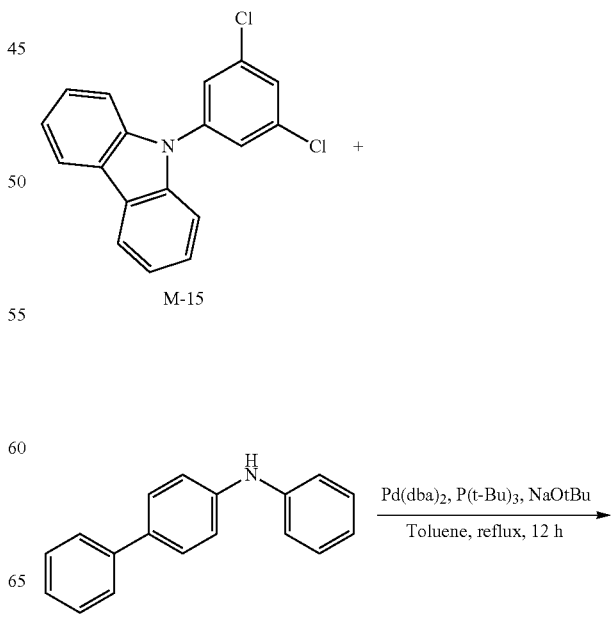

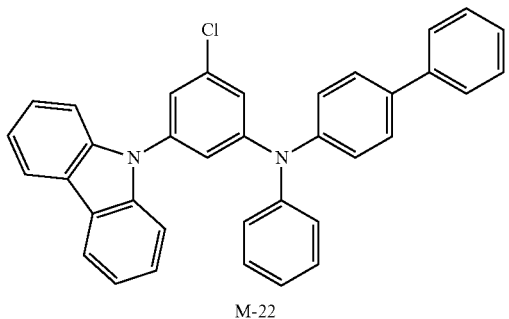

M-22

28.9 g (92.47 mmol) of the intermediate M-15, 22.7 g (92.47 mmol) of biphenyl-4-yl-phenyl amine, and 13.4 g (138.7 mmol) of sodium t-butoxide were put in a round-bottomed flask and dissolved by adding 463 ml of toluene thereto. Then, 0.133 g (0.231 mmol) of Pd(dba)$_2$ and 0.094 g (0.462 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 38.1 g of a target compound of a white solid intermediate M-22 (a yield of 79%).

(Calculation value: 520.17 g/mol, measurement value: M+=520.36 g/mol)

Synthesis of Compound for Organic Photoelectric Device

The compounds respectively represented by Chemical Formulas A-1 to A-300, B-1 to B-20, C-1 to C-12, D-1 to D-8, E-1 to E-28 and F-1 to F-20 were synthesized according to a method of the following formulas 1 to 6. Specific compounds according to one embodiment of the present invention were provided in the following [Table 1].

[General Formula 1] Synthesis of Compounds A-1 to A-291 and A-300

[General Formula 1-1]

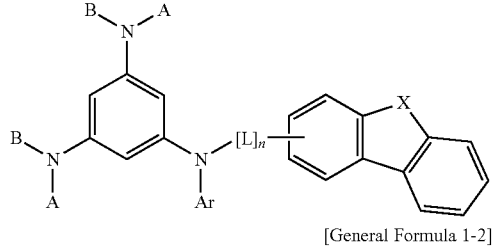

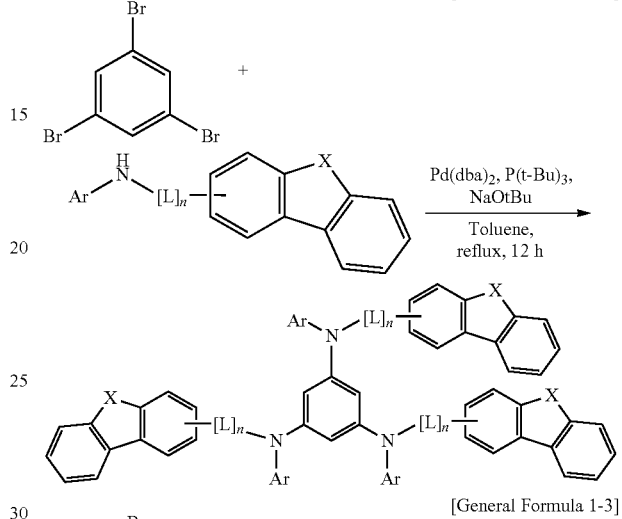

[General Formula 1-2]

[General Formula 1-3]

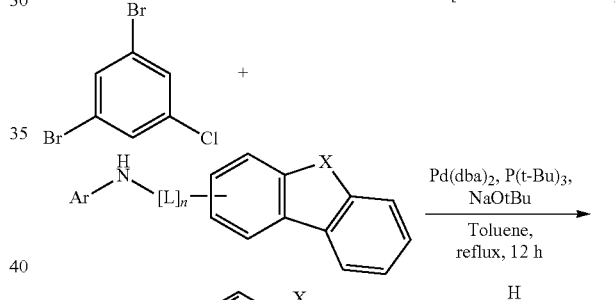

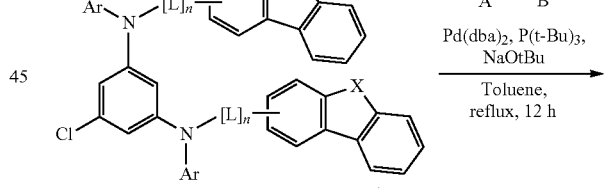

[General Formula 1-4]

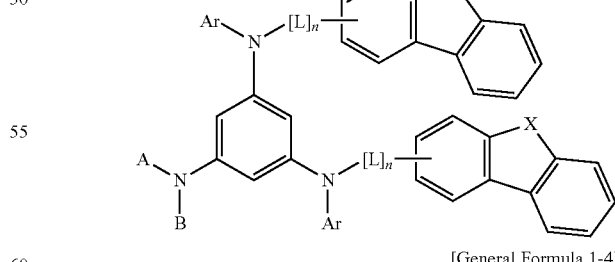

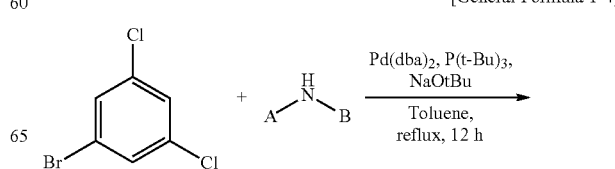

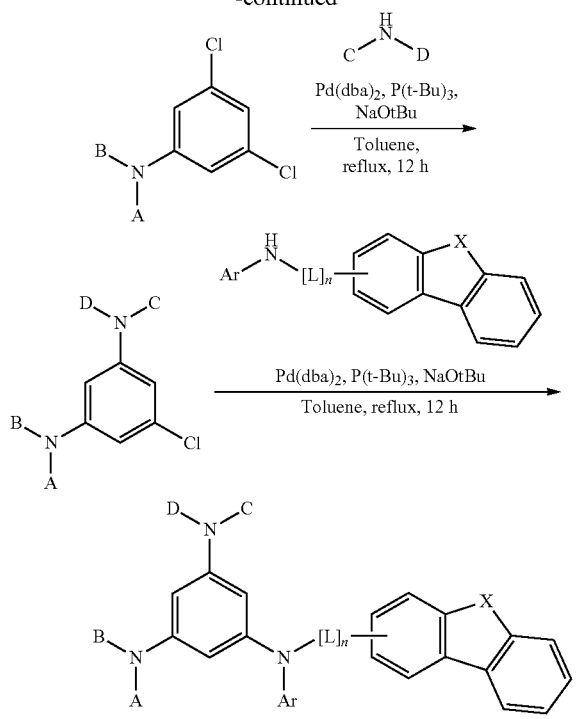
A, B = Aryl, Hetero aryl
C, D = Aryl, Hetero aryl
n = 0-3
X = O, S
Ar, L = Aryl, Hetero aryl
[General Formula 2] Synthesis of Compounds B-1 to B-20
[General Formula 2-1]
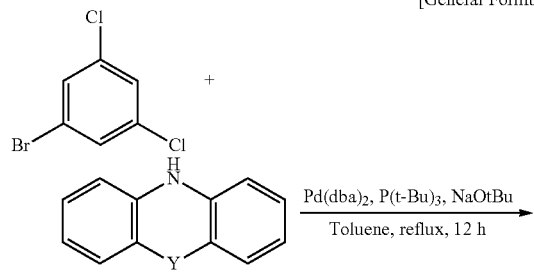
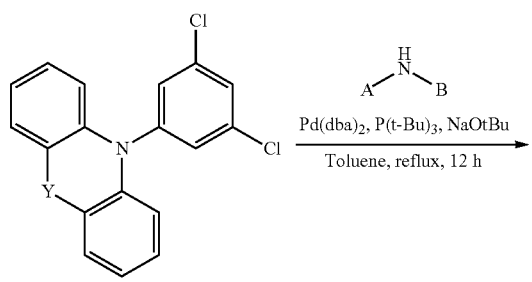
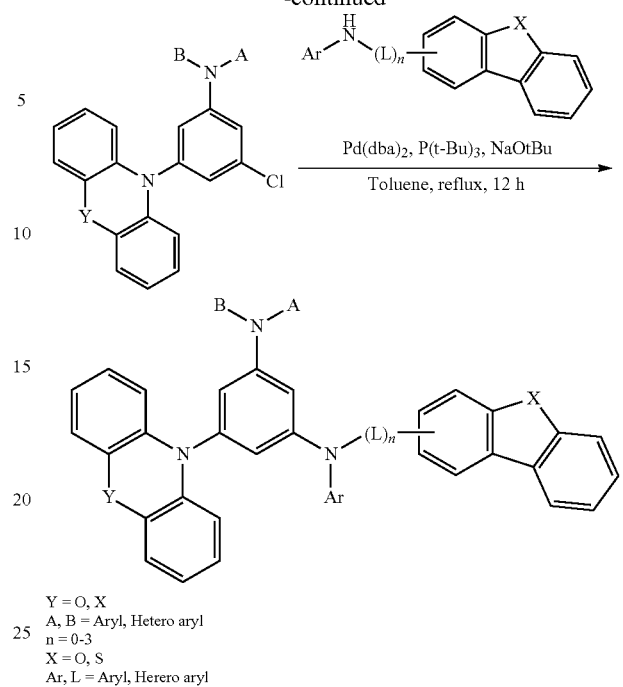
Y = O, X
A, B = Aryl, Hetero aryl
n = 0-3
X = O, S
Ar, L = Aryl, Hetero aryl
[General Formula 2-2]
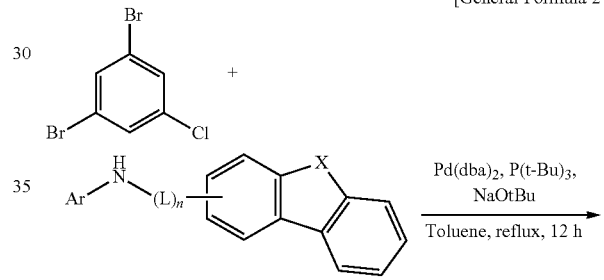
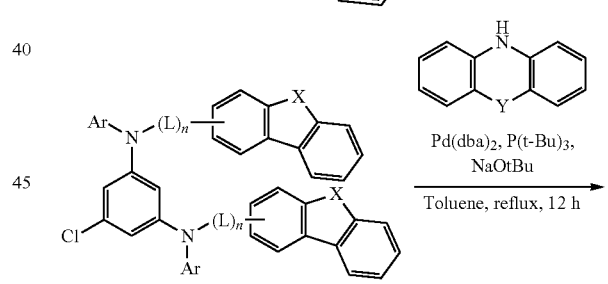
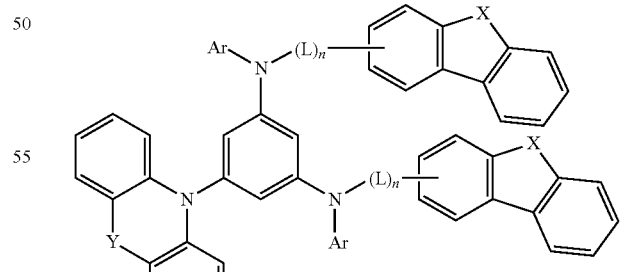
A, B = Aryl, Hetero aryl
Y = O, S
n = 0-3
X = O, S
Ar, L = Aryl, Hetero aryl

[General Formula 3] Synthesis of Compounds C-1 to C-12
[General Formula 3-1]
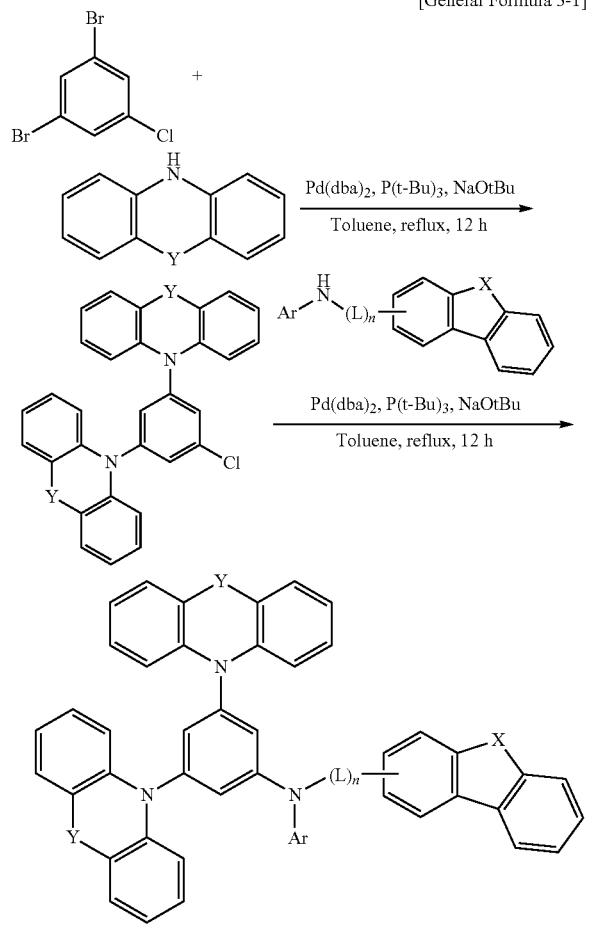
A, B = Aryl, Hetero aryl
Y = O, S
n = 0-3
X = O, S
Ar, L = Aryl, Hetero aryl
[General Formula 3-2]
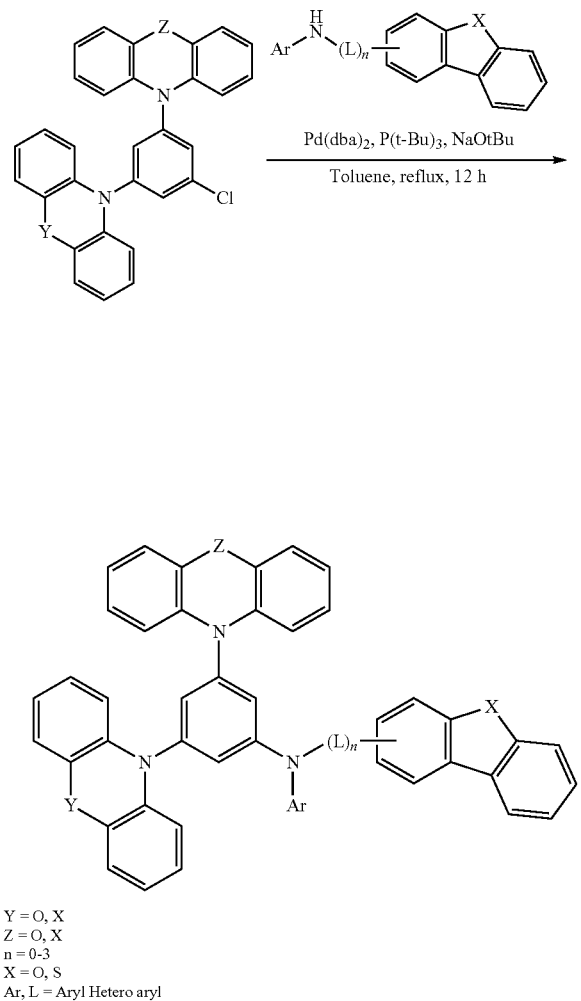
Y = O, X
Z = O, X
n = 0-3
X = O, S
Ar, L = Aryl Hetero aryl
[General Formula 4] Synthesis of Compounds D-1 to D-8
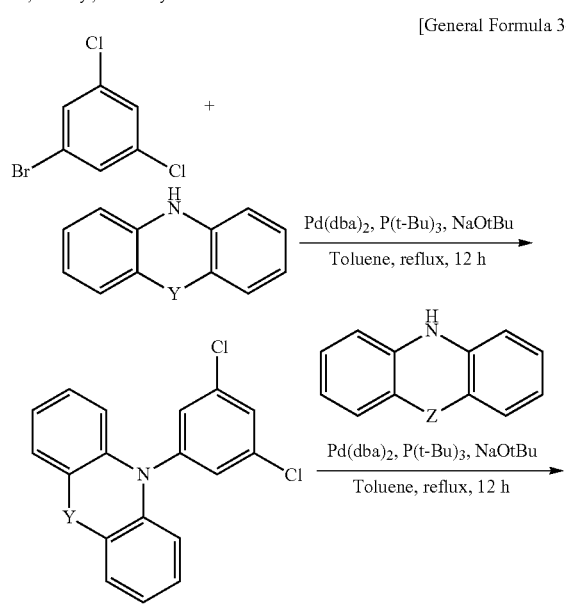
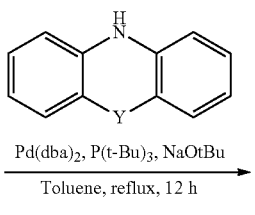

189
-continued
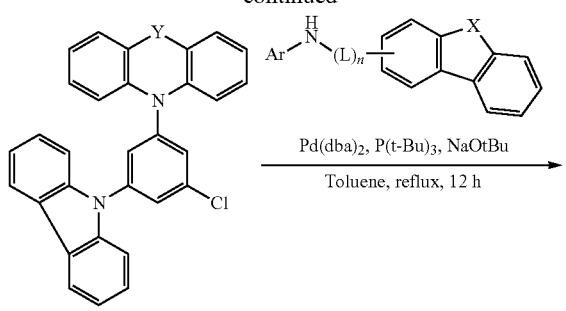
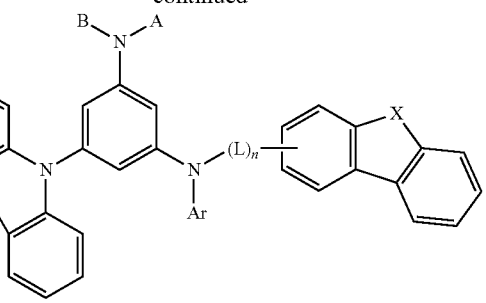
A, B = Aryl, Hetero aryl
n = 0-3
X = O, S
Ar, L = Aryl, Hetero aryl
[General Formula 5-2]
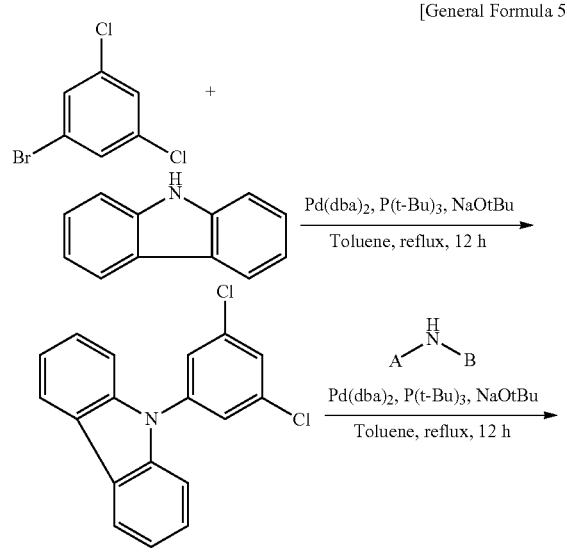
Y = O, X
n = 0-3
X = O, S
Ar, L = Aryl Hetero aryl
[General Formula 5] Synthesis of Compounds E-1 to E-28
[General Formula 5-1]
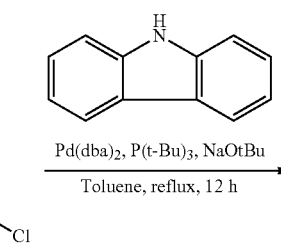
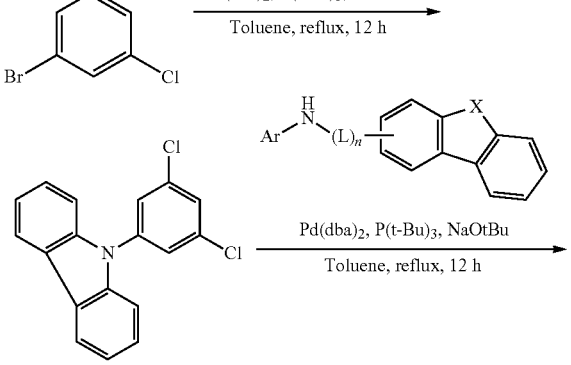
190
-continued
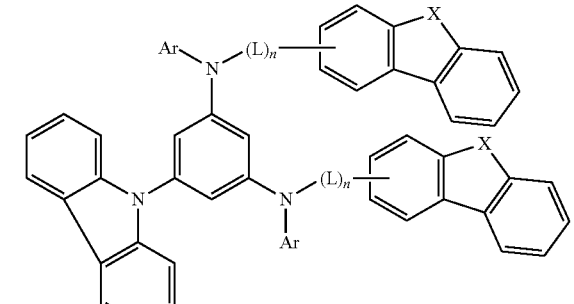
n = 0-3
X = O, S
Ar, L = Aryl, Hetero aryl
[General Formula 6] Synthesis of F-1 to F-20 Compounds
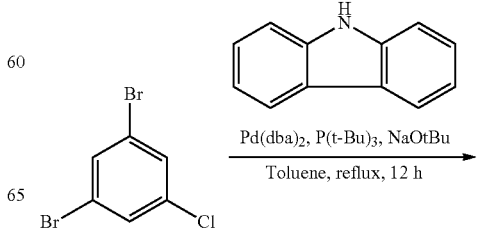
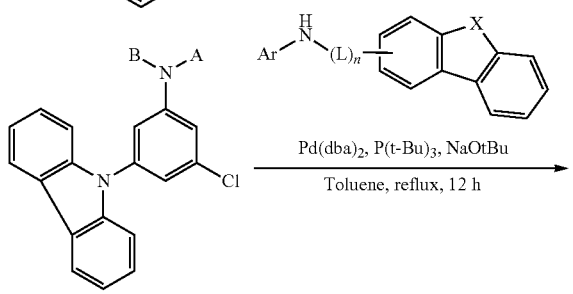

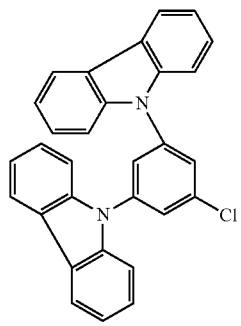 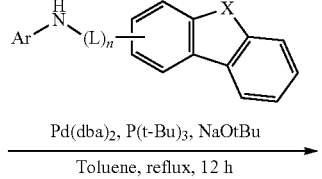 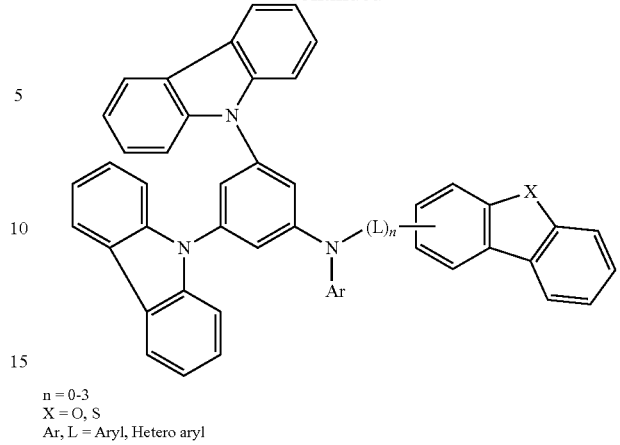
n = 0-3
X = O, S
Ar, L = Aryl, Hetero aryl
TABLE 1
| Syn-thesis method | halogen compound | Final synthesis reaction intermediate aryl amine |
|---|---|---|
| General Formula 1-1 | 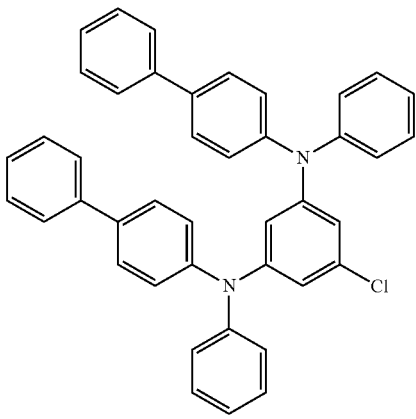 | 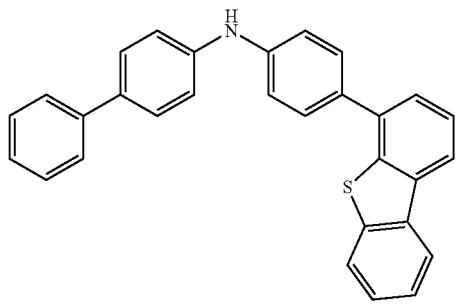 |
| General Formula 1-2 | 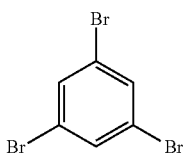 | 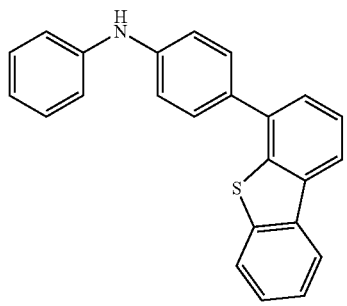 |

TABLE 1-continued
| General Formula 1-3 | 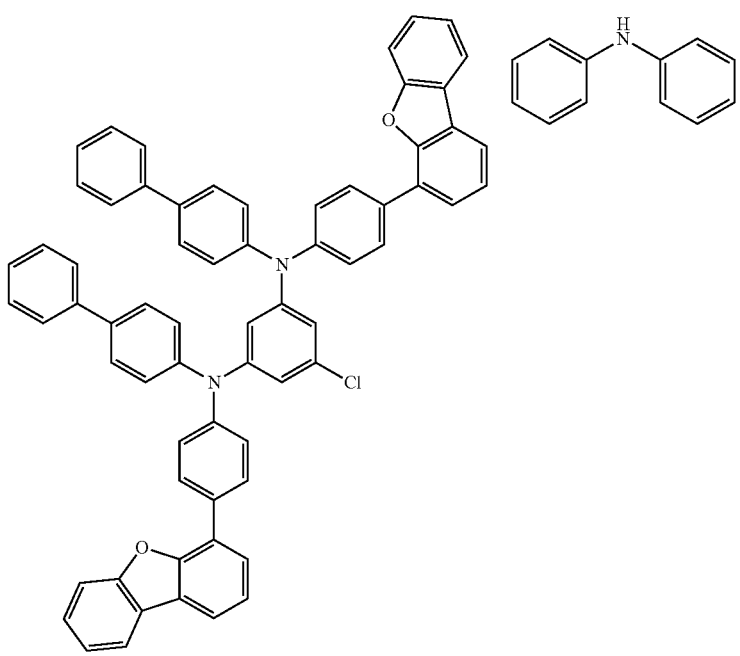 |
| General Formula 1-4 | 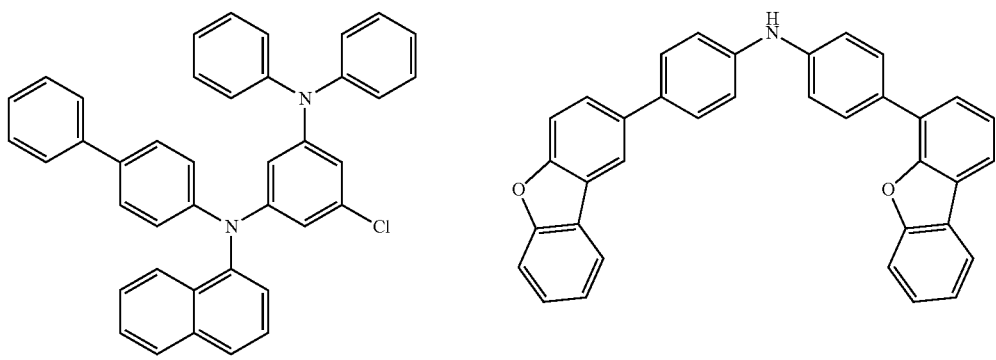 |
| General Formula 2-1 | 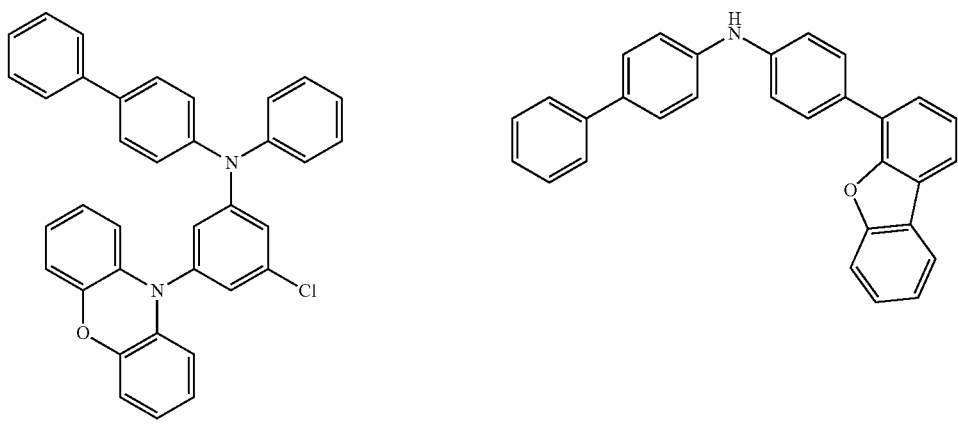 |

TABLE 1-continued
| General Formula 2-2 | 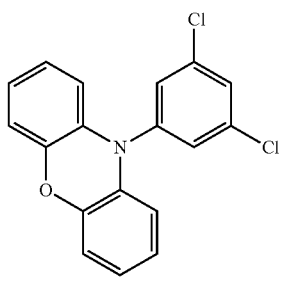 | 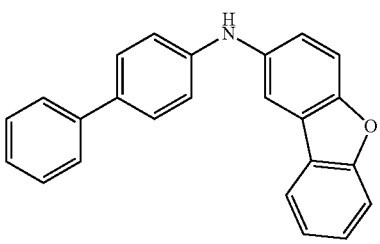 |
| General Formula 3-1 | 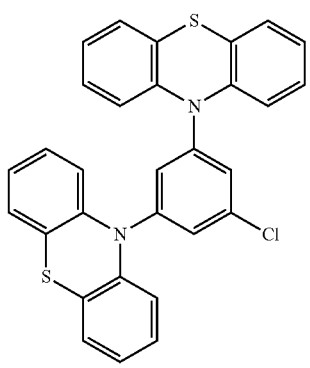 | 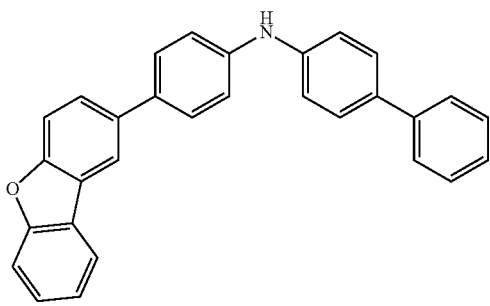 |
| General Formula 3-2 | 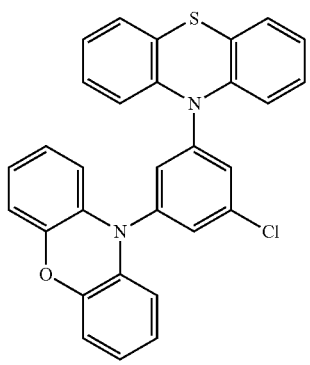 | 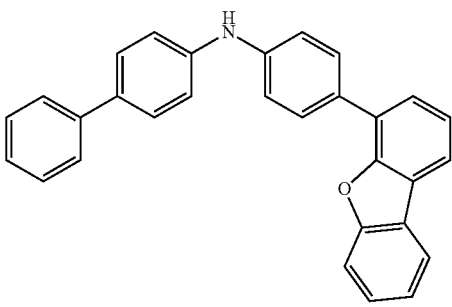 |
| General Formula 4 | 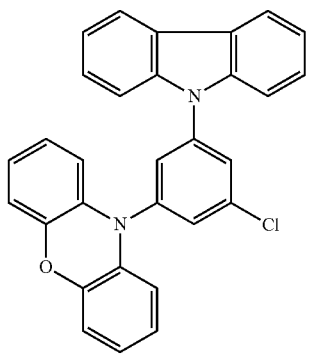 | 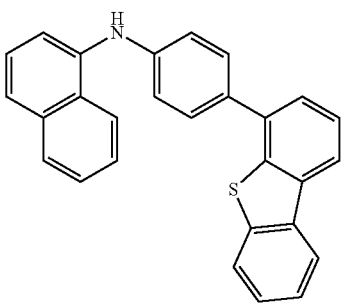 |

TABLE 1-continued
General Formula 5-1
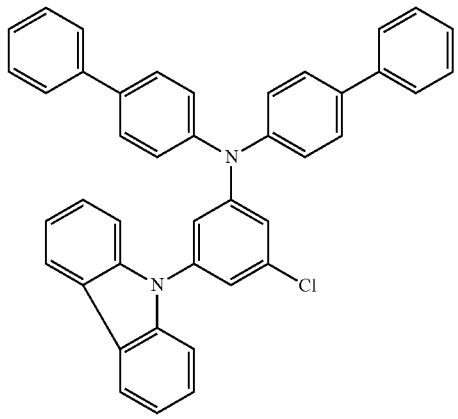
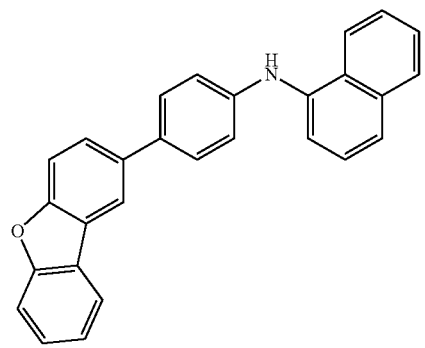
General Formula 5-2
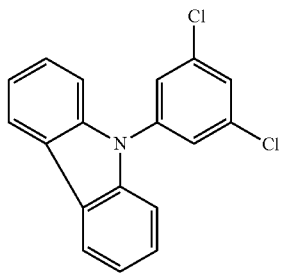
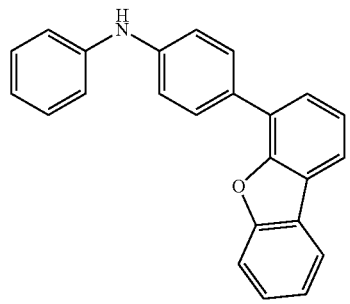
General Formula 6
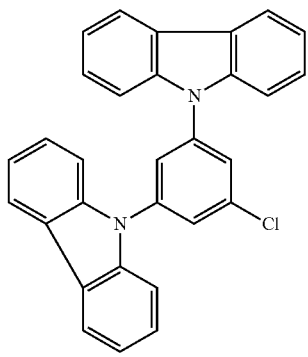
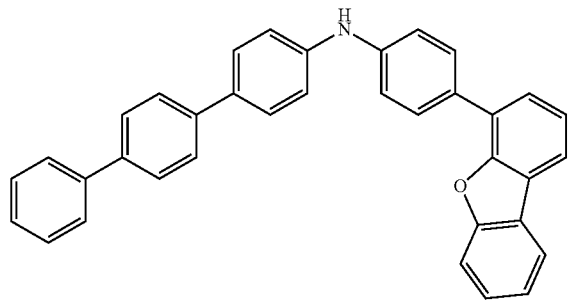

TABLE 1-continued

| Synthesis method | Final product compound structure | Nos. | Measurement value MS[M+] |
|---|---|---|---|
| General Formula 1-1 | | A-38 | 989.42 |
| General Formula 1-2 | | A-251 | 1125.51 |

TABLE 1-continued
| General Formula 1-3 | 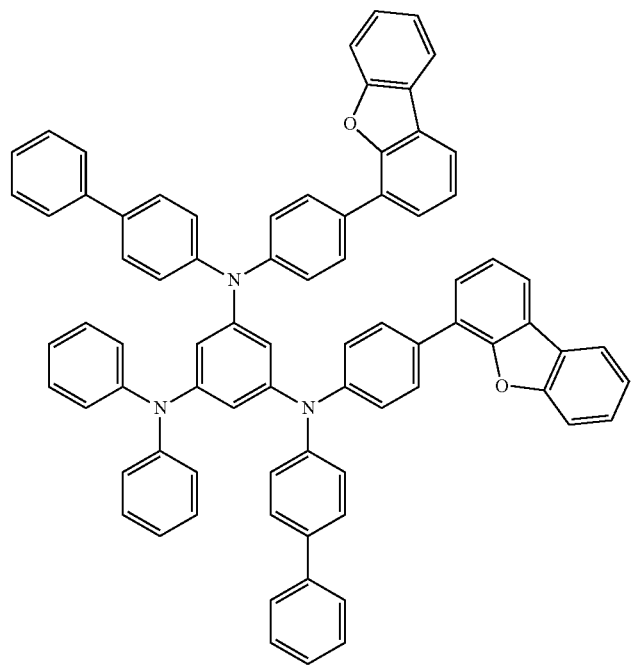 | A-209 | 1063.49 |
| General Formula 1-4 | 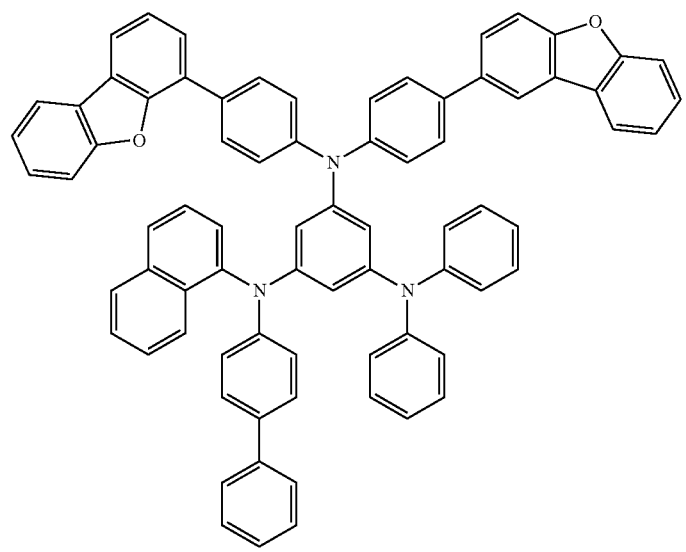 | A-203 | 1037.58 |

TABLE 1-continued
| | | | |
|---|---|---|---|
| General Formula 2-1 | 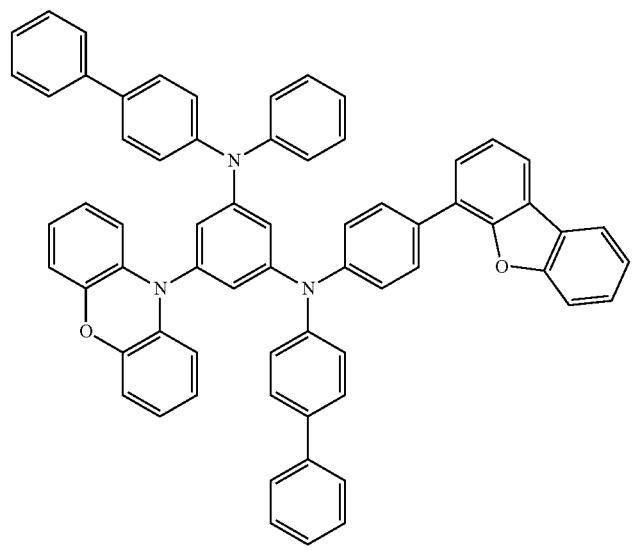 | B-3 | 911.57 |
| General Formula 2-2 | 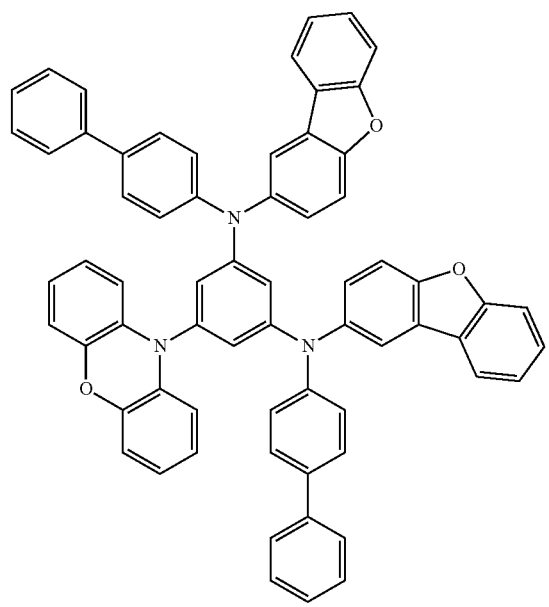 | B-10 | 925.59 |
| General Formula 3-1 | 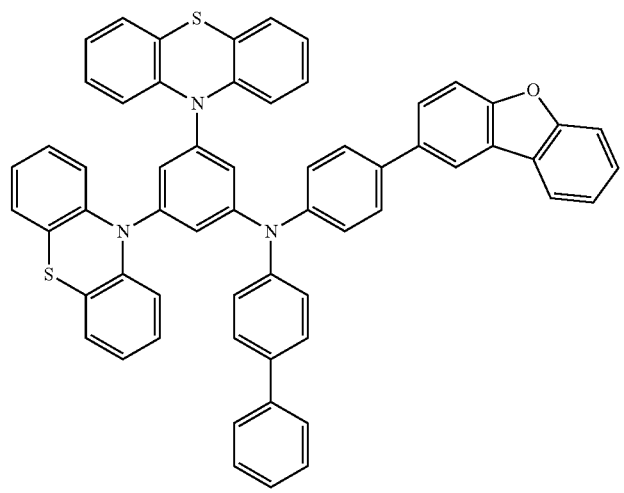 | C-4 | 881.43 |

TABLE 1-continued
| | | | |
|---|---|---|---|
| General Formula 3-2 | 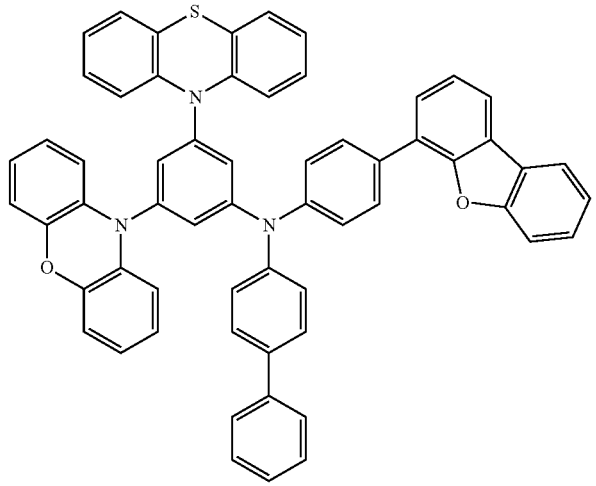 | C-9 | 865.51 |
| General Formula 4 | 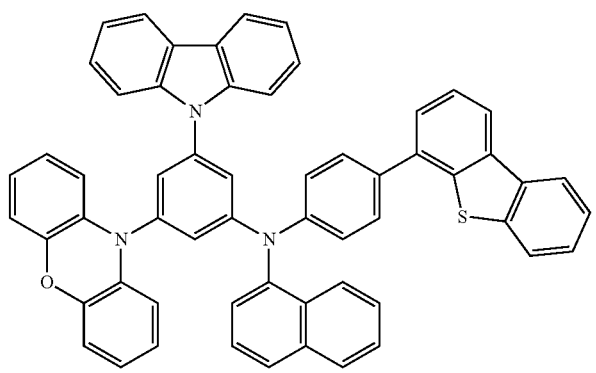 | D-3 | 823.55 |
| General Formula 5-1 | 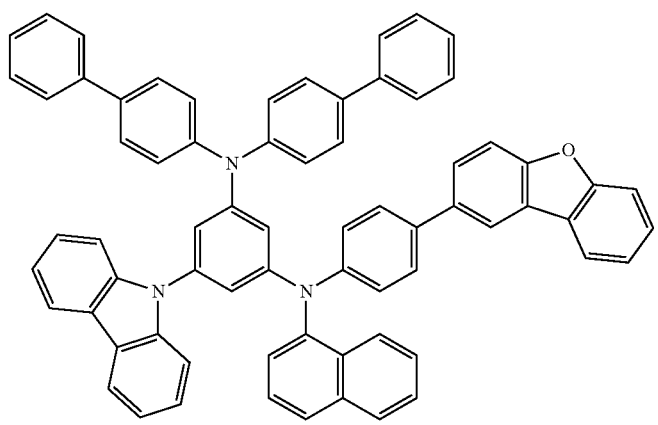 | E-8 | 945.62 |

TABLE 1-continued
| | | | |
|---|---|---|---|
| General Formula 5-2 | 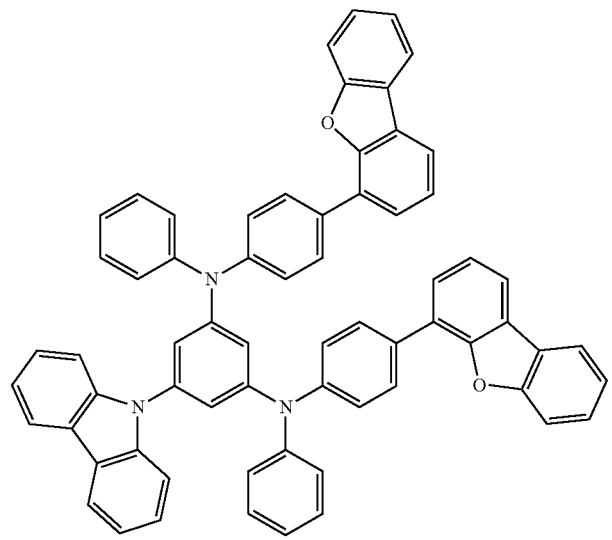 | E-17 | 909.63 |
| General Formula 6 | 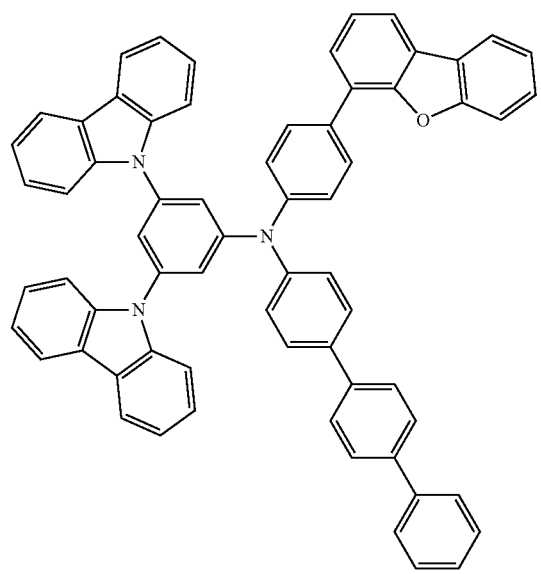 | F-12 | 893.57 |

Example 1: Synthesis of Compound A-34

The compound A-34 was synthesized through the following Reaction Scheme 1.

[Reaction Scheme 1]

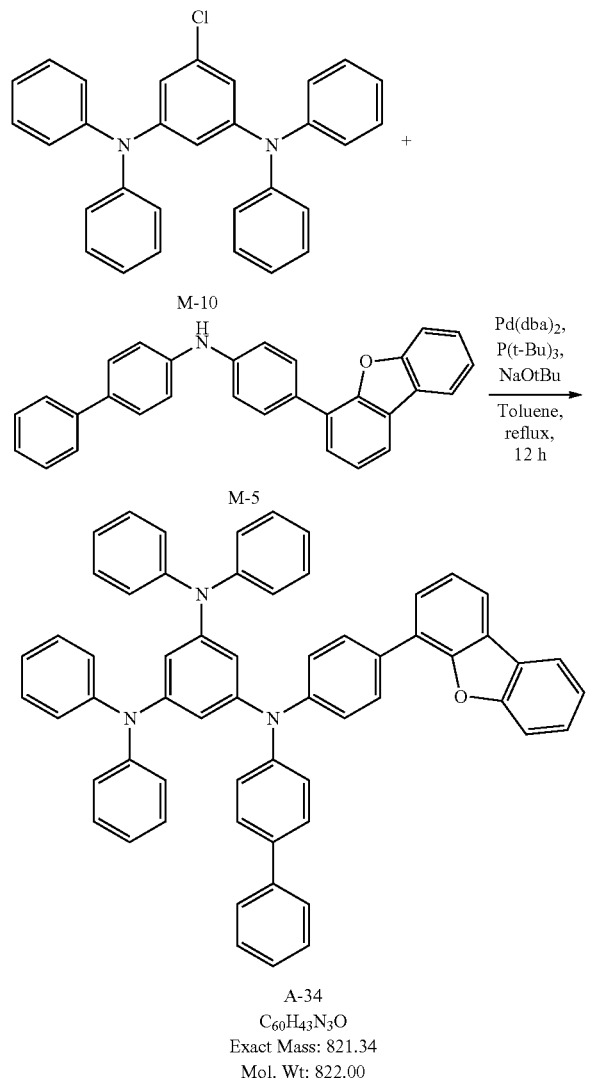

10 g (22.37 mmol) of the intermediate M-10, 9.2 g (22.37 mmol) of the intermediate M-5, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (82 of a volume ratio) through silica gel column chromatography, obtaining 16.9 g of a target compound of a white solid compound A-34 (a yield of 92%).

(Calculation value: 821.34 g/mol, Measurement value: M+=821.46 g/mol)

Example 2: Synthesis of Compound A-104

The compound A-104 was synthesized through the following Reaction Scheme 2.

[Reaction Scheme 2]

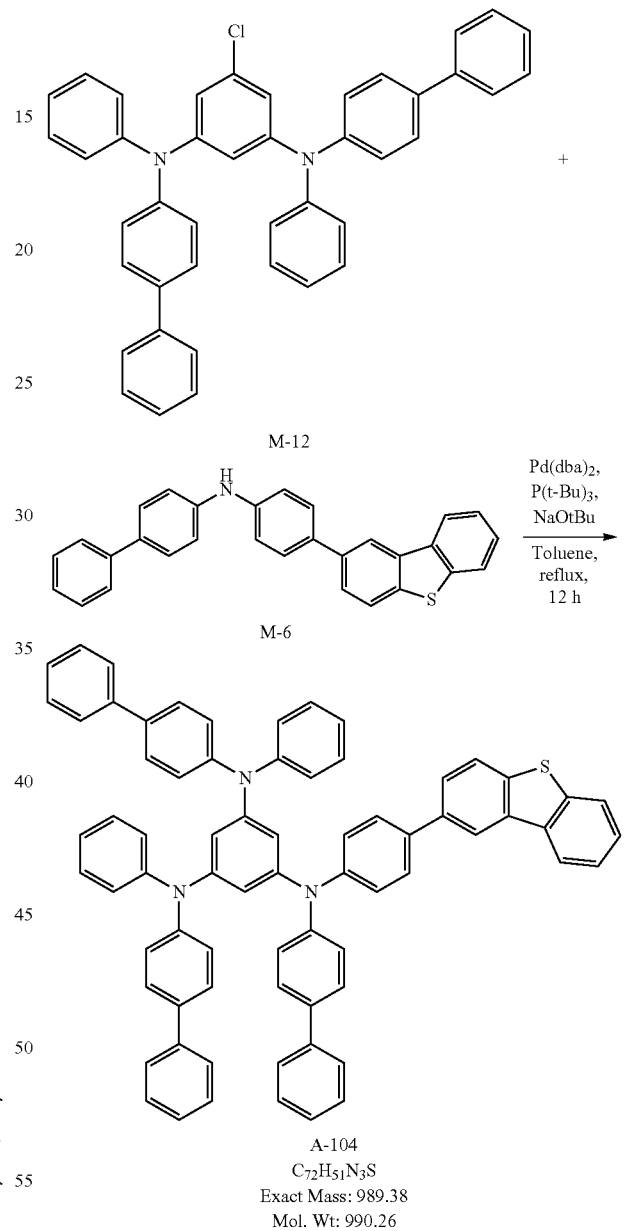

13.4 g (22.37 mmol) of the intermediate M-12, 9.6 g (22.37 mmol) of the intermediate M-6, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 20.6 g of a target compound of a white solid compound A-104 (a yield of 93%).

(Calculation value: 989.38 g/mol, Measurement value: M+=989.45 g/mol)

Example 3: Synthesis of Compound A-201

The compound A-201 was synthesized through the following Reaction Scheme 3.

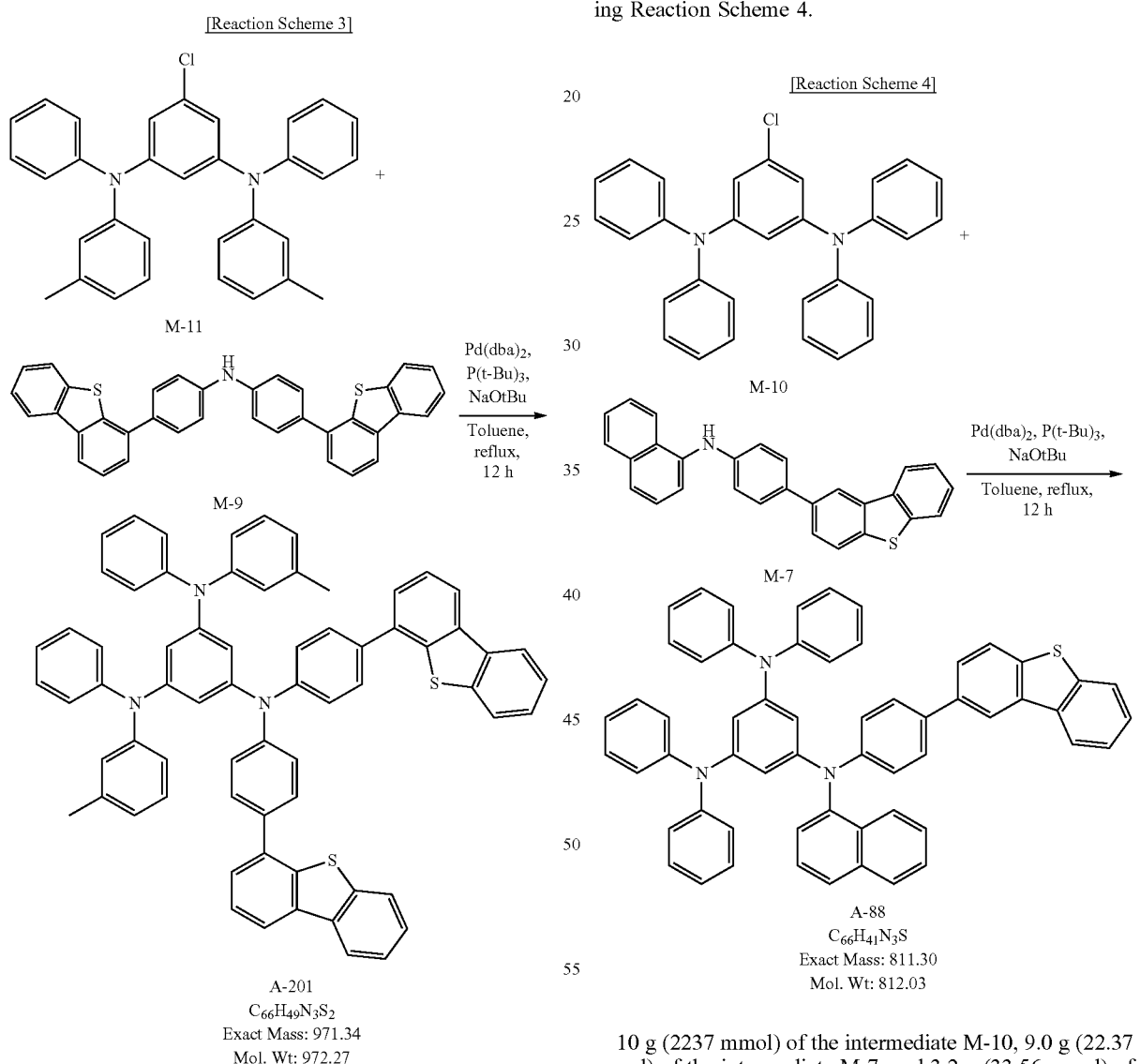

10.6 g (22.37 mmol) of the intermediate M-11, 11.9 g (22.37 mmol) of intermediate M-9, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 19.8 g of a target compound of a white solid compound A-201 (a yield of 91%).

(Calculation value: 971.34 g/mol, Measurement value: M+=971.51 g/mol)

Example 4: Synthesis of Compound A-88

The compound A-88 was synthesized through the following Reaction Scheme 4.

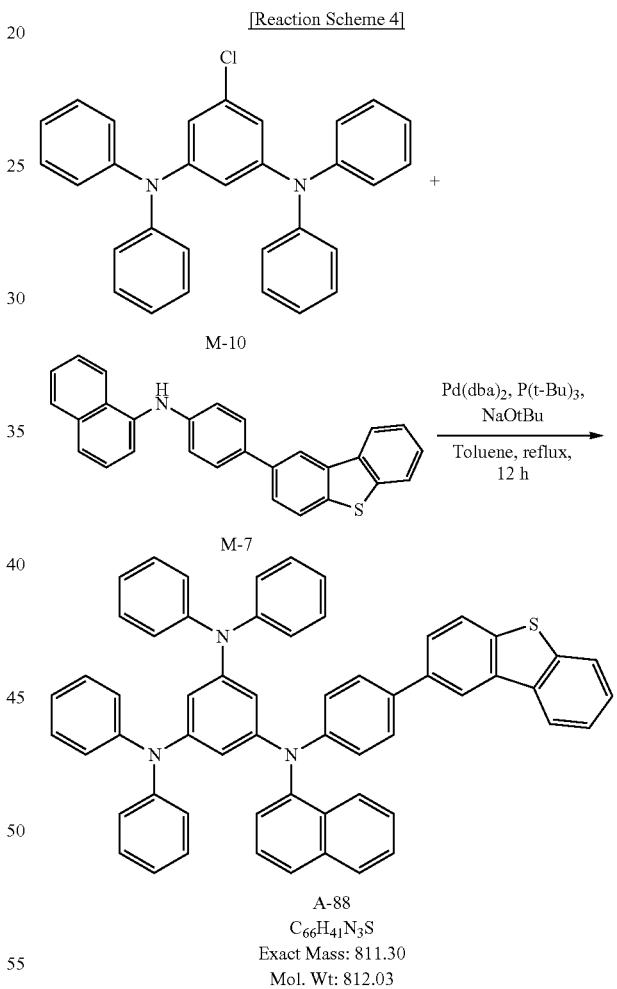

10 g (2237 mmol) of the intermediate M-10, 9.0 g (22.37 mmol) of the intermediate M-7, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 16.5 g of a target compound of a white solid compound A-88 (a yield of 91%).

(Calculation value: 811.30 g/mol, Measurement value: M+=811.61 g/mol)

Example 5: Synthesis of Compound B-17

The compound B-17 was synthesized through the following Reaction Scheme 5.

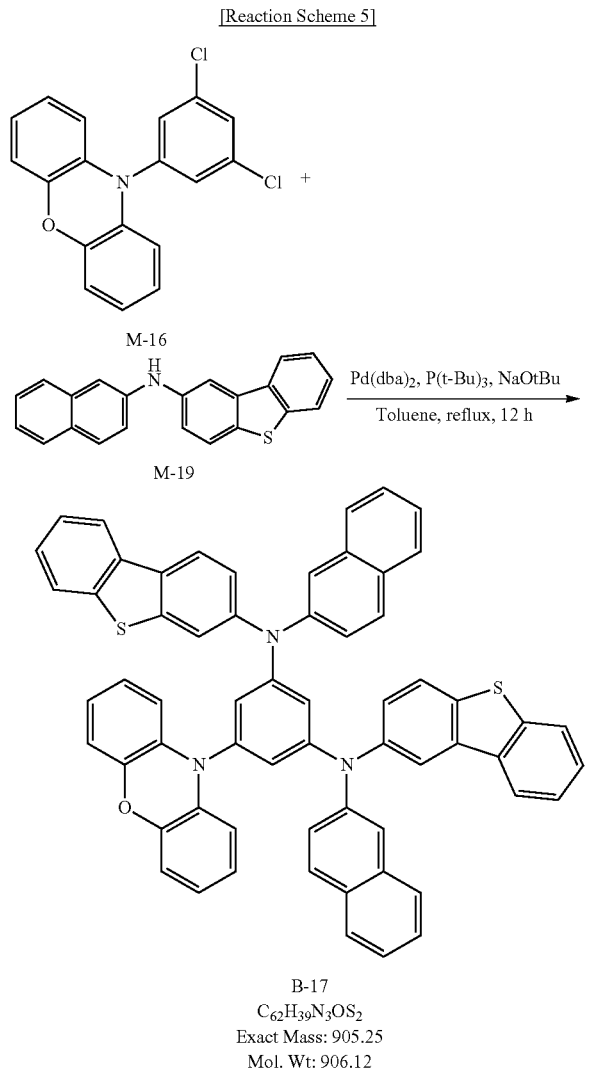

Example 6: Synthesis of Compound C-8

The compound C-8 was synthesized through the following Reaction Scheme 6.

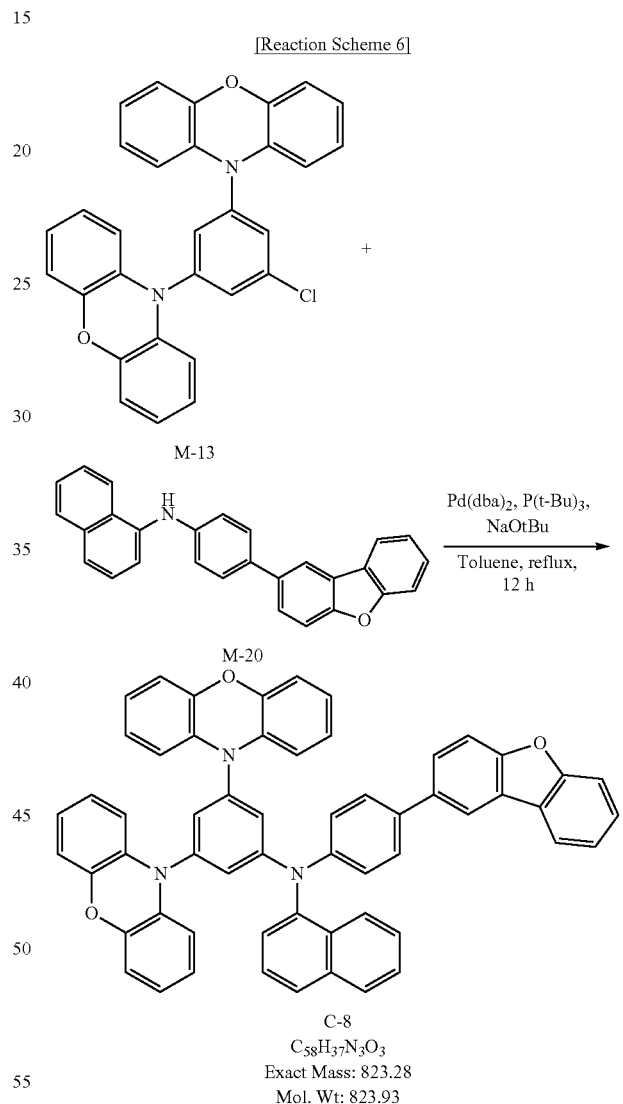

was dried with magnesium sulfate, filtered and concentrated under a reduced pressure. Then, a product therefrom was purified with n-hexane/dichloromethane (8:2 of a volume ratio) through silica gel column chromatography, obtaining 19.1 g of a target compound of a light yellow solid compound B-17 (a yield of 94%).

(Calculation value: 905.25 g/mol, Measurement value: M+=905.49 g/mol)

7.3 g (22.37 mmol) of the intermediate M-16, 14.6 g (44.74 mmol) of the intermediate M-19, and 6.4 g (67.11 mmol) of sodium t-butoxide were put in a round-bottomed flask and dissolved by adding 250 ml of toluene thereto. Then, 0.258 g (0.448 mmol) of Pd(dba)$_2$ and 0.182 g (0.896 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom 10.6 g (22.37 mmol) of the intermediate M-13, 8.6 g (22.37 mmol) of the intermediate M-20, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 17 g of a target compound of a white solid compound C-8 (a yield of 92%).

(Calculation value: 823.28 g/mol, Measurement value: M+=823.41 g/mol)

Example 7: Synthesis of Compound D-6

The compound D-6 was synthesized through the following Reaction Scheme 7.

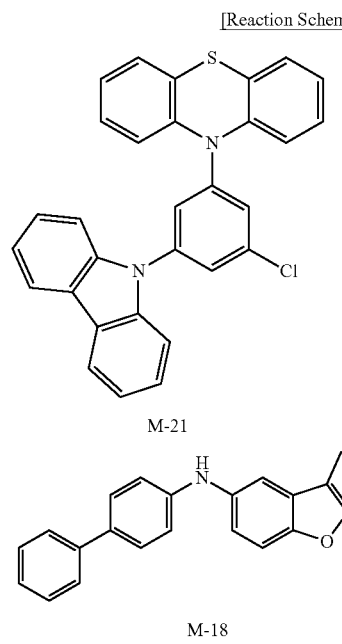

10.6 g (22.37 mmol) of the intermediate M-21, 7.5 g (22.37 mmol) of the intermediate M-18, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 16.1 g of a target compound of a light yellow solid compound D-6 (a yield of 93%).

(Calculation value: 773.25 g/mol, Measurement value: M+=773.51 g/mol)

Example 8: Synthesis of Compound E-25

The compound E-25 was synthesized through the following Reaction Scheme 8.

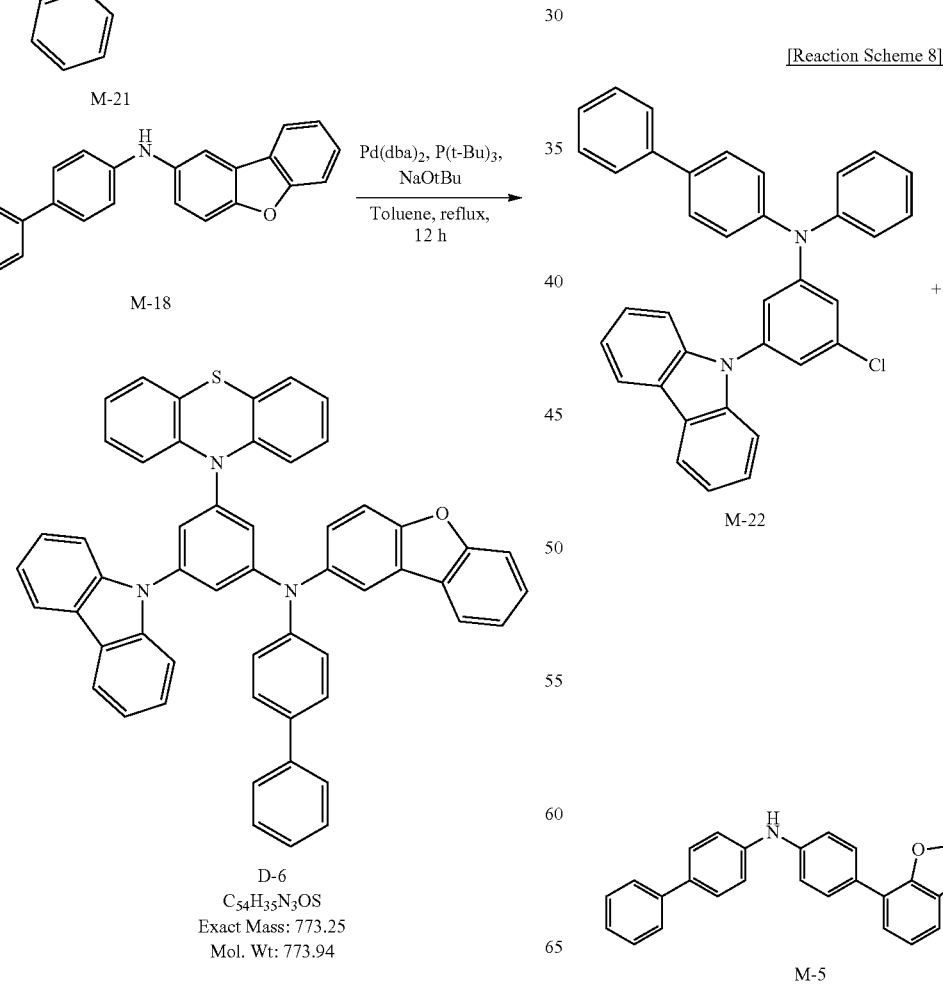

-continued

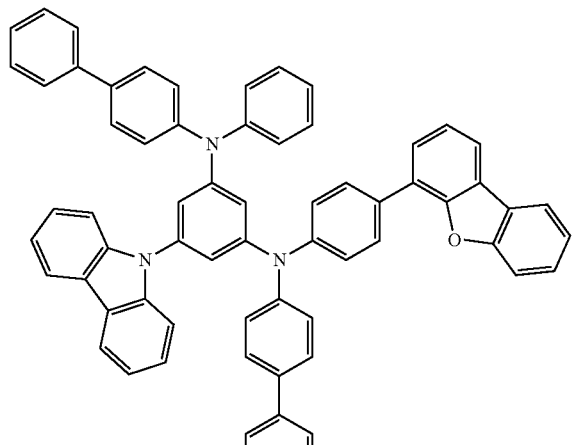

E-25
C$_{66}$H$_{45}$N$_3$O
Exact Mass: 895.36
Mol. Wt: 896.08

11.7 g (22.37 mmol) of the intermediate M-22, 9.2 g (22.37 mmol) of the intermediate M-5, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with toluene and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 18 g of a target compound of a white solid compound E-25 (a yield of 90%).

(Calculation value: 895.36 g/mol, Measurement value: M+=895.48 g/mol)

Example 9: Synthesis of Compound F-2

The compound F-2 was synthesized through the following Reaction Scheme 9.

[Reaction Scheme 9]

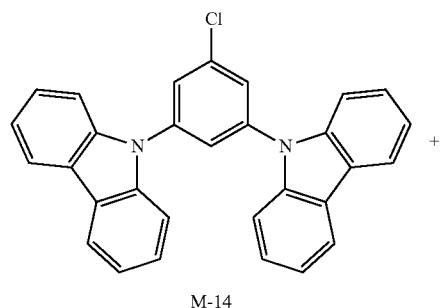

M-14

+

-continued

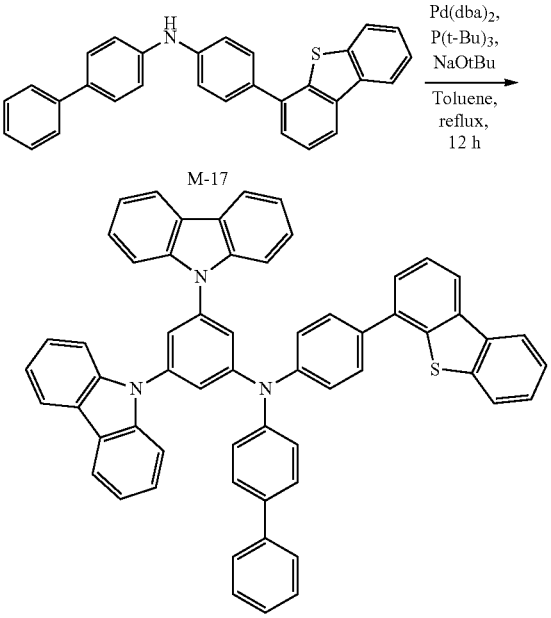

9.9 g (22.37 mmol) of the intermediate M-14, 9.6 g (22.37 mmol) of the intermediate M-17, and 3.2 g (33.56 mmol) of sodium t-butoxide were put in a round-bottomed flask and dissolved by adding 250 ml of toluene thereto. Then, 0.129 g (0.224 mmol) of Pd(dba)$_2$ and 0.091 g (0.448 mmol) of tri-tertiary-butylphosphine were sequentially added thereto, and the mixture was refluxed and agitated under a nitrogen atmosphere for 12 hours. When the reaction was complete, the resultant was extracted with ethylacetate and distilled water, and an organic layer obtained therefrom was dried with magnesium sulfate, filtered and concentrated under a reduced pressure. Then, a product therefrom was purified with n-hexane/dichloromethane (8:2 of a volume ratio) through silica gel column chromatography, obtaining 17.5 g of a target compound of a white solid compound F-2 (a yield of 94%).

(Calculation value: 833.29 g/mol, Measurement value: M+=833.42 g/mol)

(Analysis and Characteristics of Prepared Compound)

1) Measurement of Molecular Weight

The molecular weight of a compound was measured to analyze its structure by using LC-MS.

2) 1H-NMR Result Analysis

Figure 3:
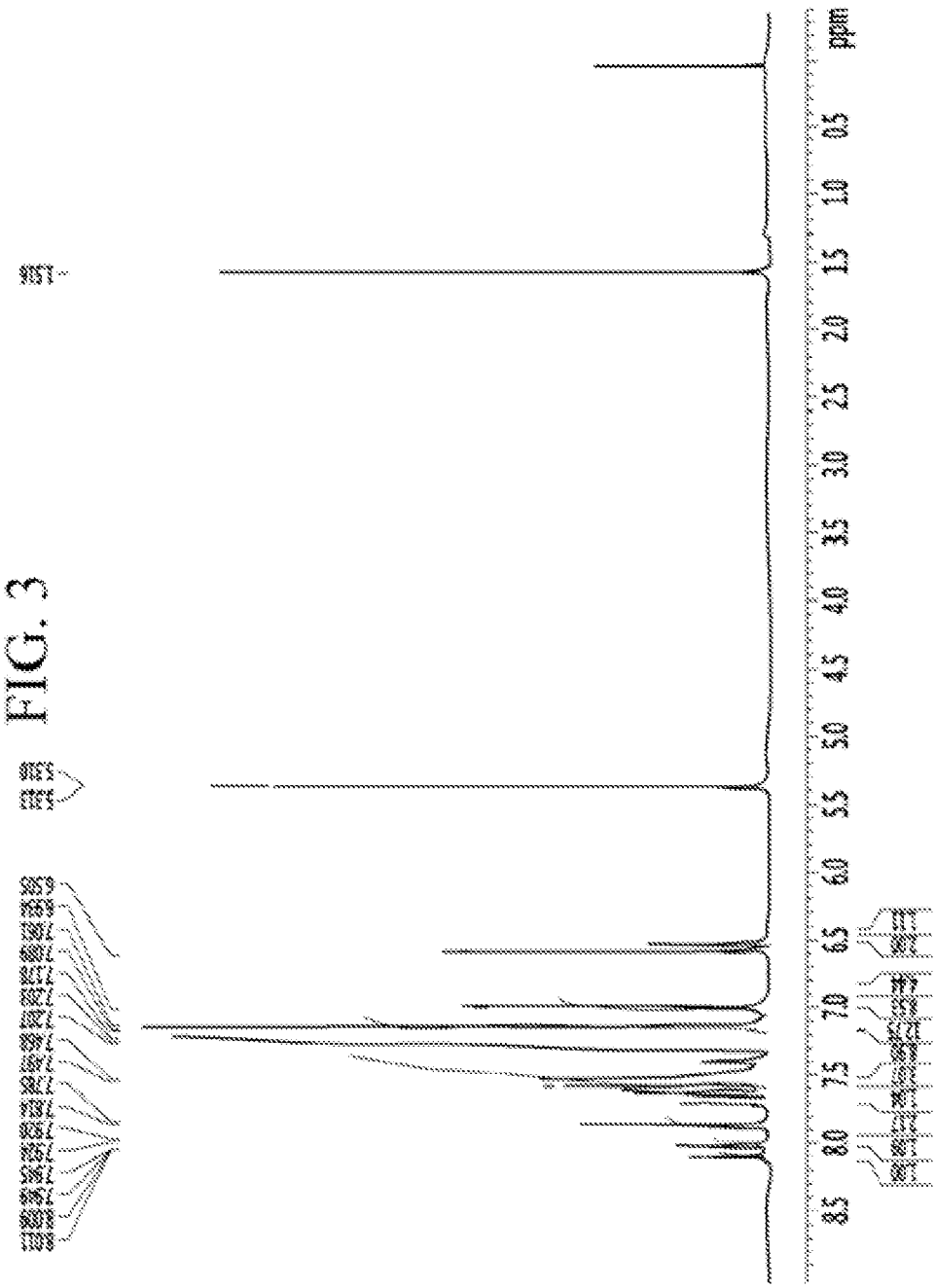
FIG. 3 shows an $^1$H-NMR result of a compound A-34 according to Example 1.

In order to analyse the structure of the compound, the compound according to Example 1 was dissolved in a CD2Cl2 solvent, and its 1H-NMR was measured by using a 300 MHz NMR equipment. The results are provided in FIG. 3.

3) Fluorescence Characteristic Analysis

Figure 4:
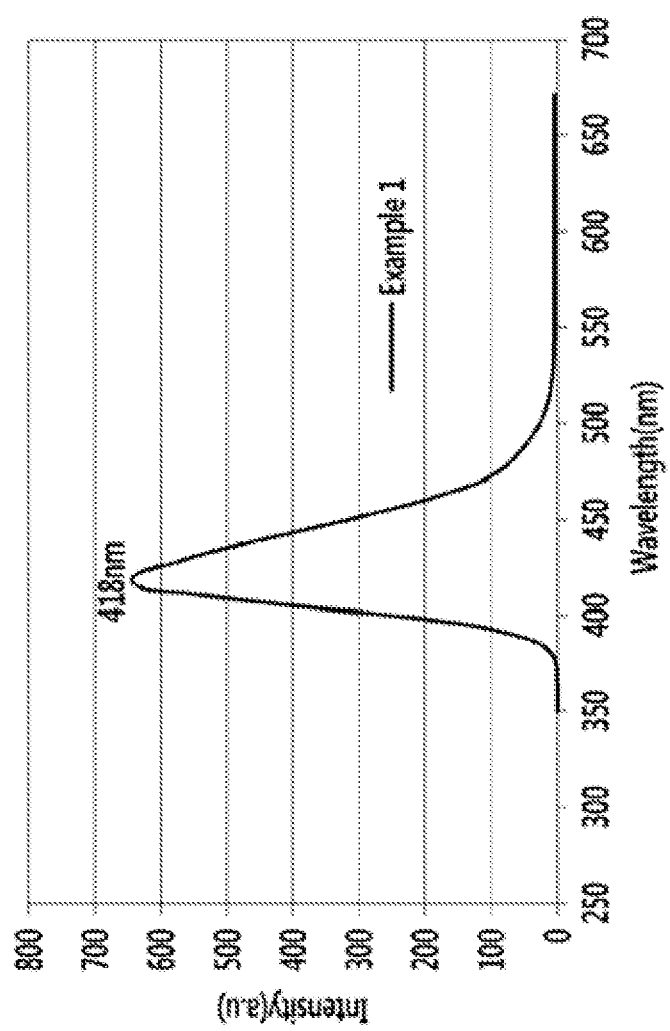
FIG. 4 shows a PL (photoluminescence) wavelength measurement result of the compound A-34 according to Example 1.

The compound according to Example 1 was dissolved in THF, and its PL (photoluminescence) wavelength was measured by using HITACHI F-4500 to analyse fluorescence characteristics. The result was provided in FIG. 4.

(Manufacture of Organic Light Emitting Diode)
Manufacture of Green Organic Light Emitting Element Example 10

A glass substrate coated with a 1500 Å-thick ITO (Indium tin oxide) thin film was cleaned with distilled water ultrasonic wave. Then, the substrate was ultrasonic wave-washed with a solvent such as isopropyl alcohol, acetone, methanol and the like solvent, dried, then, moved to a plasma cleaner, cleaned with oxygen plasma for 5 minutes and then, moved to a vacuum depositor. This ITO transparent electrode as used as an anode, and a 700 Å-thick hole injection and transport layer was formed on the ITO substrate by vacuum-depositing N,N'-di(1-naphthyl)-N,N'-diphenylbenzidine [NPB]. Subsequently, the compound A-34 according to Example 1 was vacuum-deposited to form a 100 Å-thick auxiliary hole transport layer (HTL). On the auxiliary hole transport layer (HTL), 300 Å-thick emission layer was formed by using (4,4'-N,N'-dicarbazole)biphenyl [CBP] as a host and doping it with 5 wt % of tri(2-phenylpyridine) iridium (III) [Ir(ppy)$_3$] as a dopant.

Then, A 50 Å-thick hole blocking layer was formed by vacuum-depositing biphenoxy-bis(8-hydroxyquinoline)aluminum [Balq] on the emission layer. On the hole blocking layer, a 250 Å-thick electron transport layer (ETL) was formed by vacuum-depositing tris(8-hydroxyquinoline)aluminum [Alq$_3$], and on the electron transport layer (ETL), a cathode was formed by sequentially vacuum-depositing LiF to be 10 Å thick and Al to be 100 Å thick, manufacturing an organic light emitting element.

The organic light emitting element had a five organic thin layered structure and specifically, a structure of Al 1000 Å/LiF 10 Å/Alq$_3$ 250 Å/Balq 50 Å/EML. [CBP:Ir(ppy)$_3$=95:5] 300 Å/A-34 100 Å/NPB 700 Å/ITO 1500 Å.

Example 11

An organic light emitting element was manufactured according to the same method as Example 10 except for using the compound A-104 according to Example 2 instead of the compound A-34 according to Example 1.

Example 12

An organic light emitting element was manufactured according to the same method as Example 10 except for using the compound A-201 according to Example 3 instead of the compound A-34 according to Example 1.

Example 13

An organic light emitting element was manufactured according to the same method as Example 10 except for using the compound D-6 according to Example 7 instead of the compound A-34 according to Example 1.

Example 14

An organic light emitting element was manufactured according to the same method as Example 10 except for using the compound E-25 according to Example 8 instead of the compound A-34 according to Example 1.

Example 15

An organic light emitting element was manufactured according to the same method as Example 10 except for using the compound F-2 according to Example 9 instead of the compound A-34 according to Example 1.

Comparative Example 1

An organic light emitting element was manufactured according to the same method as Example 10 except for using N,N'-di(1-naphthyl)-N,N'-diphenylbenzidine [NPB] instead of the compound A-34 according to Example 1.

Comparative Example 2

An organic light emitting element was manufactured according to the same method as Example 10 except for using TDAB instead of the compound A-34 according to Example 1.

Manufacture of Red Organic Light Emitting Diode

Example 16

A glass substrate coated with 1500 Å-thick ITO (Indium tin oxide) thin film was cleaned with distilled water ultrasonic wave. After washing with distilled water, the substrate was ultrasonic wave-cleaned with a solvent such as isopropyl alcohol, acetone, methanol and the like, dried, moved to a plasma cleaner, cleaned for 5 minutes by using oxygen plasma and then, moved to a vacuum depositor. This ITO transparent electrode was used as an anode, a 600 Å-thick hole injection layer (HIL) was formed by vacuum-depositing 4,4'-bis[N-[4-{N,N-bis(3-methylphenyl)amino}-phenyl]-N-phenylamino]biphenyl [DNTPD] on the ITO substrate. Subsequently, a 200 Å-thick hole transport layer (HTL) was formed by vacuum-depositing N,N'-di(1-naphthyl)-N,N'-diphenylbenzidine [NPB]. On the hole transport layer (HTL), a 100 Å-thick auxiliary hole transport layer (HTL) was formed by vacuum-depositing the compound A-34 according to Example 1. On the auxiliary hole transport layer (HTL), a 300 Å-thick emission layer was formed by using (4,4'-N,N'-dicarbazole)biphenyl [CBP] as a host and doping it with 7 wt % of bis(2-phenylquinoline) (acetylacetonate)iridium(III) [Ir(pq)$_2$acac] as a dopant.

Then, on the emission layer, a 50 Å-thick hole blocking layer was formed by vacuum-depositing biphenoxy-bis(8-hydroxyquinoline)aluminum [Balq]. On the hole blocking layer, a 250 Å-thick electron transport layer (ETL) was formed by vacuum-depositing tris(8-hydroxyquinoline)aluminum [Alq$_3$], and a cathode was formed on the electron transport layer (ETL) by sequentially vacuum-depositing LiF to be 10 Å thick and Al to be 100 Å-thick, manufacturing an organic light emitting element.

The organic light emitting element had a six organic thin layered structure and specifically, a structure of Al 1000 Å/LiF 10 Å/Alq$_3$ 250 Å/Balq 50 Å/EML[CBP: Ir (pq)$_2$acac=93:7] 300 Å/A-34 100 Å/NPB 700 Å/DNTPD 600 Å/ITO 1500 Å.

Example 17

An organic light element was manufactured according to the same method as Example 16 except for using the compound A-104 according to Example 2 instead of the compound A-34 according to Example 1.

Example 18

An organic light element was manufactured according to the same method as Example 16 except for using the compound A-88 according to Example 4 instead of the compound A-34 according to Example 1.

Example 19

An organic light element was manufactured according to the same method as Example 16 except for using the compound B-17 according to Example 5 instead of the compound A-34 according to Example 1.

Example 20

An organic light element was manufactured according to the same method as Example 16 except for using the compound C-8 according to Example 6 instead of the compound A-34 according to Example 1.

Example 21

An organic light element was manufactured according to the same method as Example 16 except for using the compound E-25 according to Example 8 instead of the compound A-34 according to Example 1.

Example 22

An organic light element was manufactured according to the same method as Example 16 except for using the compound F-2 according to Example 9 instead of the compound A-34 according to Example 1.

Comparative Example 3

An organic light element was manufactured according to the same method as Example 16 except for using N,N'-di(1-naphthyl)-N,N'-diphenylbenzidine [NPB] instead of the compound A-34 according to Example 1.

Comparative Example 4

An organic light emitting element was manufactured according to the same method as Example 16 except for using TDAB instead of the compound A-34 according to Example 1.

The DNTPD, NPB, TDAB, CBP, Balq, Alq3, Ir(ppy)3, Ir(pq)2acac respectively used for the organic light emitting elements had the following structures.

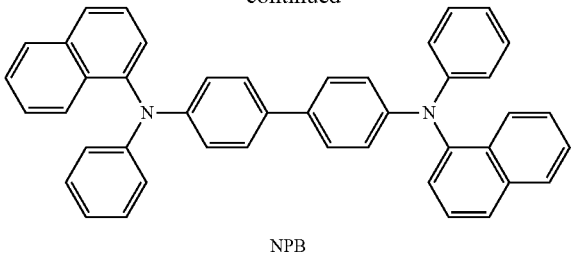

NPB

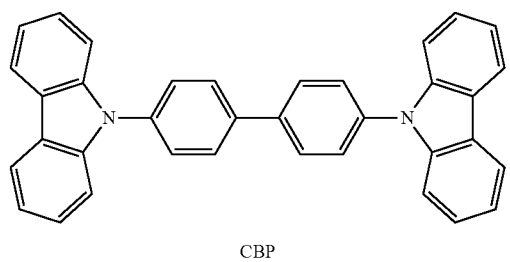

CBP

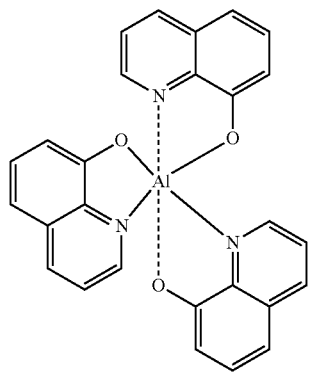

Alq3

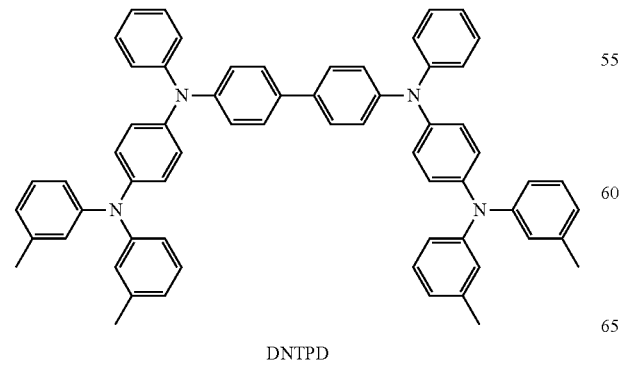

DNTPD

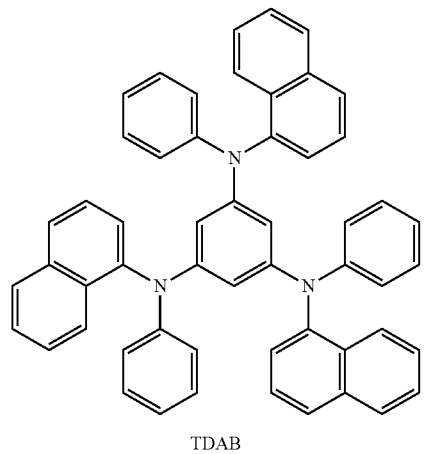

TDAB

-continued

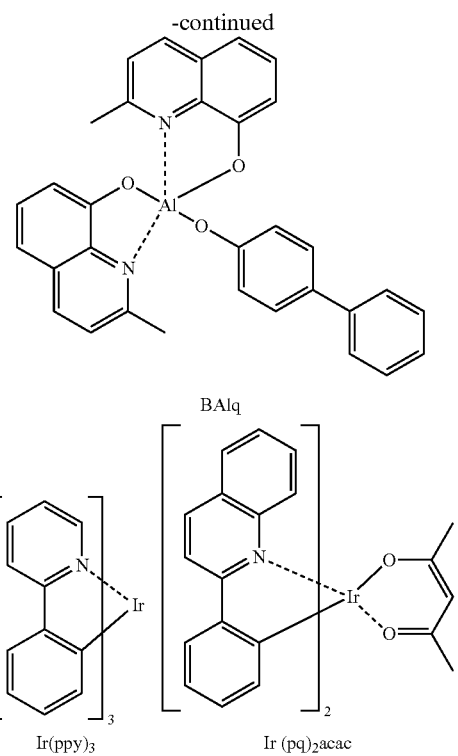

BAlq

Ir(ppy)₃   Ir (pq)₂acac (Performance Measurement of Organic Light Emitting Element)

Current density and luminance changes depending on a voltage and luminous efficiency of each organic light emitting element according to Examples 10 to 22 and Comparative Examples 1 to 4 were measured. The measurements were specifically performed in the following method, and the results were provided in the following Tables 2 and 3.

(1) Measurement of Current Density Change Depending on Voltage Change

The obtained organic light emitting elements were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting elements was increased from 0 V to 10 V.

(3) Measurement of Luminous Efficiency

Current efficiency (cd/A) and power efficiency (lm/W) at the same luminance (cd/m²) were calculated by using the luminance, current density, and voltages (V) from the items (1) and (2).

(4) Life-span

Half-life life-spans of the organic light emitting elements were measured as a time when their luminance decreased down to ½ relative to the initial luminance (cd/m²) after emitting the green organic light emitting elements of Examples 10 to 15, Comparative Example 1 and Comparative Example 2 at 3,000 nit as the initial luminance (cd/m²) and T80 life-spans of the organic light emitting elements were measured as a time when their luminance decreased down to 80% relative to the initial luminance (cd/m²) after emitting the red organic light emitting elements of Examples 16 to 22, Comparative Example 3 and Comparative Example 4 at 1,000 nit as the initial luminance (cd-m²), and measuring their luminance decrease depending on time with a Polanonix life-span measurement system.

TABLE 2

| Devices | Hole transport layer (HTL) | Auxiliary hole transport layer (HTL) | Driving voltage (V) | Luminous efficiency (cd/A) | EL peak (nm) | Half life-span (h) @3000 nit |
|---|---|---|---|---|---|---|
| Example 10 | NPB | A-34 | 7.1 | 37.5 | 516 | 240 |
| Example 11 | NPB | A-104 | 6.9 | 39.1 | 516 | 249 |
| Example 12 | NPB | A-201 | 7.2 | 38.8 | 516 | 249 |
| Example 13 | NPB | D-16 | 7.0 | 35.1 | 516 | 221 |
| Example 14 | NPB | E-25 | 7.1 | 39.6 | 516 | 261 |
| Example 15 | NPB | F-2 | 7.4 | 40.3 | 516 | 253 |
| Comparative Example 1 | NPB | NPB | 8.2 | 25.8 | 516 | 175 |
| Comparative Example 2 | NPB | TDAB | 8.1 | 24.1 | 516 | 169 |

(Driving Voltage and Luminous Efficiency are Measured at 1,000 nit)

Referring to the result of [Table 2], the organic light emitting elements according to Examples 10 to 15 using an auxiliary hole transport layer (HTL) formed of the compound according to the present invention showed improved luminous efficiency and life-span compared with the green phosphorescent organic light emitting element using no auxiliary hole transport layer (HTL) according to Comparative Example 1. In particular, the organic light emitting element according to an exemplary embodiment of the present invention showed at least 36% and at most 56% increased luminous efficiency compared with the one according to Comparative Example 1 and also, at least 31% to at most 54% increased life-span compared with the one using conventionally-known TDAB as an auxiliary hole transport layer (HTL) according to Comparative Example 2 and thus, turned out to be sufficiently commercialized, considering that life-span, of an organic light emitting element is the most important factor for the commercialization.

TABLE 3

| Devices | Hole transport layer (HTL) | Auxiliary hole transport layer (HTL) | Driving voltage (V) | Luminous efficiency (cd/A) | EL peak (nm) | T80 life-span (h) @1000 nit |
|---|---|---|---|---|---|---|
| Example 16 | NPB | A-34 | 8.3 | 18.6 | 600 | 845 |
| Example 17 | NPB | A-104 | 8.0 | 18.4 | 600 | 867 |
| Example 18 | NPB | A-88 | 8.2 | 17.5 | 600 | 855 |
| Example 19 | NPB | B-17 | 7.8 | 18.7 | 600 | 800 |
| Example 20 | NPB | C-8 | 8.2 | 17.3 | 600 | 835 |
| Example 21 | NPB | E-25 | 8.1 | 18.9 | 600 | 872 |
| Example 22 | NPB | F-2 | 8.3 | 18.5 | 600 | 880 |

TABLE 3-continued

| Devices | Hole transport layer (HTL) | Auxiliary hole transport layer (HTL) | Driving voltage (V) | Luminous efficiency (cd/A) | EL peak (nm) | T80life-span (h) @1000 nit |
|---|---|---|---|---|---|---|
| Comparative Example 3 | NPB | NPB | 8.7 | 15.1 | 600 | 720 |
| Comparative Example 4 | NPB | TDAB | 8.5 | 16.0 | 600 | 630 |

(Driving Voltage and Luminous Efficiency are Measured at 1,000 nit)

Referring to the result of [Table 3], the organic light emitting elements using the compound of the present invention as an auxiliary hole transport layer (HTL) according to Examples 16 to 22 showed improved luminous efficiency and life-span compared with the red phosphorescent organic light emitting element using no auxiliary hole transport layer (HTL) according to Comparative Example 3. Particularly, exemplary embodiments of the present invention largely improved luminous efficiency by at least 14% to at most 25% compared with Comparative Example 3 and also, increased luminous efficiency by at least 8% to at most 18% and a life-span by at least 27% to at most 40% compared with Comparative Example 4 using TDAB as an auxiliary hole transport layer (HTL) but decreased a driving voltage and thus, generally improved main characteristics of a red phosphorescent diode. Considering that life-span of a diode is the most important factor for the commercialization, the results of the exemplary embodiments turned out to be sufficient for the commercialization.

While this invention has been described in connection with what is presently considered to be practical exemplary embodiments, it is so be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

What is claimed is:

1. A compound represented by Chemical Formula 1:

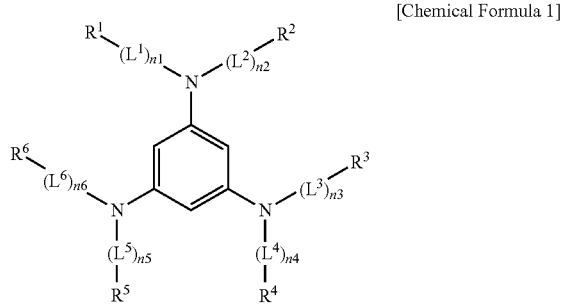

[Chemical Formula 1]

wherein, in Chemical Formula 1,
L$^1$ to L$^6$ are each independently a substituted or unsubstituted C6 to C30 arylene group, or a substituted or unsubstituted C2 to C30 heteroarylene group except a substituted or unsubstituted fluorenylene group,
n1 to n6 are each independently integers ranging from 0 to 3,
R$^1$ to R$^6$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group,
provided that one of n1 to n6 is an integer of 1 to 3, and the one of R$^1$ to R$^6$ that corresponds to the one of n1 to n6 is a substituent represented by Chemical Formula 2,

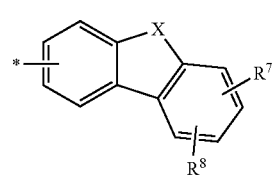

[Chemical Formula 2]

wherein, in Chemical Formula 2,
X is O or S,
R$^7$ or R$^8$ are selected from hydrogen, deuterium, a substituted or unsubstituted C1 to C30 alkyl group, a substituted or unsubstituted C6 to C30 aryl group and a substituted or unsubstituted C2 to C30 heteroaryl group,
* indicates a point where the substituent is linked to a carbon atom or an atom except carbon,
R$^1$ and R$^2$ are independently present or are linked to each other to form a condensed ring,
R$^3$ and R$^4$ are independently present or are linked to each other to form a condensed ring,
R$^5$ and R$^6$ are independently present or are linked to each other to form a condensed ring, and
when one of R$^1$ to R$^6$ is a substituted or unsubstituted fluorenyl group, the substituted or unsubstituted fluorenyl group is not directly bonded with the "N" of Chemical Formula 1.

2. The compound of claim 1, wherein Chemical Formula 1 is represented by one of Chemical Formulae 9 to 14:

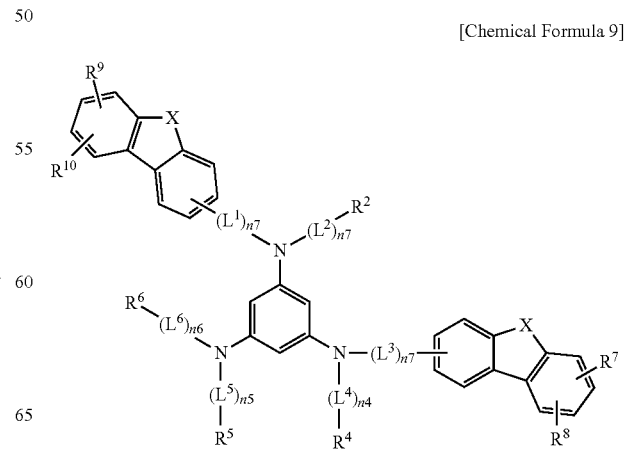

[Chemical Formula 9]

-continued

[Chemical Formula 10]

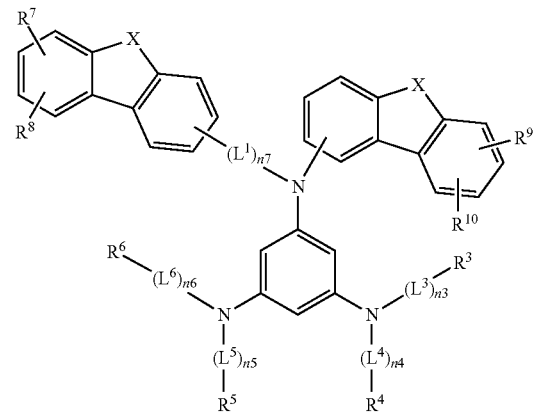

[Chemical Formula 11]

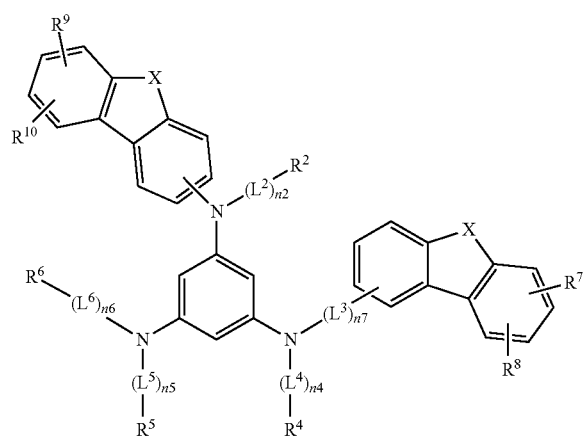

[Chemical Formula 12]

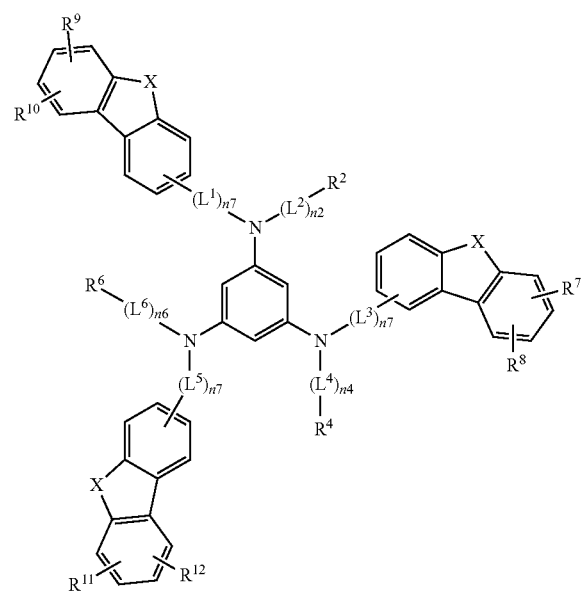

-continued

[Chemical Formula 13]

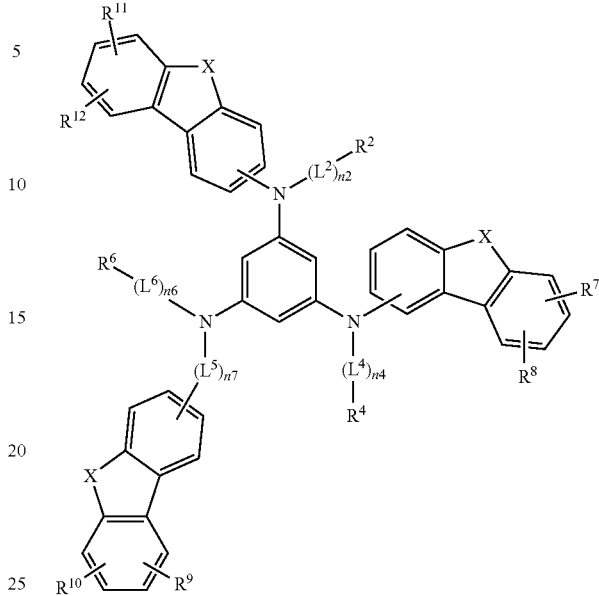

[Chemical Formula 14]

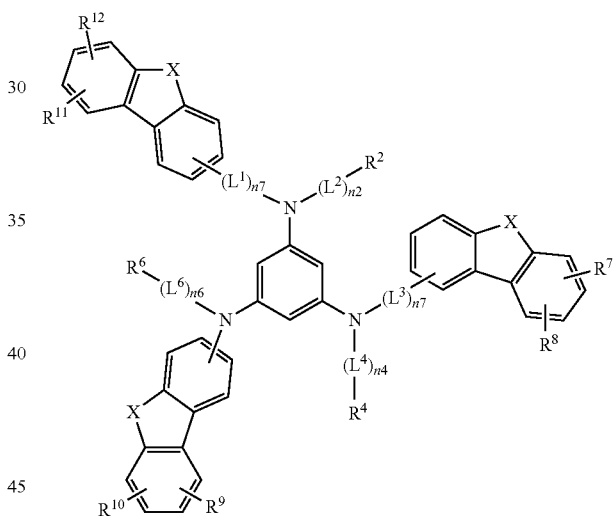

wherein, in Chemical Formulae 9 to 14, $L^1$ to $L^6$ are each independently a substituted or unsubstituted C6 to C30 arylene group, or a substituted or unsubstituted C2 to C30 heteroarylene group except a substituted or unsubstituted fluorenylene group, n2 to n6 are each independently integers ranging from 0 to 3, n7 is an integer of 1 to 3, $R^2$ to $R^6$ are each independently selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, and a substituted or unsubstituted silyl group, X is O or S, $R^7$ to $R^{12}$ are independently selected from hydrogen, deuterium, a substituted or unsubstituted C1 to C30 alkyl group, a substituted or unsubstituted C6 to C30 aryl group and a substituted or unsubstituted C2 to C30 heteroaryl group, and when one of $R^2$ to $R^6$ is a substituted or unsubstituted fluorenyl group, the substituted or unsubstituted fluorenyl group is not directly bonded with the "N" of Chemical Formula 1.

3. The compound of claim 1, wherein Chemical Formula 1 is represented by one of Chemical Formulae 15 and 18:

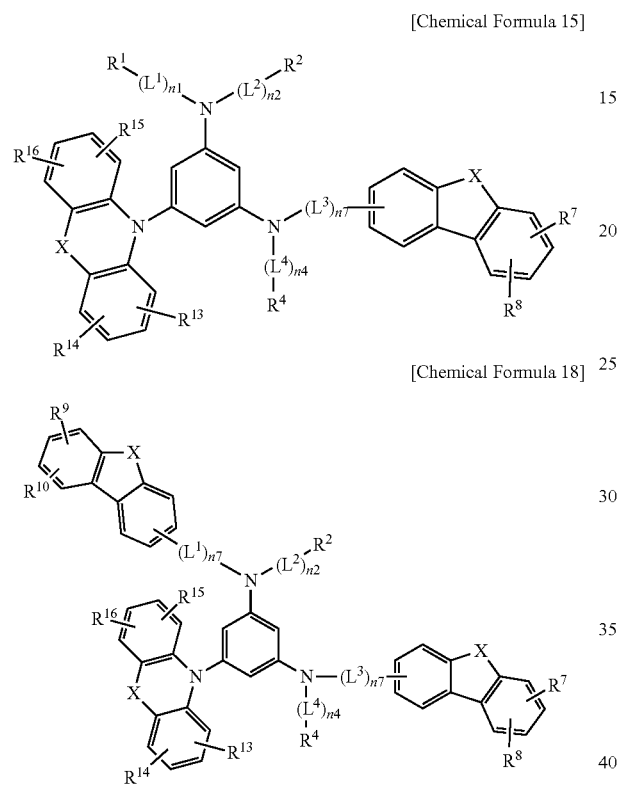

[Chemical Formula 15]

[Chemical Formula 18]

wherein, in Chemical Formulae 15 and 18, $L^1$ to $L^4$ are each independently a substituted or unsubstituted C6 to C30 arylene group, or a substituted or unsubstituted C2 to C30 heteroarylene group except a substituted or unsubstituted fluorenylene group, n1, n2, and n4 are each independently integers ranging from 0 to 3, n7 is an integer of 1 to 3, $R^1$, $R^2$ and $R^4$ are each independently selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group and a substituted or unsubstituted silyl group, X is O or S, $R^7$ to $R^{10}$ and $R^{13}$ to $R^{16}$ are independently selected from hydrogen, deuterium, a substituted or unsubstituted C1 to C30 alkyl group, a substituted or unsubstituted C6 to C30 aryl group and a substituted or unsubstituted C2 to C30 heteroaryl group, and when one of $R^1$, $R^2$ and $R^4$ is a substituted or unsubstituted fluorenyl group, the substituted or unsubstituted fluorenyl group is not directly bonded with the "N" of Chemical Formula 1.

4. The compound of claim 1, wherein Chemical Formula 1 is represented by one of Chemical Formulae 19 to 21:

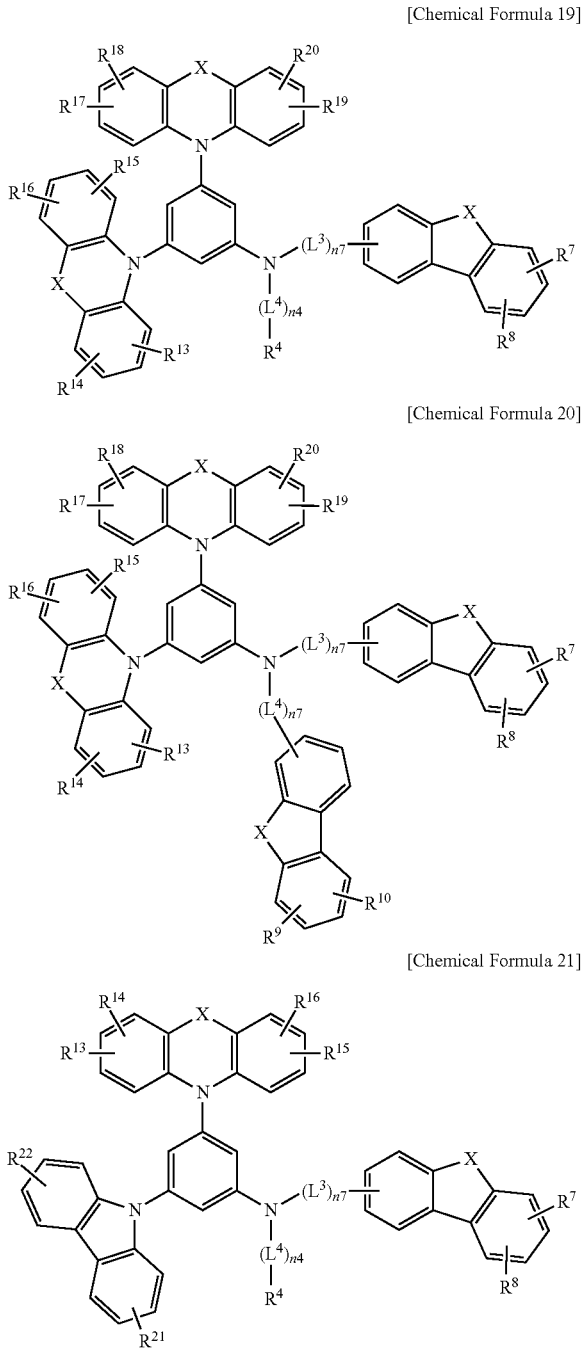

[Chemical Formula 19]

[Chemical Formula 20]

[Chemical Formula 21]

wherein, in Chemical Formulae 19 to 21, $L^3$ and $L^4$ are each independently a substituted or unsubstituted C6 to C30 arylene group, or a substituted or unsubstituted C2 to C30 heteroarylene group except a substituted or unsubstituted fluorenylene group, n4 is an integer of 0 to 3, n7 is an integer of 1 to 3, $R^4$ is selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group and a substituted or unsubstituted silyl group, X is O or S, $R^7$ to $R^{10}$ and $R^{13}$ to $R^{22}$ are independently selected from hydrogen, deuterium, a substituted or unsubstituted C1 to C30 alkyl group, a substituted or unsubstituted C6 to C30 aryl group and a substituted or unsubstituted C2 to C30 heteroaryl group, and when $R^4$ is a substituted or unsubstituted fluorenyl group, the substituted or unsubstituted fluorenyl group is not directly bonded with the "N" of Chemical Formula 1.

5. The compound of claim 1, wherein Chemical Formula 1 is represented by one of Chemical Formulae 22, 24, and 25:

[Chemical Formula 22]

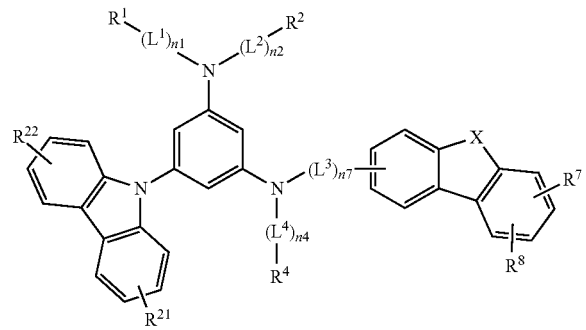

[Chemical Formula 24]

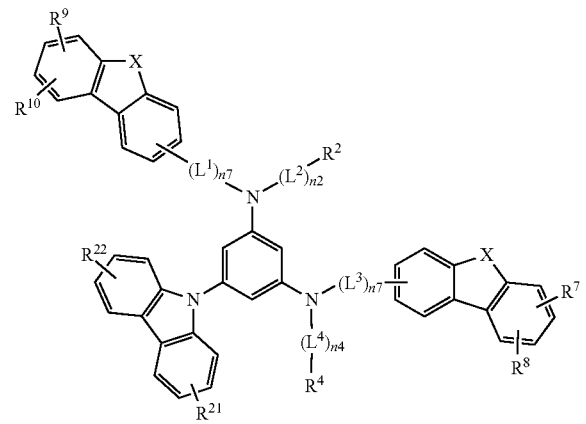

[Chemical Formula 25]

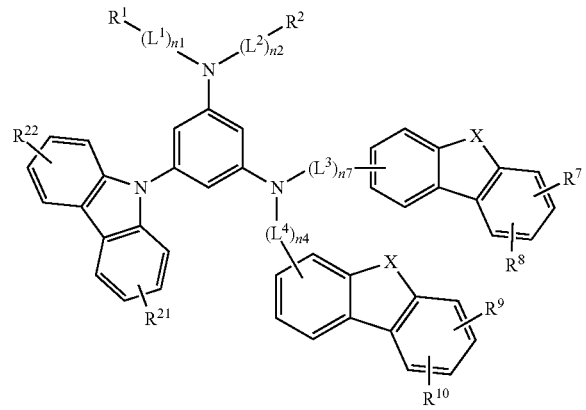

wherein, in Chemical Formulae 22, 24, and 25, $L^1$ to $L^4$ are each independently a substituted or unsubstituted C6 to C30 arylene group, or a substituted or unsubstituted C2 to C30 heteroarylene group except a substituted or unsubstituted fluorenylene group, n1, n2 and n4 are integers of 0 to 3, n7 is an integer of 1 to 3, $R^1$, $R^2$ and $R^4$ are selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group and a substituted or unsubstituted silyl group, X is O or S, $R^7$ to $R^{10}$, $R^{21}$ and $R^{22}$ are independently selected from hydrogen, deuterium, a substituted or unsubstituted C1 to C30 alkyl group, a substituted or unsubstituted C6 to C30 aryl group and a substituted or unsubstituted C2 to C30 heteroaryl group, and when one of $R^1$, $R^2$ and $R^4$ is a substituted or unsubstituted fluorenyl group, the substituted or unsubstituted fluorenyl group is not directly bonded with the "N" of Chemical Formula 1.

6. The compound of claim 1, wherein Chemical Formula 1 is represented by one of Chemical Formulae 27 and 28:

[Chemical Formula 27]

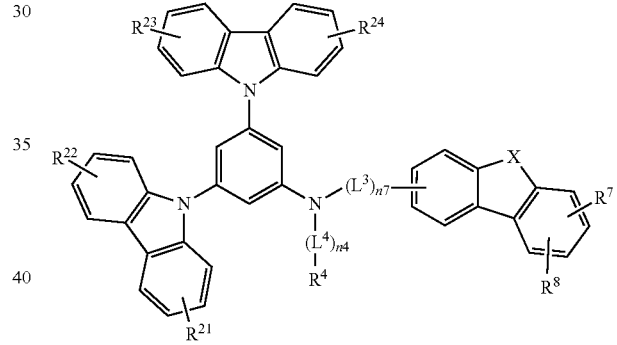

[Chemical Formula 28]

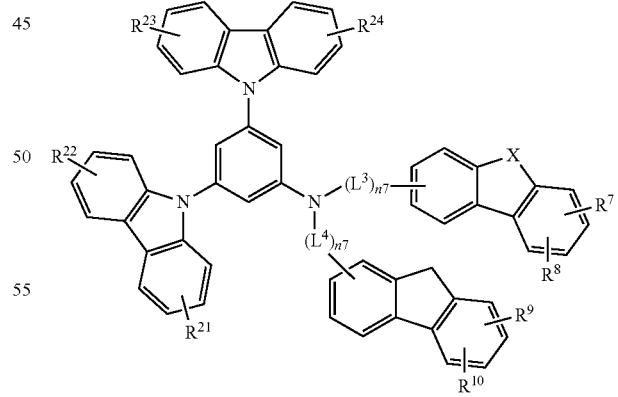

wherein, in Chemical Formulae 27 and 28, $L^3$ and $L^4$ are each independently a substituted or unsubstituted C6 to C30 arylene group, or a substituted or unsubstituted C2 to C30 heteroarylene group except a substituted or unsubstituted fluorenylene group, n4 is an integer of 0 to 3, n7 is an integer of 1 to 3, $R^4$ is selected from hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group and a substituted or unsubstituted silyl group, X is O or S, $R^7$ to $R^{10}$ and $R^{21}$ to $R^{24}$ are independently selected from hydrogen, deuterium, a substituted or unsubstituted C1 to C30 alkyl group, a substituted or unsubstituted C6 to C30 aryl group and a substituted or unsubstituted C2 to C30 heteroaryl group, and when $R^4$ is a substituted or unsubstituted fluorenyl group, the substituted or unsubstituted fluorenyl group is not directly bonded with the "N" of Chemical Formula 1.

7. The compound of claim 2, wherein $L^1$ and $L^3$ of Chemical Formula 9; $L^1$ of Chemical Formula 10; $L^3$ of Chemical Formula 11; $L^1$, $L^3$ and $L^5$ of Chemical Formula 12; $L^5$ of Chemical Formula 13; and $L^1$ and $L^3$ of Chemical Formula 14 are each independently a substituted or unsubstituted C6 to C30 arylene group, or a substituted or unsubstituted C2 to C30 heteroarylene group except a substituted or unsubstituted fluorenylene group.

8. The compound of claim 3, wherein $L^3$ of Chemical Formula 15, $L^1$ and $L^3$ of Chemical Formula 18 are each independently a substituted or unsubstituted C6 to C30 arylene group, or a substituted or unsubstituted C2 to C30 heteroarylene group except a substituted or unsubstituted fluorenylene group.

9. The compound of claim 4, wherein $L^3$ of Chemical Formula 19, $L^3$ and $L^4$ of Chemical Formula 20, $L^3$ of Chemical Formula 21 are each independently a substituted or unsubstituted C6 to C30 arylene group, or a substituted or unsubstituted C2 to C30 heteroarylene group except a substituted or unsubstituted fluorenylene group.

10. The compound of claim 5, wherein $L^3$ of Chemical Formula 22, $L^1$ and $L^3$ of Chemical Formula 24, $L^3$ and $L^4$ of Chemical Formula 25 are each independently a substituted or unsubstituted C6 to C30 arylene group, or a substituted or unsubstituted C2 to C30 heteroarylene group except a substituted or unsubstituted fluorenylene group.

11. The compound of claim 6, wherein $L^3$ of Chemical Formula 27 and $L^3$ and $L^4$ of Chemical Formula 28 are each independently a substituted or unsubstituted C6 to C30 arylene group, or a substituted or unsubstituted C2 to C30 heteroarylene group except a substituted or unsubstituted fluorenylene group.

12. The compound of claim 1, wherein:
at least one of n1 to n6 is an integer of 1 to 3, and
the $L^1$ to $L^6$ are each independently a substituted or unsubstituted C6 to C30 arylene group except a substituted or unsubstituted fluorenylene group.

13. The compound of claim 1, wherein the $R^1$ to $R^6$ are each independently hydrogen, or a substituted or unsubstituted C6 to C30 aryl group, wherein when the aryl group is a fluorenyl group, the fluorenyl group is not directly bonded with the "N" of Chemical Formula 1.

14. The compound of claim 1, wherein Chemical Formula 1 is represented by one of the following compounds

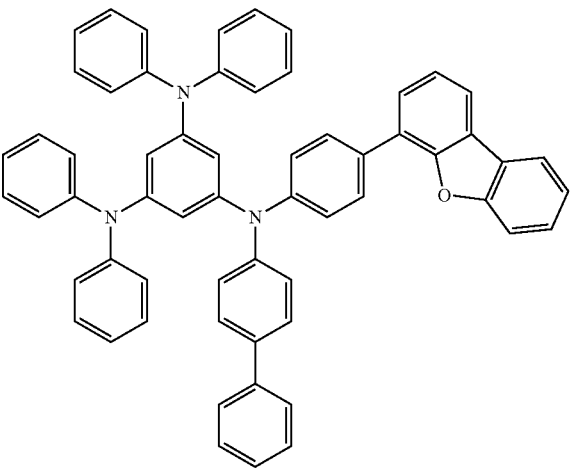
[A-34]

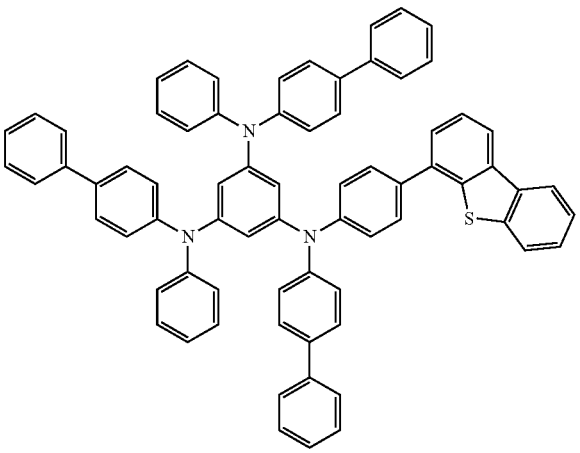
[A-38]

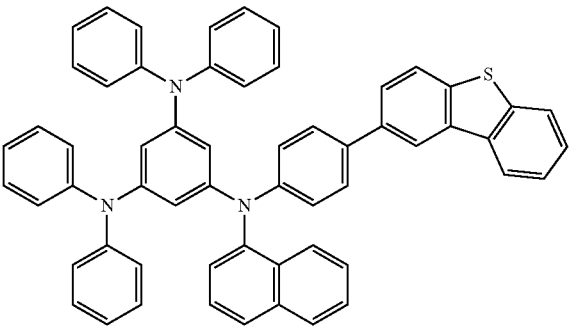
[A-88]

[A-104]
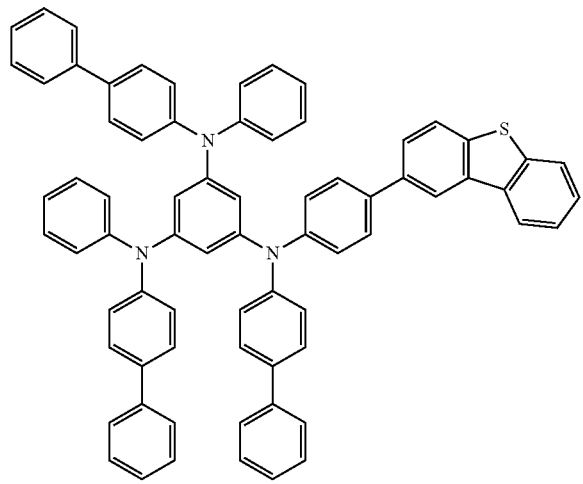
[A-209]
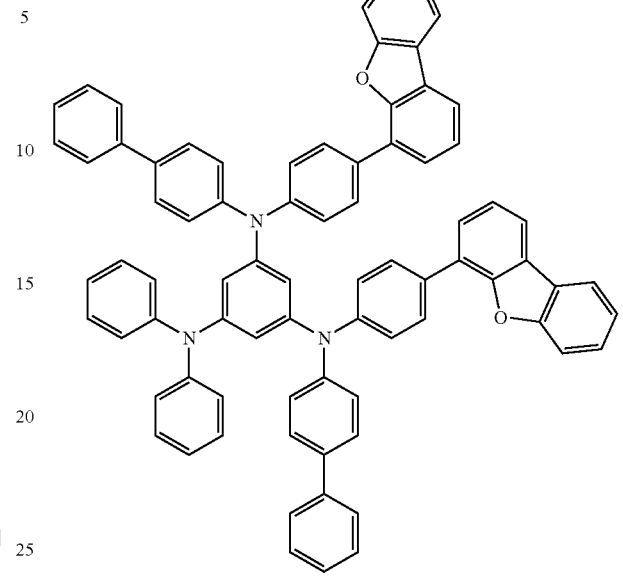
[A-201]
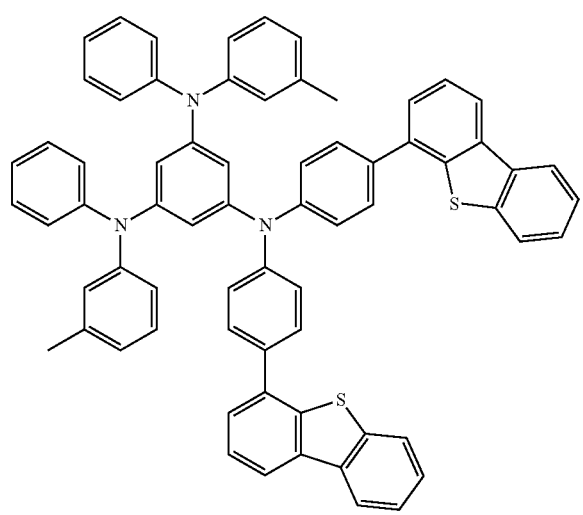
[A-251]
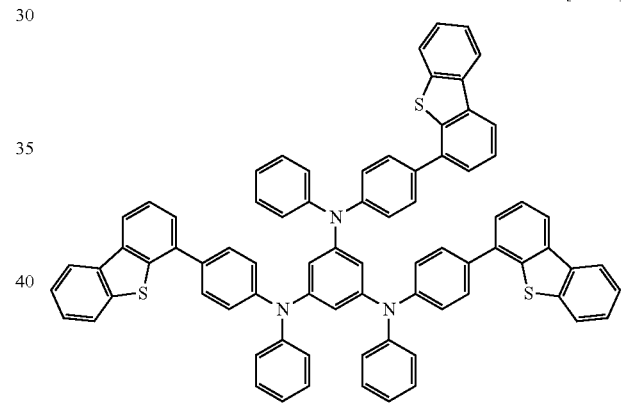
[A-203]
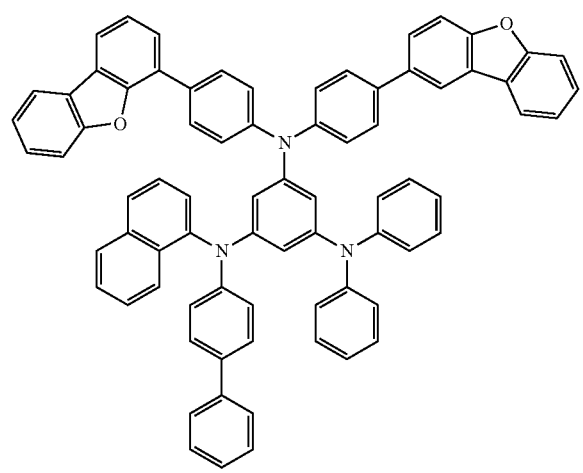
[B-3]
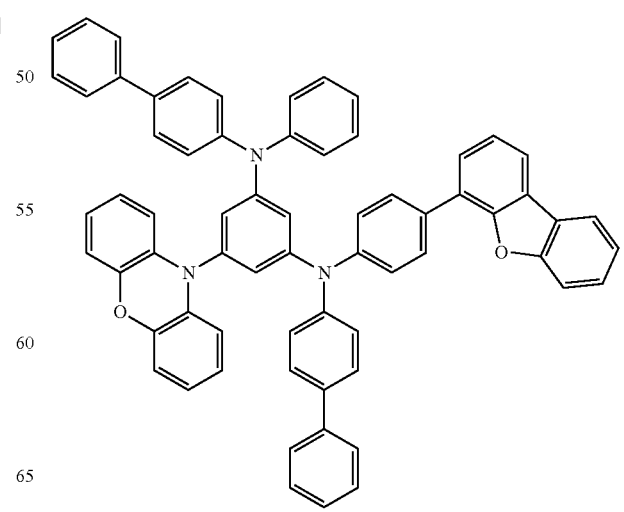

[C-4]
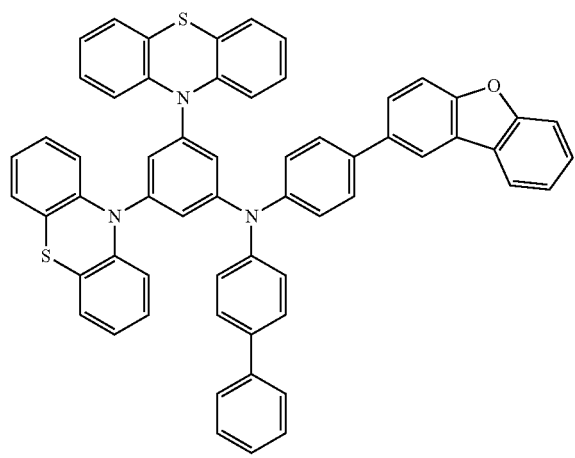
[C-8]
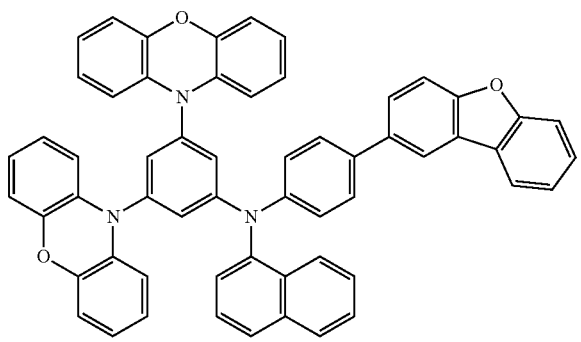
[C-9]
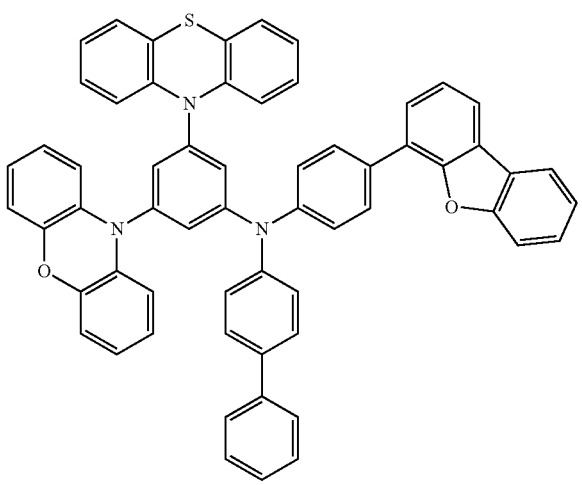
[D-3]
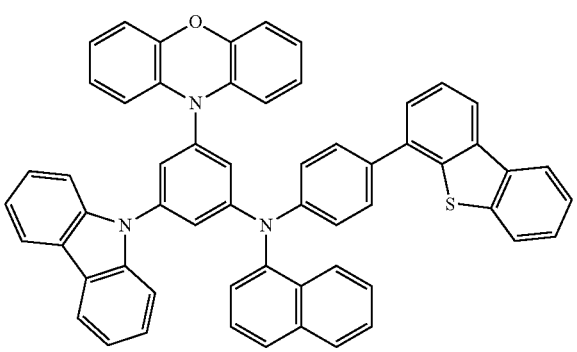
[E-8]
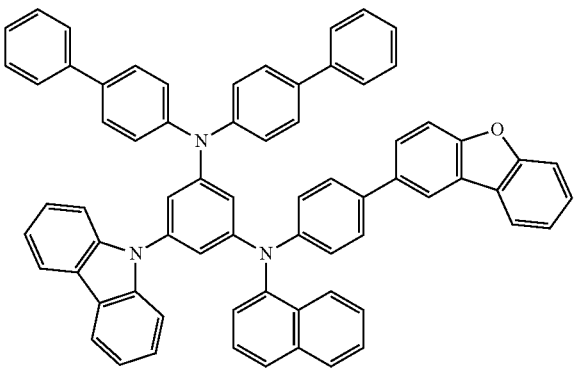
[E-17]
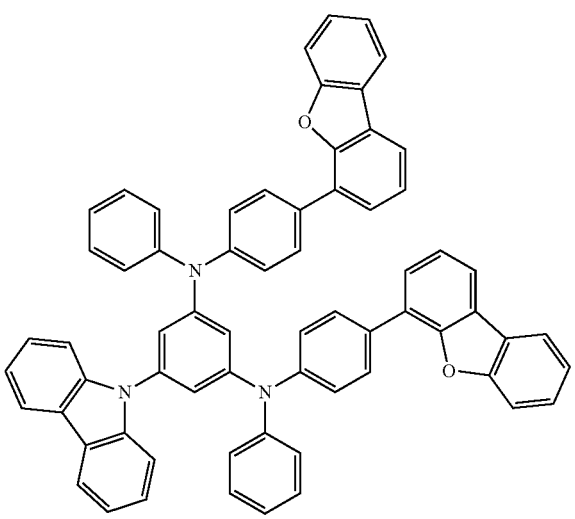

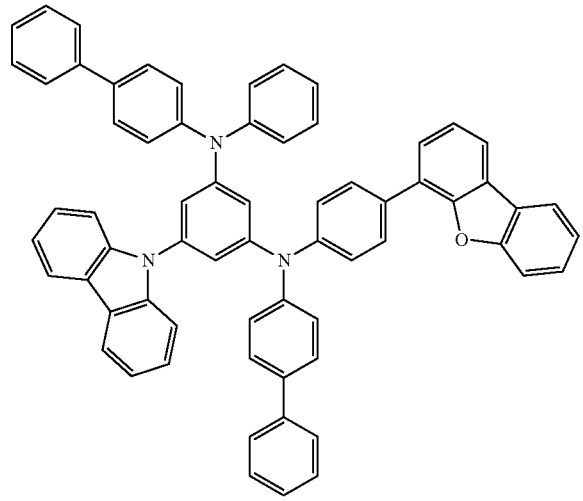
[E-25]

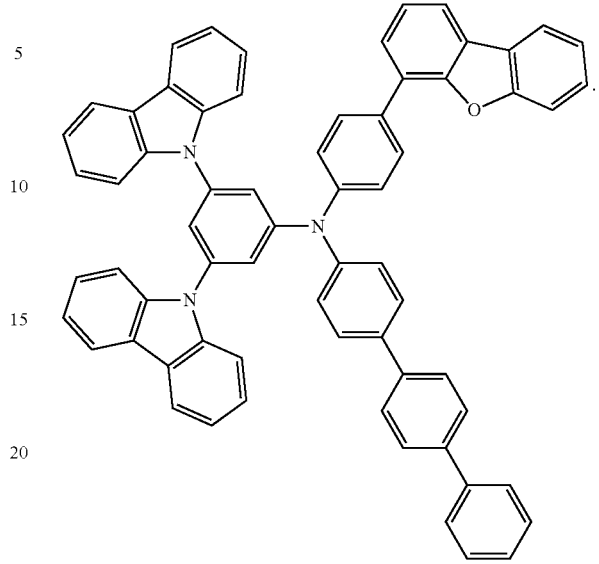
[F-12]

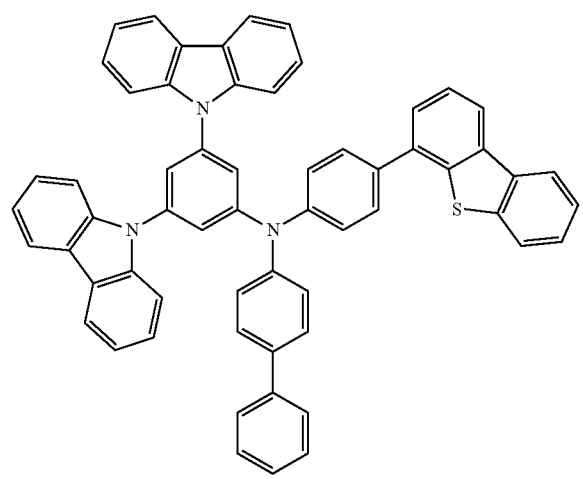
[F-2]

15. An organic light emitting element comprising
an anode, a cathode and at least one organic thin layer between the anode and the cathode,
wherein at least one layer of the organic thin layer includes the compound of claim 1.

16. The organic light emitting element of claim 15, wherein the organic thin layer is an electron injection layer (EIL), an electron transport layer (ETL), a hole injection layer (HIL), a hole transport layer (HTL), an auxiliary hole transport layer (HTL), or emission layer.

17. The organic light emitting element of claim 15, wherein the organic thin layer is an auxiliary hole transport layer (HTL).

18. The organic light emitting element of claim 15, wherein the compound is used as a host in an emission layer.

19. A display device comprising the organic light emitting element of claim 15.

* * * * *